(12) United States Patent
Hudson et al.

(10) Patent No.: US 9,657,012 B2
(45) Date of Patent: May 23, 2017

(54) FAAH INHIBITORS

(75) Inventors: Colleen Hudson, Malden, MA (US); Timothy C. Barden, Salem, MA (US); James Jia, Somerville, MA (US); Ara Mermerian, Melrose, MA (US); Bo Peng, Arlington, MA (US); Jane Yang, Boxborough, MA (US); Xiang Y. Yu, Acton, MA (US); Kevin Sprott, Needham, MA (US); Angelika Fretzen, Somerville, MA (US)

(73) Assignee: Ironwood Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/996,807

(22) PCT Filed: Dec. 22, 2011

(86) PCT No.: PCT/US2011/066972
§ 371 (c)(1),
(2), (4) Date: Feb. 4, 2014

(87) PCT Pub. No.: WO2012/088469
PCT Pub. Date: Jun. 28, 2012

(65) Prior Publication Data
US 2015/0175599 A1  Jun. 25, 2015

Related U.S. Application Data

(60) Provisional application No. 61/426,362, filed on Dec. 22, 2010, provisional application No. 61/446,808, filed on Feb. 25, 2011.

(51) Int. Cl.
| | | |
|---|---|---|
| *C07D 401/14* | (2006.01) | |
| *A61K 31/444* | (2006.01) | |
| *A61K 31/4439* | (2006.01) | |
| *C07D 471/04* | (2006.01) | |
| *C07D 401/12* | (2006.01) | |
| *C07D 403/12* | (2006.01) | |
| *C07D 403/14* | (2006.01) | |
| *A61K 31/4045* | (2006.01) | |
| *A61K 31/497* | (2006.01) | |
| *A61K 31/501* | (2006.01) | |
| *A61K 31/506* | (2006.01) | |
| *A61K 45/06* | (2006.01) | |
| *C07D 209/14* | (2006.01) | |

(52) U.S. Cl.
CPC ........ *C07D 471/04* (2013.01); *A61K 31/4045* (2013.01); *A61K 31/444* (2013.01); *A61K 31/4439* (2013.01); *A61K 31/497* (2013.01); *A61K 31/501* (2013.01); *A61K 31/506* (2013.01); *A61K 45/06* (2013.01); *C07D 209/14* (2013.01); *C07D 401/12* (2013.01); *C07D 401/14* (2013.01); *C07D 403/12* (2013.01); *C07D 403/14* (2013.01)

(58) Field of Classification Search
None
See application file for complete search history.

(56) References Cited

U.S. PATENT DOCUMENTS

| | | |
|---|---|---|
| 3,856,967 A | 12/1974 | Allais et al. |
| 3,946,029 A | 3/1976 | Descamps et al. |
| 4,105,777 A | 8/1978 | Allais et al. |
| 4,460,777 A | 7/1984 | Renfroe |
| 5,639,780 A | 6/1997 | Lau et al. |
| 5,965,582 A | 10/1999 | Lebaut et al. |
| 6,008,231 A | 12/1999 | Lebaut et al. |
| 6,069,156 A | 5/2000 | Oku et al. |
| 6,232,327 B1 | 5/2001 | Nickel et al. |
| 6,245,761 B1 | 6/2001 | Britton et al. |
| 6,251,923 B1 | 6/2001 | Hofgen et al. |
| 6,432,987 B2 | 8/2002 | Gunther et al. |
| 6,500,853 B1 | 12/2002 | Seehra et al. |
| 6,589,954 B1 | 7/2003 | Mavunkel et al. |
| 6,693,119 B2 | 2/2004 | Nickel et al. |
| 6,753,342 B2 | 6/2004 | Menta et al. |
| 6,867,209 B1 | 3/2005 | Mavunkel et al. |
| 6,903,104 B2 | 6/2005 | Chen et al. |
| 7,056,943 B2 | 6/2006 | Elokdah et al. |
| 7,067,536 B2 | 6/2006 | Hofgen et al. |
| 7,074,817 B2 | 7/2006 | Elokdah et al. |
| 7,205,299 B2 | 4/2007 | Gerlach et al. |

(Continued)

FOREIGN PATENT DOCUMENTS

| | | |
|---|---|---|
| CN | 101016294 | 8/2007 |
| WO | 99/43654 | 9/1999 |

(Continued)

OTHER PUBLICATIONS

Ajuebor, et al., "Cyclooxygenase-2-derived prostaglandin D2 is an early anti-inflammatory signal in experimental colitis," Am. J. Physiol. Gastrointest. Live Physiol., 279:G238-G244 (2000).
Arora, et al., "Eosinophilic Esophagitis: Asthma of the Esophagus?" Clin. Gastroint. & Hepatol. 2(7): 523-530 (2004).
Bahr, et al., "Targeting the endocannabinoid system in treating brain disorders," Expert Opin. Investig. Drugs 15(4):351-365 (2006).
Beilstein Institute for Organic Chemistry, Database Assession No. BRN453331, Compound: 2-(1-benzyl-5-methoxy-2-methyl-indol-3-yl)-2-oxo-N-phenyl-acetamide, Domschke et al., Chemische Berichte 94:2353-2355 (1961).

(Continued)

*Primary Examiner* — Alicia L Otton
(74) *Attorney, Agent, or Firm* — Peter Korakas; Karen E. Brown

(57) ABSTRACT

The present disclosure relates to compounds useful as inhibitors of the enzyme Fatty Acid Amide Hydrolase (FAAH). The disclosure also provides pharmaceutically acceptable compositions comprising the compounds of the disclosure and methods of using the compositions in the treatment or prevention of various disorders. Compounds of the invention are described in Table 1.

4 Claims, No Drawings

(56) References Cited

U.S. PATENT DOCUMENTS

| | | |
|---|---|---|
| 7,211,588 B2 | 5/2007 | Gerlach et |
| 7,229,986 B2 | 6/2007 | Ishihara et al. |
| 7,365,081 B2 | 4/2008 | Emig et al. |
| 7,452,910 B2 | 11/2008 | Nickel et al. |
| 7,528,165 B2 | 5/2009 | Hsieh et al. |
| 2002/0022218 A1 | 2/2002 | Li et al. |
| 2002/0161025 A1 | 10/2002 | Lebaut et al. |
| 2003/0162825 A1 | 8/2003 | Heefner et al. |
| 2004/0009990 A1 | 1/2004 | Higgins et al. |
| 2004/0266760 A1 | 12/2004 | Hoefgen et al. |
| 2006/0052390 A1 | 3/2006 | Schreiner et al. |
| 2006/0058296 A1 | 3/2006 | Higgins et al. |
| 2006/0110462 A1 | 5/2006 | Papadopoulos et al. |
| 2007/0203220 A1 | 8/2007 | Crandall et al. |
| 2010/0074955 A1 | 3/2010 | Buschmann et al. |
| 2010/0197708 A1 | 8/2010 | Talley et al. |
| 2010/0240718 A1 | 9/2010 | Lehr et al. |
| 2010/0256082 A1 | 10/2010 | Schotzinger |
| 2012/0088793 A1 | 4/2012 | Ghosh et al. |

FOREIGN PATENT DOCUMENTS

| | | | |
|---|---|---|---|
| WO | 99/43672 | 9/1999 | |
| WO | 00/51685 | 9/2000 | |
| WO | 00/67802 | 9/2000 | |
| WO | 01/32621 | 5/2001 | |
| WO | 01/44182 | 6/2001 | |
| WO | 01/44184 | 6/2001 | |
| WO | 01/44185 | 6/2001 | |
| WO | 01/81306 | 11/2001 | |
| WO | 02/08225 | 1/2002 | |
| WO | 03/022280 | 3/2003 | |
| WO | 03/066047 | 8/2003 | |
| WO | 2005/000875 | 1/2005 | |
| WO | 2005/014542 | 2/2005 | |
| WO | 2006/015263 | 2/2006 | |
| WO | 2006/015867 | 2/2006 | |
| WO | 2006/036994 | 4/2006 | |
| WO | 2006/091862 | 8/2006 | |
| WO | 2007/022501 | 2/2007 | |
| WO | 2008/008732 | 1/2008 | |
| WO | 2008/019357 | 2/2008 | |
| WO | 2008/066807 | 6/2008 | |
| WO | 2008/100867 | 8/2008 | |
| WO | 2008/157740 | 12/2008 | |
| WO | 2009/051666 | 4/2009 | |
| WO | 2010/109287 | 9/2010 | |
| WO | 2011/047156 | 4/2011 | |
| WO | 2011/123719 | 10/2011 | |
| WO | WO 2012/088431 | * 6/2012 | ........... C07D 401/12 |

OTHER PUBLICATIONS

Black, et al., "From indomethacin to a selective cox-2 inhibitor: development of indolalkanoic . . . " Biorg. & Medicin. Chem. Lett. 6(6):725-730 (1996).

Chen, et al., "Flavoenzymes inhibited by indomethacin" Drug Metab. & Drug Interac. 11(2):153-160, 1994.

Cravatt, et al., "Fatty acid amide hydrolase: an emerging therapeutic target in the endocannibinoid system", Curr. Opin. in Chem. Biol. 7:469-475 (2003).

Deutsch, et al., "The fatty acid amide hydrolase (FAAH)" Prostaglandins, Leukotrienes and Essential Fatty Acids 66 (2&3):201-210 (2002).

Domschke et al., "Notiz zur Darstellung einiger (1-Benzyl-2-methyl-5-methoxyindolyl-(3)]-glyoxylsaureamide" Chemische Berichte. 94:2353-2355 (1961).

Duggan, et al., "The metabolism of indomethacin in man" J. of Pharmacol. & Exper. Ther. 181(3):563-575 (1972).

Fride, et al., "Pharmacological activity of the cannabinoid receptor antagonist, anandamide, a brain constituent" Eur. J. of Pharm. 231:313-314 (1993).

Harman, et al., "The metabolites of indomethacin, a new anti-inflammatory drug" J. Pharmacol. Exp. Therap. 143:215-220 (1964).

Hecht, et al., "Heterologous desensitization of T cell functions by CCR5 and CXCR4 ligands: . . . " Intl. Immunology 15(1):29-38 (2003).

Helleberg, L., "Clinical Pharmacokinetics of Indomethacin" Clin. Pharm. 6:245-258 (1981).

Huang, et al., "Sequence variants of the gene encoding chemoattractant receptor expressed on Th2 cells (CRTH2) are . . . " Human Mol. Genet. 13(21):2691-2697 (2004).

Kiehl, et al., "Tissue eosinophilia in acute and chronic atopic dermatitis: a morphometric approach . . . " British J. of Dermatol. 145:720-729 (2001).

Lau, et al., "From indomethacin to a selective cox-2 inhibitor" Advances in Experimental Medicine and Biology 407:73-78 (1997).

Menciu, et al., "New N-(pyridin-4-yl)-(indol-3-yl) acetamides and propanamides as antiallergic agents" J. Med. Chem. 42(4):638-648 (1999).

Monneret, et al., "15R-Methyl-Prostaglandin D2 is a potent and selective CRTH2/DP2 receptor . . . " J. of Pharmacol. & Experim. Ther. 304(1):349-355 (2003).

Nagata, et al., "CRTH2, an orphan receptor of T-helper-2-cells, is expressed on basophils . . . " FEBS Letters 459:195-199 (1999).

Olgen, et al., "Synthesis and antioxidant properties of novel N-substituted indole-2-carboxamide and indole-3-acetamide derivatives" Archlv Der Pharmazie 7:331-338 (2002).

Shen, et al., "Non-Steroid Anti-Inflammatory Agents" J. Amer. Chem. Soc. 85:488-489 (1963).

Shen, T. et al., "Chemical and Biological Studies on Indomethacin, Sulindac and their Analogs" Adv. in Drug Res. 12:89-245 (1977).

Shichijo, et al., "Chemoattractant Receptor-Homologous Molecule Expressed on TH2 Cells Activation . . . " J. of Pharmacol. & Exper. Ther. 307(2):518-525 (2003).

Strachman, et al., "Synthesis of Indomethacin Metabolites" J. Med. Chem. 7(6):799-800 (1964).

Stubbs, et al., "Indomethacin Causes Prostaglandin D2-like and Eotaxin-like Selective Responses . . . " J. of Biol. Chem. 277(29):26012-26020 (2002).

Touhey, et al., "Structure-activity relationshipof indomethacin analogues of MRP-1, COX-1 and COX-2 inhibition: . . . " Eur. J. of Cancer 38:1661-1670 (2002).

Walker, et al., "Pain modulation by release of the endogenous cannabinoid anandamide" PNAS 96(21):12198-12203 (1999).

Weber, et al., "Formation of Prostamides from Anandamide in FAAH Knockout Mice Analyzed by HPLC . . . " J. of Lipid Res. 45:757-763 (2004).

Wei, et al., "A second fatty acid amide hydrolase with variable distribution among placental mammals" J. of Biol. Chem. 281(48):36569-36578 (2006).

Yoshimura-Uchiyama, et al., "Differential modulation of human basophile functions through prostaglandin D2 receptors . . . " Clin. Exp. Allergy 34:1283-1290 (2004).

ISR PCT US08/67588 dated Dec. 26, 2008.
ISR PCT US07/75332 dated May 7, 2008.
ISR PCT US06/32573 dated May 23, 2007.
ISR PCT US06/62265 dated Oct. 16, 2008.
Chemical Abstracts Service Registry No. 857495-43-3, STN Entry Date Jul. 28, 2005.

* cited by examiner

FAAH INHIBITORS

PRIORITY CLAIM

This application is a national phase application of PCT/US2011/066972, filed on Dec. 22, 2011, which claims priority to U.S. Provisional Application Ser. No. 61/446,808, filed Feb. 25, 2011, and 61/426,362 filed Dec. 22, 2010. The entire contents of the aforementioned applications are incorporated herein by reference.

TECHNICAL FIELD

The present disclosure relates to indole and azaindole compounds useful as inhibitors of the enzyme Fatty Acid Amide Hydrolase (FAAH). The disclosure also provides pharmaceutically acceptable compositions comprising the compounds of the disclosure and methods of using the compositions in the treatment of various disorders.

BACKGROUND

The endocannabinoid (eCB) system has been implicated in a variety of processes including cell signaling, memory encoding, compensatory mechanisms, and immunosuppressant and anti-inflammatory responses. The eCB system comprises at least two receptors: the CB1 cannabinoid receptor, widely distributed in the brain, and present in some peripheral organs, and the CB2 receptor, found principally in the periphery and immune systems and in some regions of the brain. The endogenous agonists of these receptors are the endogenous cannabinoids (eCBs), a family of lipids comprising the fatty acid anandamide (AEA) as well as other fatty acids.

Endocannabinoid-degrading enzymes, including fatty acid amide hydrolase (FAAH), are responsible for cleaving and deactivating eCBs in vivo. FAAH is an integral membrane protein that is expressed in high levels in several brain regions, especially in the neurons of the hippocampus, cerebellum, neocortex and olfactory bulb. FAAH is the principal enzyme responsible for the hydrolysis of AEA in vivo and is also capable of hydrolyzing a wide variety of other substrates. It is known that inhibiting FAAH can lead to increases in fatty acids, including AEA, which could enhance cannabinoid signals within the eCB system. It has also been demonstrated that a number of fatty acid amides can induce analgesia in acute and chronic animal models of pain. Thus, increasing the level of AEA and other fatty acid amides (e.g., N-palmitoyl ethanolamide, N-oleoylethanol amide and oleamide) by inhibiting FAAH may lead to an increase in the nociceptive threshold. For these reasons, inhibitors of FAAH are useful in the treatment of pain. Inhibitors of FAAH might also be useful in the treatment of other disorders involving deregulation of the eCB system (e.g., depression, anxiety, eating disorders, gastrointestinal and cardiovascular disorders, inflammation, excitotoxic insult, brain trauma and fibromyalgia), and may avoid some of the side effects typically associated with CB receptor agonists (e.g., catalepsy or hypothermia).

In addition, previous studies have demonstrated that eCBs can control spasticity and provide neuroprotection in multiple sclerosis rodent models. Thus, certain FAAH inhibitors may be useful agents for treating symptoms or achieving disease modification changes in multiple sclerosis. There is also evidence that when FAAH activity is reduced or absent, AEA acts as a substrate for COX-2, which can convert it to a prostamide. Thus, certain prostamides may be elevated in the presence of an FAAH inhibitor. Given that certain prostamides are associated with reduced intraocular pressure and ocular hypotensivity, FAAH inhibitors may also be useful agents for treating glaucoma.

SUMMARY

The compounds of the instant disclosure and their pharmaceutically acceptable salts thereof are useful as FAAH inhibitors. They are selected from the group consisting of:

TABLE I

| Structure | Compound Number |
|---|---|
| 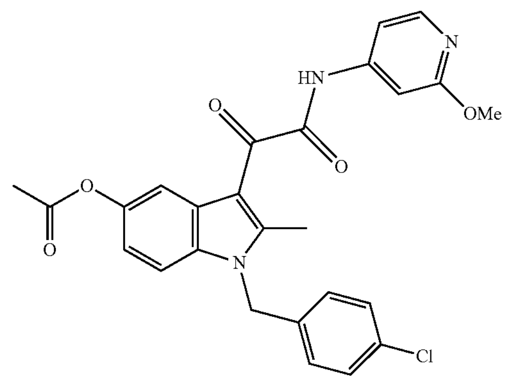 [SMILES: COc1cc(NC(=O)C(=O)c2c(C)n(Cc3ccc(Cl)cc3)c3ccc(OC(C)=O)cc23)ccn1] | 1 |
| 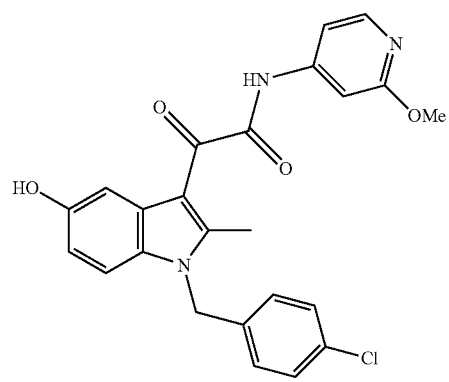 [SMILES: COc1cc(NC(=O)C(=O)c2c(C)n(Cc3ccc(Cl)cc3)c3ccc(O)cc23)ccn1] | 2 |
| 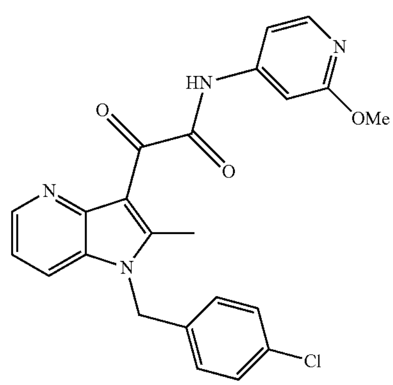 [SMILES: COc1cc(NC(=O)C(=O)c2c(C)n(Cc3ccc(Cl)cc3)c3cccnc23)ccn1] | 3 |

TABLE I-continued

| Structure | Compound Number |
|---|---|
| (structure) | 4 |
| (structure) | 5 |
| (structure) | 6 |
| (structure) | 7 |
| (structure) | 8 |
| (structure) | 9 |
| (structure) | 10 |
| (structure) | 11 |

TABLE I-continued

| Structure | Compound Number |
|---|---|
| (5-methoxy-2-methyl-1-((5-chloropyrazin-2-yl)methyl)-1H-indol-3-yl) N-(2-methoxypyridin-4-yl) oxoacetamide | 12 |
| (5-methoxy-6-fluoro-2-methyl-1-((3,5-dichloropyridin-2-yl)methyl)-1H-indol-3-yl) N-(2-methoxypyridin-4-yl) oxoacetamide | 13 |
| (5-methoxy-6-fluoro-2-methyl-1-(2,4-difluorobenzyl)-1H-indol-3-yl) N-(2-methoxypyridin-4-yl) oxoacetamide | 14 |
| (5-cyano-2-methyl-1-(4-chlorobenzyl)-1H-indol-3-yl) N-(2-methoxypyridin-4-yl) oxoacetamide | 15 |
| (5-methoxy-2-methyl-1-(pyridin-4-ylmethyl)-1H-indol-3-yl) N-(2-methoxypyridin-4-yl) oxoacetamide | 16 |
| (5-dimethylamino-2-methyl-1-(4-chlorobenzyl)-1H-indol-3-yl) N-(2-methoxypyridin-4-yl) oxoacetamide | 17 |
| (5-bromo-2-methyl-1-(4-chlorobenzyl)-1H-indol-3-yl) N-(2-methoxypyridin-4-yl) oxoacetamide | 18 |
| (5-nitro-2-methyl-1-(4-chlorobenzyl)-1H-indol-3-yl) N-(2-methoxypyridin-4-yl) oxoacetamide | 19 |

TABLE I-continued

| Structure | Compound Number |
|---|---|
| (5-amino-1-(4-chlorobenzyl)-2-methylindol-3-yl with oxoacetamide linked to 2-methoxypyridin-4-yl) | 20 |
| (5-trifluoromethyl-1-(4-chlorobenzyl)-2-methylindol-3-yl with oxoacetamide linked to 2-methoxypyridin-4-yl) | 21 |
| (5-acetamido-1-(4-chlorobenzyl)-2-methylindol-3-yl with oxoacetamide linked to 2-methoxypyridin-4-yl) | 22 |
| (5-trifluoromethoxy-1-(4-chlorobenzyl)-2-methylindol-3-yl with oxoacetamide linked to 2-methoxypyridin-4-yl) | 23 |
| (5-diethylamino-1-(4-chlorobenzyl)-2-methylindol-3-yl with oxoacetamide linked to 2-methoxypyridin-4-yl) | 24 |
| (5-(methylaminomethyl)-1-(4-chlorobenzyl)-2-methylindol-3-yl with oxoacetamide linked to 2-methoxypyridin-4-yl) | 25 |
| (5-(dimethylaminomethyl)-1-(4-chlorobenzyl)-2-methylindol-3-yl with oxoacetamide linked to 2-methoxypyridin-4-yl) | 26 |
| (5-vinyl-1-(4-chlorobenzyl)-2-methylindol-3-yl with oxoacetamide linked to 2-methoxypyridin-4-yl) | 27 |

TABLE I-continued

| Structure | Compound Number |
|---|---|
| (structure) | 28 |
| (structure) | 29 |
| (structure) | 30 |
| (structure) | 31 |
| (structure) | 32 |
| (structure) | 33 |
| (structure) | 34 |
| (structure) | 35 |

TABLE I-continued
| Structure | Compound Number |
|---|---|
| 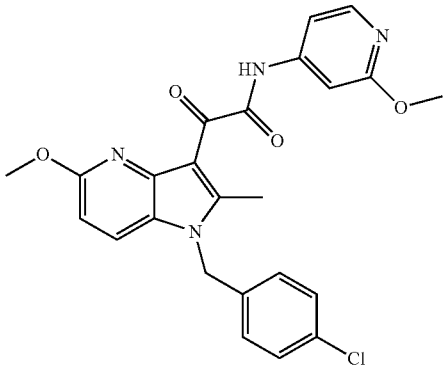 | 36 |
| 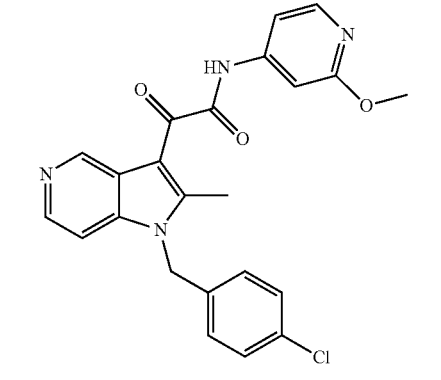 [SMILES: COc1cc(NC(=O)C(=O)c2c(C)n(Cc3ccc(Cl)cc3)c3ccncc23)ccn1] | 37 |
| 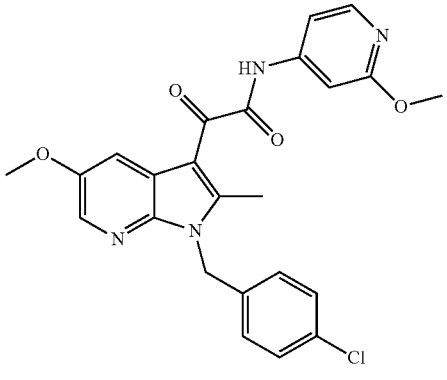 | 38 |
| 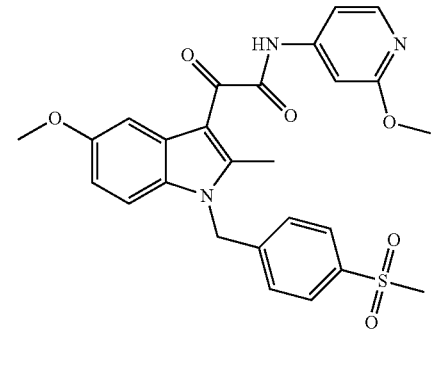 | 39 |
| 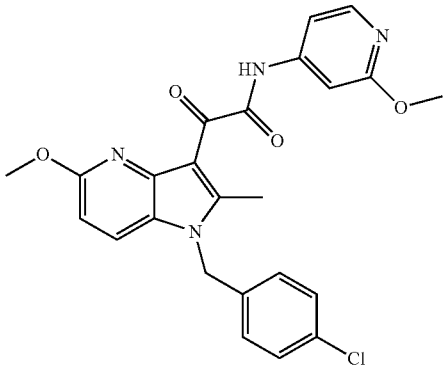 | 40 |
| 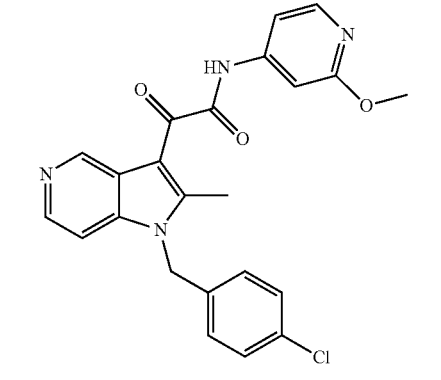 [SMILES: COc1cc(NC(=O)C(=O)c2c(C)n(Cc3ccc(Cl)cc3)c3ccncc23)ccn1] | 41 |
| 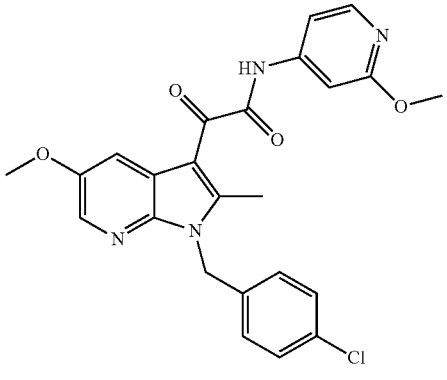 | 42 |
| 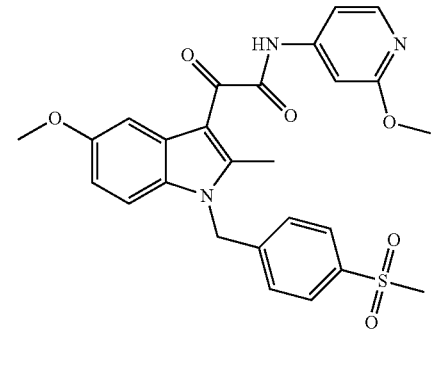 | 43 |

TABLE I-continued

| Structure | Compound Number |
|---|---|
| (structure) | 44 |
| (structure) | 45 |
| (structure) | 46 |
| (structure) | 47 |
| (structure) | 48 |
| (structure) | 49 |
| (structure) | 50 |
| (structure) | 51 |

TABLE I-continued
| Structure | Compound Number |
|---|---|
| 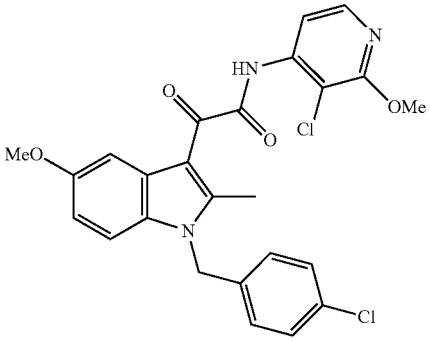 [SMILES: COc1ccc2c(c1)c(C(=O)C(=O)Nc1ccnc(OC)c1Cl)c(C)n2Cc1ccc(Cl)cc1] | 52 |
| 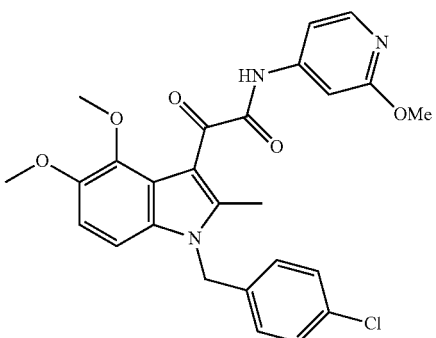 | 53 |
| 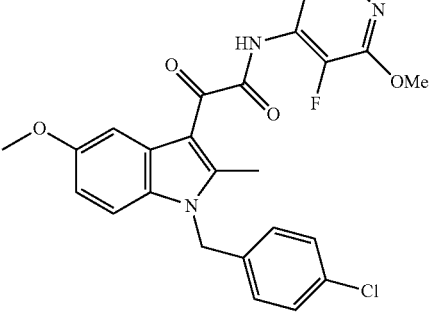 | 54 |
| 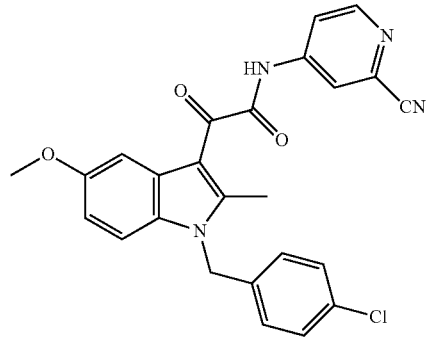 [SMILES: COc1ccc2c(c1)c(C(=O)C(=O)Nc1ccnc(C#N)c1)c(C)n2Cc1ccc(Cl)cc1] | 55 |
| 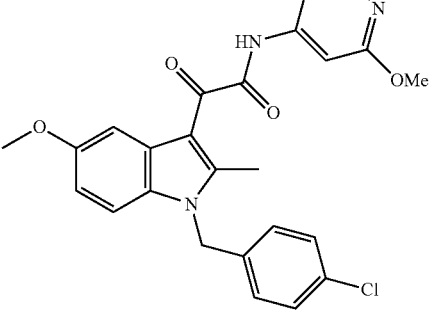 | 56 |
| 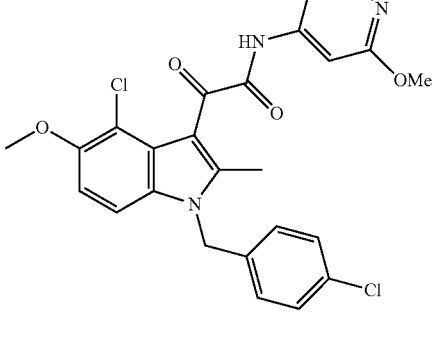 | 57 |
| 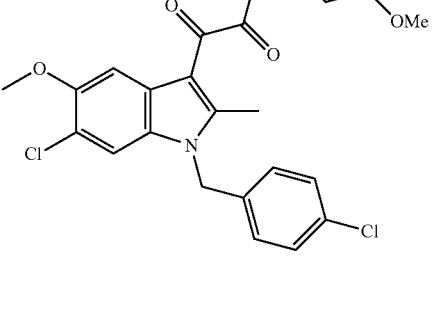 | 58 |
| 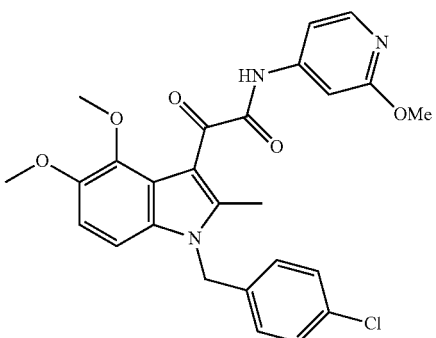 | 59 |

TABLE I-continued

| Structure | Compound Number |
|---|---|
| (5-methoxy-6-chloro-2-methyl-1-((5-chloropyridin-2-yl)methyl)-1H-indol-3-yl)-N-(2-methoxypyridin-4-yl) glyoxylamide | 60 |
| (5-methyl-2-methyl-1-((5-chloropyridin-2-yl)methyl)-1H-indol-3-yl)-N-(2-methoxypyridin-4-yl) glyoxylamide | 61 |
| (5-nitro-2-methyl-1-((5-chloropyridin-2-yl)methyl)-1H-indol-3-yl)-N-(2-methoxypyridin-4-yl) glyoxylamide | 62 |
| (5-chloro-2-methyl-1-((5-chloropyridin-2-yl)methyl)-1H-indol-3-yl)-N-(2-methoxypyridin-4-yl) glyoxylamide | 63 |

| Structure | Compound Number |
|---|---|
| (5-methoxy-6-fluoro-2-methyl-1-((5-chloropyridin-2-yl)methyl)-1H-indol-3-yl)-N-(2-methoxypyridin-4-yl) glyoxylamide | 64 |
| (5-amino-2-methyl-1-((5-chloropyridin-2-yl)methyl)-1H-indol-3-yl)-N-(2-methoxypyridin-4-yl) glyoxylamide | 65 |
| (5-dimethylamino-2-methyl-1-((5-chloropyridin-2-yl)methyl)-1H-indol-3-yl)-N-(2-methoxypyridin-4-yl) glyoxylamide | 66 |
| (5-chloro-6-methoxy-2-methyl-1-((5-chloropyridin-2-yl)methyl)-1H-indol-3-yl)-N-(2-methoxypyridin-4-yl) glyoxylamide | 67 |

TABLE I-continued
| Structure | Compound Number |
|---|---|
| 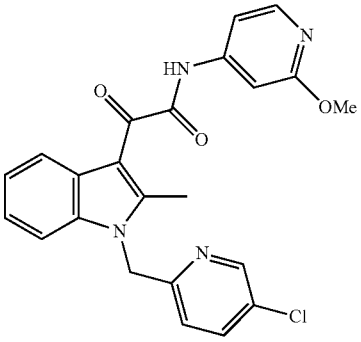 [SMILES: COc1cc(NC(=O)C(=O)c2c(C)n(Cc3ccc(Cl)cn3)c3ccccc23)ccn1] | 68 |
| 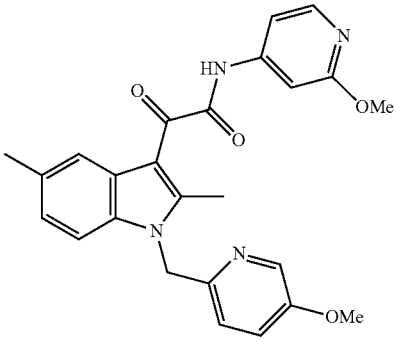 [SMILES: COc1ccc(Cn2c(C)c(C(=O)C(=O)Nc3ccnc(OC)c3)c3cc(C)ccc32)nc1] | 69 |
| 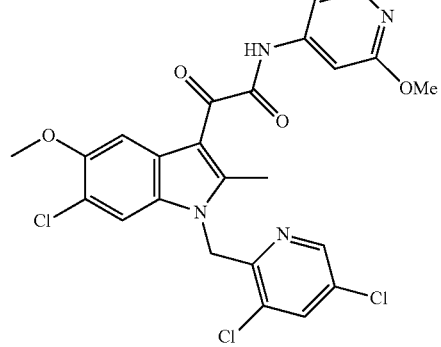 | 70 |
| 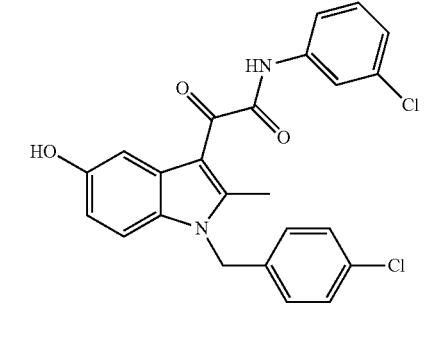 [SMILES: Cc1c(C(=O)C(=O)Nc2cccc(Cl)c2)c2cc(O)ccc2n1Cc1ccc(Cl)cc1] | 71 |
| 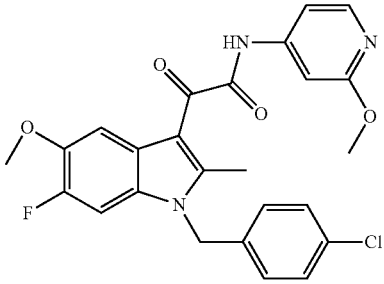 [SMILES: COc1cc(NC(=O)C(=O)c2c(C)n(Cc3ccc(Cl)cc3)c3cc(F)c(OC)cc23)ccn1] | 72 |
| 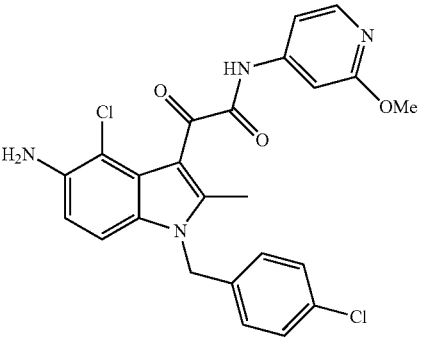 [SMILES: COc1cc(NC(=O)C(=O)c2c(C)n(Cc3ccc(Cl)cc3)c3ccc(N)c(Cl)c23)ccn1] | 73 |
| 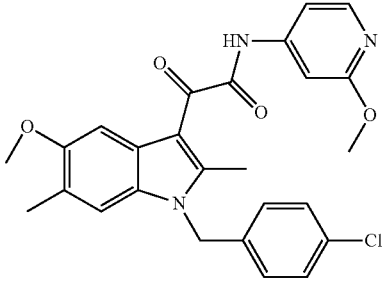 [SMILES: COc1cc(NC(=O)C(=O)c2c(C)n(Cc3ccc(Cl)cc3)c3cc(C)c(OC)cc23)ccn1] | 74 |
| 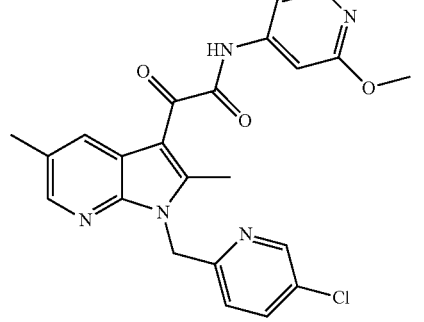 | 75 |

TABLE I-continued

| Structure | Compound Number |
|---|---|
| 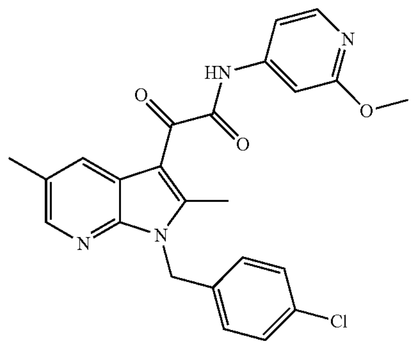 | 76 |
| 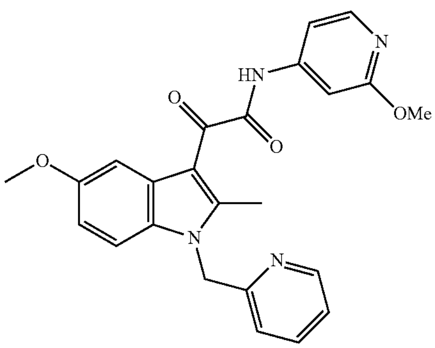 [SMILES: COc1ccc2c(c1)c(C(=O)C(=O)Nc1ccnc(OC)c1)c(C)n2Cc1ccccn1] | 77 |
| 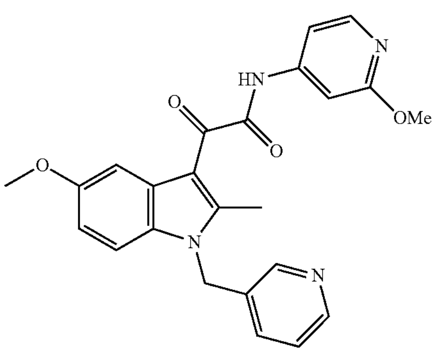 [SMILES: COc1ccc2c(c1)c(C(=O)C(=O)Nc1ccnc(OC)c1)c(C)n2Cc1cccnc1] | 78 |
| 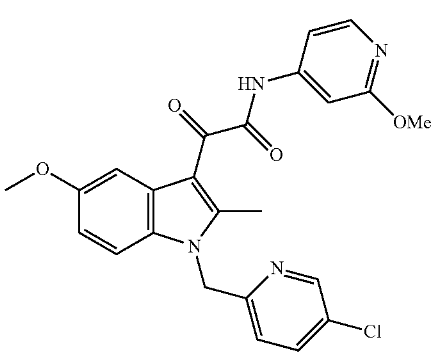 [SMILES: COc1ccc2c(c1)c(C(=O)C(=O)Nc1ccnc(OC)c1)c(C)n2Cc1ccc(Cl)cn1] | 79 |
| | 80 |
| | 81 |
| | 82 |
| | 83 |

TABLE I-continued
| Structure | Compound Number |
|---|---|
| 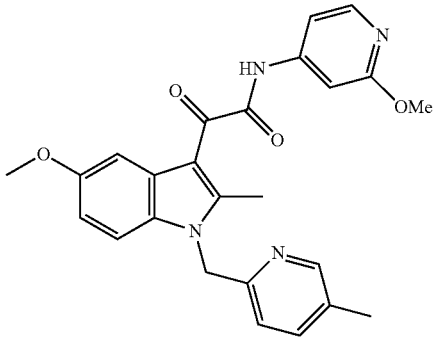 [SMILES: COc1ccc2c(c1)c(C(=O)C(=O)Nc1ccnc(OC)c1)c(C)n2Cc1ccc(C)cn1] | 84 |
| 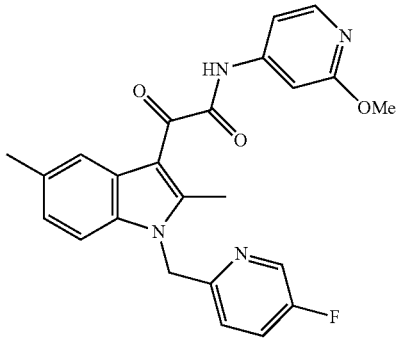 [SMILES: COc1cc(NC(=O)C(=O)c2c(C)n(Cc3ccc(F)cn3)c3ccc(C)cc23)ccn1] | 85 |
| 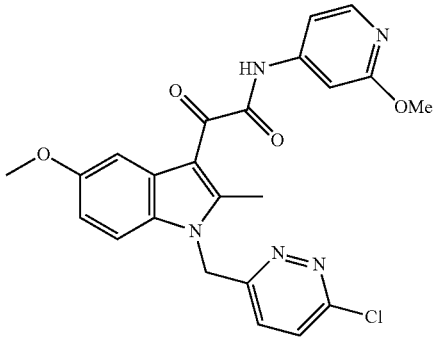 [SMILES: COc1ccc2c(c1)c(C(=O)C(=O)Nc1ccnc(OC)c1)c(C)n2Cc1ccc(Cl)nn1] | 86 |
| 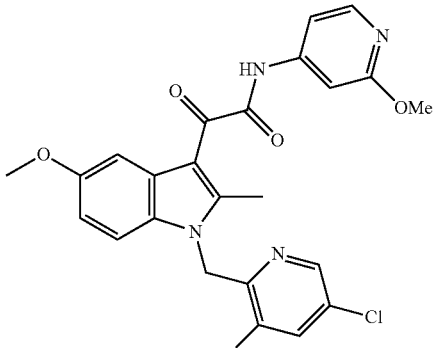 | 87 |
| 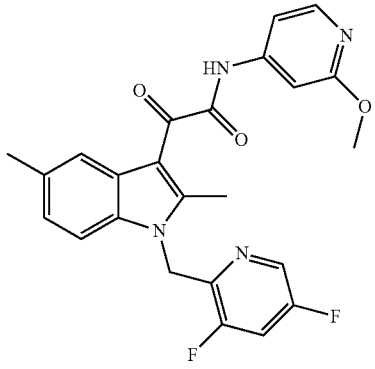 [SMILES: COc1cc(NC(=O)C(=O)c2c(C)n(Cc3ncc(F)cc3F)c3ccc(C)cc23)ccn1] | 88 |
| 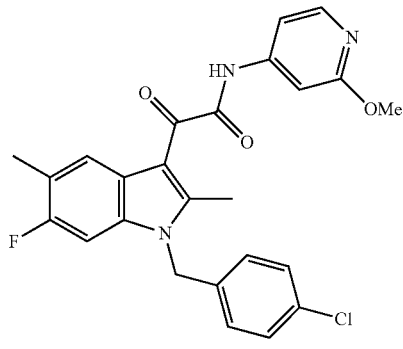 [SMILES: COc1cc(NC(=O)C(=O)c2c(C)n(Cc3ccc(Cl)cc3)c3cc(F)c(C)cc23)ccn1] | 89 |
| 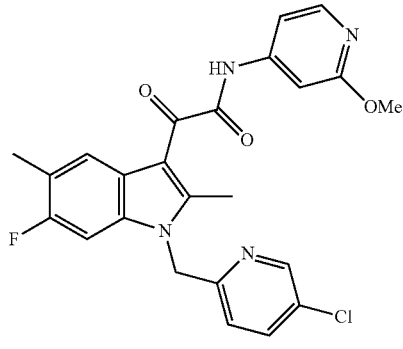 | 90 |
| 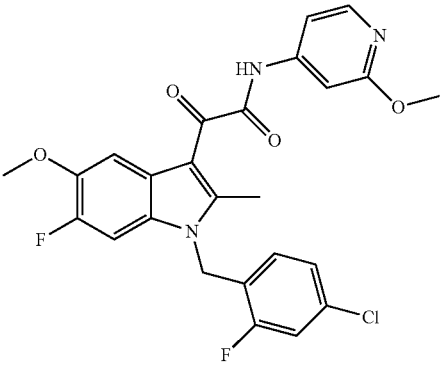 | 91 |

TABLE I-continued
| Structure | Compound Number |
|---|---|
| 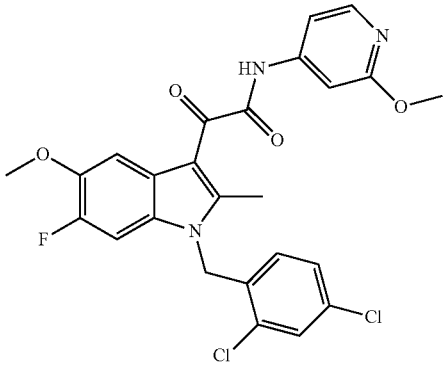 | 92 |
| 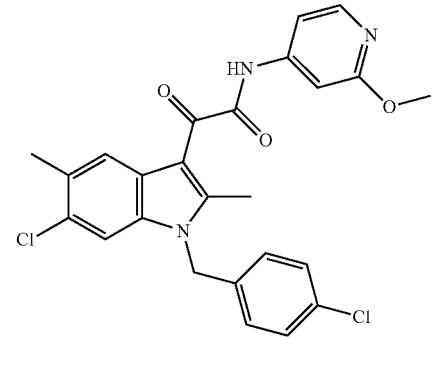 | 93 |
| 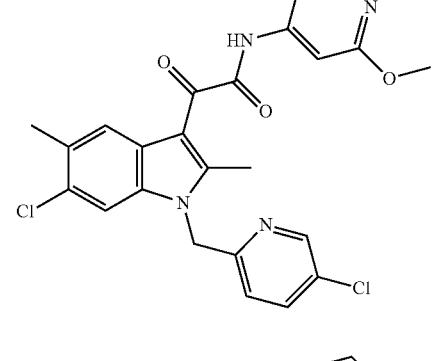 | 94 |
| 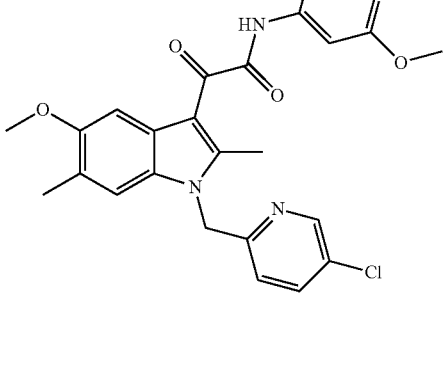 | 95 |
| 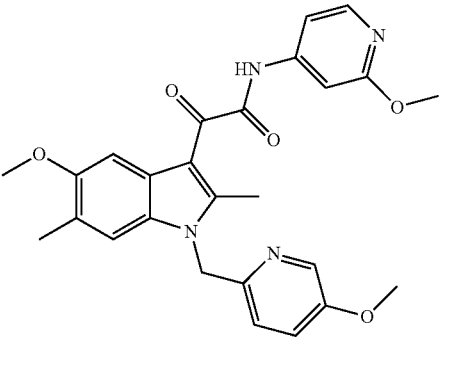 | 96 |
| 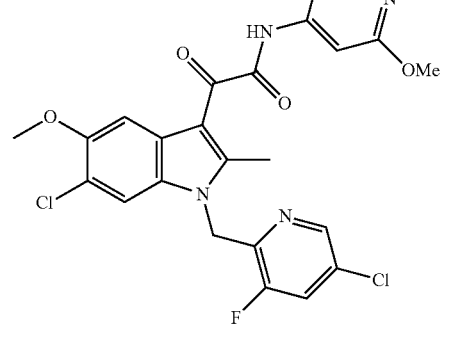 | 97 |
| 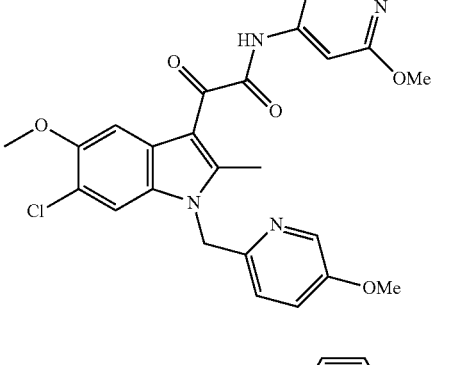 | 98 |
| 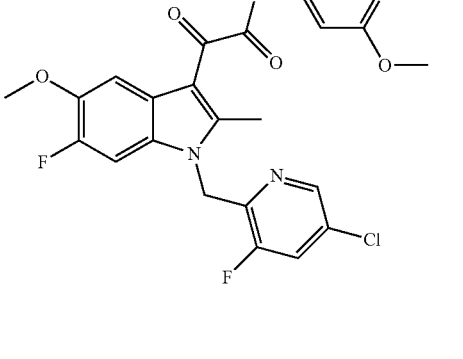 | 99 |

TABLE I-continued

| Structure | Compound Number |
|---|---|
| (structure) | 100 |
| (structure) | 101 |

A further aspect of the disclosure includes pharmaceutical compositions comprising one or more of said compounds of Table 1, alone or in combination with one or more additional therapeutic agents.

In another aspect, the compounds of Table 1 described herein and their pharmaceutically acceptable compositions are useful in methods for treating or lessening the severity of a variety of diseases or disease symptoms, including pain, inflammation, progressive central nervous system or neurological diseases, and autoimmune diseases.

In another aspect, the compounds of Table 1 and their pharmaceutical compositions can be used in combination therapy.

The invention also relates to methods for the treatment or prevention of pain; autoimmune disorders; disease-states or indications that are accompanied by inflammatory processes; gastrointestinal diseases or disorders; pruritus; substance abuse-related syndromes, disorders, diseases or withdrawal symptoms; psychiatric disorders; neurological or neurodegenerative disorders; ocular disorders; appetite-related disorders; gynecological disorders, urinary system disorders and sleep disorders; by using one of the compounds or pharmaceutical composition of the invention, either alone or in combination therapy.

DETAILED DESCRIPTION

Reference will now be made in detail to certain embodiments of the invention, examples of which are illustrated in the accompanying structures and formulae. While the invention will be described in conjunction with the disclosed embodiments, it will be understood that they are not intended to limit the invention to those embodiments. Rather, the invention is intended to cover all alternatives, modifications and equivalents that may be included within the scope of the present invention as defined by the claims. The present invention is not limited to the methods and materials described herein but include any methods and materials similar or equivalent to those described herein that could be used in the practice of the present invention. In the event that one or more of the incorporated literature references, patents or similar materials differ from or contradict this application, including but not limited to defined terms, term usage, described techniques or the like, this application controls.

DESCRIPTION OF EXEMPLARY COMPOUNDS

Definitions and General Terminology

For purposes of this disclosure, the chemical elements are identified in accordance with the Periodic Table of the Elements, CAS version, and the *Handbook of Chemistry and Physics*, 75th Ed. (1994). Additionally, general principles of organic chemistry are described in *Organic Chemistry*, Thomas Sorrell, University Science Books, Sausalito: 1999, and *March's Advanced Organic Chemistry*, 5th Ed., Smith, M. B. and March, J., eds. John Wiley & Sons, New York: 2001, which are herein incorporated by reference in their entirety.

As described herein, compounds of the invention may optionally be substituted with one or more substituents, such as illustrated generally below, or as exemplified by particular classes, subclasses, and species of the invention. The phrase "optionally substituted" is used interchangeably with the phrase "substituted or unsubstituted." In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. If a substituent radical or structure is not identified or defined as "optionally substituted", the substituent radical or structure is not substituted. As it will be apparent to one of ordinary skill in the art, groups such as —H, halogen, —$NO_2$, —CN, —OH, —$NH_2$ or —$OCF_3$ would not be substitutable groups.

The phrase "up to", as used herein, refers to zero or any integer number that is equal to or less than the number following the phrase. For example, optionally substituted with "up to 3" means substituted with 0, 1, 2, or 3 substituents. As described herein, a specified number range of atoms includes any integer therein. For example, a group having from 1-4 atoms could have 1, 2, 3 or 4 atoms. It will be understood by one of ordinary skill in the art that when a group is characterized as substituted (as opposed to optionally substituted) with, e.g., "up to 3" substituents, it can only be substituted with 1, 2 or 3 substituents.

When any variable occurs more than one time at any position, its definition on each occurrence is independent from every other occurrence.

Selection of substituents and combinations envisioned by this disclosure are only those that result in the formation of stable or chemically feasible compounds. Such choices and combinations will be apparent to those of ordinary skill in the art and may be determined without undue experimentation. The term "stable", as used herein, refers to compounds that are not substantially altered when subjected to conditions that allow for their production, detection, and, in some embodiments, their recovery, purification, and use for one or more of the purposes disclosed herein. In some embodiments, a stable compound or chemically feasible compound is one that is not substantially altered when kept at a temperature of 25° C. or less, in the absence of moisture or other chemically reactive conditions, for at least a week.

A compound, such as the compounds of the invention or other compounds herein disclosed, may be present in its free form (e.g., an amorphous form or polymorphs). Under certain conditions, compounds may also form salts, and/or other multi-component crystalline forms (e.g., solvates (e.g., hydrates) and co-crystals). As used herein, the term co-form is synonymous with the term multi-component crystalline form. When one of the components in the co-form has clearly transferred a proton to the other component, the resulting co-form is referred to as a "salt". When both compounds in a multi-component crystalline form are independently solids at room temperature, the resulting co-form is referred to as a "co-crystal". In co-crystals, no proton transfer takes place between the different components of the co-form. The formation of a salt or a co-crystal is determined by how large is the difference in the pKas between the partners that form the mixture. As used herein, a "solvate" refers to an association or complex of one or more solvent molecules and a compound disclosed herein (or its salts or co-crystals). A "hydrate" is a particular type of solvate in which the solvent is water. Examples of solvents that can form solvates include, but are not limited to: water, isopropanol, ethanol, methanol, dimethyl sulfoxide (DMSO), ethyl acetate, acetic acid, ethanolamine, tetrahydrofuran (THF), dichloromethane (DCM), N,N-dimethylformamide (DMF).

Unless only one of the isomers is drawn or named specifically, structures depicted herein are also meant to include all stereoisomeric (e.g., enantiomeric, diastereomeric, atropoisomeric and cis-trans isomeric) forms of the structure, for example, the R and S configurations for each asymmetric center, Ra and Sa configurations for each asymmetric axis, (Z) and (E) double bond configurations, and cis and trans conformational isomers. Therefore, single stereochemical isomers as well as racemates, and mixtures of enantiomers, diastereomers, and cis-trans isomers (double bond or conformational) of the present compounds are within the scope of the present disclosure. Unless otherwise stated, all tautomeric forms of the compounds of the present disclosure are within the scope of the disclosure.

The present disclosure also embraces isotopically labeled compounds that are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine, and iodine, such as $^2$H, 3H, C, $^{13}$C, $^{14}$C, $^{13}$N $^{15}$N $^{15}$O, $^{17}$O, $^{18}$O, $^{32}$P, $^{33}$P, $^{35}$S, $^{18}$F, $^{36}$Cl, $^{123}$I, and $^{125}$I, respectively. Certain isotopically labeled compounds of the present invention (e.g., those labeled with $^3$H and $^{14}$C) are useful in compound and/or substrate tissue distribution assays. Tritiated (i.e., $^3$H) and carbon-14 (i.e., $^{14}$C) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron-emitting isotopes such as $^{15}$O, $^{13}$N, $^{11}$C, and $^{18}$F are useful for positron emission tomography (PET) studies to examine substrate receptor occupancy. Isotopically labeled compounds of the present invention can generally be prepared by following procedures analogous to those disclosed in the Examples herein by substituting an isotopically labeled reagent for a non-isotopically labeled reagent.

The terms "aliphatic" or "aliphatic group", as used herein, mean a straight-chain (i.e., unbranched) or branched, substituted or unsubstituted hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms. In other embodiments, aliphatic groups contain 1-4 aliphatic carbon atoms and in yet other embodiments, aliphatic groups contain 1-3 aliphatic carbon atoms. Suitable aliphatic groups include, but are not limited to, linear or branched, substituted or unsubstituted alkyl, alkenyl, or alkynyl groups. Specific examples of aliphatic groups include, but are not limited to: methyl, ethyl, propyl, butyl, isopropyl, isobutyl, vinyl, sec-butyl, tert-butyl, butenyl, propargyl, acetylene and the like.

The term "alkyl", as used herein, refers to a saturated linear or branched-chain monovalent hydrocarbon radical. Unless otherwise specified, an alkyl group contains 1-20 carbon atoms (e.g., 1-20 carbon atoms, 1-10 carbon atoms, 1-8 carbon atoms, 1-6 carbon atoms, 1-4 carbon atoms or 1-3 carbon atoms). Examples of alkyl groups include, but are not limited to, methyl, ethyl, n-propyl, isopropyl, n-butyl, isobutyl, s-butyl, t-butyl, pentyl, hexyl, heptyl, octyl and the like.

The term "alkenyl" refers to a linear or branched-chain monovalent hydrocarbon radical with at least one site of unsaturation, i.e., a carbon-carbon, sp$^2$ double bond, wherein the alkenyl radical includes radicals having "cis" and "trans" orientations, or alternatively, "E" and "Z" orientations. Unless otherwise specified, an alkenyl group contains 2-20 carbon atoms (e.g., 2-20 carbon atoms, 2-10 carbon atoms, 2-8 carbon atoms, 2-6 carbon atoms, 2-4 carbon atoms or 2-3 carbon atoms). Examples include, but are not limited to, vinyl, allyl and the like.

The term "alkynyl" refers to a linear or branched monovalent hydrocarbon radical with at least one site of unsaturation, i.e., a carbon-carbon sp triple bond. Unless otherwise specified, an alkynyl group contains 2-20 carbon atoms (e.g., 2-20 carbon atoms, 2-10 carbon atoms, 2-8 carbon atoms, 2-6 carbon atoms, 2-4 carbon atoms or 2-3 carbon atoms). Examples include, but are not limited to, ethynyl, propynyl, and the like.

The term "carbocyclic" refers to a ring system formed only by carbon and hydrogen atoms. Unless otherwise specified, throughout this disclosure, carbocycle is used as a synonym of "non-aromatic carbocycle" or "cycloaliphatic"). In some instances, the term can be used in the phrase "aromatic carbocycle", and in this case it refers to an "aryl group" as defined below.

The term "cycloaliphatic" (or "non-aromatic carbocycle", "non-aromatic carbocyclyl", "non-aromatic carbocyclic") refers to a cyclic hydrocarbon that is completely saturated or that contains one or more units of unsaturation but which is not aromatic, and which has a single point of attachment to the rest of the molecule. Unless otherwise specified, a cycloaliphatic group may be monocyclic, bicyclic, tricyclic, fused, spiro or bridged. In one embodiment, the term "cycloaliphatic" refers to a monocyclic $C_3$-$C_{12}$ hydrocarbon or a bicyclic $C_7$-$C_{12}$ hydrocarbon. In some embodiments, any individual ring in a bicyclic or tricyclic ring system has 3-7 members. Suitable cycloaliphatic groups include, but are not limited to, cycloalkyl, cycloalkenyl, and cycloalkynyl. Examples of aliphatic groups include cyclopropyl, cyclobutyl, cyclopentyl, cyclopentenyl, cyclohexyl, cyclohexenyl, cycloheptyl, cycloheptenyl, norbornyl, cyclooctyl, cyclononyl, cyclodecyl, cycloundecyl, cyclododecyl, and the like.

The term "cycloaliphatic" also includes polycyclic ring systems in which the non-aromatic carbocyclic ring can be "fused" to one or more aromatic or non-aromatic carbocyclic or heterocyclic rings or combinations thereof, as long as the radical or point of attachment is on the non-aromatic carbocyclic ring.

The term "heterocycle" (or "heterocyclyl" or "heterocyclic"), as used herein, refers to a ring system in which one or more ring members are an independently selected heteroatom, which is completely saturated or that contains one or more units of unsaturation but which is not aromatic, and which has a single point of attachment to the rest of the molecule. Unless otherwise specified, through this disclosure, heterocycle is used as a synonym of "non-aromatic heterocycle". In some instances the term can be used in the phrase "aromatic heterocycle", and in this case it refers to a "heteroaryl group" as defined below. The term heterocycle also includes fused, spiro or bridged heterocyclic ring systems. Unless otherwise specified, a heterocycle may be monocyclic, bicyclic or tricyclic. In some embodiments, the heterocycle has 3-18 ring members in which one or more ring members is a heteroatom independently selected from oxygen, sulfur or nitrogen, and each ring in the system contains 3 to 7 ring members. In other embodiments, a heterocycle may be a monocycle having 3-7 ring members (2-6 carbon atoms and 1-4 heteroatoms) or a bicycle having 7-10 ring members (4-9 carbon atoms and 1-6 heteroatoms). Examples of bicyclic heterocyclic ring systems include, but are not limited to: adamantanyl, 2-oxa-bicyclo[2.2.2]octyl, 1-aza-bicyclo[2.2.2]octyl.

As used herein, the term "heterocycle" also includes polycyclic ring systems wherein the heterocyclic ring is fused with one or more aromatic or non-aromatic carbocyclic or heterocyclic rings, or with combinations thereof, as long as the radical or point of attachment is in the heterocyclic ring.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydro-imidazol-2-one.

As used herein, the term "aryl" (as in "aryl ring" or "aryl group"), used alone or as part of a larger moiety, as in "aralkyl", "aralkoxy", "aryloxyalkyl", refers to a carbocyclic ring system wherein at least one ring in the system is aromatic and has a single point of attachment to the rest of the molecule. Unless otherwise specified, an aryl group may be monocyclic, bicyclic or tricyclic and contain 6-18 ring members. The term also includes polycyclic ring systems where the aryl ring is fused with one or more aromatic or non-aromatic carbocyclic or heterocyclic rings, or with combinations thereof, as long as the radical or point of attachment is in the aryl ring. Examples of aryl rings include, but are not limited to, phenyl, naphthyl, indanyl, indenyl, tetralin, fluorenyl, and anthracenyl. An optionally substituted "aralkyl" can be substituted on both the alkyl and the aryl portion. For instance, unless otherwise indicated, as used in this disclosure, an optionally substituted aralkyl is attached to the rest of the molecule through the alkyl chain and optionally substituted in the aryl portion. The same principle applies, for example, to a substituted aralkoxy, which would be attached to the rest of the molecule through the oxygen of the alkoxy and substituted on the aryl portion. A substituted aryloxyalkyl would be attached to the rest of the molecule through the alkyl chain and substituted on the aryl ring, which in turn would be attached to the alkyl chain through an oxygen atom.

The term "heteroaryl" (or "heteroaromatic" or "heteroaryl group" or "aromatic heterocycle") used alone or as part of a larger moiety as in "heteroaralkyl" or "heteroarylalkoxy" refers to a ring system wherein at least one ring in the system is aromatic and contains one or more heteroatoms, wherein each ring in the system contains 3 to 7 ring members and which has a single point of attachment to the rest of the molecule. Unless otherwise specified, a heteroaryl ring system may be monocyclic, bicyclic or tricyclic and have a total of five to fourteen ring members. In one embodiment, all rings in a heteroaryl system are aromatic. Also included in this definition are heteroaryl radicals where the heteroaryl ring is fused with one or more aromatic or non-aromatic carbocyclic or heterocyclic rings, or combinations thereof, as long as the radical or point of attachment is in the heteroaryl ring. A bicyclic 6,5 heteroaromatic system, as used herein, for example, is a six-membered heteroaromatic ring fused to a second five-membered ring wherein the radical or point of attachment is on the six-membered ring.

Heteroaryl rings include, but are not limited to the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, benzopyrazinyl, benzopyranonyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

As used herein, "cyclo" (or "cyclic", or "cyclic moiety") encompasses mono-, bi- and tri-cyclic ring systems including cycloaliphatic, heterocyclic, aryl or heteroaryl, each of which has been previously defined.

"Fused" bicyclic ring systems comprise two rings which share two adjoining ring atoms.

"Bridged" bicyclic ring systems comprise two rings which share three or four adjacent ring atoms. As used herein, the term "bridge" refers to a bond or an atom or a chain of atoms connecting two different parts of a molecule. The two atoms that are connected through the bridge (usually but not always, two tertiary carbon atoms) are referred to as "bridgeheads". Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.03.7]nonyl.

"Spiro" bicyclic ring systems share only one ring atom (usually a quaternary carbon atom).

The term "ring atom" refers to an atom such as C, N, O or S that is part of the ring of an aromatic group, a cycloaliphatic group or a heteroaryl ring. A "substitutable ring atom" is a ring carbon or nitrogen atom bonded to at least one hydrogen atom. The hydrogen can be optionally replaced with a suitable substituent group. Thus, the term "substitutable ring atom" does not include ring nitrogen or carbon atoms which are shared when two rings are fused. In addition, "substitutable ring atom" does not include ring carbon or nitrogen atoms when the structure depicts that they are already attached to one or more moiety other than hydrogen and no hydrogens are available for substitution.

"Heteroatom" refers to one or more of oxygen, sulfur, nitrogen, phosphorus, or silicon, including any oxidized form of nitrogen, sulfur, phosphorus, or silicon, the quaternized form of any basic nitrogen, or a substitutable nitrogen of a heterocyclic or heteroaryl ring, for example, N (as in 3,4-dihydro-2H-pyrrolyl), NH (as in pyrrolidinyl) or NR+ (as in N-substituted pyrrolidinyl).

In some embodiments, two independent occurrences of a variable may be taken together with the atom(s) to which each variable is bound to form a 5-8-membered, heterocyclyl, aryl, or heteroaryl ring or a 3-8-membered cycloalkyl ring. Exemplary rings that are formed when two independent occurrences of a substituent are taken together with the atom(s) to which each variable is bound include, but are not limited to the following: a) two independent occurrences of a substituent that are bound to the same atom and are taken together with that atom to form a ring, where both occurrences of the substituent are taken together with the atom to which they are bound to form a heterocyclyl, heteroaryl, carbocyclyl or aryl ring, wherein the group is attached to the rest of the molecule by a single point of attachment; and b) two independent occurrences of a substituent that are bound to different atoms and are taken together with both of those atoms to form a heterocyclyl, heteroaryl, carbocyclyl or aryl ring, wherein the ring that is formed has two points of attachment with the rest of the molecule.

For example, where a phenyl group is substituted with two occurrences of $R_o$ as in Formula D1:

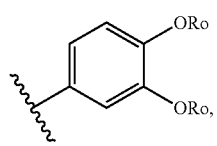

these two occurrences of $OR_o$ are taken together with the carbon atoms to which they are bound to form a fused 6-membered oxygen containing ring as in Formula D2:

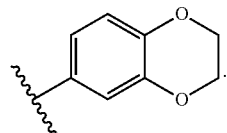

It will be appreciated that a variety of other rings can be formed when two independent occurrences of a substituent are taken together with the atom(s) to which each substituent is bound and that the examples detailed above are not intended to be limiting.

In some embodiments, an alkyl or aliphatic chain can be optionally interrupted with another atom or group. This means that a methylene unit of the alkyl or aliphatic chain can optionally be replaced with said other atom or group. Unless otherwise specified, the optional replacements form a chemically stable compound. Optional interruptions can occur both within the chain and/or at either end of the chain; i.e., both at the point of attachment(s) to the rest of the molecule and/or at the terminal end. Two optional replacements can also be adjacent to each other within a chain so long as it results in a chemically stable compound. Unless otherwise specified, if the replacement or interruption occurs at a terminal end of the chain, the replacement atom is bound to an H on the terminal end. For example, if —$CH_2CH_2CH_3$ were optionally interrupted with —O—, the resulting compound could be —$OCH_2CH_3$, —$CH_2OCH_3$, or —$CH_2CH_2OH$. In another example, if the divalent linker —$CH_2CH_2CH_2$— were optionally interrupted with —O—, the resulting compound could be —$OCH_2CH_2$—, —$CH_2OCH_2$—, or —$CH_2CH_2O$—. The optional replacements can also completely replace all of the carbon atoms in a chain. For example, a $C_3$ aliphatic can be optionally replaced by —$N(R^\$)$—, —$C(O)$—, and —$N(R^\$)$— to form —$N(R^\$)C(O)N(R^\$)$— (a urea).

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., $R^XO(O)C$-alkyl, is an example of a carboxy group used terminally. A group is internal when the group is present in the middle of a substituent at the end of the substituent bound to the rest of the chemical structure. Alkylcarboxy (e.g., alkyl-C(O)O— or alkyl-O(CO)—) and alkylcarboxyaryl (e.g., alkyl-C(O)O-aryl- or alkyl-O(CO)-aryl-) are examples of carboxy groups used internally.

As described herein, a bond drawn from a substituent to the center of one ring within a multiple-ring system (as shown below), represents substitution of the substituent at any substitutable position in any of the rings within the multiple ring system. For example, formula D3 represents possible substitution in any of the positions shown in formula D4:

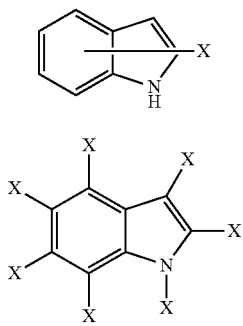

This also applies to multiple ring systems fused to optional ring systems (which would be represented by dotted lines). For example, in Formula D5, X is an optional substituent both for ring A and ring B.

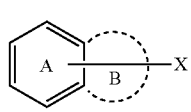

If, however, two rings in a multiple ring system each have different substituents drawn from the center of each ring, then, unless otherwise specified, each substituent only represents substitution on the ring to which it is attached. For example, in Formula D6, Y is an optional substituent for ring A only, and X is an optional substituent for ring B only.

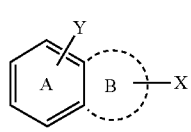

As used herein, the terms "alkoxy" or "alkylthio" refer to an alkyl group, as previously defined, attached to the molecule, or to another chain or ring, through an oxygen ("alkoxy," e.g., O-alkyl) or a sulfur ("alkylthio," e.g., S-alkyl) atom. The terms $C_{n\text{-}m}$ "alkoxyalkyl", $C_{n\text{-}m}$ "alkoxyalkenyl", $C_{n\text{-}m}$ "alkoxyaliphatic", and $C_{n\text{-}m}$ "alkoxyalkoxy" mean alkyl, alkenyl, aliphatic or alkoxy, as the case may be, substituted with one or more alkoxy groups, wherein the total number of carbons between the alky and alkoxy, alkenyl and alkoxy, aliphatic and alkoxy or alkoxy and alkoxy, as the case may be, is between the values of n and m. When these moieties are optionally substituted they can be substituted in either of the portions on both sides of the oxygen or sulfur. For example, an optionally substituted $C_4$ alkoxyalkyl could be, for instance, —CH$_2$CH$_2$OCH$_2$(Me)CH$_3$ or —CH$_2$(OH)OCH$_2$CH$_2$CH$_3$; a $C_5$ alkoxyalkenyl could be, for instance, =CHCH$_2$OCH$_2$CH$_2$CH$_3$ or =CHCH$_2$CH$_2$OCH$_2$CH$_3$.

The terms "aryloxy", "arylthio", "benzyloxy" or "benzylthio", refer to an aryl or benzyl group attached to the molecule, or to another chain or ring, through an oxygen ("aryloxy", "benzyloxy," e.g., —O-Ph, —OCH$_2$Ph) or sulfur ("arylthio," e.g., —S-Ph, —S—CH$_2$Ph) atom. For instance, the terms "aryloxyalkyl", "benzyloxyalkyl" "aryloxyalkenyl" and "aryloxyaliphatic" mean alkyl, alkenyl or aliphatic, as the case may be, substituted with one or more aryloxy or benzyloxy groups, as the case may be. In this case, the number of atoms for each aryl, aryloxy, alkyl, alkenyl or aliphatic will be indicated separately. Thus, a 5-6-membered aryloxy($C_{1\text{-}4}$alkyl) is a 5-6 membered aryl ring, attached via an oxygen atom to a $C_{1\text{-}4}$ alkyl chain which, in turn, is attached to the rest of the molecule via the terminal carbon of the $C_{1\text{-}4}$ alkyl chain.

An optionally substituted "aralkyl" can potentially be substituted on both the alkyl and the aryl portion. Unless otherwise indicated, as used in this disclosure, an optionally substituted aralkyl is attached to the rest of the molecule through the alkyl chain and optionally substituted in the aryl portion. The same principle applies, for example, to a substituted aralkoxy, which would be attached to the rest of the molecule through the oxygen of the alkoxy and substituted on the aryl portion. A substituted aryloxyalkyl would be attached to the rest of the molecule through the alkyl chain and substituted on the aryl ring, which in turn would be attached to the alkyl chain through an oxygen atom. For example, an optionally substituted 6-membered aryloxy ($C_3$alkyl) group could be, for instance, —(CH$_3$)$_2$CH$_2$-[p-(MeO)-Ph]; an optionally substituted 6-membered heteroaryloxy($C_4$alkyl) could, for instance, be —CH$_2$CH$_2$CH$_2$—O-(3-F-2-pyrydyl) or —CH(CH$_3$)—O—CH$_2$CH$_2$-(5,6-dimethyl-1,3-pyrimidine). If the alkyl chain on the "aralkyl" group is also substituted that will be specifically indicated. For instance an optionally substituted 6-membered heteroaryloxy($C_4$alkyl) that is also optionally substituted on the alkyl would be referred to as "an optionally substituted 6-membered heteroaryloxy($C_4$alkyl), wherein said $C_4$ alkyl chain is optionally substituted." An example of this latter group could be 5,6-dimethyl-1,3-pyrimidine-O—CF(CH$_3$)—CH(OH)CH$_2$, wherein the alkyl chain is substituted with F and with —OH.

As used herein, the terms "halogen" or "halo" mean F, Cl, Br, or I.

The terms "haloalkyl", "haloalkenyl", "haloaliphatic", and "haloalkoxy" mean alkyl, alkenyl, aliphatic or alkoxy, as the case may be, substituted with one or more halogen atoms. For example, a $C_{1\text{-}3}$ haloalkyl could be CFHCH$_2$CHF$_2$ and a $C_{1\text{-}2}$ haloalkoxy could be —OC(Br)HCHF$_2$. This term includes perfluorinated alkyl groups, such as —CF$_3$ and —CF$_2$CF$_3$.

As used herein, the term "cyano" refers to —CN or —C≡N.

The terms "cyanoalkyl", "cyanoalkenyl", "cyanoaliphatic", and "cyanoalkoxy" mean alkyl, alkenyl, aliphatic or alkoxy, as the case may be, substituted with one or more cyano groups. For example, a $C_{1\text{-}3}$ cyanoalkyl could be —C(CN)$_2$CH$_2$CH$_3$ and a $C_{1\text{-}2}$ cyanoalkenyl could be =CHC(CN)H$_2$.

As used herein, an "amino" group refers to —NH$_2$.

The terms "aminoalkyl", "aminoalkenyl", "aminoaliphatic", and "aminoalkoxy" mean alkyl, alkenyl, aliphatic or alkoxy, as the case may be, substituted with one or more amino groups. For example, a $C_1$-3 aminoalkyl could be —CH(NH$_2$)CH$_2$CH$_2$NH$_2$ and a $C_{1\text{-}2}$ aminoalkoxy could be —OCH$_2$CH$_2$NH$_2$.

The terms "hydroxyl" or "hydroxy" refer to —OH.

The terms "hydroxyalkyl", "hydroxyalkenyl", "hydroxyaliphatic", and "hydroxyalkoxy" mean alkyl, alkenyl, aliphatic or alkoxy, as the case may be, substituted with one or more —OH groups. For example a $C_{1\text{-}3}$ hydroxyalkyl could be —CH$_2$(CH$_2$OH)CH$_3$ and a $C_4$ hydroxyalkoxy could be —OCH$_2$C(CH$_3$)(OH)CH$_3$.

As used herein, an "aroyl" or "heteroaroyl" refers to a —C(O)-aryl or a —C(O)— heteroaryl. The aryl and heteroaryl portion of the aroyl or heteroaroyl is optionally substituted as previously defined.

As used herein, a "carbonyl", used alone or in connection with another group refers to C(O)— or —C(O)H. For example, as used herein, an "alkoxycarbonyl," refers to a group such as —C(O)O(alkyl).

As used herein, an "oxo" refers to =O, wherein oxo is usually, but not always, attached to a carbon atom (e.g., it can also be attached to a sulfur atom forming a sulfoxide or a sulfone). An aliphatic chain can be optionally interrupted by a carbonyl group or can optionally be substituted by an oxo group, and both expressions refer to the same: e.g., —CH₂—C(O)—CH₃.

As used herein, in the context of resin chemistry (e.g., using solid resins or soluble resins or beads), the term "linker" refers to a bifunctional chemical moiety attaching a compound to a solid support or soluble support.

In all other situations, a "linker", as used herein, refers to a divalent group in which the two free valences are on different atoms (e.g., carbon or heteroatom) or are on the same atom but can be substituted by two different substituents. For example, a methylene group can be a $C_1$ alkyl linker (—CH₂—) which can be substituted by two different groups, one for each of the free valences (e.g., as in Ph-CH₂-Ph, wherein methylene acts as a linker between two phenyl rings). Ethylene can be a $C_2$ alkyl linker (—CH₂CH₂—) wherein the two free valences are on different atoms. The amide group, for example, can act as a linker when placed in an internal position of a chain (e.g., —CONH—). A linker can be the result of interrupting an aliphatic chain by certain functional groups or of replacing methylene units on said chain by said functional groups. E.g., a linker can be a $C_{1-6}$ aliphatic chain in which up to two methylene units are substituted by —C(O)— or —NH— (as in —CH₂—NH—CH₂—C(O)—CH₂— or —CH₂—NH—C(O)—CH₂—). An alternative way to define the same —CH₂—NH—CH₂—C(O)—CH₂— and —CH₂—NH—C(O)—CH₂— groups is as a $C_3$ alkyl chain optionally interrupted by up to two —C(O)— or —NH— moieties. Cyclic groups can also form linkers: e.g., a 1,6-cyclohexanediyl can be a linker between two R groups, as in

Divalent groups of the type =CH—R or =C—R₂, wherein both free valences are in the same atom and are attached the same substituent, are also possible. In this case, they will be referred to by their IUPAC accepted names. For instance, an alkylidene (such as, for example, a methylidene (=CH₂) or an ethylidene (=CH—CH₃)) would not be encompassed by the definition of a linker in this disclosure.

The term "protecting group", as used herein, refers to an agent used to temporarily block one or more desired reactive sites in a multifunctional compound. In certain embodiments, a protecting group has one or more, or preferably all, of the following characteristics: a) reacts selectively in good yield to give a protected substrate that is stable to the reactions occurring at one or more of the other reactive sites; and b) is selectively removable in good yield by reagents that do not attack the regenerated functional group. Exemplary protecting groups are detailed in Greene, T. W., Wuts, P. G. in *Protective Groups in Organic Synthesis,* 3rd Ed., John Wiley & Sons, New York: 1999, the entire contents of which are hereby incorporated by reference. The term "nitrogen protecting group", as used herein, refers to an agents used to temporarily block one or more desired nitrogen reactive sites in a multifunctional compound. Preferred nitrogen protecting groups also possess the characteristics exemplified above, and certain exemplary nitrogen protecting groups are also detailed in Chapter 7 in Greene, T. W., Wuts, P. G. in *Protective Groups in Organic Synthesis,* 3rd Ed., John Wiley & Sons, New York: 1999, the entire contents of which are hereby incorporated by reference.

As used herein, the term "displaceable moiety" or "leaving group" refers to a group that is associated with an aliphatic or aromatic group as defined herein and is subject to being displaced by nucleophilic attack by a nucleophile.

As used herein, "amide coupling agent" or "amide coupling reagent" means a compound that reacts with the hydroxyl moiety of a carboxy moiety thereby rendering it susceptible to nucleophilic attack. Exemplary amide coupling agents include DIC (diisopropylcarbodiimide), EDCI (1-Ethyl-3-(3-dimethylaminopropyl)carbodiimide), DCC (dicyclohexylcarbodiimide), BOP (Benzotriazol-1-yloxy-tris(dimethylamino)-phosphonium hexafluorophosphate), pyBOP ((Benzotriazol-1-yloxy)tripyrrolidinophosphonium Hexafluorophosphate), etc.

The compounds of the invention are defined herein by their chemical structures and/or chemical names. Where a compound is referred to by both a chemical structure and a chemical name, and the chemical structure and chemical name conflict, the chemical structure is determinative of the compound's identity.

In one aspect, the invention relates to the compounds selected from Table 1, or pharmaceutically acceptable salts thereof.

TABLE 1

| Structure | Compound Number |
|---|---|
| 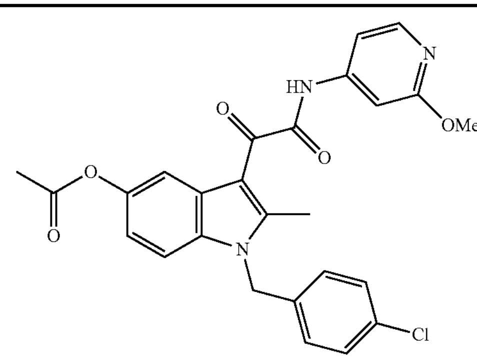 | 1 |

TABLE 1-continued

| Structure | Compound Number |
|---|---|
| (5-hydroxy-2-methyl-1-(4-chlorobenzyl)indol-3-yl N-(2-methoxypyridin-4-yl)oxoacetamide) | 2 |
| (2-methyl-1-(4-chlorobenzyl)pyrrolo[3,2-b]pyridin-3-yl N-(2-methoxypyridin-4-yl)oxoacetamide) | 3 |
| (5-carboxy-2-methyl-1-(4-chlorobenzyl)indol-3-yl N-(2-methoxypyridin-4-yl)oxoacetamide) | 4 |
| (5-acetyl-2-methyl-1-(4-chlorobenzyl)indol-3-yl N-(2-methoxypyridin-4-yl)oxoacetamide) | 5 |
| (5-(N,N-dimethylcarbamoyl)-2-methyl-1-(4-chlorobenzyl)indol-3-yl N-(2-methoxypyridin-4-yl)oxoacetamide) | 6 |
| (5-(N-Boc-N-methylamino)-2-methyl-1-(4-chlorobenzyl)indol-3-yl N-(2-methoxypyridin-4-yl)oxoacetamide) | 7 |
| (5-(hydroxymethyl)-2-methyl-1-(4-chlorobenzyl)indol-3-yl N-(2-methoxypyridin-4-yl)oxoacetamide) | 8 |
| (5-(methylamino)-2-methyl-1-(4-chlorobenzyl)indol-3-yl N-(2-methoxypyridin-4-yl)oxoacetamide) | 9 |

TABLE 1-continued
| Structure | Compound Number |
|---|---|
| 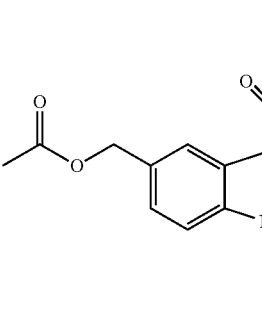 | 10 |
| 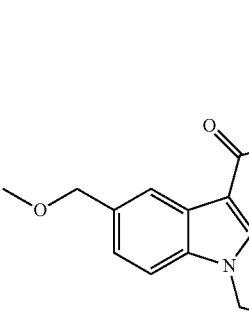 | 11 |
| 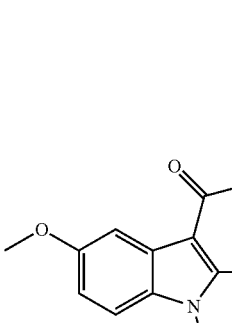 | 12 |
| 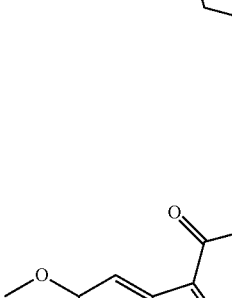 | 13 |
| | 14 |
| | 15 |
| | 16 |
| | 17 |

TABLE 1-continued

| Structure | Compound Number |
|---|---|
| (5-bromo-2-methyl-1-(4-chlorobenzyl)-1H-indol-3-yl)-N-(2-methoxypyridin-4-yl)-2-oxoacetamide | 18 |
| (5-nitro-2-methyl-1-(4-chlorobenzyl)-1H-indol-3-yl)-N-(2-methoxypyridin-4-yl)-2-oxoacetamide | 19 |
| (5-amino-2-methyl-1-(4-chlorobenzyl)-1H-indol-3-yl)-N-(2-methoxypyridin-4-yl)-2-oxoacetamide | 20 |
| (5-trifluoromethyl-2-methyl-1-(4-chlorobenzyl)-1H-indol-3-yl)-N-(2-methoxypyridin-4-yl)-2-oxoacetamide | 21 |
| (5-acetamido-2-methyl-1-(4-chlorobenzyl)-1H-indol-3-yl)-N-(2-methoxypyridin-4-yl)-2-oxoacetamide | 22 |
| (5-trifluoromethoxy-2-methyl-1-(4-chlorobenzyl)-1H-indol-3-yl)-N-(2-methoxypyridin-4-yl)-2-oxoacetamide | 23 |
| (5-diethylamino-2-methyl-1-(4-chlorobenzyl)-1H-indol-3-yl)-N-(2-methoxypyridin-4-yl)-2-oxoacetamide | 24 |
| (5-(methylaminomethyl)-2-methyl-1-(4-chlorobenzyl)-1H-indol-3-yl)-N-(2-methoxypyridin-4-yl)-2-oxoacetamide | 25 |

TABLE 1-continued

| Structure | Compound Number |
|---|---|
| 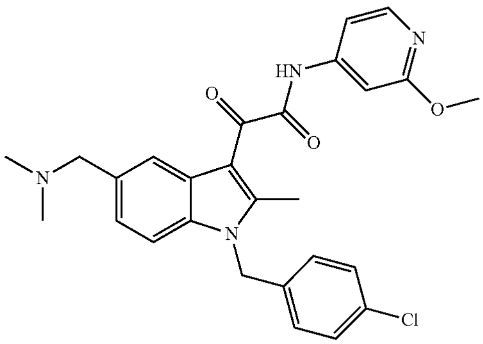 | 26 |
| 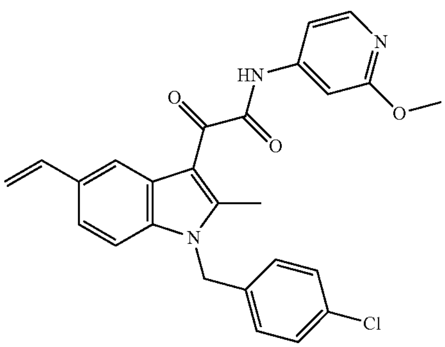 [SMILES: C=Cc1ccc2c(c1)c(C(=O)C(=O)Nc1ccnc(OC)c1)c(C)n2Cc1ccc(Cl)cc1] | 27 |
| 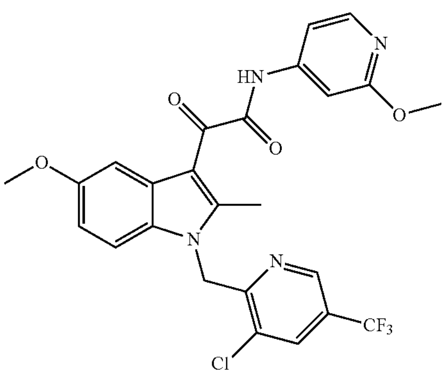 | 28 |
| 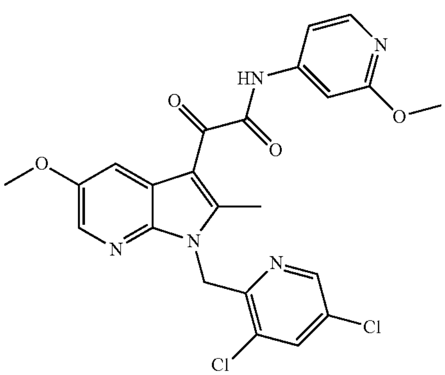 | 29 |
| | 30 |
| | 31 |
| | 32 |
| | 33 |

TABLE 1-continued

| Structure | Compound Number |
|---|---|
| (structure) | 34 |
| (structure) | 35 |
| (structure) | 36 |
| (structure) | 37 |
| (structure) | 38 |
| (structure) | 39 |
| (structure) | 40 |
| (structure) | 41 |

TABLE 1-continued

| Structure | Compound Number |
|---|---|
| (5-methoxy-2-methyl-1-(2,4-dichlorobenzyl)-7-azaindol-3-yl glyoxylamide with 2-methoxypyridin-4-yl) | 42 |
| (5-methoxy-2-methyl-1-((5-methoxypyridin-2-yl)methyl)indol-3-yl glyoxylamide with 2-methoxypyridin-4-yl) | 43 |
| (5,6-dimethoxy-2-methyl-1-(4-chlorobenzyl)indol-3-yl glyoxylamide with 2-methoxypyridin-4-yl) | 44 |
| (4-methoxy-2-methyl-1-(4-chlorobenzyl)indol-3-yl glyoxylamide with 2-methoxypyridin-4-yl) | 45 |
| (5-methoxy-2-methyl-1-(4-chlorobenzyl)indol-3-yl glyoxylamide with 2-methoxypyrimidin-4-yl) | 46 |
| (5-methoxy-2-methyl-1-(4-chlorobenzyl)indol-3-yl glyoxylamide with 2-chloro-6-methoxypyridin-4-yl) | 47 |
| (6-methoxy-2-methyl-1-(4-chlorobenzyl)indol-3-yl glyoxylamide with 2-methoxypyridin-4-yl) | 48 |
| (2-methyl-1-(4-chlorobenzyl)-7-azaindol-3-yl glyoxylamide with 2-methoxypyridin-4-yl) | 49 |

TABLE 1-continued

| Structure | Compound Number |
|---|---|
| (structure) | 50 |
| (structure) | 51 |
| (structure) | 52 |
| (structure) | 53 |
| (structure) | 54 |
| (structure) | 55 |
| (structure) | 56 |
| (structure) | 57 |

TABLE 1-continued

| Structure | Compound Number |
|---|---|
| (structure) | 58 |
| (structure) | 59 |
| (structure) | 60 |
| (structure) | 61 |
| (structure) | 62 |
| (structure) | 63 |
| (structure) | 64 |
| (structure) | 65 |

TABLE 1-continued

| Structure | Compound Number |
|---|---|
| (structure) | 66 |
| (structure) | 67 |
| (structure) | 68 |
| (structure) | 69 |
| (structure) | 70 |
| (structure) | 71 |
| (structure) | 72 |
| (structure) | 73 |

TABLE 1-continued

| Structure | Compound Number |
|---|---|
| (structure) | 74 |
| (structure) | 75 |
| (structure) | 76 |
| (structure) | 77 |
| (structure) | 78 |
| (structure) | 79 |
| (structure) | 80 |
| (structure) | 81 |

TABLE 1-continued

| Structure | Compound Number |
|---|---|
| (structure) | 82 |
| (structure) | 83 |
| (structure) | 84 |
| (structure) | 85 |
| (structure) | 86 |
| (structure) | 87 |
| (structure) | 88 |
| (structure) | 89 |

TABLE 1-continued

| Structure | Compound Number |
|-----------|-----------------|
| 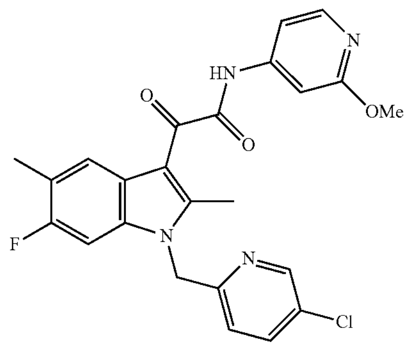 [SMILES: COc1cc(NC(=O)C(=O)c2c(C)n(Cc3ccc(Cl)cn3)c3cc(F)c(C)cc23)ccn1] | 90 |
| 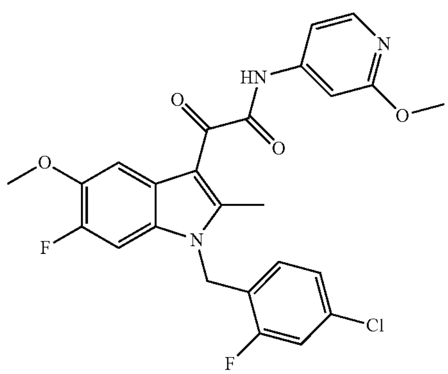 | 91 |
| 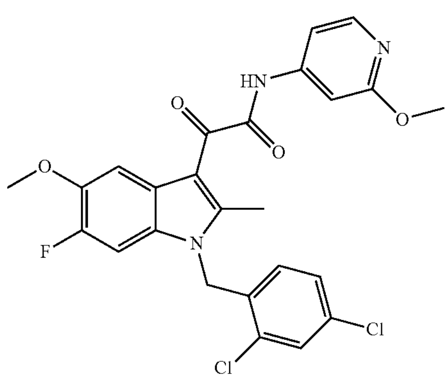 | 92 |
| 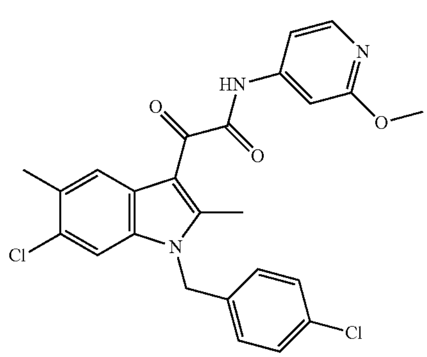 | 93 |
| | 94 |
| | 95 |
| | 96 |
| | 97 |

TABLE 1-continued

| Structure | Compound Number |
|---|---|
| (structure) | 98 |
| (structure) | 99 |
| (structure) | 100 |
| (structure) | 101 |

In another embodiment, the compounds of Table 1 or pharmaceutically acceptable salts thereof are selected from those with compound numbers 13, 28, 29, 30, 31, 32, 33, 34, 40, 41, 43, 60, 61, 62, 63, 64, 65, 66, 67, 68, 69, 70, 75, 77, 79, 81, 82, 84, 85, 87, 88, 90, 94, 95, 96, 97, 98, 99, 100, and 101.

In another embodiment, the compounds of Table 1 or pharmaceutically acceptable salts thereof are selected from those with compound numbers 13, 28, 29, 30, 32, 33, 34, 40, 41, 43, 60, 61, 64, 69, 70, 75, 77, 79, 81, 82, 84, 85, 87, 88, 90, 94, 95, 96, 97, 98, 99, 100, or 101.

In another embodiment, the compounds of Table 1 or pharmaceutically acceptable salts thereof are selected from those with compound numbers 13, 29, 30, 33, 34, 41, 60, 61, 62, 63, 64, 65, 66, 67, 68, 70, 75, 79, 81, 82, 85, 87, 88, 90, 94, 95, 97, 99, and 101.

In another embodiment, the compounds of Table 1 or pharmaceutically acceptable salts thereof are selected from those with compound numbers 13, 28, 29, 32, 34, 40, 41, 43, 60, 61, 77, 79, 81, 82, 84, 87, and 100.

In another embodiment, the compounds of Table 1 or pharmaceutically acceptable salts thereof are selected from those with compound numbers 29, 34, 41, 77, 79, 81, 82, and 87.

In another embodiment, the compounds of Table 1 or pharmaceutically acceptable salts thereof are selected from those with compound numbers 34, 41, 77, 79, 81, 82, and 87. In a further embodiment, the compound advantageously displays one or more of the selected attributes (i) decreased affinity for binding to the CB1 receptor, (ii) decreased inhibition of the hERG channel, or (iii) increased plasma exposure profile, see for example Tables 4, 5, and 6. In still a further embodiment, the compound advantageously displays one or more of the selected attributes (i) a decreased affinity for binding to the CB1 receptor as compared to other known FAAH inhibitors, (ii) a decreased inhibition of the hERG channel as compared to other known FAAH inhibitors, or (iii) an increased plasma exposure profile as compared to other known FAAH inhibitors.

Methods of Preparing the Compounds:

The compounds of Table 1 may be prepared according to the schemes and examples depicted and described below. Unless otherwise specified, the starting materials and various intermediates may be obtained from commercial sources, prepared from commercially available compounds or prepared using well-known synthetic methods.

General Synthetic Methods and General Synthetic Schemes

General synthetic procedures for the compounds of this invention are described below. The synthetic schemes are presented as examples and do not limit the scope of the invention in any way.

General Synthetic Routes and Procedures

General Route 1: (contains general procedures A, B, C and D)

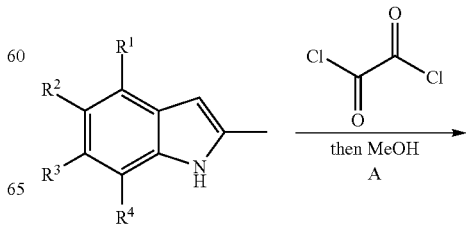

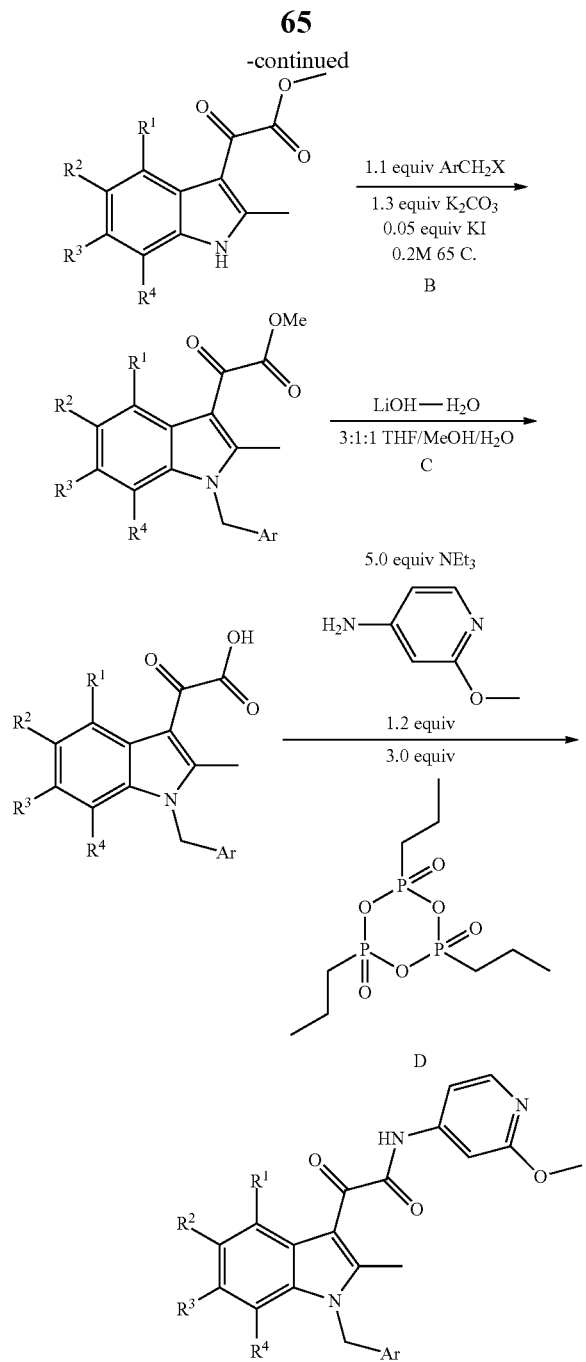

Formation of indole 3-ketoester (General Procedure A)

To a 0° C. solution of the appropriate indole (1.0 equiv) in dichloromethane (0.1 M) was added neat oxalyl dichloride (2.0 equiv). The reaction was stirred at 0° C. for 20 minutes, after which LCMS of the methanolysis product indicated complete conversion to the acid chloride (by presence of methyl ketoester). The reaction was concentrated to dryness, reconstituted in dichloromethane (0.1 M), cooled to 0° C. and then treated with excess methanol (10-30 equiv). The product was isolated via filtration of the observed precipitate or extracted with ethyl acetate (3×), dried (sodium sulfate), filtered and concentrated to afford the corresponding ketoester as a solid.

N-alkylation of Indole 3-ketoester (General Procedure B)

A slurry of the indole 3-ketoester (1.0 equiv), appropriate benzyl bromide or chloride (1.1 equiv), potassium iodide (0.05 equiv) and potassium carbonate (1.3 equiv) was heated at 65° C. in either N,N-dimethylformamide or acetonitrile (0.1-0.2 M) until LCMS analysis indicated completion of the reaction (2-5 hours). The reaction mixture was cooled to room temperature, diluted in water, extracted with ethyl acetate (3×), dried (sodium sulfate), filtered and concentrated to a residue. Purification was achieved by silica gel chromatography using ethyl acetate in hexanes to afford the desired alkylation product.

Saponification of Indole 3-ketoester (General Procedure C)

To a 0° C. solution of the N-alkylated indole 3-ketoester in 3:1:1 THF:methanol:water (0.1 M) was added solid lithium hydroxide monohydrate (1.5 equiv). The reaction was monitored by LCMS analysis until completion (0.2-3 hours) after which the solvent was removed in vacuo and the resulting residue was diluted in water. This solution was washed with ethyl acetate (1-3×), and the aqueous layer was acidified with 3M aqueous hydrochloric acid solution (1.5 equiv), back-extracted with ethyl acetate (3×), dried (sodium sulfate), filtered and concentrated to afford desired N-alkylated ketoacid as a solid. This material was used in the next step without further purification.

1-propanephosphonic Acid Anhydride Cyclic Trimer (T3P)-Mediated Ketoamide Coupling (General Procedure D)

To a room-temperature solution of N-alkylated indole-3-ketoacid (1.0 equiv) in acetonitrile or DMF (0.1-0.2 M) was successively added triethylamine (5.0 equiv), 2-methoxypyridin-4-amine (1.2 equiv), and a 50% ethyl acetate solution of 1-propanephosphonic acid anhydride cyclic trimer (T3P) (3.0 equiv). The reaction was stirred at room temperature or heated to 60° C. while monitoring the reaction for completeness (1-12 hours). The reaction was diluted in brine, extracted with ethyl acetate (3×), dried (sodium sulfate), filtered and concentrated. Purification was achieved by silica gel chromatography using ethyl acetate in hexanes or a 7:1 solution of acetonitrile/methanol in dichloromethane. The desired N-alkylated 3-ketoamide was isolated as a solid.

General Route 2: (contains general procedures E, F, C and D)

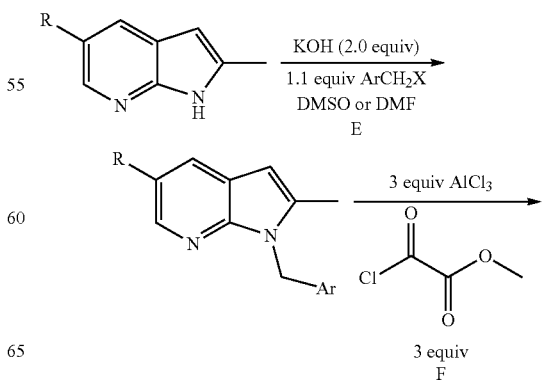

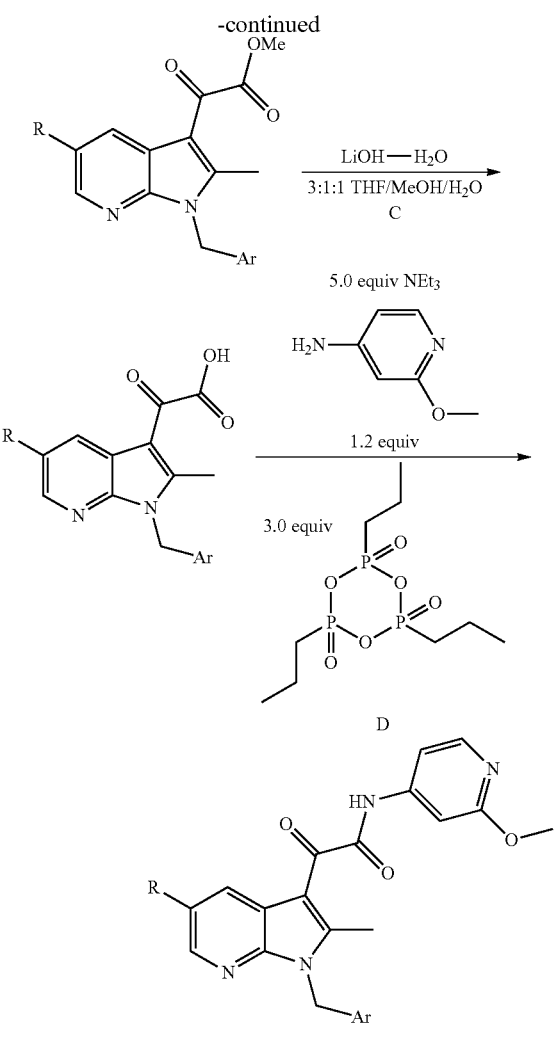

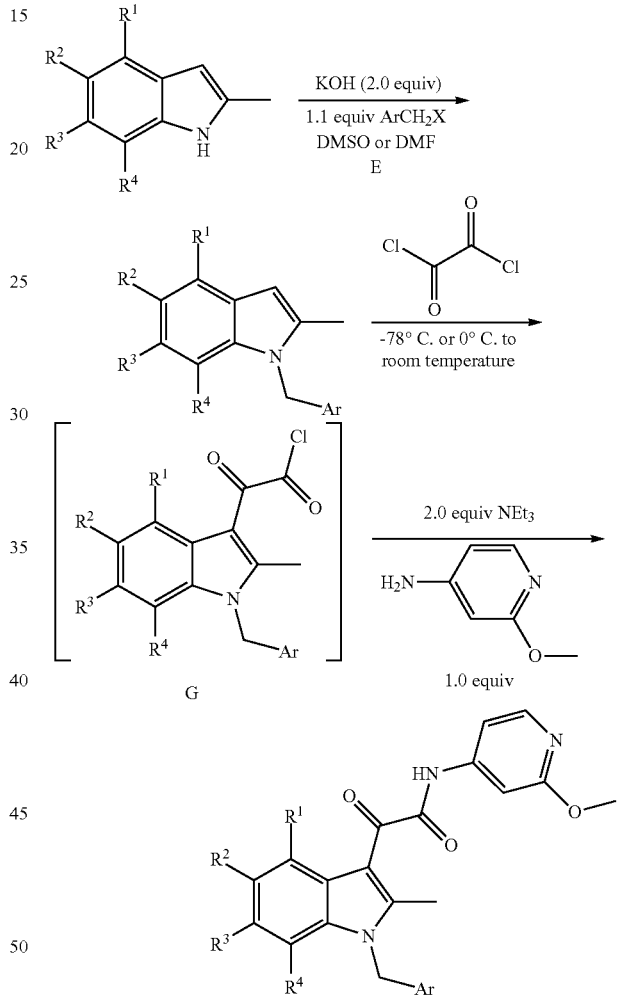

bilize the reaction mixture) was stirred at room temperature with LCMS monitoring until completion or the reaction was achieved (1-12 hours). The reaction was then poured into ice-water, extracted with dichloromethane (3×), dried (sodium sulfate), and concentrated. The material was either used crude or purified using silica gel chromatography using ethyl acetate in hexanes to afford the desired N-alkylated azaindole 3-ketoester. (In certain cases, the acid is the major product observed with only a trace of the ester product present).

General Route 3: (contains general procedures E and G)

N-Alkylation of Azaindole Core (General Procedure E)

To a 0° C. solution of the appropriate azaindole (1.0 equiv) in DMSO or DMF (0.2-0.3 M) was added powdered potassium hydroxide (2.0 equiv). The reaction was warmed to room temperature and stirred for one hour after which the appropriate benzyl bromide or chloride (1.1 equiv) was added. The mixture was monitored by LCMS analysis until completion (1-4 hours), after which the reaction mixture was diluted in water, extracted with ethyl acetate (3×), dried (sodium sulfate), filtered and concentrated. Purification was achieved by silica gel chromatography using ethyl acetate in hexanes to afford the desired N-alkylated azaindole.

Friedel-Crafts Acylation of N-alkylated Azaindole (General Procedure F)

To a stirred suspension of aluminum trichloride (3.0 equiv) in dichloromethane (0.1 M) at 0° C. was added a solution of N-alkylated azaindole (1.0 equiv) in dichloromethane (0.1 M). The reaction mixture was warmed to room temperature and stirred for one hour, after which methyl 2-chloro-2-oxoacetate (3.0 equiv) was added. The resulting solution or suspension (for cases of non-homogeneous reactions, 1-2 mL of acetonitrile was added to solu-

Direct Formation of N-alkylated Indole-3 Ketoamide (General Procedure G)

To a cooled (−78° C. or 0° C.) solution of the appropriate indole (1.0 equiv) in dichloromethane (0.05-0.1 M) was added oxalyl chloride (1-2 equiv). The reaction progress was monitored by LCMS (methanol as solvent for aliquot) indicating the presence of a ketoacid chloride intermediate. The reaction was concentrated to dryness, reconstituted in dichloromethane (0.05-0.1 M), and cooled to 0° C. To this cooled mixture was successively added 2-methoxypyridin-4-amine (1.0 equiv), followed by triethylamine (2.0 equiv). The reaction progress was monitored by LCMS for completion (30-60 minutes), after which the reaction was diluted in water and extracted with dichloromethane (3×), dried (sodium sulfate), filtered and concentrated. Purification was achieved by silica gel chromatography using ethyl acetate in hexanes to afford the desired N-alkylated indole-3-ketoamide product as a solid.

rotary evaporation. The remaining residue was taken up in ethyl acetate and washed with 1N sodium hydroxide solution (2×), washed with water (3×), dried (sodium sulfate), filtered and concentrated. Purification was achieved by silica gel column chromatography using ethyl acetate in hexanes to afford the desired indole as a solid.

General Route 4: Indole/Azaindole core constructions (contains general procedures H, J, K and M):

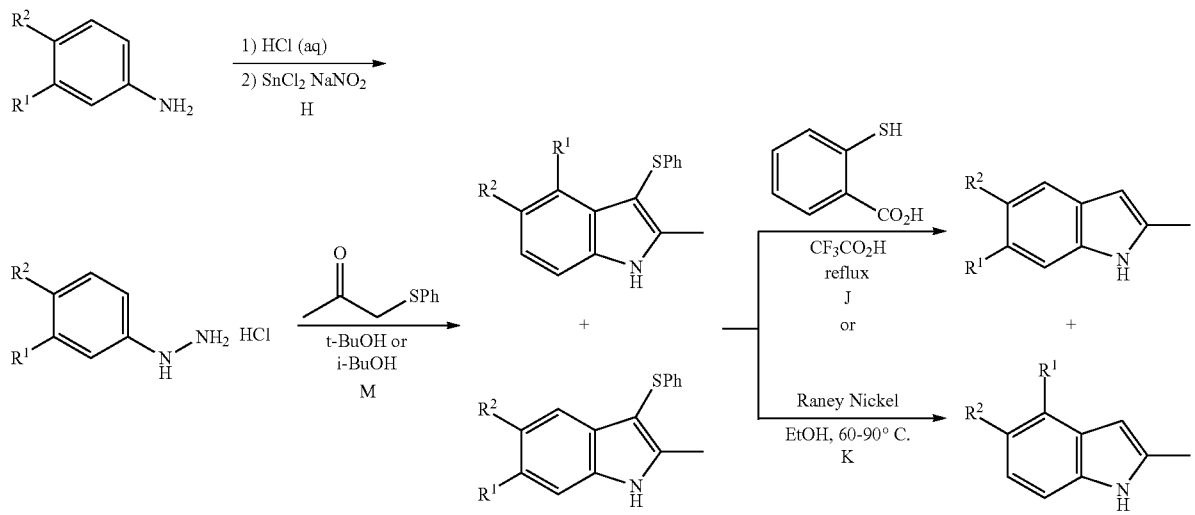

Aryl Hydrazine Formation (General Procedure H)

A solution of the aniline (1.0 equiv) in concentrated hydrochloric acid (2.0-3.0 M) was stirred at room temperature for 2 hours, after which the mixture was cooled to 0° C. A solution of sodium nitrite (1.1-1.2 equiv) in water (4 M) was added dropwise over 45 minutes, while maintaining an internal temperature of <5° C. After an additional hour of stirring at 0° C., a solution of tin (II) dichloride dihydrate (4.2 equiv) in concentrated hydrochloric acid (~6 M) was added. The reaction was allowed to stir and was warmed up to room temperature, then stored at 5° C. overnight (12 hours). The resulting precipitate was filtered, washed with water (2×), then ethanol (3×) and dried thoroughly to the desired arylhydrazine hydrochloride salt.

Indole Cyclization (General Procedure M)

A suspension of the arylhydrazine hydchloride (1.4 equiv) and thiophenyl acetone (1.0 equiv) in tert-butanol or isobutyl alcohol (0.5 M) was heated to 90° C. for 1 hour. The reaction mixture was then cooled to room temperature, filtered through celite, diluted with ethyl acetate and successively washed with water (2×50 mL) and saturated sodium chloride solution (2×50 mL), dried (sodium sulfate), filtered and concentrated. Purification was achieved by silica gel chromatography using ethyl acetate in hexanes to afford the appropriate indole 3-thiophenyl product.

Desulfurization of 3-thiophenyl Indole Derivatives (General Procedure J)

A slurry of the 3-thiophenyl indole (1.0 equiv) and 2-mercaptobenzoic acid (2.0 equiv) and in trifluoroacetic acid (0.1-0.2 M) was stirred at room temperature for 30 minutes, after which the trifluoroacetic acid was removed by

Desulfurization of 3-thiophenyl Indole Derivatives (General Procedure K)

To a solution of the 3-thiophenyl indole (1.0 equiv) in ethanol (0.1 M) was added a suspension of Raney Nickel in water (20-30 equiv). The suspension was heated to 90° C. while monitoring by LCMS for completion of reaction (1-5 hours), after which the reaction was cooled to room temperature, filtered through celite, washed with ethyl acetate (3×50 mL), and concentrated. Purification was achieved by silica gel chromatography using ethyl acetate in hexanes to afford the desired indole as a solid.

Pharmaceutically Acceptable Salts:

The phrase "pharmaceutically acceptable salt," as used herein, refers to pharmaceutically acceptable organic or inorganic salts of a compound selected from Table 1. For use in medicine, the salts of the compounds selected from Table 1 will be pharmaceutically acceptable salts. Other salts may, however, be useful in the preparation of the compounds selected from Table 1 or of their pharmaceutically acceptable salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

Pharmaceutically acceptable salts of the compounds described herein include those derived from suitable inorganic and organic acids and bases. In some embodiments, the salts can be prepared in situ during the final isolation and purification of the compounds. In other embodiments the salts can be prepared from the free form of the compound in a separate synthetic step.

When the compound selected from Table 1 is acidic or contains a sufficiently acidic bioisostere, suitable pharmaceutically acceptable salts are salts prepared from non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particular embodiments include ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When the compound selected from Table 1 is basic or contains a sufficiently basic bioisostere, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particular embodiments include citric, hydrobromic, hydrochloric, maleic, phosphoric, sulfuric and tartaric acids. Other exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

The preparation of the pharmaceutically acceptable salts described above and other typical pharmaceutically acceptable salts is more fully described by Berg et al., "Pharmaceutical Salts," *J. Pharm. Sci.*, 1977:66:1-19, incorporated herein by reference in its entirety.

Pharmaceutical Compositions and Methods of Administration:

The compounds disclosed herein, and their pharmaceutically acceptable salts, thereof, may be formulated as pharmaceutical compositions or "formulations".

In a second aspect, the invention comprises a pharmaceutical composition comprising a compound as discussed above, or a pharmaceutically acceptable salt thereof, and a pharmaceutically acceptable carrier, vehicle or adjuvant. In a further embodiment, the pharmaceutical composition further comprises at least one additional therapeutic agent. In other embodiments, the pharmaceutical composition further comprises an additional therapeutic agent which is chosen from the group consisting of painkillers, non-steroidal anti-inflammatory drugs (NSAIDs), cannabinoid receptor agonists, opiate receptor agonists, anti-infective agents, sodium channel blockers, N-type calcium channel blockers, local anesthetics, VR1 agonists and antagonists, agents used for migraines, topical agents used in the treatment of localized pruritus, anti-inflammatory and/or immunosuppressive agents, agents designed to treat tobacco abuse (e.g., nicotine receptor partial agonists and nicotine replacement therapies), ADD/ADHD agents, agents to treat alcoholism, such as opioid antagonists, agents for reducing alcohol withdrawal symptoms such as benzodiazepines and beta-blockers, antihypertensive agents such as ACE inhibitors and Angiotensin II Receptor blockers, Renin inhibitors, vasodilators, agents used to treat glaucoma such as direct-acting Miotics (cholinergic agonists), indirect acting Miotics (cholinesterase inhibitors), Carbonic anhydrase inhibitors, selective adrenergic agonists, Osmotic diuretics, antidepressants such as SSRIs, tricyclic antidepressants, and dopaminergic antidepressants, cognitive improvement agents, acetylcholinesterase inhibitors, anti-emetic agents (e.g., 5HT3 antagonists), neuroprotective agents, neuroprotective agents currently under investigation, antipsychotic medications, agents used for multiple sclerosis, disease-modifying anti-rheumatic drugs (DMARDS), biological response modifiers (BRMs), COX-2 selective inhibitors, COX-1 inhibitors, immunosuppressives, PDE4 inhibitors, corticosteroids, histamine H1 receptor antagonists, histamine H2 receptor antagonists, proton pump inhibitors, leukotriene antagonists, 5-lipoxygenase inhibitors, nicotinic acetylcholine receptor agonists, P2X3 receptor antagonists, NGF agonists and antagonists, NK1 and NK2 antagonists, NMDA antagonists, potassium channel modulators, GABA modulators, anti-cancer agents such as tyrosine kinase inhibitors, anti-hyperlipidemia drugs, appetite suppressing agents, anti-diabetic medications such as insulin, GI (gastrointestinal) agents, and serotonergic and noradrenergic modulators.

A typical formulation is prepared by mixing a compound selected from Table 1, or a pharmaceutically acceptable salt, solvate, co-crystal or pro-drug thereof, and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound selected from Table 1 is being formulated. Solvents are generally selected based on solvents recognized by persons skilled in the art as safe (e.g., GRAS-Generally Regarded as Safe) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc., and mixtures thereof. The formulations may also include other types of excipients such as one or more buffers, stabilizing agents, antiadherents, surfactants, wetting agents, lubricating agents, emulsifiers, binders, suspending agents, disintegrants, fillers, sorbents, coatings (e.g., enteric or slow release) preservatives, antioxidants, opaquing agents, glidants, processing aids, colorants, sweeteners, perfuming agents, flavoring agents and other known additives to provide an elegant presentation of the drug (e.g., a compound selected from Table 1 or pharmaceutical composition thereof) or aid in the manufacturing of the pharmaceutical product (i.e., medicament).

The formulations may be prepared using conventional dissolution and mixing procedures. For example, the bulk drug substance (e.g., compound selected from Table 1, a pharmaceutically acceptable salt, solvate, co-crystal or pro-drug thereof, or a stabilized form of the compound, such as a complex with a cyclodextrin derivative or other known complexation agent) is dissolved in a suitable solvent in the presence of one or more of the excipients described above. A compound having the desired degree of purity is optionally mixed with pharmaceutically acceptable diluents, carriers, excipients or stabilizers, in the form of a lyophilized formulation, milled powder, or an aqueous solution. Formulation may be conducted by mixing at ambient temperature at the appropriate pH, and at the desired degree of purity, with physiologically acceptable carriers. The pH of the formulation depends mainly on the particular use and the concentration of compound, but may range from about 3 to about 8.

The compound selected from Table 1 or a pharmaceutically acceptable salt thereof is typically formulated into pharmaceutical dosage forms to provide an easily controllable dosage of the drug and to enable patient compliance with the prescribed regimen. Pharmaceutical formulations of compounds selected from Table 1, or a pharmaceutically acceptable salt, solvate, co-crystal or pro-drug thereof, may be prepared for various routes and types of administration. Various dosage forms may exist for the same compound, since different medical conditions may warrant different routes of administration. The amount of active ingredient that may be combined with the carrier material to produce a single dosage form will vary depending upon the subject treated and the particular mode of administration. For example, a time-release formulation intended for oral administration to humans may contain approximately 1 to 1000 mg of active material compounded with an appropriate and convenient amount of carrier material which may vary from about 5 to about 95% of the total composition (weight: weight). The pharmaceutical composition can be prepared to provide easily measurable amounts for administration. For example, an aqueous solution intended for intravenous infusion may contain from about 3 to 500 g of the active ingredient per milliliter of solution in order that infusion of a suitable volume at a rate of about 30 mL/hr can occur. As a general proposition, the initial pharmaceutically effective amount of the inhibitor administered will be in the range of about 0.01-100 mg/kg per dose, namely about 0.1 to 20 mg/kg of patient body weight per day, with the typical initial range of compound used being 0.3 to 15 mg/kg/day.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. The therapeutically or pharmaceutically effective amount of the compound to be administered will be governed by such considerations, and is the minimum amount necessary to ameliorate, cure or treat the disease or disorder or one or more of its symptoms.

The pharmaceutical compositions selected from Table 1 will be formulated, dosed, and administered in a fashion, i.e., in amounts, concentrations, schedules, courses, vehicles, and route(s) of administration consistent with good medical practice. Factors for consideration in this context include the particular disorder being treated, the particular human or other mammal being treated, the clinical condition of the individual patient, the cause of the disorder, the site of delivery of the agent, the method of administration, the scheduling of administration, and other factors known to medical practitioners, such as the age, weight, and response of the individual patient.

The term "prophylactically effective amount" refers to an amount effective in preventing or substantially lessening the chances of acquiring a disease or disorder or in reducing the severity of the disease or disorder or one or more of its symptoms before it is acquired or before the symptoms develop. Roughly, prophylactic measures are divided between primary prophylaxis (to prevent the development of a disease) and secondary prophylaxis (whereby the disease has already developed and the patient is protected against worsening of its severity).

Acceptable diluents, carriers, excipients, and stabilizers are those that are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, e.g., hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in *Remington's: The Science and Practice of Pharmacy*, 21$^{st}$ Edition, University of the Sciences in Philadelphia, Eds., 2005 (hereafter "Remington's").

"Controlled drug delivery systems" supply the drug to the body in a manner precisely controlled to suit the drug and the conditions being treated. The primary aim is to achieve a therapeutic drug concentration at the site of action for the desired duration of time. The term "controlled release" is often used to refer to a variety of methods that modify release of drug from a dosage form. This term includes preparations labeled as "extended release", "delayed release", "modified release" or "sustained release".

"Sustained-release preparations" are the most common applications of controlled release. Suitable examples of sustained-release preparations include semipermeable matrices of solid hydrophobic polymers containing the compound, wherein the matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers, and poly-D-(−)-3-hydroxybutyric acid.

"Immediate-release preparations" may also be prepared. The objective of these formulations is to get the drug into the bloodstream and to the site of action as rapidly as possible. For instance, for rapid dissolution, most tablets are designed to undergo rapid disintegration to granules and subsequent disaggregation to fine particles. This provides a larger surface area exposed to the dissolution medium, resulting in a faster dissolution rate.

Implantable devices coated with a compound of this invention are another embodiment of the present invention. The compounds may also be coated on implantable medical devices, such as beads, or co-formulated with a polymer or other molecule, to provide a "drug depot", thus permitting the drug to be released over a longer time period than administration of an aqueous solution of the drug. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

The formulations include those suitable for the administration routes detailed herein. The formulations may conveniently be presented in unit dosage form and may be prepared by any of the methods well known in the art of pharmacy. Techniques and formulations generally are found in Remington's. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product.

The terms "administer", "administering" or "administration" in reference to a compound, composition or formulation of the invention mean introducing the compound into the system of the animal in need of treatment. When a compound of the invention is provided in combination with one or more other active agents, "administration" and its variants are each understood to include concurrent and/or sequential introduction of the compound and the other active agents.

The compositions described herein may be administered systemically or locally, e.g.: orally (e.g., using capsules, powders, solutions, suspensions, tablets, sublingual tablets and the like), by inhalation (e.g., with an aerosol, gas, inhaler, nebulizer or the like), to the ear (e.g., using ear drops), topically (e.g., using creams, gels, liniments, lotions, ointments, pastes, transdermal patches, etc.), ophthalmically (e.g., with eye drops, ophthalmic gels, ophthalmic ointments), rectally (e.g., using enemas or suppositories), nasally, buccally, vaginally (e.g., using douches, intrauterine devices, vaginal suppositories, vaginal rings or tablets, etc.), via an implanted reservoir or the like, or parenterally depending on the severity and type of the disease being treated. The term "parenteral" as used herein includes, but is not limited to, subcutaneous, intravenous, intramuscular, intra-articular, intra-synovial, intrasternal, intrathecal, intra-hepatic, intralesional and intracranial injection or infusion techniques. Preferably, the compositions are administered orally, intraperitoneally or intravenously.

The pharmaceutical compositions described herein may be orally administered in any orally acceptable dosage form including, but not limited to, capsules, tablets, aqueous suspensions or solutions. Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution-retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. Tablets may be uncoated or may be coated by known techniques, including microencapsulation, to mask an unpleasant taste or to delay disintegration and adsorption in the gastrointestinal tract and thereby provide a sustained action over a longer period. For example, a time-delay material such as glyceryl monostearate or glyceryl distearate alone or with a wax may be employed. A water soluble taste-masking material such as hydroxypropyl-methylcellulose or hydroxypropyl-cellulose may be employed.

Formulations of a compound selected from Table 1 that are suitable for oral administration may be prepared as discrete units such as tablets, pills, troches, lozenges, aqueous or oil suspensions, dispersible powders or granules, emulsions, hard or soft capsules, e.g., gelatin capsules, syrups or elixirs. Formulations of a compound intended for oral use may be prepared according to any method known to the art for the manufacture of pharmaceutical compositions.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The active compounds can also be in microencapsulated form with one or more excipients as noted above.

When aqueous suspensions are required for oral use, the active ingredient is combined with emulsifying and suspending agents. If desired, certain sweetening and/or flavoring agents may be added. Syrups and elixirs may be formulated with sweetening agents, for example glycerol, propylene glycol, sorbitol or sucrose. Such formulations may also contain a demulcent, a preservative, flavoring and coloring agents and antioxidant.

Sterile injectable forms of the compositions described herein (e.g., for parenteral administration) may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers that are commonly used in the manufacture of pharmaceutically acceptable solid, liquid, or other dosage forms may also be used for the purposes of injectable formulations.

Oily suspensions may be formulated by suspending the compound selected from Table 1 in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents, such as those set forth above, and flavoring agents may be added to provide a palatable oral preparation. These compositions may be preserved by the addition of an antioxidant such as butylated hydroxyanisol or alpha-tocopherol.

Aqueous suspensions of compounds selected from Table 1 contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxyc-etanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

The injectable formulations can be sterilized, for example, by filtration through a bacteria-retaining filter, or by incorporating sterilizing agents in the form of sterile solid compositions that can be dissolved or dispersed in sterile water or other sterile injectable medium prior to use.

In order to prolong the effect of a compound described herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsuled matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot-injectable formulations are also prepared by entrapping the compound in liposomes or microemulsions that are compatible with body tissues.

The injectable solutions or microemulsions may be introduced into a patient's bloodstream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

Compositions for rectal or vaginal administration are preferably suppositories, which can be prepared by mixing the compounds described herein with suitable non-irritating excipients or carriers, such as cocoa butter, beeswax, polyethylene glycol or a suppository wax that are solid at ambient temperature but liquid at body temperature and therefore melt in the rectum or vaginal cavity and release the active compound. Other formulations suitable for vaginal administration may be presented as pessaries, tampons, creams, gels, pastes, foams or sprays.

The pharmaceutical compositions described herein may also be administered topically, especially when the target of treatment includes areas or organs readily accessible by topical application, including diseases of the eye, the ear, the skin, or the lower intestinal tract. Suitable topical formulations are readily prepared for each of these areas or organs.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel. Topical application for the lower intestinal tract can be effected in a rectal suppository formulation (see above) or in a suitable enema formulation. Topically transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH-adjusted sterile saline, or, preferably, as solutions in isotonic, pH-adjusted sterile saline, either with or without a preservative such as benzylalkonium chloride. Alternatively, for ophthalmic uses, the pharmaceutical compositions may be formulated in an ointment such as petrolatum. For treatment of the eye or other external tissues, e.g., mouth and skin, the formulations may be applied as a topical ointment or cream containing the active ingredient(s) in an amount of, for example, 0.075 to 20% w/w. When formulated in an ointment, the active ingredients may be employed with either an oil-based, paraffinic or a water-miscible ointment base.

Alternatively, the active ingredients may be formulated in a cream with an oil-in-water cream base. If desired, the aqueous phase of the cream base may include a polyhydric alcohol, i.e., an alcohol having two or more hydroxyl groups such as propylene glycol, butane-1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of emulsions prepared using compounds selected from Table 1 may be constituted from known ingredients in a known manner. While the phase may comprise merely an emulsifier (otherwise known as an emulgent), it desirably comprises a mixture of at least one emulsifier with a fat or an oil or with both a fat and an oil. A hydrophilic emulsifier may be included together with a lipophilic emulsifier which acts as a stabilizer. In some embodiments, the emulsifier includes both an oil and a fat. Together, the emulsifier(s) with or without stabilizer(s) make up the so-called emulsifying wax, and the wax together with the oil and fat make up the so-called emulsifying ointment base, which forms the oily dispersed phase of the cream formulations. Emulgents and emulsion stabilizers suitable for use in the formulation of compounds selected from Table 1 include Tween™-60, Span™-80, cetostearyl alcohol, benzyl alcohol, myristyl alcohol, glyceryl mono-stearate and sodium lauryl sulfate.

The pharmaceutical compositions may also be administered by nasal aerosol or by inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. Formulations suitable for intrapulmonary or nasal administration have a mean particle size, for example, in the range of 0.1 to 500 microns (including particles with a mean particle size in a range between 0.1 and 500 microns in micron increments such as 0.5, 1, 30, 35 microns, etc.), and are administered by rapid inhalation through the nasal passage or by inhalation through the mouth so as to reach the alveolar sacs.

For use, the pharmaceutical composition (or formulation) may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as recited herein, or an appropriate fraction thereof, of the active ingredient.

In another aspect, a compound selected from Table 1 or a pharmaceutically acceptable salt thereof may be formulated in a veterinary composition comprising a veterinary carrier. Veterinary carriers are materials useful for the purpose of administering the composition and may be solid, liquid or gaseous materials that are otherwise inert or acceptable in the veterinary art and are compatible with the active ingredient. These veterinary compositions may be administered parenterally, orally or by any other desired route.

Therapeutic Methods:

The terms, "disease", "disorder", and "condition" may be used interchangeably here to refer to a condition where an increase in the concentration of an endogenous cannabinoid (eCB) might be beneficial or a condition that can be treated by a FAAH inhibitor.

As used herein, the terms "subject" and "patient" are used interchangeably. The terms "subject" and "patient" refer to an animal (e.g., a bird such as a chicken, quail or turkey, or a mammal), preferably a "mammal" including a non-primate (e.g., a cow, pig, horse, sheep, rabbit, guinea pig, rat, cat, dog, and mouse) and a primate (e.g., a monkey, chimpanzee and a human), and more preferably a human. In one embodiment, the subject is a non-human animal such as a farm animal (e.g., a horse, cow, pig or sheep), or a pet (e.g., a dog, cat, guinea pig or rabbit). In a preferred embodiment, the subject is a "human".

The term "biological sample", as used herein, includes, without limitation, in vivo or ex vivo cell cultures or extracts thereof; biopsied material obtained from a mammal or extracts thereof; blood, saliva, urine, feces, semen, tears, lymphatic fluid, ocular fluid, vitreous humor or other body fluids or extracts thereof.

"Treat", "treating" or "treatment" with regard to a disorder or disease refers to alleviating or abrogating the cause and/or the effects of the disorder or disease. As used herein, the terms "treat", "treatment" and "treating" refer to the reduction or amelioration of the progression, severity and/or duration of a condition wherein an increase in the concentration of eCB might be beneficial or that can be treated with a FAAH inhibitor, or the amelioration of one or more symptoms (preferably, one or more discernible symptoms)

of said condition, resulting from the administration of one or more therapies (e.g., one or more therapeutic agents such as a compound or composition of the invention). In specific embodiments, the terms "treat", "treatment" and "treating" refer to the amelioration of at least one measurable physical parameter of condition wherein an increase in the concentration of eCB might be beneficial or a condition that can be treated with a FAAH inhibitor. In other embodiments the terms "treat", "treatment" and "treating" refer to the inhibition of the progression of said condition, either physically by, e.g., stabilization of a discernible symptom, physiologically by, e.g., stabilization of a physical parameter, or both.

As used herein, the terms "prevent", "preventing" and "prevention" with regard to a disorder or disease refer to averting the cause and/or effects of a disease or disorder prior to the disease or disorder manifesting itself. The terms "prophylaxis" or "prophylactic use", as used herein, refer to any medical or public health procedure whose purpose is to prevent, rather than treat or cure a disease. As used herein, the terms "prevent", "prevention" and "preventing" refer to the reduction in the risk of acquiring or developing a given condition, or the reduction or inhibition of the recurrence or said condition in a subject who is not ill, but who has been or may be near a person with the disease.

The term "chemotherapy" refers to the use of medications, e.g., small molecule drugs (rather than e.g., "vaccines") for treating a disorder or disease.

The term "chemoprophylaxis" refers to the use of medications, e.g., small molecule drugs (rather than e.g., "vaccines") for the prevention of a disorder or disease.

In one embodiment, the methods of the invention are a preventative or "pre-emptive" measure to a patient, preferably a human, having a predisposition to developing a condition or symptom that can be improved by an increase in the concentration of an eCB or treated with a FAAH inhibitor.

Also described are methods for treating or preventing various disorders with a composition that includes any of the various embodiments of the compound selected from Table 1. Among the disorders or symptoms that can be treated or prevented are:

pain (e.g., acute pain, chronic pain, neurogenic pain, dental pain, menstrual pain, dysmenorrheal pain, visceral pain, abdominal pain, pelvic pain, abdominal discomfort, neuropathic pain, headache, migraines, allodynia, hyperalgesia, post operative pain (e.g., associated with orthopedic surgery, gynecological surgery, abdominal surgery, incisions, oral surgery), back pain, pain caused by inflammation (e.g., arthritis, osteoarthritis, spondylitis, rheumatoid arthritis, Crohn's disease, irritable bowel syndrome, pain associated with injury, burns or trauma, and pain associated with fibromyalgia);

anxiety, depression, an impulse control disorder (e.g., pathological gambling, compulsive shopping, hypersexuality), a compulsion disorder, a dopamine dysregulation syndrome, an eating disorder (e.g., anorexia and bulimia);

obesity (e.g., by appetite suppression), elevated intraocular pressure (e.g., glaucoma), a cardiovascular disorder (e.g., hypertension);

an inflammatory disorder (e.g., allergy (e.g., food allergy, respiratory inflammation, inflammation of the skin and gastrointestinal inflammation), asthma, Crohn's disease);

emesis (e.g., as a side effect of chemotherapy), some cancers, excitotoxic insult (e.g., in cerebral ischemia, seizure and edema due to traumatic brain injury), asphyxia;

addictive behaviors, sleep disorders, epilepsy, epileptiform-induced damage, progressive CNS diseases (e.g., Parkinson's, motor neuron disorders, amyotrophic lateral sclerosis (ALS), Huntington's and motor dysfunction, dyskinesia); hyperactivity disorders, restless leg syndrome, periodic limb movement disorder;

gastrointestinal disorders (e.g., attenuation of cholera induced fluid accumulation, nausea, vomiting, gastric ulcers, diarrhea, paralytic ileus, IBS, IBD, colitis, and gastro-esophageal reflux conditions);

urinary system disorders (e.g. overactive bladder and interstitial cystitis);

and autoimmune disorders (e.g., multiple sclerosis).

The compounds and pharmaceutical compositions described herein can be used alone or in combination therapy for the treatment or prevention of pain. The pain can be chronic pain, acute pain, perioperative pain (e.g., associated with surgery), postoperative pain (e.g., associated with orthopedic surgery, gynecological surgery, abdominal surgery, incisions, oral surgery), visceral pain, abdominal pain, abdominal discomfort, pelvic pain, inflammatory pain, cancer pain, headache pain, pain associated with cough, neuropathic pain, deafferentation pain, chronic nociceptive pain, dental pain (such as odontalgia), bone pain, joint pain (e.g., osteoarthritis or rheumatoid arthritis), myofascial pain (e.g., muscular injury, fibromyalgia), pain associated with fibromyalgia, labor pain, pain associated with injuries, trauma, allergies, dermatitis, immunodeficiency, Hodgkin's disease, Myasthenia gravis, nephrotic syndrome, scleroderma, or thyroiditis, central and peripheral pathway mediated pain, pain associated with or the result of injury or age, menstrual pain, neurogenic pain, dysmenorrheal pain, migraines, allodynia, hyperalgesia, back pain, pain caused by inflammation (e.g., arthritis, osteoarthritis, spondylitits, rheumatoid arthritis, Crohn's disease and irritable bowel syndrome), and pain associated with burns.

Neuropathic pain is initiated or caused by a primary lesion or dysfunction in the peripheral or central nervous systems. It can occur in the peripheral nerves, dorsal roots, spinal cord and certain regions of the brain. It can also result from a peripheral nerve disorder such as neuroma, nerve compression, nerve crush, nerve stretch or incomplete nerve transfection. It can be associated with neuronal lesions, such as those induced by diabetes, HIV, herpes infection, nutritional deficiencies or a stroke. Chronic neuropathic pain can result from injury and/or inflammation such as chronic lower back pain. Acute neuropathic pain includes, for example, traumatic pain (e.g., bone fracture pain, sprains, strains and soft tissue damage), muscle pain, burn pain, and sun burn pain. Neuropathic pain can also be associated with, for example, nerve injury, head trauma, hyperalgesia, allodynia, dysesthesias, sciatica, amputation (e.g., phantom limb syndrome, stump pain), fibromyalgia, chemotherapeutic neuropathy, cancer pain (e.g., tumors of the brainstem, thalamus or cortex), AIDS-related neuropathy, painful traumatic mononeuropathy, painful polyneuropathy, multiple sclerosis, root avulsions, post-thoracotomy syndrome. It can be the result of a central nervous system injury (such as pain in stroke or spinal cord injury patients). Neuropathic pain also includes lower back pain, toxin induced pain, neurogenic pain, thalamic pain syndrome, repetitive motion pain (e.g., carpal tunnel syndrome) or pain induced by post-mastectomy syndrome, by surgery or by radiation. Neuralgia is a type of neuropathic pain that is thought to be linked to four possible mechanisms: ion gate malfunctions; a nerve becoming mechanically sensitive and creating an ectopic signal; cross signals between large and small fibers; and malfunction due to damage in the central processor. Under the general heading of neuralgia are trigeminal neuralgia (TN), atypical trigeminal neuralgia (ATN), and post-herpetic neuralgia (caused by shingles or herpes). Neuralgia is also involved in disorders such as sciatica and brachial plexopathy with neuropathia. Neuralgias that do not involve the trigeminal nerve are occipital neuralgia and glossopharyngeal neuralgia. Neuropathic pain also includes referred pain.

Visceral, abdominal or pelvic pain or discomfort includes, for example, pancreas pain (e.g., pain associated with pancreatitis), urological pain (e.g., associated with interstitial cystitis, urinary bladder pain, prostate pain), renal pain (e.g., renal colic, pain caused by kidney stones), gynecological pain (e.g., dysmenorrhea, menstrual cramps, menstruation, endometriosis, ovarian pain), gastrointestinal pain (e.g., pain associated with irritable bowel syndrome (IBS; with all its variants), Crohn's disease, celiac disease, ulcerative colitis, peptic ulcers, stomach pain, rectal pain, bowel pain, intestinal pain, intestinal cramps, gastritis and non-ulcer dyspepsia), angina, myocardial ischemia. Visceral pain also includes non-cardiac chest pain and referred pain. Also included is abdominal, visceral or pelvic pain caused by cancer, bacterial infections, parasitic infections, surgery, trauma, medications, gallstones, and diverticulitis or digestive disorders. Inflammatory pain includes both inflammatory pain that is a significant component of a disorder or disease and that that is considered a minor component or symptom. For example, inflammatory pain induced by or associated with disorders such as osteoarthritis, rheumatic fever, rheumatoid arthritis, rheumatic disease, tendonitis, juvenile arthritis, spondylitis, gouty arthritis, psoriatic arthritis, interstitial cystitis, peripheral neuritis, mucositis, fibromyalgia, pancreatitis, enteritis, diverticulitis, cellulites, bone fractures, post-operative ileus, Crohn's Disease, ulcerative colitis, cholecystitis, teno-synovitis, gout, vulvodynia, fibromyalgia, sprains and strains, systemic lupus erythematosus, myositis, bronchitis and influenza and other viral infections such as the common cold. Inflammatory pain also includes sympathetically maintained pain, pain due to venomous and non-venomous snake bite, spider bite or insect sting, sports injury pain, sprain pain, joint pain, myofascial pain (muscular injury, fibromyalgia), musculoskeletal pain, and pain due to inflammatory bowel diseases. Among the inflammatory pain disorders that can be treated are included some autoimmune disorders or diseases.

Cancer pain can be induced by or associated with tumors such as lymphatic leukemia, Hodgkin's disease, malignant lymphoma, osteosarcoma, bone cancer, lymphogranulomatoses, lymphosarcoma, solid malignant tumors, and extensive metastases. Chemotherapy pain is a side effect of chemotherapy treatments.

Headache pain includes cluster headache, migraines with and without aura, tension type headache, headaches caused by injury or infection, hangovers, and headaches with unknown origins.

The compounds and pharmaceutical compositions described herein can be used alone or in combination therapy for the treatment or prevention of inflammatory disorders, including, for example, chronic and acute inflammatory disorders. Examples of disorders with inflammatory components include asthma, atopic allergy, allergy, atherosclerosis, bronchial asthma, eczema, glomerulonephritis, graft vs. host disease, hemolytic anemia, osteoarthritis, sepsis, septic shock (e.g., as antihypovolemic and/or antihypotensive agents), systemic lupus erythematosus, stroke, transplantation of tissue and organs, vasculitis, interstitial cystitis, diabetic retinopathy and ventilator induced lung injury. The compounds and pharmaceutical compositions described herein can also be used alone or in combination therapy for the treatment or prevention of disease-states or indications that are accompanied by inflammatory processes such as:

(1) Lung diseases: e.g., asthma, bronchitis, allergic rhinitis, emphysema, adult respiratory distress syndrome (ARDS), pigeon fancier's disease, farmer's lung, chronic obstructive pulmonary disease (COPD), asthma including allergic asthma (atopic or non-atopic) as well as exercise-induced bronchoconstriction, occupational asthma, viral- or bacterial exacerbation of asthma, other non-allergic asthmas and "wheezy-infant syndrome", pneumoconiosis, including aluminosis, anthracosis, asbestosis, chalicosis, ptilosis, siderosis, silicosis, tabacosis and byssinosis;

(2) Rheumatic diseases or autoimmune diseases or musculoskeletal diseases: e.g., all forms of rheumatic diseases, especially rheumatoid arthritis, acute rheumatic fever, and polymyalgia rheumatica; reactive arthritis; rheumatic soft tissue diseases; inflammatory soft tissue diseases of other genesis; arthritic symptoms in degenerative joint diseases (arthroses); tendinitis, bursitis, osteoarthritis, traumatic arthritis, gout (metabolic arthritis); collagenoses of any genesis, e.g., systemic lupus erythematosus, scleroderma, polymyositis, dermatomyositis, Sjogren syndrome, Still disease, Felty syndrome; and osteoporosis and other bone resorption diseases;

(3) Allergic diseases including all forms of allergic reactions, e.g., allergic rhinitis, allergic conjunctivitis, infectious parasitic, angioneurotic edema, hay fever, insect bites, allergic reactions to drugs, blood derivatives, contrast agents, etc., anaphylactic shock (anaphylaxis), urticaria, angioneurotic edema, delayed or immediate hypersensitivity, and contact dermatitis;

(4) Vascular diseases: e.g., panarteritis nodosa, polyarteritis nodosa, periarteritis nodosa, arteritis temporalis, Wegner granulomatosis, giant cell arthritis, atherosclerosis, reperfusion injury and erythema nodosum, myocardial ischemia, thrombosis.

(5) Dermatological diseases: e.g., dermatitis, psoriasis, sunburn, burns, and eczema;

(6) Renal, urinary and pancreatic diseases: e.g., nephrotic syndrome and all types of nephritis (such as glomerulonephritis); pancreatitis; bladder hyper-reflexia following bladder inflammation; other renal diseases that can be treated by the compounds and compositions herein described include urinary incontinence or vesicle inflammation, uresesthesia urgency, overactive bladder, urinary frequency, interstitial cystitis or chronic prostatitis;

(7) Hepatic diseases: e.g., acute liver cell disintegration; acute hepatitis of various genesis (such as viral, toxic, drug-induced) and chronically aggressive and/or chronically intermittent hepatitis, liver fibrosis associated with liver injury or disease, including fibrosis caused or exacerbated by alcoholic liver cirrhosis, chronic viral hepatitis, non-alcoholic steatohepatitis and primary liver cancer;

(8) Gastrointestinal diseases: e.g., ulcers, inflammatory bowel diseases, regional enteritis (Crohn's disease), ulcerative colitis, gastritis, aphthous ulcer, celiac disease, regional ileitis, ileus, esophagitis, NSAID-induced ulcer, non-ulcerative dyspepsia and gastroesophageal reflux disease;

(9) Neurodegenerative diseases: e.g., treatment/reduction of neurodegeneration following stroke, cardiac arrest, pulmonary bypass, traumatic brain injury, edema, spinal cord injury, cerebral ischemia, seizures, neurodegeneration associated with multiple sclerosis, or the like, neuroprotection, neurogenesis;

(10) Eye diseases: e.g., allergic keratitis, uveitis, or iritis, conjunctivitis, blepharitis, neuritis nervi optici, choroiditis, glaucoma and sympathetic ophthalmia;

(11) Diseases of the ear, nose, and throat (ENT) area: e.g., tinnitus, allergic rhinitis or hay fever, gingivitis, otitis externa, caused by contact eczema, infection, etc., and otitis media;

(12) Progressive central nervous system or neurological diseases: e.g., brain edema, particularly tumor-related brain edema, multiple sclerosis, spasticity associated with multiple sclerosis, acute encephalomyelitis, meningitis, acute spinal cord injury, trauma; cognitive disorders such as dementia, particularly degenerative dementia (including senile dementia, Alzheimer's disease, Parkinson's disease and Creutzfeldt-Jacob disease, Huntington's chorea, Pick's disease, amyotrophic lateral sclerosis (ALS)), vascular dementia (including multi-infarct dementia and dementia associated with intracranial space occupying lesions, infections and related conditions such as HIV infection); Guillain-Barre syndrome, myasthenia gravis, stroke, and various forms of seizures (such as nodding spasms), hyperactivity, dyskinesias;

(13) Blood diseases: e.g., acquired hemolytic anemia, aplastic anemia, and idiopathic thrombocytopenia;

(14) Tumor diseases: e.g., acute lymphatic leukemia, Hodgkin's disease, malignant lymphoma, lymphogranulomatoses, lymphosarcoma, solid malignant tumors, colorectal polyps, and extensive metastases; other proliferative disorders such as diabetic retinopathy and tumor angiogenesis (e.g., wet macular degeneration).

(15) Endocrine diseases: e.g., endocrine opthalmopathy, endocrine orbitopathia, thyrotoxic crisis, Thyroiditis de Quervain, Hashimoto thyroiditis, Morbus Basedow, granulomatous thyroiditis, struma lymphomatosa, Graves disease, type I diabetes (such as insulin-dependent diabetes); organ and tissue transplantations and graft vs. host diseases;

(16) Severe states of shock: e.g., septic shock, anaphylactic shock, and systemic inflammatory response syndrome (SIRS);

(17) Viral or bacterial parasitic infectious disease: for example, AIDS and meningitis; and

(18) Various other disease-states or conditions including, restenosis following percutaneous transluminal coronary angioplasty, acute and chronic pain, atherosclerosis, reperfusion injury, congestive heart failure, myocardial infarction, thermal injury, multiple organ injury secondary to trauma, necrotizing enterocolitis and syndromes associated with hemodialysis, leukopheresis, granulocyte transfusion, sarcoidosis, gingivitis, pyrexia; edema resulting from trauma associated with burns, sprains or fracture, cerebral edema and angioedema, and diabetes (such as diabetic vasculopathy, diabetic neuropathy, diabetic retinopathy, post capillary resistance and diabetic symptoms associated with insulitis (e.g., hyperglycemia, diuresis, proteinuria and increased nitrite and kallikrein urinary excretion)).

The compounds and compositions herein described can be used alone or in combination therapy for the treatment of gastrointestinal (GI) diseases or disorders: e.g., functional gastrointestinal disorders, ulcers, inflammatory bowel diseases (IBD), regional enteritis (Crohn's disease), ulcerative colitis, diarrhea, gastritis, aphthous ulcer, celiac disease, regional ileitis, ileus, functional dyspepsia, diverticulitis, gastrointestinal bleeding, irritable bowel syndrome (IBS), non-ulcerative dyspepsia and gastroesophageal reflux disease.

The compounds and pharmaceutical compositions described herein can be used alone or in combination therapy for the treatment or prevention of pruritus (itch). For example, pruritus originated in the skin (dermal pruritus), neuropathic pruritus, neurogenic or psychogenic pruritus would all be included. Pruritus (itching) can be a symptom of primary skin diseases or of systemic disease. Skin diseases notorious for causing intense pruritus include scabies, pediculosis, insect bites, urticaria, atopic and contact dermatitis, lichen planus, miliaria, and dermatitis herpetiformis. In other cases pruritus is prominent without any identifiable skin lesions: e.g., dry skin (especially in elderly people), systemic disease, and use of certain drugs can generate pruritus. Systemic diseases that cause generalized pruritus include cholestatic diseases, uremia, polycythemia vera, and hematologic malignancies. Pruritus may also occur during the later months of pregnancy. Barbiturates, salicylates, morphine and cocaine can cause pruritus. Less well-defined causes of pruritus include hyper- and hypothyroidism, diabetes, iron deficiency, and internal cancers of many types.

The compounds and pharmaceutical compositions described herein can be used alone or in combination therapy for the treatment or prevention of substance abuse related syndromes, disorders or diseases include, including, for example, drug abuse and drug withdrawal. Abused substances can include alcohol, amphetamines, amphetamine-like substances, caffeine, cannabis, cocaine, hallucinogens, inhalants, opioids, nicotine (and/or tobacco products), heroin, barbiturates, phencyclidine (or phencyclidine-like compounds), sedative-hypnotics, benzodiazepines, or combinations of any of the foregoing. The compounds and pharmaceutical compositions can also be used to treat withdrawal symptoms and substance-induced anxiety or mood disorder. In addition, they can be used to reduce tobacco craving; treat nicotine dependency, addiction, or withdrawal; or aid in the cessation or lessening of tobacco in a subject in need thereof.

The compounds and pharmaceutical compositions described herein can be used alone or in combination therapy for the treatment or prevention of psychiatric disorders, such as depressions (including major depressive disorder, bipolar depression, unipolar depression, single or recurrent major depressive episodes (e.g., with or without psychotic features, catatonic features, and/or melancholic features), postpartum onset, seasonal affective disorder, dysthymic disorders (e.g., with early or late onset and with or without atypical features), neurotic depression and social phobia, depression accompanying dementia, depression associated with fibromyalgia, anxiety, psychosis, social affective disorders, and/or cognitive disorders); manic-depressive psychoses, bipolar disorders, extreme psychotic states (such as mania, schizophrenia, and excessive mood swings where behavioral stabilization is desired); post-traumatic stress disorder; panic disorder; compulsive disorders (e.g., obsessive compulsive disorder, stereotypic, selfinjurious and repetitive behaviors, trichtillomania), pyschiatric tremors such as dyskinesia, dyskinesia associated with Parkinson's disease, dystonia or spasticity, dystonia or spasticity associated with multiple sclerosis. The compounds and pharmaceutical compositions described herein can also be used alone or in combination therapy for the treatment or prevention of attention disorders such as ADHD (attention deficit hyperactivity disorders), hyperactivity, hyperactivity disorders, restless leg syndrome, periodic limb movement disorder, autism, anxiety states, generalized anxiety, an impulse control disorder (e.g. pathological gambling, compulsive shopping, hypersexuality), a compulsion disorder, a dopamine dysregulation syndrome, agoraphobia, as well as those behavioral states characterized by social withdrawal. They can also be used for the treatment of psychiatric tremors, for instance dyskinesias (e.g., associated with Parkinson's disease), dystonia or spasticity (e.g., associated with multiple sclerosis).

The compounds and pharmaceutical compositions described herein can be used alone or in combination therapy for the treatment or prevention of an autoimmune disease or disorder or at least one symptom associated with said disease or disorder, including, for example, alopecia areata (also known as systemic sclerosis (SS)), amyloses, amyotrophic lateral sclerosis, ankylosing spondylarthritis, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, connective tissue diseases, crest syndrome, Crohn's disease, Degos' disease, dermatomyositis-juvenile, discoid lupus, essential mixed cryoglobulinemia, fibromyalgia-fibromyositis, graft vs. host disease, transplantation rejection, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, lupus erythematosus, Meniere's disease, multiple sclerosis, myasthenia gravis, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, reactional arthritis, Reiter's syndrome, rheumatic fever, rheumatoid arthritis, sarcoidosis, scleroderma (progressive systemic sclerosis (PSS), Sjogren's syndrome, stiff-man syndrome, systemic lupus erythematosus, Takayasu arteritis, temporal arteritis/giant cell arteritis, ulcerative colitis, undifferentiated spondylarthritis, uveitis, vitiligo, and Wegener's granulomatosis. The compounds and pharmaceutical compositions described herein can be used alone or in combination therapy for neuroprotection in individuals suffering from multiple sclerosis or other autoimmune diseases.

The compounds and pharmaceutical compositions described herein can be used alone or in combination therapy for the treatment or prevention of neurological or neurodegenerative disorders. Examples of neurodegenerative diseases include dementia, particularly degenerative dementia (including senile dementia, Alzheimer's disease, Pick's disease, Huntingdon's chorea, Parkinson's disease, prion disease and Creutzfeldt-Jakob disease, motor neuron disease; vascular dementia (including multi-infarct dementia); as well as dementia associated with intracranial space occupying lesions; trauma; infections and related conditions (including HIV infection); dementia in Parkinson's disease; metabolism; toxins; anoxia and vitamin deficiency; and mild cognitive impairment associated with aging, particularly Age-Associated Memory Impairment. Examples of neurological disorders include amyotrophic lateral sclerosis (ALS), multiple sclerosis, spascity associated with multiple sclerosis, epilepsy, ischemia, traumatic head or brain injury, brain inflammation, eye injury, stroke and neuroinflammation. The compounds and compositions here described can also be used for the treatment/reduction of neurodegeneration or decreased brain activity associated with stroke, cardiac arrest, pulmonary bypass, traumatic brain injury, hypoxia, hypoglycemia, gas poisoning, drug intoxication, diabetes mellitus, edema, spinal cord injury, cerebral ischemia, cerebral infarction, cerebral hemorrhage, subarachnoid hemorrhage, seizures, neurodegeneration associated with multiple sclerosis, or the like.

The compounds and pharmaceutical compositions described herein can be used alone or in combination therapy for the treatment or prevention of ocular disorders including, for example, glaucoma (such as normal tension glaucoma), glaucoma-associated intraocular pressure retinitis, retinopathies, uveitis, and acute injury to the eye tissue (e.g., conjunctivitis). Ocular disorders also include neurodegenerative disease conditions of the retina and the optic nerve, for example, in patients presenting risk factors for glaucoma, such as high intraocular pressure, family history of glaucoma, glaucoma in the contralateral eye and high myopia.

The compounds and compositions described herein can also be used, alone or in combination therapy, to treat or prevent appetite related disorders such as emesis, vomiting and nausea, food behavioral problems or feeding disorders (e.g., anorexias, cachexias, wasting conditions and bulimia) and obesity or obesity-related disorders (e.g., diabetes type II, hyperlipidemia).

Certain gynecological disorders can be treated by inhibition of uterus contraction caused by hormones and prostanoid-induced muscle contraction using compounds or compositions described herein, for example, premature labor, menstrual cramps, menstrual irregularity, dysmenorrhea.

Some sleep disorders can be treated with compounds or compositions described herein, for example insomnia, night terrors, nightmares, vivid dreaming, restlessness, bruxism, somnambulism, narcolepsy, circadian rhythm adjustment disorders, and the like. Also contemplated are sleep disorders associated with neurological or mental disorders or with pain.

Cardiovascular diseases that can be treated with the compounds and compositions of the invention include myocardial ischemia, thrombosis, hypertension or cardiac arrhythmias.

Compounds and compositions of the invention are also useful for veterinary treatment of companion animals, exotic animals and farm animals, including, without limitation, dogs, cats, mice, rats, hamsters, gerbils, guinea pigs, rabbits, horses, pigs and cattle.

In another embodiment, the invention provides a method of inhibiting FAAH in a biological sample, comprising contacting said biological sample with a compound or composition of the invention. Use of a FAAH inhibitor in a biological sample is useful for a variety of purposes known to one of skill in the art. Examples of such purposes include, without limitation, biological assays and biological specimen storage.

Combination Therapies:

The compounds and pharmaceutical compositions described herein can be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent.

When co-administered with other agents, e.g., when co-administered with another pain medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range from between about 0.001 to about 100 mg/kg body weight/day, from about 0.001 to about 50 mg/kg body weight/day, from about 0.001 to about 30 mg/kg body weight/day, from about 0.001 to about 10 mg/kg body weight/day.

When combination therapy is employed, an effective amount can be achieved using a first amount of a compound selected from Table 1 or a pharmaceutically acceptable salt, solvate (e.g., hydrate), co-crystal or pro-drug thereof and a second amount of an additional suitable therapeutic agent (e.g., an agent to treat pain).

In one embodiment of this invention, the compound selected from Table 1 and the additional therapeutic agent, are each administered in an effective amount (i.e., each in an amount which would be therapeutically effective if administered alone). In another embodiment, the compounds selected from Table 1 and the additional therapeutic agent, are each administered in an amount which alone does not provide a therapeutic effect (a sub-therapeutic dose). In yet another embodiment, the compounds selected from Table 1 can be administered in an effective amount, while the additional therapeutic agent is administered in a sub-therapeutic dose. In still another embodiment, the compounds selected from Table 1 can be administered in a sub-therapeutic dose, while the additional therapeutic agent, for example, a suitable cancer-therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Co-administration encompasses administration of the first and second amounts of the compounds in an essentially simultaneous manner, such as in a single pharmaceutical composition, for example, a capsule or tablet having a fixed ratio of first and second amounts, or in multiple, separate capsules or tablets for each. In addition, such co-administration also encompasses use of each compound in a sequential manner in either order. When co-administration involves the separate administration of the first amount of a compound of Table 1 and a second amount of an additional therapeutic agent, the compounds are administered sufficiently close in time to have the desired therapeutic effect. For example, the period of time between each administration that can result in the desired therapeutic effect, can range from minutes to hours and can be determined taking into account the properties of each compound such as potency, solubility, bioavailability, plasma half-life and kinetic profile. For example, a compound selected from Table 1 and the second therapeutic agent can be administered in any order within about 24 hours of each other, within about 16 hours of each other, within about 8 hours of each other, within about 4 hours of each other, within about 1 hour of each other or within about 30 minutes of each other.

More specifically, a first therapy (e.g., a prophylactic or therapeutic agent such as a compound described herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks prior to), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks subsequent to) the administration of a second therapy (e.g., a prophylactic or therapeutic agent such as an anti-cancer agent) to a subject.

Additional therapeutic agents that can be combined with compounds described herein include, without limitation:

FAAH inhibitors: e.g., OL-135, LY2183240, URB-597, CAY-10402, PF-750, BMS-469908, SSR-411298, TK-25, PF-04457845, PF-3845, SA-47, JNJ-245, JNJ-28833155 and JNJ-1661010;

painkillers such as acetaminophen or paracetamol;

non-steroidal anti-inflammatory drugs (NSAIDs) such as propionic acid derivatives (alminoprofen, benoxaprofen, bucloxic acid, carprofen, fenhufen, fenoprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (meclofenamic acid, mefenamic acid, and tolfenamic acid), biphenyl-carboxylic acid derivatives, oxicams (isoxicam, meloxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone), and COX-2 inhibitors, such as the coxibs (celecoxib, deracoxib, valdecoxib, rofecoxib, parecoxib and etoricoxib);

other pain relieving agents such as gabapentin, topical capsaicin, tanezumab, esreboxetine;

opiate receptor agonists such as morphine, propoxyphene (Darvon™), tramadol, buprenorphin;

cannabinoid receptor agonists such as dronabinol, Δ9-THC, CP-55940, WIN-55212-2, HU-210;

anti-infective agents;

sodium channel blockers such as carbamazepine, mexiletine, lamotrigine, pregabalin, tectin, NW-1029, CGX-1002;

N-type calcium channel blockers such as ziconotide, NMED-160, SPI-860; serotonergic and noradrenergic modulators such as SR-57746, paroxetine, duloxetine, clonidine, amitriptyline, citalopram;

local anesthetics such as ambroxol, lidocaine;

VR1 agonists and antagonists such as NGX-4010, WL-1002, ALGRX-4975, WL-10001, AMG-517;

agents used for migraines, such as sumatriptan, zolmitriptan, naratriptan, eletriptan, rauwolscine, yohimbine, metoclopramide;

topical agents used in the treatment of localized pruritus: e.g., camphor/menthol lotions or creams containing 0.125 to 0.25% menthol, doxepin (e.g., Sinequan™, Zonalon™), phenol (e.g., Cepastat®, Chloraseptic® gargle, Ulcerease), 0.5 to 2%, pramoxine (e.g., Anusol™ ointment, Proctofoam-NS, Tronolane™ Cream, Tucks™ Hemorrhoidal), eutectic mixture of local anesthetics (EMLA), and corticosteroids;

anti-inflammatory and/or immunosuppressive agents such as methotrexate, cyclosporin A (including, for example, cyclosporin microemulsion), tacrolimus, corticosteroids, statins, interferon beta, Remicade™ (infliximab), Enbrel™ (etanercept) and Humira™ (adalimumab);

agents designed to treat tobacco abuse: e.g., nicotine receptor partial agonists, bupropion hypochloride (also known under the tradename Zyban™) and nicotine replacement therapies;

ADD/ADHD agents: e.g., Ritalin™ (methylphenidate hydrochloride), Strattera™ (atomoxetine hydrochloride), Concerta™ (methylphenidate hydrochloride) and Adderall™ (amphetamine aspartate; amphetamine sulfate; dextroamphetamine saccharate; and dextroamphetamine sulfate);

agents to treat alcoholism, such as opioid antagonists (e.g., naltrexone (also known under the tradename ReVia M) and nalmefene), disulfiram (also known under the tradename Antabuse™), and acamprosate (also known under the tradename Campral™));

agents for reducing alcohol withdrawal symptoms such as benzodiazepines, beta-blockers, clonidine, carbamazepine, pregabalin, and gabapentin (Neurontin™);

antihypertensive agents: e.g., ACE inhibitors and Angiotensin II Receptor blockers such as benazepril, captopril, enalapril, fosinopril, lisinopril, candesartan, eprosartan, irbesartan, losartan, olmesartan, telmisartan, valsartan, renin inhibitors such as aliskiren, vasodilators such as minoxidil;

agents used to treat glaucoma: e.g., direct-acting miotics (cholinergic agonists), indirect acting miotics (cholinesterase inhibitors), carbonic anhydrase inhibitors (e.g., acetazolamide, methazolamide, brinzolamide, dorzolamide, selective adrenergic agonists (e.g., apraclonidine, brimonidine), beta-blockers (timolol, betaxolol, carteolol, levobetaxolol, levobunolol, metipranolol), osmotic diuretics (e.g., glycerin, mannitol);

antidepressants: e.g., SSRIs (e.g., fluoxetine, citalopram, femoxetine, fluvoxamine, paroxetine, indalpine, sertraline, zimeldine), tricyclic antidepressants (e.g., imipramine, amitriptiline, chlomipramine and nortriptiline), dopaminergic antidepressants (e.g., bupropion and aminepetine), SNRIs (e.g., venlafaxine and reboxetine);

cognitive improvement agents: e.g., donepezil hydrochloride (Aricept™) and other acetylcholinesterase inhibitors;

anti-emetic agents: e.g., 5HT3 antagonists such as ondansetron, granisetron, metoclopramide;

neuroprotective agents: e.g., memantine, L-dopa, bromocriptine, pergolide, talipexol, pramipexol, cabergoline, neuroprotective agents currently under investigation including anti-apoptotic drugs (CEP 1347 and CTCT346), lazaroids, bioenergetics, antiglutamatergic agents and dopamine receptors. Other clinically evaluated neuroprotective agents are, e.g., the monoamine oxidase B inhibitors selegiline and rasagiline, dopamine agonists, and the complex I mitochondrial fortifier coenzyme Q10;

antipsychotic medications: e.g., ziprasidone (Geodon™), risperidone (Risperdal™), and olanzapine (Zyprexa™);

agents used for multiple sclerosis such as beta-interferon (e.g., Avonex™, Betaseron™) baclofen and Copaxone™;

disease-modifying anti-rheumatic drugs (DMARDS) such as methotrexate, azathioptrine, leflunomide, pencillinamine, gold salts, mycophenolate mofetil, cyclophosphamide, CP-690,550; biological response modifiers (BRMs) such as Enbrel™, Remicade™, IL-1 antagonists; NSAIDS such as piroxicam, naproxen, indomethacin, ibuprofen and the like; COX-2 selective inhibitors such as Celebrex™; COX-1 inhibitors such as Feldene™; immunosuppressives such as steroids, cyclosporine, tacrolimus, rapamycin and the like;

PDE4 inhibitors such as theophylline, drotaverine hydrochloride, cilomilast, roflumilast, denbufylline, rolipram, tetomilast, enprofylline, arofylline, cipamfylline, tofimilast, filaminast, piclamilast, (R)-(+)-4-[2-(3-cyclopentyloxy-4-methoxyphenyl)-2-phenylethyl]pyridine, mesopram, N-(3,5-dichloro-4-pyridinyl)-2-[1-(4-fluorobenzyl)-5-hydroxy-1H-indol-3-yl]-2-oxoacetamide, CDC-801 (Celgene), CC-1088 (Celgene), Lirimilast, ONO-6126 (Ono), CC-10004 (Celgene) and MN-001 (Kyorin), ibudilast and pentoxifylline, for use in treating inflammation, lung disorders and as bronchodilators;

corticosteroids such as betamethasone, budesonide, cortisone, dexamethasone, hydrocortisone, methylprednisolone, prednisolone, prednisone and triamcinolone;

histamine H1 receptor antagonists such as bromopheniramine, chlorpheniramine, dexchlorpheniramine, triprolidine, clemastine, diphenhydramine, diphenylpyraline, tripelennamine, hydroxyzine, methdiazine, promethazine, trimeprazine, azatadine, cyproheptadine, antazoline, pheniramine pyrilamine, astemizole, terfenadine, loratadine, cetirizine, desloratadine, fexofenadine and levocetirizine;

histamine H2 receptor antagonists such as cimetidine, famotidine and ranitidine;

proton pump inhibitors such as omeprazole, pantoprazole and esomeprazole;

leukotriene antagonists and 5-lipoxygenase inhibitors such as zafirlukast, montelukast, pranlukast and zileuton;

nicotinic acetylcholine receptor agonists such as ABT-202, A-366833, ABT-594; BTG-102, A-85380, CGX1204;

P2X3 receptor antagonists such as A-317491, ISIS-13920, AZD-9056;

NGF agonists and antagonists such as RI-724, RI-1024, AMG-819, AMG-403, PPH 207;

NK1 and NK2 antagonists such as DA-5018, R-116301; CP-728663, ZD-2249;

NMDA antagonist such as NER-MD-11, CNS-5161, EAA-090, AZ-756, CNP-3381; potassium channel modulators such as CL-888, ICA-69673, retigabine;

GABA modulators such as lacosamide and propofol;

anti-cancer agents such as tyrosine kinase inhibitors imatinib (Gleevec™/Glivec™) and gefitinib (Iressa™);

anti hyperlipidemia drugs such as statins, ezetimibe, niacin and bile acid sequestrants;

appetite suppressing agents: e.g., sibutramine, taranabant, rimobamant;

anti-diabetic medications such as insulin, tolbutamide (Orinase™), acetohexamide (Dymelor™), tolazamide (Tolinase™), chlorpropamide (Diabinese™), glipizide (Glucotrol™), glyburide (Diabeta™, Micronase™, Glynase™), glimepiride (Amaryl™), gliclazide (Diamicron™), repaglinide (Prandin™), nateglinide (Starlix™), pramlintide (Symlin™) and exenatide (Byetta™);

serotonergic and noradrenergic modulators such as SR-57746, paroxetine, duloxetine, clonidine, amitriptyline, citalopram, flibanserin; and GI agents: e.g., laxatives (e.g., lubiprostone (Amitiza™), Fybogel®, Regulan®, Normacol® and the like), a gastrointestinal agent used for the treatment of idiopathic chronic constipation and constipation-predominant IBS, GI motility stimulants (e.g., domperidone, metoclopramide, mosapride, itopride), antispasmodic drugs (e.g., anticholinergics such as hyoscyamine or dicyclomine); anti-diarrheal medicines such loperamide (Imodium™) and bismuth subsalicylate (as found in Pepto Bismol™ and Kaopectate™), GCC (Guanylate Cyclase C) agonists (e.g., linaclotide), 5HT4 agonists (e.g., tegasarod), 5HT3 antagonists (e.g., alosetron, ramosetron, ondansetron).

EXAMPLES

General Analytical Techniques

LC/MS was run on a Waters Acquity system using a Polar C18 column, and 5 to 60% acetonitrile/water over 5 min. The ionization method for the MS was electrospray.

Automated column chromatography was run using an ISCO system. One of the Companion, Combiflash, or Combiflash Rf was used in each case.

Microwave reactions were run on a Personal Chemistry Optimizer, at 0-240° C., a power of 0-300 W and a pressure of 0-21 bar.

HPLC for purification was run on a Varian Prepstar instrument using the following conditions:

Solvent A: 0.1% Trifluoroacetic acid in water
Solvent B: 0.1% Trifluoroacetic acid in acetonitrile

| Time | % Solvent A | % Solvent B | Flow | Inject wait |
|------|-------------|-------------|------|-------------|
| 0:00 | 90 | 10 | 15 | x |
| 35:00 | 5 | 95 | 15 | |
| 43:00 | 5 | 95 | 15 | |
| 45:00 | 95 | 5 | 15 | |
| 50:00 | 98 | 2 | 0 | |

All references provided in the Examples are herein incorporated by reference in their entirety. As used herein, all abbreviations, symbols and conventions are consistent with those used in the contemporary scientific literature. See, e.g., Janet S. Dodd, ed., *The ACS Style Guide: A Manual for Authors and Editors*, 2$^{nd}$ Ed., Washington, D.C.: American Chemical Society, 1997, herein incorporated by reference in its entirety.

Example 1

See Route 1, Procedures A, B, C and D 2-(1-((5-chloropyrazin-2-yl)methyl)-5-methoxy-2-methyl-1H-indol-3-yl)-N-(2-methoxypyridin-4-yl)-2-oxoacetamide (12)

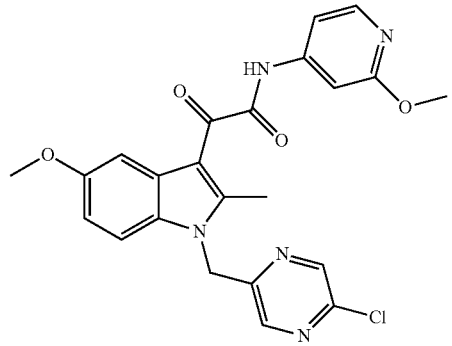

To a solution of 5-methoxy-2-methyl-1H-indole (3.45 g, 21.4 mmol) in dichloromethane (100 mL) at 0° C. was added oxalyl chloride (2.06 mL, 23.5 mmol). After 30 minutes, the reaction was warmed to room temperature, and LCMS analysis indicated the presence of the ketoacid chloride (via analysis of the methanolysis product). The reaction mixture was concentrated to dryness and then reconstituted in dichloromethane (100 mL) and cooled to 0° C. Methanol (8.00 mL, 198 mmol) was added after which the reaction mixture was warmed to room temperature, resulting in the formation of a solid precipitate, which was filtered and washed with hexanes and dried to afford methyl 2-(5-methoxy-2-methyl-1H-indol-3-yl)-2-oxoacetate (4.08 g, 16.5 mmol, 77% yield) as a light pink solid. No further purification of this material was necessary. $^1$H NMR (400 MHz, CDCl$_3$) δ (ppm): 8.49 (br. s, 1H), 7.59 (d, 1H), 7.22 (d, 1H), 6.88 (dd, 1H), 3.98 (s, 3H), 3.87 (s, 3H), 2.45 (s, 3H).

A solution of methyl 2-(5-methoxy-2-methyl-1H-indol-3-yl)-2-oxoacetate (672 mg, 2.72 mmol), (5-chloropyrazin-2-yl)methyl methanesulfonate (787 mg, 3.53 mmol), potassium carbonate (451 mg, 3.26 mmol), and potassium iodide (22.6 mg, 0.136 mmol) in N,N-dimethylformamide (15 mL) was heated at 65° C. for six hours, after which the reaction was diluted in water and treated with saturated sodium chloride solution, extracted with ethyl acetate (3×100 mL), dried (sodium sulfate), filtered and concentrated to a dark brown oil. Purification was achieved by silica gel chromatography (Luknova 80 g, 20 mL/min) using 30 to 100% ethyl acetate in hexanes over 60 minutes. The product, methyl 2-(1-((5-chloropyrazin-2-yl)methyl)-5-methoxy-2-methyl-1H-indol-3-yl)-2-oxoacetate (818 mg, 2.19 mmol, 80% yield) was isolated as a tan solid. $^1$H NMR (400 MHz, CDCl$_3$) δ (ppm): 8.54 (d, 1H), 8.05 (s, 1H), 7.54 (d, 1H), 7.16 (d, 1H), 6.88 (dd, 1H), 5.44 (s, 2H), 3.99 (s, 3H), 3.86 (s, 3H), 2.87 (s, 3H).

To a solution of methyl 2-(1-((5-chloropyrazin-2-yl)methyl)-5-methoxy-2-methyl-1H-indol-3-yl)-2-oxoacetate (810 mg, 2.167 mmol) in tetrahydrofuran (9.3 mL), methanol (3.1 mL), and water (3.1 mL) was added lithium hydroxide monohydrate (136 mg, 3.25 mmol). The reaction mixture was stirred at room temperature for 3 hours, after which it was concentrated to a residue, reconstituted in water and washed with ethyl acetate (3×50 mL). The aqueous layer was acidified with 3M hydrochloric acid solution, back-extracted with ethyl acetate (3×100 mL), dried (sodium sulfate), filtered, and concentrated to afford 2-(1-((5-chloropyrazin-2-yl)methyl)-5-methoxy-2-methyl-1H-indol-3-yl)-2-oxoacetic acid (737 mg, 2.05 mmol, 95% yield) as a tan solid. $^1$H NMR (400 MHz, CD$_3$CN) δ (ppm): 8.52 (d, 1H), 8.37 (d, 1H), 7.59 (d, 1H), 7.37 (d, 1H), 6.90 (dd, 1H), 5.56 (s, 2H), 3.84 (s, 3H), 3.86 (s, 3H), 2.69 (s, 3H). [Carboxylic acid proton was not observed in the $^1$H NMR spectrum]. LCMS: 1.62 min: [ES]$^-$ found 358.20.

To a solution of 2-(1-((5-chloropyrazin-2-yl)methyl)-5-methoxy-2-methyl-1H-indol-3-yl)-2-oxoacetic acid (500 mg, 1.39 mmol) and triethylamine (969 µL, 6.95 mmol) in acetonitrile (6.9 mL) was added 2-methoxypyridin-4-amine (190 mg, 1.53 mmol) followed by a 50% in ethyl acetate solution of T3P (2.48 mL, 4.17 mmol). The resulting solution was stirred at room temperature for 4 hours, after which LCMS analysis indicated that the reaction was complete. Water was added to the reaction mixture after which it was extracted with ethyl acetate (3×50 mL), dried (sodium sulfate), filtered and concentrated to a residue. Purification was achieved by silica gel chromatography (Luknova 80 g, 20 mL/min) using 30 to 100% ethyl acetate in hexanes over 60 minutes to afford 2-(1-((5-chloropyrazin-2-yl)methyl)-5-methoxy-2-methyl-1H-indol-3-yl)-N-(2-methoxypyridin-4-yl)-2-oxoacetamide (435 mg, 0.934 mmol, 67% yield) as a yellow solid. $^1$H NMR (400 MHz, CDCl$_3$) δ (ppm): 9.03 (br. s, 1H), 8.55 (d, 1H), 8.14 (d, 1H), 8.05 (s, 1H), 7.76 (d, 1H), 7.25 (d, 1H), 7.15 (d, 2H), 6.89 (dd, 1H), 5.46 (s, 2H), 3.96 (s, 3H), 3.87 (s, 3H), 2.77 (s, 3H). LCMS: 2.50 min, [ES]$^-$ found 464.30.

Example 2

See General Route 2, Procedure E, F, C and D 2-(1-(4-chlorobenzyl)-2-methyl-1H-pyrrolo[3,2-b]pyridin-3-yl)-N-(2-methoxypyridin-4-yl)-2-oxoacetamide (3)

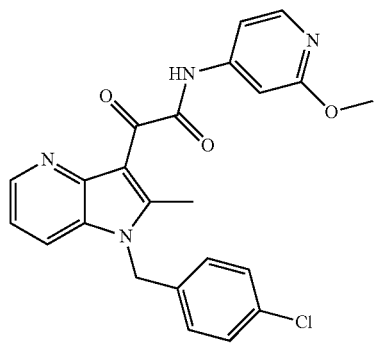 [SMILES: COc1cc(NC(=O)C(=O)c2c(C)n(Cc3ccc(Cl)cc3)c3cccnc23)ccn1]

To a solution of 2-methyl-1H-pyrrolo[3,2-b]pyridine (74.4 mg, 0.563 mmol) and 4-chlorobenzyl chloride (0.0780 mL, 0.619 mmol) in DMSO (8 mL) at room temperature was added powdered potassium hydroxide (69.5 mg, 1.24 mmol). The reaction was stirred at room temperature for 12 hours, after which LCMS analysis indicated that the reaction was complete. The reaction mixture was diluted in water and extracted with dichloromethane (3×50 mL), dried (sodium sulfate), filtered and concentrated to a clear residue. Purification was achieved by silica gel chromatography using 30 to 90% ethyl acetate in hexanes over 80 minutes affording 1-(4-chlorobenzyl)-2-methyl-1H-pyrrolo[3,2-b]pyridine (64.2 mg, 0.250 mmol, 44% yield) as an off-white solid. $^1$H NMR (400 MHz, CDCl$_3$) δ (ppm): 8.41 (dd, 1H), 7.41 (d, 1H), 7.24 (d, 2H), 7.01 (dd, 1H), 6.86 (d, 2H), 6.54 (s, 1H), 5.27 (s, 2H), 2.41 (s, 3H).

To a solution of 1-(4-chlorobenzyl)-2-methyl-1H-pyrrolo[3,2-b]pyridine (341 mg, 1.33 mmol) in dichloromethane (25 mL) was added aluminum trichloride (886 mg, 6.65 mmol). The mixture was stirred at room temperature for 20 minutes, after which ethyl oxalyl chloride (0.744 mL, 6.65 mmol) was added. The reaction mixture was stirred at room temperature for an additional three hours, after which it was poured over ice and extracted with ethyl acetate (3×50 mL), dried (sodium sulfate) filtered and concentrated to afford 2-(1-(4-chlorobenzyl)-2-methyl-1H-pyrrolo[3,2-b]pyridin-3-yl)-2-oxoacetic acid (76.5 mg, 0.233 mmol, 18% yield) an off-white solid. This material was used without any purification in the next step. The intended product of this reaction, ethyl 2-(1-(4-chlorobenzyl)-2-methyl-1H-pyrrolo[3,2-b]pyridin-3-yl)-2-oxoacetate, was observed in trace amounts and was not isolated from the reaction mixture. $^1$H NMR (400 MHz, CDCl$_3$) δ (ppm): 8.44 (dd, 1H), 7.41 (dd, 1H), 7.20 (d, 2H), 7.04 (dd, 1H), 6.84 (d, 2H), 6.54 (s, 1H), 5.27 (s, 2H), 2.77 (s, 3H) [Carboxylic acid proton not detected in 1H NMR]. LCMS: 2.18 min, [ES]$^-$ found 327.10.

To a solution of 2-(1-(4-chlorobenzyl)-2-methyl-1H-pyrrolo[3,2-b]pyridin-3-yl)-2-oxoacetic acid (76.5 mg, 0.218 mmol) in acetonitrile (7 mL) was added triethylamine (0.304 mL, 2.18 mmol), 2-methoxypyridin-4-amine (29.8 mg, 0.240 mmol), followed by a 50% ethyl acetate solution of T3P (972 mg, 1.53 mmol). The reaction was heated to 60° C. for 2 hours, after which additional triethylamine (0.304 mL, 2.18 mmol) and T3P solution (972 mg, 1.53 mmol) were added. The reaction mixture was stirred at 60° C. for 12 hours, after which it was diluted in water, extracted with ethyl acetate (3×50 mL), dried (sodium sulfate), filtered and concentrated to a residue. Purification was achieved by silica gel chromatography (Luknova 40 g, 20 mL/min) using 10 to 60% ethyl acetate in hexanes over 60 minutes. 2-(1-(4-chlorobenzyl)-2-methyl-1H-pyrrolo[3,2-b]pyridin-3-yl)-N-(2-methoxypyridin-4-yl)-2-oxoacetamide (31 mg, 0.071 mmol, 33% yield) was isolated as a light-tan solid. $^1$H NMR (400 MHz, CDCl$_3$) δ (ppm): 12.5 (br. s, 1H), 8.55 (dd, 1H), 8.08 (d, 1H), 7.55 (dd, 1H), 7.23-7.29 (m, 4H), 7.18 (dd, 1H), 6.87 (d, 2H), 5.34 (s, 2H), 3.90 (s, 3H), 2.70 (s, 3H).

Example 3

See General Route 3, Procedure E and G 2-(1-(4-chlorobenzyl)-5-cyano-2-methyl-1H-indol-3-yl)-N-(2-methoxypyridin-4-yl)-2-oxoacetamide (15)

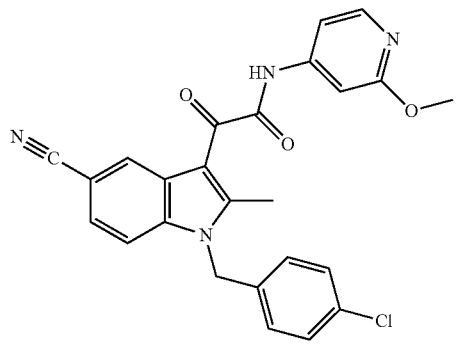 [SMILES: COc1cc(NC(=O)C(=O)c2c(C)n(Cc3ccc(Cl)cc3)c3ccc(C#N)cc23)ccn1]

To a room temperature solution of 2-methyl-1H-indole-5-carbonitrile (1.89 g, 12.1 mmol) and 1-chloro-4-(chloromethyl)benzene (1.53 mL, 12.1 mmol) in DMSO (40.3 mL) was added powdered potassium hydroxide (1.39 g, 24.2 mmol). The reaction mixture was stirred at room temperature for 12 hours, which it was diluted in water, extracted with dichloromethane (3×50 mL), dried (sodium sulfate), filtered and concentrated to a clear residue. Purification was achieved by silica gel chromatography using 10 to 60% ethyl acetate in hexanes over 75 minutes to afford 1-(4-chlorobenzyl)-2-methyl-1H-indole-5-carbonitrile (2.75 g, 9.80 mmol, 81% yield) as an off-white solid. $^1$H NMR (400 MHz, CDCl$_3$) δ (ppm): 7.88 (d, 1H), 7.34 (dd, 1H), 7.26 (d, 2H), 7.20 (d, 1H), 6.86 (d, 2H), 6.41 (s, 1H), 5.29 (s, 2H), 2.30 (s, 3H).

To a room temperature solution of 1-(4-chlorobenzyl)-2-methyl-1H-indole-5-carbonitrile (360 mg, 1.28 mmol) in dichloromethane (25 mL) was added N,N-dimethylformamide (1 drop), followed by drop-wise addition (over 30 minutes) of a solution of oxalyl chloride (0.559 mL, 6.41 mmol) in dichloromethane (25 mL). The reaction mixture was stirred at room temperature for 2 hours, after which it was concentrated to dryness affording a brown solid. This solid was reconstituted in dichloromethane (25 mL), resulting in a dark brown solution to which triethylamine (0.894 mL, 6.41 mmol) and 2-methoxypyridin-4-amine (0.251 g, 2.02 mmol) were added. The reaction mixture was allowed to stir for 12 hours at room temperature, after which it was quenched by the addition of saturated sodium bicarbonate solution (200 mL), extracted with dichloromethane (3×100 mL), dried (magnesium sulfate), filtered, and concentrated to a solid. Purification was achieved by silica gel chromatography using 5 to 20% of a 7:1 mixture of acetonitrile:methanol in dichloromethane over 60 minutes to afford 2-(1-(4-chlorobenzyl)-5-cyano-2-methyl-1H-indol-3-yl)-N-(2-methoxypyridin-4-yl)-2-oxoacetamide (248 mg, 0.540 mmol, 42% yield) as a yellow solid. $^1$H NMR (400 MHz, CDCl$_3$) δ (ppm): 9.09 (br. s, 1H), 8.57 (d, 1H), 8.15 (d, 1H), 7.47 (dd, 1H), 7.31 (s, 2H), 7.29 (s, 1H), 7.23 (d, 1H), 7.17 (dd, 1H), 6.92 (d, 2H), 5.40 (s, 2H), 3.96 (s, 3H), 2.72 (s, 3H); LCMS: [ES]$^+$ found 459.14.

Example 4a

See General Route 4, Procedure H, M and K 2-(3-fluoro-4-methoxyphenyl)hydrazine

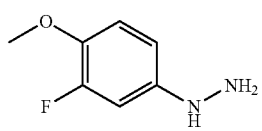

A room temperature solution of 3-fluoro-4-methoxyaniline (25.0 g, 177 mmol) in concentrated 12M aqueous hydrochloric acid solution (60 mL) was stirred for two hours, after which it was cooled to 0° C. to which a solution of sodium nitrite (14.2 g, 205 mmol), in water (50 mL), was added, drop-wise over 45 minutes, with internal temperature monitoring such that the reaction temperature does not warm above 5° C. After stirring for one hour at 0° C., the reaction mixture was poured slowly into a 0° C. pre-made solution of tin(II) chloride dihydrate (168 g, 744 mmol) in concentrated 12M aqueous hydrochloric acid solution (125 mL). The reaction mixture was allowed to warm up to room temperature, after which it was stored in the freezer overnight (12 hours), leading to the formation of a precipitate. This dark brown solid was successively washed with water (2×100 mL) and diethyl ether (3×100 mL), and dried to afford crude 2-(3-fluoro-4-methoxyphenyl)hydrazine hydrochloride as a pasty brown solid (note that this crude solid can also be used directly in the next step). As part of the purification and isolation process, the crude hydrazine hydrochloride salt was reconstituted in water (100 mL) and 3M aqueous sodium hydroxide solution (200 mL), extracted with diethyl ether (2×200 mL), washed with successively with saturated sodium bicarbonate solution (2×100 mL), water (2×20 mL) and saturated sodium chloride solution (2×20 mL), dried (sodium sulfate), filtered and concentrated to afford 2-(3-fluoro-4-methoxyphenyl)hydrazine as a light yellow solid (15.0 g, 96.1 mmol, 54% yield. $^1$H NMR (400 MHz, CDCl$_3$) δ (ppm): 6.87 (m, 1H), 6.66 (dd, 1H), 6.49-6.53 (m, 1H), 5.06 (br. s, 1H), 3.83 (s, 3H), 3.55 (br. s, 2H).

A portion of 2-(3-fluoro-4-methoxyphenyl)hydrazine (5.00 g, 32.0 mmol) was dissolved in absolute ethanol (50 mL), to which a solution hydrogen chloride (15 mL, 2.5M in ethanol) was added. The resulting precipitate was filtered, washed with ethyl acetate (2×40 mL), and dried to afford 2-(3-fluoro-4-methoxyphenyl)hydrazine hydrochloride as an off-white solid (4.7 g).

6-fluoro-5-methoxy-2-methyl-3-(phenylthio)-1H-indole

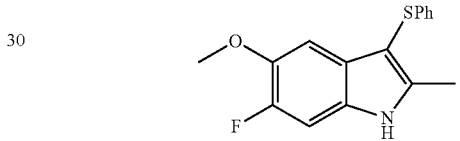

A slurry of (3-fluoro-4-methoxyphenyl)hydrazine hydrochloride (1.86 g, 9.65 mmol) and 1-(phenylthio)propan-2-one (1.13 g, 6.80 mmol) in isobutyl alcohol (25 mL) was heated to 90° C. The reaction mixture was then cooled to room temperature, diluted with ethyl acetate (200 mL), extracted with ethyl acetate (2×150 mL), washed with water (2×100 mL), brine (2×100 mL), dried (sodium sulfate), filtered and concentrated to an orange residue. Purification was achieved by silica gel chromatography (ISCO 80 g, 60 mL/min) using 5 to 50% ethyl acetate in hexanes over 40 minutes to afford 6-fluoro-5-methoxy-2-methyl-3-(phenylthio)-1H-indole (1.39 g, 4.84 mmol, 68% yield) as a yellow solid. $^1$H NMR (400 MHz, CDCl$_3$) δ (ppm): 8.17 (br. s, 1H), 7.15-7.19 (m, 2H), 7.11 (d, 1H), 7.00-7.08 (m, 4H), 3.86 (s, 3H), 2.48 (s, 3H).

6-fluoro-5-methoxy-2-methyl-1H-indole

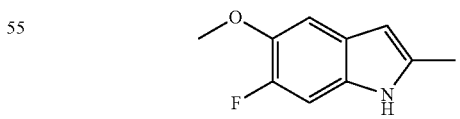

To a slurry of Raney nickel (7.40 g, 126 mmol, 50% solution in water) in absolute ethanol (40 mL) was added solid 6-fluoro-5-methoxy-2-methyl-3-(phenylthio)-1H-indole (1.39 g, 4.84 mmol). The reaction suspension was heated to 90° C. for five hours, after which it was cooled too room temperature, filtered through celite, washed with ethyl acetate (3×20 mL), and concentrated to a solid. Purification was achieved by silica gel chromatography (ISCO 40 g, 40 mL/min) using 5 to 70% ethyl acetate in hexanes over 30 minutes to afford 6-fluoro-5-methoxy-2-methyl-1H-indole (0.690 g, 3.85 mmol, 80% yield) as a white solid. $^1$H NMR (400 MHz, CDCl$_3$) δ (ppm): 7.76 (br. s, 1H), 7.00-7.06 (m, 2H), 6.13 (s, 1H), 3.88 (s, 3H), 2.41 (s, 3H).

Example 4b

See General Route 4, Procedure J 1-(4-chlorobenzyl)-2-methyl-5-(trifluoromethyl)-1H-indole

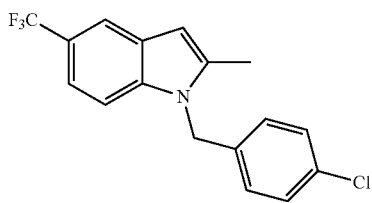 [SMILES: Cc1cc2cc(C(F)(F)F)ccc2n1Cc1ccc(Cl)cc1]

To a solution of 1-(4-chlorobenzyl)-2-methyl-3-(phenylthio)-5-(trifluoromethyl)-1H-indole (0.212 g, 0.491 mmol) in trifluoroacetic acid (3.3 mL) was added 2-mercaptobenzoic acid (0.151 g, 0.982 mmol). The reaction mixture was stirred at room temperature for two hours, after which the trifluoroacetic acid was removed in vacuo. The remaining residue was reconstituted in ethyl acetate (50 mL), washed successively with aqueous 1M sodium hydroxide solution (3×30 mL) and water (1×50 mL), dried (sodium sulfate), filtered and concentrated to a residue. Purification was achieved using silica gel chromatography (ISCO 40 g) using 0 to 30% ethyl acetate in hexanes over 45 minutes to afford 1-(4-chlorobenzyl)-2-methyl-5-(trifluoromethyl)-1H-indole (0.0370 g, 0.114 mmol, 23% yield) as a tan solid. $^1$H NMR (400 MHz, CDCl$_3$) δ (ppm): 7.85 (s, 1H), 7.49-7.51 (m, 1H), 7.21-7.35 (m, 3H), 6.87 (d, 2H), 6.42 (s, 1H), 5.30 (s, 2H), 2.38 (d, 3H).

The following compounds were prepared according to general route 1:

2-(5-methoxy-1-((5-methoxypyridin-2-yl)methyl)-2-methyl-1H-indol-3-yl)-N-(2-methoxypyridin-4-yl)-2-oxoacetamide (43)

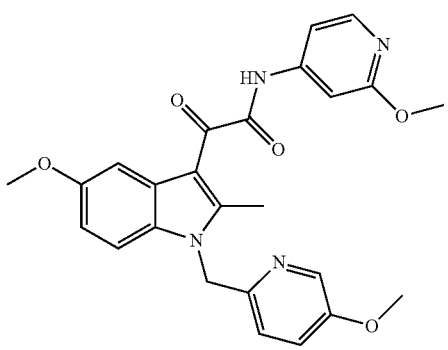

2-(5-methoxy-1-((5-methoxypyridin-2-yl)methyl)-2-methyl-1H-indol-3-yl)-N-(2-methoxypyridin-4-yl)-2-oxoacetamide was synthesized as a yellow-gold solid using general route 1. $^1$H NMR (400 MHz, CDCl$_3$) δ (ppm): 10.43 (s, 1H), 8.34 (s, 1H), 8.22 (d, 1H), 7.73 (s, 1H), 7.44 (d, 2H), 7.36 (dd, 1H), 7.14 (d, 1H), 6.79-6.86 (m, 2H), 5.59 (s, 2H), 4.06 (s, 3H), 3.89 (s, 3H), 3.81 (s, 3H), 2.62 (s, 3H).

2-(1-((5-chloro-3-fluoropyridin-2-yl)methyl)-2,5-dimethyl-1H-indol-3-yl)-N-(2-methoxypyridin-4-yl)-2-oxoacetamide (33)

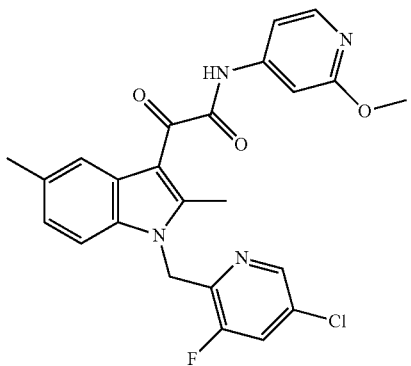

2-(1-((5-chloro-3-fluoropyridin-2-yl)methyl)-2,5-dimethyl-1H-indol-3-yl)-N-(2-methoxypyridin-4-yl)-2-oxoacetamide was synthesized as a solid in using general route 1. $^1$H NMR (400 MHz, CDCl$_3$) δ (ppm): 9.01 (s, 1H), 8.29-8.30 (m 1H), 8.14 (d, 1H), 7.93 (d, 1H), 7.48 (dd, 1H), 7.25-7.27 (m, 2H), 7.16 (dd, 1H), 7.05 (d, 1H), 5.47 (d, 2H), 3.97 (s, 3H), 2.84 (s, 2H), 2.44 (s, 3H).

2-(6-fluoro-5-methoxy-1-((5-methoxypyridin-2-yl)methyl)-2-methyl-1H-indol-3-yl)-N-(2-methoxypyridin-4-yl)-2-oxoacetamide (32)

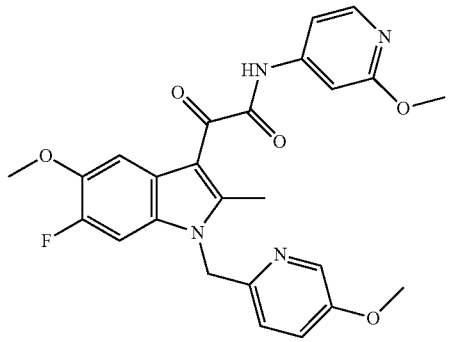

2-(6-fluoro-5-methoxy-1-((5-methoxypyridin-2-yl)methyl)-2-methyl-1H-indol-3-yl)-N-(2-methoxypyridin-4-yl)-2-oxoacetamide was synthesized as a yellow solid using general route 1. $^1$H NMR (400 MHz, CDCl$_3$) δ (ppm): 9.09 (s, 1H), 8.27 (s, 1H), 8.14 (s, 1H), 7.87 (s, 1H), 7.06-7.28 (m, 4H), 6.73 (s, 1H), 5.33 (s, 2H), 3.84 (d, 6H), 3.82 (s, 3H).

101

2-(1-((3,5-dichloropyridin-2-yl)methyl)-6-fluoro-5-methoxy-2-methyl-1H-indol-3-yl)-N-(2-methoxypyridin-4-yl)-2-oxoacetamide (13)

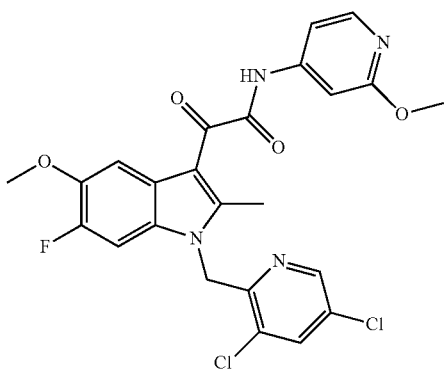

To a 0° C. solution of 6-fluoro-5-methoxy-2-methyl-1H-indole (132 mg, 0.737 mmol) in dichloromethane (10 mL) was added neat oxalyl dichloride (0.129 ml, 1.47 mmol). The reaction was stirred at 0° C. for 20 minutes, after which LCMS analysis indicated completion of the reaction (analysis via methanolysis product). The reaction mixture was concentrated to dryness, then reconstituted in dichloromethane (10 mL), to which methanol (1.0 mL, 25 mmol) was added. The reaction was extracted with dichloromethane (1×30 mL), then with ethyl acetate (2×50 mL), dried (sodium sulfate), filtered and concentrated to afford methyl 2-(6-fluoro-5-methoxy-2-methyl-1H-indol-3-yl)-2-oxoacetate (172 mg, 0.648 mmol, 88% yield) as a pinkish-tan solid. $^1$H NMR (400 MHz, CDCl$_3$) δ (ppm): 8.49 (br. s, 1H), 7.59 (d, 1H), 7.22 (d, 1H), 6.88 (dd, 1H), 3.98 (s, 3H), 3.87 (s, 3H), 2.45 (s, 3H).

This compound was synthesized as a tan solid in 99% yield starting from methyl 2-(6-fluoro-5-methoxy-2-methyl-1H-indol-3-yl)-2-oxoacetate, 3,5-dichloro-2-(chloromethyl)pyridine, and N,N-dimethylformamide as the solvent using general procedure B. The product was used in the subsequent step without any purification.

2-(1-((3,5-dichloropyridin-2-yl)methyl)-6-fluoro-5-methoxy-2-methyl-1H-indol-3-yl)-2-oxoacetic acid was synthesized as a pink solid in 89% yield starting methyl 2-(1-((3,5-dichloropyridin-2-yl)methyl)-6-fluoro-5-methoxy-2-methyl-1H-indol-3-yl)-2-oxoacetate using general procedure C. The material was used in the subsequent step without any purification.

2-(1-((3,5-dichloropyridin-2-yl)methyl)-6-fluoro-5-methoxy-2-methyl-1H-indol-3-yl)-N-(2-methoxypyridin-4-yl)-2-oxoacetamide was synthesized as a light yellow solid in 53% yield starting from 2-(1-((3,5-dichloropyridin-2-yl)methyl)-6-fluoro-5-methoxy-2-methyl-1H-indol-3-yl)-2-oxoacetic acid using general procedure D. Purification was achieved by silica gel chromatography (Luknova 40 g, 20 mL/min) using 3 to 9% of a 7:1 acetonitrile/methanol solution in dichloromethane over 60 minutes. $^1$H NMR (400 MHz, CDCl$_3$) δ (ppm): 9.04 (br. s, 1H), 8.29 (d, 1H), 8.14 (d, 1H), 7.89 (d, 1H), 7.78 (d, 1H), 7.25 (d, 1H), 7.15 (dd, 1H), 6.95 (d, 1H), 5.46 (s, 2H), 3.96 (s, 3H), 3.95 (s, 3H), 2.73 (s, 3H).

102

2-(1-(2,4-difluorobenzyl)-6-fluoro-5-methoxy-2-methyl-1H-indol-3-yl)-N-(2-methoxypyridin-4-yl)-2-oxoacetamide (14)

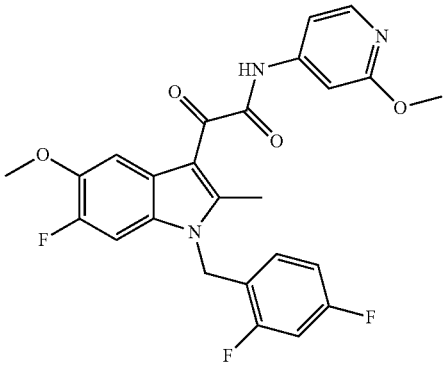

This compound was synthesized as a yellow solid in 26% yield starting from methyl 2-(6-fluoro-5-methoxy-2-methyl-1H-indol-3-yl)-2-oxoacetate using general route 1. $^1$H NMR (400 MHz, CDCl$_3$) δ (ppm): 8.99 (br. s, 1H), 8.07 (d, 1H), 7.81 (d, 1H), 7.18 (d, 1H), 7.08 (dd, 1H), 6.91 (d, 1H), 6.81-6.87 (m, 1H), 6.67-6.72 (m, 1H), 6.48-6.54 (m, 1H), 5.24 (s, 2H), 3.89 (s, 6H, two shifts isochronous), 2.63 (s, 3H).

2-(1-((5-chloro-3-fluoropyridin-2-yl)methyl)-5-methoxy-2-methyl-1H-indol-3-yl)-N-(2-methoxypyridin-4-yl)-2-oxoacetamide (87)

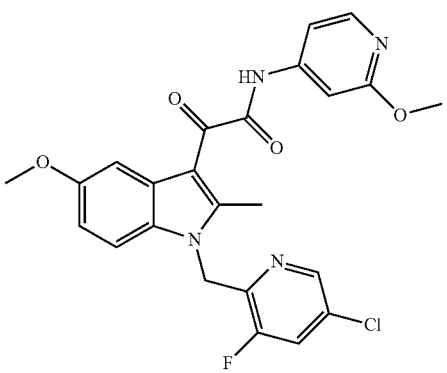

2-(1-((5-chloro-3-fluoropyridin-2-yl)methyl)-5-methoxy-2-methyl-1H-indol-3-yl)-N-(2-methoxypyridin-4-yl)-2-oxoacetamide was synthesized as a solid starting from 5-chloro-2-chloromethyl-3-fluoro-pyridine hydrochloride using general route 1. $^1$H NMR (400 MHz, CDCl$_3$) δ (ppm): 8.99 (s, 1H), 8.31 (s, 1H), 8.14 (d, 1H), 7.72 (s, 1H), 7.50 (d, 1H), 7.28 (m, 2H), 7.16 (d, 1H), 6.87 (d, 1H), 5.46 (s, 2H), 3.95 (s, 3H), 3.85 (s, 3H), 2.84 (s, 3H).

2-(1-(4-chloro-2-fluorobenzyl)-6-fluoro-5-methoxy-2-methyl-1H-indol-3-yl)-N-(2-methoxypyridin-4-yl)-2-oxoacetamide (91)

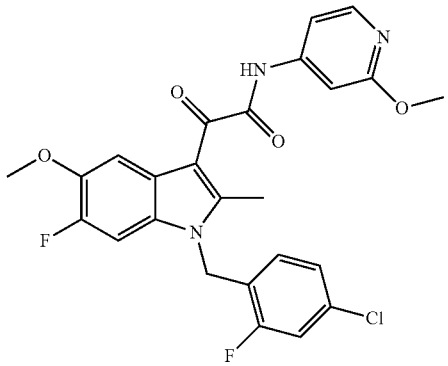

2-(1-(4-chloro-2-fluorobenzyl)-6-fluoro-5-methoxy-2-methyl-1H-indol-3-yl)-N-(2-methoxypyridin-4-yl)-2-oxoacetamide was synthesized as a yellow solid using general route 1. Purification was achieved by silica gel chromatography (Luknova 40 g, 20 mL/min) using 10 to 50% ethyl acetate in hexanes over 60 minutes. $^1$H NMR (400 MHz, CDCl$_3$) δ (ppm): $^1$H NMR (400 MHz, CDCl$_3$) δ (ppm): 9.05 (br. s, 1H), 8.16 (d, 1H), 7.90 (d, 1H), 7.25-7.27 (m, 1H), 7.20 (dd, 1H), 7.16 (dd, 1H), 7.02 (dd, 1H), 6.98 (d, 1H), 6.52 (dd, 1H), 5.33 (s, 2H), 3.97 (s, 6H, two shifts isochronous), 2.70 (s, 3H).

2-(1-(2,4-dichlorobenzyl)-6-fluoro-5-methoxy-2-methyl-1H-indol-3-yl)-N-(2-methoxypyridin-4-yl)-2-oxoacetamide (92)

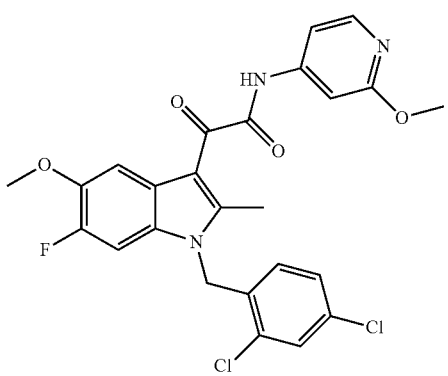

2-(1-(2,4-dichlorobenzyl)-6-fluoro-5-methoxy-2-methyl-1H-indol-3-yl)-N-(2-methoxypyridin-4-yl)-2-oxoacetamide was synthesized as a yellow solid using general route 1. Purification was achieved by silica gel chromatography (Luknova 40 g, 20 mL/min) using 10 to 50% ethyl acetate in hexanes over 60 minutes. $^1$H NMR (400 MHz, CDCl$_3$) δ (ppm): 9.06 (br. s, 1H), 8.15 (d, 1H), 7.90 (d, 1H), 7.49 (d, 1H), 7.26 (m, 1H), 7.15 (dd, 1H), 7.09 (dd, 1H), 6.90 (d, 1H), 6.28 (d, 1H), 5.33 (s, 2H), 3.97 (s, 6H, two shifts isochronous), 2.65 (s, 3H).

2-(1-((5-chloro-3-methoxypyridin-2-yl)methyl)-5-methoxy-2-methyl-1H-indol-3-yl)-N-(2-methoxypyridin-4-yl)-2-oxoacetamide (100)

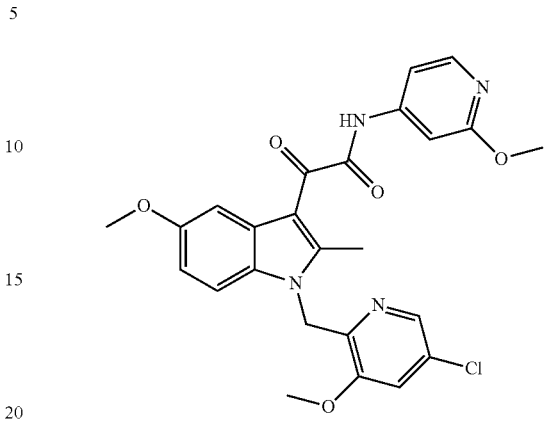

2-(1-((5-chloro-3-methoxypyridin-2-yl)methyl)-5-methoxy-2-methyl-1H-indol-3-yl)-N-(2-methoxypyridin-4-yl)-2-oxoacetamide was synthesized as a light yellow solid using general route 1. Purification was achieved by silica gel chromatography (Luknova 40 g, 20 mL/min) using 5 to 50% ethyl acetate in hexanes over 60 minutes. $^1$H NMR (400 MHz, CDCl$_3$) δ (ppm): 8.97 (br. s, 1H), 8.12 (d, 1H), 8.02 (m, 1H), 7.72 (d, 1H), 7.24-7.26 (m, 2H), 7.17 (m, 1H), 7.13 (d, 1H), 6.80 (dd, 1H), 5.39 (s, 2H), 3.94 (s, 3H), 3.88 (s, 3H), 3.83 (s, 3H), 2.77 (s, 3H).

2-(6-chloro-1-(4-chlorobenzyl)-2,5-dimethyl-1H-indol-3-yl)-N-(2-methoxypyridin-4-yl)-2-oxoacetamide (93)

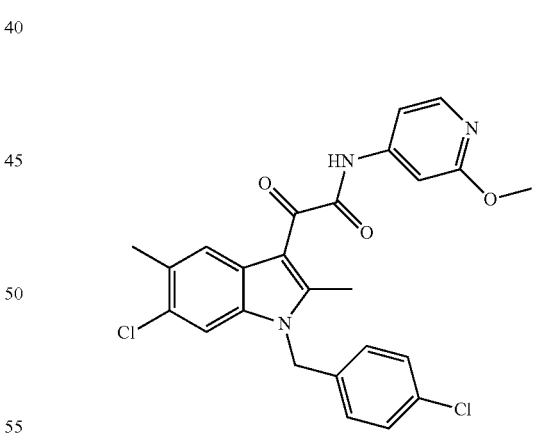

2-(6-chloro-1-(4-chlorobenzyl)-2,5-dimethyl-1H-indol-3-yl)-N-(2-methoxypyridin-4-yl)-2-oxoacetamide was synthesized as a yellow solid using general route 1. Purification was achieved by silica gel chromatography using 0 to 70% ethyl acetate in hexanes over 30 minutes. $^1$H NMR (400 MHz, CDCl$_3$) δ (ppm): 9.02 (s, 1H), 8.15 (d, 1H), 8.07 (s, 1H), 7.24-7.31 (m, 4H), 7.15-7.16 (m, 1H), 6.94 (d, 2H), 5.31 (s, 2H), 3.96 (d, 3H), 2.67 (d, 3H), 2.48 (s, 3H).

2-(6-chloro-1-((5-chloropyridin-2-yl)methyl)-2,5-dimethyl-1H-indol-3-yl)-N-(2-methoxypyridin-4-yl)-2-oxoacetamide (94)

2-(5-methoxy-1-((5-methoxypyridin-2-yl)methyl)-2,6-dimethyl-1H-indol-3-yl)-N-(2-methoxypyridin-4-yl)-2-oxoacetamide (96)

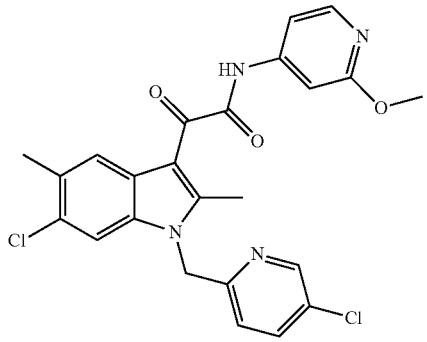

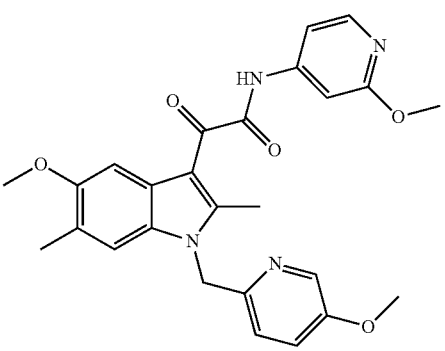

2-(6-chloro-1-((5-chloropyridin-2-yl)methyl)-2,5-dimethyl-1H-indol-3-yl)-N-(2-methoxypyridin-4-yl)-2-oxoacetamide was synthesized as a yellow solid using general route 1. Purification was achieved by silica gel chromatography using 0 to 70% ethyl acetate in hexanes over 30 minutes. $^1$H NMR (400 MHz, CDCl$_3$) δ (ppm): 9.02 (s, 1H), 8.55 (d, 1H), 8.15 (d, 1H), 8.06 (s, 1H), 7.57 (dd, 1H), 7.26 (m, 2H), 7.15 (dd, 1H), 6.72 (d, 1H), 5.41 (s, 2H), 3.97 (s, 3H), 2.72 (s, 3H), 2.47 (s, 3H).

2-(5-methoxy-1-((5-methoxypyridin-2-yl)methyl)-2,6-dimethyl-1H-indol-3-yl)-N-(2-methoxypyridin-4-yl)-2-oxoacetamide was synthesized as a yellow solid using general route 1. Purification was achieved by two successive silica gel chromatography runs, first using 10 to 70% ethyl acetate in hexanes over 35 minutes followed by 10 to 50% of a 7:1 acetonitrile:methanol solution in dichloromethane over 30 minutes. $^1$H NMR (400 MHz, (CDCl$_3$) δ (ppm): 9.20 (br. s, 1H), 8.25 (s, 1H), 8.10 (d, 1H), 7.64 (s, 1H), 7.25 (s, 1H), 7.15 (d, 1H), 7.01 (d, 1H), 6.99 (s, 1H), 6.60 (d, 1H), 5.29 (s, 2H), 3.93 (s, 3H), 3.82 (s, 3H), 3.79 (s, 3H), 2.60 (s, 3H), 2.25 (s, 3H).

2-(1-((5-chloropyridin-2-yl)methyl)-5-methoxy-2,6-dimethyl-1H-indol-3-yl)-N-(2-methoxypyridin-4-yl)-2-oxoacetamide (95)

2-(1-((3,5-difluoropyridin-2-yl)methyl)-2,5-dimethyl-1H-indol-3-yl)-N-(2-methoxypyridin-4-yl)-2-oxoacetamide (88)

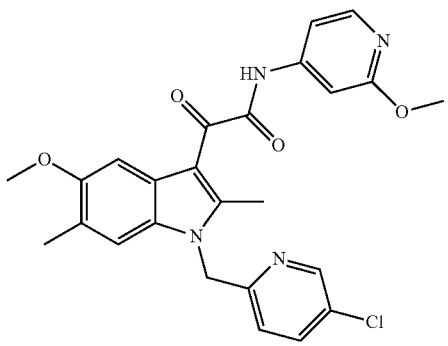

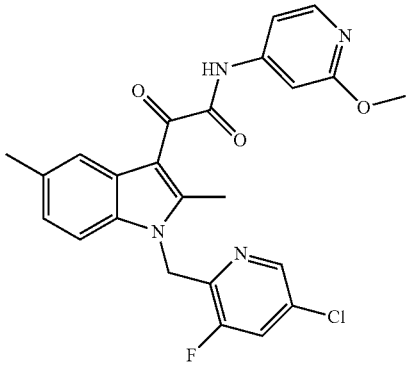

2-(1-((5-chloropyridin-2-yl)methyl)-5-methoxy-2,6-dimethyl-1H-indol-3-yl)-N-(2-methoxypyridin-4-yl)-2-oxoacetamide was synthesized as a yellow solid using general route 1. Purification was achieved by silica gel chromatography using 10 to 70% ethyl acetate in hexanes over 35 minutes. $^1$H NMR (400 MHz, CDCl$_3$) δ (ppm): 9.13 (br. s, 1H), 8.53 (s, 1H), 8.10 (d, 1H), 7.67 (s, 1H), 7.51 (d, 1H), 7.24 (s, 1H), 7.14 (d, 1H), 6.95 (s, 1H), 6.60 (d, 1H), 5.35 (s, 2H), 3.94 (s, 3H), 3.85 (s, 3H), 2.63 (s, 3H), 2.25 (s, 3H). LCMS: [M+H]$^+$. found 479.0.

2-(1-((3,5-difluoropyridin-2-yl)methyl)-2,5-dimethyl-1H-indol-3-yl)-N-(2-methoxypyridin-4-yl)-2-oxoacetamide was synthesized as a pale brown solid using general route 1. Purification was achieved by silica gel chromatography using 5 to 50% ethyl acetate in hexanes over 50 minutes. $^1$H NMR (400 MHz, CDCl$_3$) δ (ppm): 8.99 (br. s, 1H), 8.22 (s, 1H), 8.12 (d, 1H), 7.91 (s, 1H), 7.25 (m, 2H), 7.19 (dd, 1H), 7.14 (d, 1H), 7.02 (d, 1H), 5.44 (s, 2H), 3.94 (s, 3H), 2.82 (s, 3H), 2.42 (s, 3H).

2-(6-chloro-1-((5-chloro-3-fluoropyridin-2-yl)methyl)-5-methoxy-2-methyl-1H-indol-3-yl)-N-(2-methoxypyridin-4-yl)-2-oxoacetamide (97)

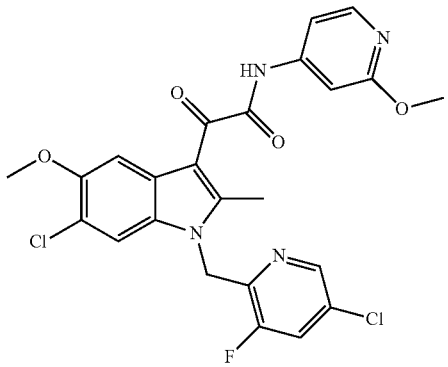

2-(6-chloro-1-((5-chloro-3-fluoropyridin-2-yl)methyl)-5-methoxy-2-methyl-1H-indol-3-yl)-N-(2-methoxypyridin-4-yl)-2-oxoacetamide was synthesized as a light yellow solid using general route 1. Purification was achieved by silica gel chromatography using 20 to 100% ethyl acetate in hexanes over 40 minutes. $^1$H NMR (400 MHz, CDCl$_3$) δ (ppm): 9.04 (br. s, 1H), 8.32 (d, 1H), 8.16 (d, 1H), 7.83 (s, 1H), 7.51 (d, 1H), 7.42 (s, 1H), 7.25 (d, 1H), 7.14 (d, 1H), 5.43 (s, 2H), 3.97 (s, 3H), 3.96 (s, 3H), 2.83 (s, 3H). LCMS, 1.85 min, [ES]$^+$ found 517.84.

2-(6-chloro-5-methoxy-1-((5-methoxypyridin-2-yl)methyl)-2-methyl-1H-indol-3-yl)-N-(2-methoxypyridin-4-yl)-2-oxoacetamide (98)

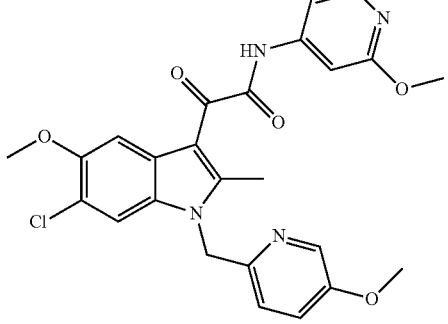

2-(6-chloro-5-methoxy-1-((5-methoxypyridin-2-yl)methyl)-2-methyl-1H-indol-3-yl)-N-(2-methoxypyridin-4-yl)-2-oxoacetamide was synthesized as a light yellow solid using general route 1. Purification was achieved by silica gel chromatography using 20 to 100% ethyl acetate in hexanes over 60 minutes. $^1$H NMR (400 MHz, CDCl$_3$) δ (ppm): 9.04 (br. s, 1H), 8.26 (d, 1H), 8.13 (d, 1H), 7.84 (s, 1H), 7.31 (s, 1H), 7.23 (d, 1H), 7.12 (d, 1H), 7.07 (d, 1H), 6.71 (d, 1H), 5.33 (s, 2H), 3.94 (s, 6H, two shifts isochronous), 3.81 (s, 3H), 2.71 (s, 3H). LCMS: [ES]$^+$ found 494.93.

2-(1-(4-chlorobenzyl)-6-fluoro-2,5-dimethyl-1H-indol-3-yl)-N-(2-methoxypyridin-4-yl)-2-oxoacetamide (89)

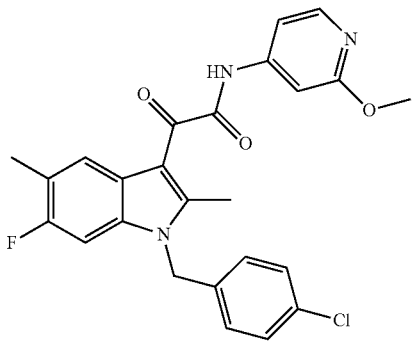

2-(1-(4-chlorobenzyl)-6-fluoro-2,5-dimethyl-1H-indol-3-yl)-N-(2-methoxypyridin-4-yl)-2-oxoacetamide was synthesized as a yellow solid using general route 1. Purification was achieved by silica gel chromatography using 5 to 80% ethyl acetate in hexanes over 35 minutes. $^1$H NMR (400 MHz, CDCl$_3$) δ (ppm): 9.03 (s, 1H), 8.15 (d, 1H), 8.01 (d, 1H), 7.30 (m, 3H), 7.15 (d, 1H), 6.95 (m, 2H), 6.88 (d, 1H), 5.28 (s, 2H), 3.96 (s, 3H), 2.67 (s, 3H), 2.38 (s, 3H).

2-(1-((5-chloropyridin-2-yl)methyl)-6-fluoro-2,5-dimethyl-1H-indol-3-yl)-N-(2-methoxypyridin-4-yl)-2-oxoacetamide (90)

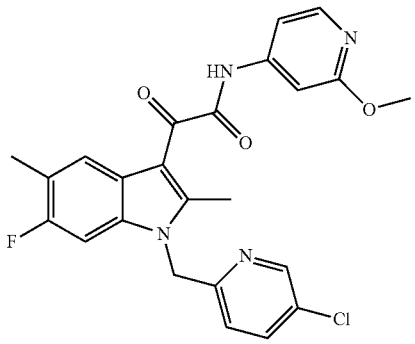

2-(1-((5-chloropyridin-2-yl)methyl)-6-fluoro-2,5-dimethyl-1H-indol-3-yl)-N-(2-methoxypyridin-4-yl)-2-oxoacetamide was synthesized as a yellow solid using general route 1. Purification was achieved by silica gel chromatography using 5 to 80% ethyl acetate in hexanes over 35 minutes. $^1$H NMR (400 MHz, CDCl$_3$) δ (ppm): 9.11 (s, 1H), 8.53 (s, 1H), 8.13 (d, 1H), 7.96 (d, 1H), 7.56 (d, 1H), 7.26 (m, 1H, isochronous with CDCl$_3$), 7.15 (d, 1H), 6.89 (d, 1H), 6.70 (d, 1H), 5.34 (s, 2H), 3.95 (s, 3H), 2.67 (s, 3H), 2.34 (s, 3H).

The following compounds were prepared according to general route 2:

2-(1-((3,5-dichloropyridin-2-yl)methyl)-5-methoxy-2-methyl-1H-pyrrolo[2,3-b]pyridin-3-yl)-N-(2-methoxypyridin-4-yl)-2-oxoacetamide (29)

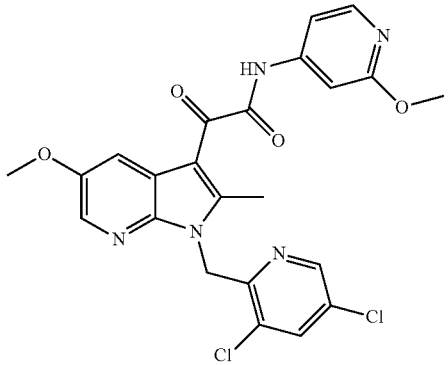

This compound was synthesized as a solid in 28% yield starting from 2-(1-((3,5-dichloropyridin-2-yl)methyl)-5-methoxy-2-methyl-1H-pyrrolo[2,3-b]pyridin-3-yl)-2-oxoacetic acid and N,N-dimethylformamide as solvent using general procedure D. $^1$H NMR (400 MHz, CDCl$_3$) δ (ppm): 9.22 (s, 1H), 8.20-8.22 (m, 2H), 8.16 (d, 1H), 8.02 (d, 1H), 7.76 (d, 1H), 7.33 (s, 1H), 7.17 (d, 1H), 5.76 (s, 2H), 4.00 (s, 3H), 3.92 (s, 3H), 2.69 (s, 3H).

2-(1-(4-chlorobenzyl)-2-methyl-1H-pyrrolo[3,2-c]pyridin-3-yl)-N-(2-methoxypyridin-4-yl)-2-oxoacetamide (37)

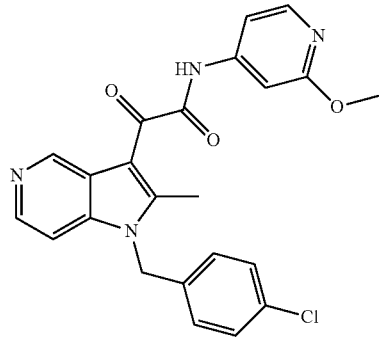 [SMILES: COc1cc(NC(=O)C(=O)c2c(C)n(Cc3ccc(Cl)cc3)c3ccncc23)ccn1]

2-(1-(4-chlorobenzyl)-2-methyl-1H-pyrrolo[3,2-c]pyridin-3-yl)-N-(2-methoxypyridin-4-yl)-2-oxoacetamide was prepared according to general route 2 as a yellow solid. $^1$H NMR (400 MHz, CD$_3$OD) δ (ppm): 9.28 (s, 1H), 8.34 (d, 1H), 8.07 (d, 1H), 7.67 (d, 1H), 7.35 (m, 3H), 7.27 (m, 1H), 7.06 (m, 2H), 5.62 (s, 2H), 3.92 (s, 3H), 2.73 (s, 3H).

2-(1-((5-chloro-3-fluoropyridin-2-yl)methyl)-5-methoxy-2-methyl-1H-pyrrolo[2,3-b]pyridin-3-yl)-N-(2-methoxypyridin-4-yl)-2-oxoacetamide (34)

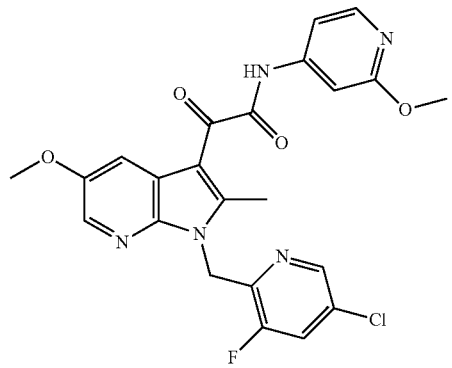

This compound was synthesized as a solid in a 44% yield starting from 2-(1-((5-chloro-3-fluoropyridin-2-yl)methyl)-5-methoxy-2-methyl-1H-pyrrolo[2,3-b]pyridin-3-yl)-2-oxoacetic acid using general procedure D. $^1$H NMR (400 MHz, CDCl$_3$) δ (ppm): 9.15 (s, 1H), 8.21 (d, 1H), 8.14-8.17 (m, 2H), 8.04 (d, 1H), 7.47-7.49 (m, 1H), 7.28 (d, 1H), 7.14-7.16 (m, 1H), 5.73 (d, 2H), 3.97 (s, 3H), 3.91 (s, 3H), 2.77 (s, 3H).

2-(1-(4-chlorobenzyl)-2-methyl-1H-pyrrolo[2,3-c]pyridin-3-yl)-N-(2-methoxypyridin-4-yl)-2-oxoacetamide (35)

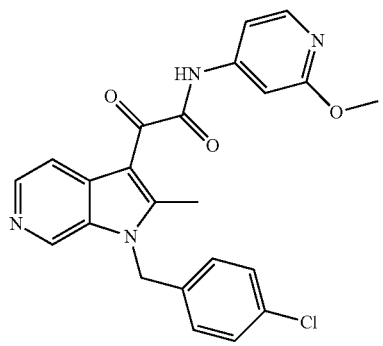 [SMILES: COc1cc(NC(=O)C(=O)c2c(C)n(Cc3ccc(Cl)cc3)c3cnccc23)ccn1]

2-(1-(4-chlorobenzyl)-2-methyl-1H-pyrrolo[2,3-c]pyridin-3-yl)-N-(2-methoxypyridin-4-yl)-2-oxoacetamide was synthesized as a yellow solid using general route 2. $^1$H NMR (400 MHz, CD$_3$OD) δ (ppm): 8.84 (s, 1H), 8.29 (d, 1H), 8.08 (d, 1H), 8.04 (d, 1H), 7.34 (m, 3H), 7.26 (m, 1H), 7.08 (m, 2H), 5.69 (s, 2H), 3.92 (s, 3H), 2.78 (s, 3H).

111

2-(5-methoxy-1-((5-methoxypyridin-2-yl)methyl)-2-methyl-1H-pyrrolo[2,3-b]pyridin-3-yl)-N-(2-methoxypyridin-4-yl)-2-oxoacetamide (40)

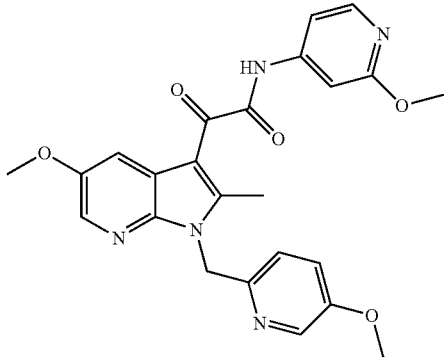

2-(5-methoxy-1-((5-methoxypyridin-2-yl)methyl)-2-methyl-1H-pyrrolo[2,3-b]pyridin-3-yl)-N-(2-methoxypyridin-4-yl)-2-oxoacetamide was synthesized as a yellow solid using general route 2. $^1$H NMR (400 MHz, CDCl$_3$) δ (ppm): 9.12 (br. s, 1H), 8.22 (d, 1H), 8.09-8.16 (m, 3H), 7.10-7.15 (m, 3H), 7.24 (m, 1H), 5.63 (s, 2H), 3.96 (s, 3H), 3.93 (s, 3H), 3.81 (s, 3H), 2.80 (s, 3H).

2-(1-((5-chloropyridin-2-yl)methyl)-5-methoxy-2-methyl-1H-pyrrolo[2,3-b]pyridin-3-yl)-N-(2-methoxypyridin-4-yl)-2-oxoacetamide (41)

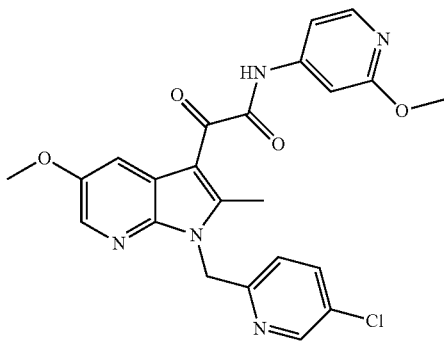

This compound was synthesized as a yellow solid in 52% yield starting from 2-(1-((5-chloropyridin-2-yl)methyl)-5-methoxy-2-methyl-1H-pyrrolo[2,3-b]pyridin-3-yl)-2-oxoacetic acid and N,N-dimethylformamide as the solvent using general procedure D. $^1$H NMR (400 MHz, CDCl$_3$) δ (ppm): 9.21 (br. s, 1H), 8.47 (m, 1H), 8.05-8.12 (m, 3H), 7.54 (dd, 1H), 7.24 (m, 1H), 7.13 (m, 1H), 7.01 (d, 1H), 5.61 (s, 2H), 3.94 (s, 3H), 3.89 (s, 3H), 2.74 (s, 3H).

112

2-(1-(2,4-dichlorobenzyl)-5-methoxy-2-methyl-1H-pyrrolo[2,3-b]pyridin-3-yl)-N-(2-methoxypyridin-4-yl)-2-oxoacetamide (42)

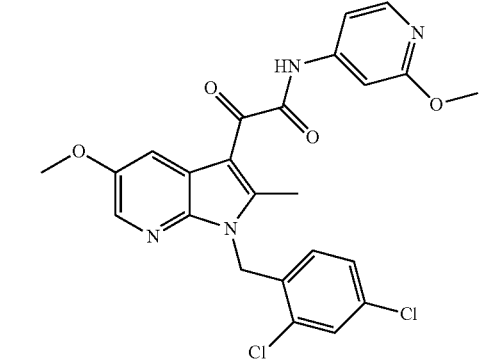

2-(1-(2,4-dichlorobenzyl)-5-methoxy-2-methyl-1H-pyrrolo[2,3-b]pyridin-3-yl)-N-(2-methoxypyridin-4-yl)-2-oxoacetamide was synthesized as a solid using general route 2. $^1$H NMR (400 MHz, CDCl$_3$) δ (ppm): 9.14 (br. s, 1H), 8.15-8.19 (m, 2H), 8.08 (d, 1H), 7.46 (d, 1H), 7.27 (d, 1H), 7.14-7.16 (m, 1H), 7.05-7.07 (m, 1H), 6.37-6.39 (m, 1H), 5.63 (s, 2H), 3.97 (s, 3H), 3.94 (s, 3H), 2.67 (s, 3H).

(1-((5-chloropyridin-2-yl)methyl)-2,5-dimethyl-1H-pyrrolo[2,3-b]pyridin-3-yl)-N-(2-methoxypyridin-4-yl)-2-oxoacetamide (75)

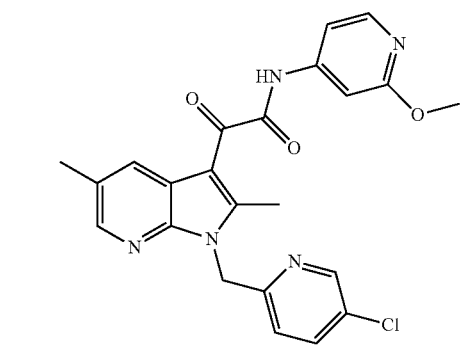

This compound was synthesized as a yellow solid in 71% yield starting from 2-(1-((5-chloropyridin-2-yl)methyl)-2,5-dimethyl-1H-pyrrolo[2,3-b]pyridin-3-yl)-2-oxoacetic acid and N,N-dimethylformamide as the solvent using general procedure D. $^1$H NMR (400 MHz, CDCl$_3$) δ (ppm): 9.15 (br. s, 1H), 8.48 (s, 1H), 8.31 (s, 1H), 8.15 (s, 1H), 8.13 (d, 1H), 7.54 (d, 1H), 7.26 (s, 1H), 7.14 (d, 1H), 7.01 (d, 1H), 5.65 (s, 2H), 3.95 (s, 3H), 2.76 (s, 3H), 2.45 (s, 3H). LCMS: [ES]$^+$ found 450.0.

2-(1-(4-chlorobenzyl)-2,5-dimethyl-1H-pyrrolo[2,3-b]pyridin-3-yl)-N-(2-methoxypyridin-4-yl)-2-oxoacetamide (76)

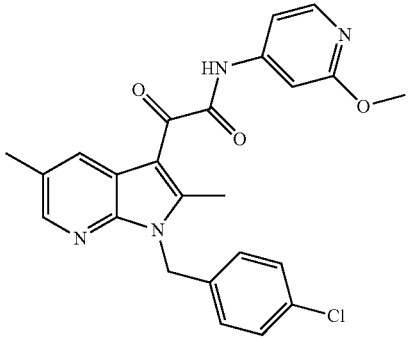

This compound was synthesized as a yellow solid in 71% yield starting from 2-(1-(4-chlorobenzyl)-2,5-dimethyl-1H-pyrrolo[2,3-b]pyridin-3-yl)-2-oxoacetic acid and N,N-dimethylformamide as the solvent using general procedure D. $^1$H NMR (400 MHz, CDCl$_3$) δ (ppm): 9.08 (br. s, 1H), 8.35 (d, 1H), 8.18 (d, 1H), 8.15 (d, 1H), 7.26 (d, 1H), 7.25 (d, 2H), 7.15 (dd, 1H), 7.06 (d, 2H), 5.57 (s, 2H), 3.97 (s, 3H), 2.71 (s, 3H), 2.49 (s, 3H). LCMS: [M+H]$^+$ found 449.0.

The Following Compounds or the Precursors to them were Prepared According to General Route 3

2-(5-methoxy-2-methyl-1-(pyridin-4-ylmethyl)-1H-indol-3-yl)-N-(2-methoxypyridin-4-yl)-2-oxoacetamide (16)

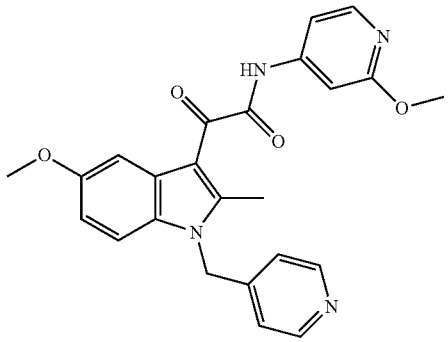

To a solution of 5-methoxy-2-methyl-1H-indole (500 mg, 3.10 mmol) in N,N-dimethylformamide (200 mL) was carefully added a 60% dispersion in mineral oil of sodium hydride (248 mg, 6.20 mmol), followed by 4-(bromomethyl)pyridine hydrobromide (785 mg, 3.10 mmol). The reaction mixture was stirred at 80° C. for 48 hours after which it was quenched by the addition of saturated sodium bicarbonate solution (50 mL) extracted with dichloromethane (3×20 mL), dried (magnesium sulfate), filtered, and concentrated to a residue. Purification was achieved by silica gel chromatography using 5 to 20% of a 7:1 acetonitrile:methanol solution in dichloromethane over 60 minutes to afford 5-methoxy-2-methyl-1-(pyridin-4-ylmethyl)-1H-indole (0.324 g, 1.28 mmol, 41% yield) as a yellow solid. $^1$H NMR (400 MHz, CDCl$_3$) δ (ppm): 8.49 (dd, 2H), 7.05 (d, 1H), 6.99 (d, 1H), 6.83 (m, 2H), 6.76 (dd, 1H), 6.29 (s, 1H), 5.26 (s, 2H), 3.84 (s, 3H). LCMS: [ES]$^+$ found 253.13.

2-(5-methoxy-2-methyl-1-(pyridin-4-ylmethyl)-1H-indol-3-yl)-N-(2-methoxypyridin-4-yl)-2-oxoacetamide was synthesized as a yellow solid in 7% yield starting from 5-methoxy-2-methyl-1-(pyridin-4-ylmethyl)-1H-indole using general procedure G. $^1$H NMR MHz, CDCl$_3$) δ (ppm): 9.03 (br. s, 1H), 8.55 (dd, 2H), 8.14 (d, 1H), 7.80 (d, 1H), 7.26 (d, 1H), 7.15 (dd, 1H), 7.07 (d, 1H), 6.92 (d, 2H), 6.88 (dd, 1H), 5.37 (s, 2H), 3.96 (s, 3H), 3.89 (s, 3H), 2.68 (s, 3H); LCMS: [ES]$^+$ found 431.20.

2-(1-(4-chlorobenzyl)-2-methyl-5-nitro-1H-indol-3-yl)-N-(2-methoxypyridin-4-yl)-2-oxoacetamide (19)

To a solution of 2-methyl-5-nitro-1H-indole (1.00 g, 5.68 mmol) in acetonitrile (11.4 mL) was added potassium carbonate (1.57 g, 11.4 mmol), and 4-chlorobenzyl chloride (0.914 g, 5.68 mmol). The reaction mixture was heated to 70° C. for 16 hours after which it was complete as shown by LCMS analysis. The reaction was cooled to room temperature, diluted with water, then concentrated to remove the acetonitrile, leading to the formation of a precipitate. This sold was filtered and dried to afford 1-(4-chlorobenzyl)-2-methyl-5-nitro-1H-indole as a solid (1.50 g, 4.99 mmol, 88% yield).

2-(1-(4-chlorobenzyl)-2-methyl-5-nitro-1H-indol-3-yl)-N-(2-methoxypyridin-4-yl)-2-oxoacetamide was synthesized using 1-(4-chlorobenzyl)-2-methyl-5-nitro-1H-indole following general procedure G to yield 2-(1-(4-chlorobenzyl)-2-methyl-5-nitro-1H-indol-3-yl)-N-(2-methoxypyridin-4-yl)-2-oxoacetamide as a solid in 44% yield. $^1$H NMR (400 MHz, CDCl$_3$) δ (ppm): 9.17 (d, 1H), 9.12 (s, 1H), 8.15-8.18 (m, 2H), 7.30-7.33 (m, 3H), 7.25-7.27 (m, 1H), 7.20 (dd, 1H), 6.94 (d, 2H), 5.43 (s, 2H), 3.99 (s, 3H), 2.75 (s, 3H).

2-(5-bromo-1-(4-chlorobenzyl)-2-methyl-1H-indol-3-yl)-N-(2-methoxypyridin-4-yl)-2-oxoacetamide (18)

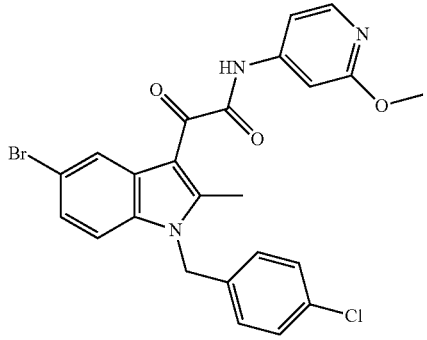

To a solution of 5-bromo-2-methyl-1H-indole (2.05 g, 9.76 mmol) in acetonitrile (35 mL) was added 1-chloro-4-(chloromethyl)benzene (7.65 mL, 9.76 mmol) followed by potassium carbonate (4.05 g, 29.3 mmol). The reaction mixture was heated to 70° C. for 16 hours after which it was cooled to room temperature, diluted with water (75 mL), extracted with dichloromethane (3×100 mL), dried (sodium sulfate), filtered and concentrated. Purification was achieved by silica gel chromatography using 0 to 50% ethyl acetate in hexanes to afford 5-bromo-1-(4-chlorobenzyl)-2-methyl-1H-indol as an orange solid in 35% yield.

2-(5-bromo-1-(4-chlorobenzyl)-2-methyl-1H-indol-3-yl)-N-(2-methoxypyridin-4-yl)-2-oxoacetamide was synthesized as a solid in 22% yield using general procedure G. $^1$H NMR (400 MHz, CDCl$_3$) δ (ppm): 9.07 (s, 1H), 8.37 (s, 1H), 8.15 (d, 1H), 7.26-7.34 (m, 4H), 7.16 (d, 1H), 7.08 (d, 1H), 6.92 (d, 2H), 5.33 (s, 2H), 3.97 (s, 3H), 2.68 (s, 3H).

2-(1-((3,5-dichloropyridin-2-yl)methyl)-2-methyl-1H-indol-3-yl)-N-(2-methoxypyridin-4-yl)-2-oxoacetamide (31)

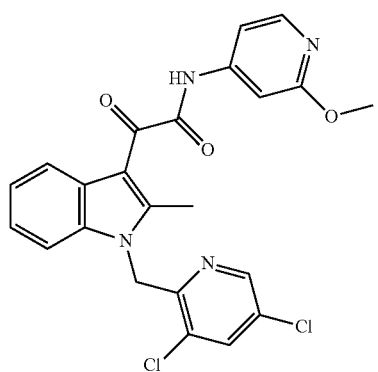 [SMILES: COc1cc(NC(=O)C(=O)c2c(C)n(Cc3ncc(Cl)cc3Cl)c3ccccc23)ccn1]

2-(1-((3,5-dichloropyridin-2-yl)methyl)-2-methyl-1H-indol-3-yl)-N-(2-methoxypyridin-4-yl)-2-oxoacetamide was synthesized as a solid using general route 3. $^1$H NMR (400 MHz, CDCl$_3$) δ (ppm): 9.03 (s, 1H), 8.27 (d, 1H), 8.12-8.18 (m, 2H), 7.77 (d, 1H), 7.26 (m, 2H), 7.17-7.24 (m, 3H), 5.54 (s, 2H), 3.97 (s, 3H), 2.76 (s, 3H).

2-(1-((3,5-dichloropyridin-2-yl)methyl)-2,5-dimethyl-1H-indol-3-yl)-N-(2-methoxypyridin-4-yl)-2-oxoacetamide (30)

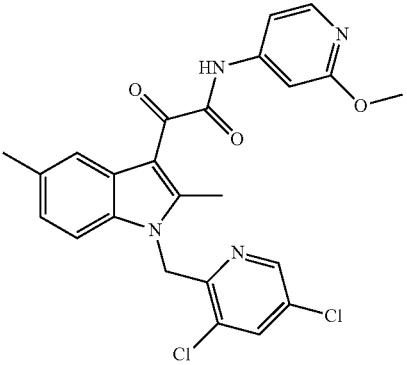

2-(1-((3,5-dichloropyridin-2-yl)methyl)-2,5-dimethyl-1H-indol-3-yl)-N-(2-methoxypyridin-4-yl)-2-oxoacetamide was synthesized as a solid using general route 3. $^1$H NMR (400 MHz, CDCl$_3$) δ (ppm): 9.03 (s, 1H), 8.26 (d, 1H), 8.14 (d, 1H), 7.98 (s, 1H), 7.76 (d, 1H), 7.28 (d, 1H), 7.16 (dd, 1H), 7.01-7.08 (m, 2H), 5.51 (s, 2H), 3.97 (s, 3H), 2.73 (s, 3H), 2.45 (s, 3H).

1-((3-chloro-5-(trifluoromethyl)pyridin-2-yl)methyl)-5-methoxy-2-methyl-1H-indole (28)

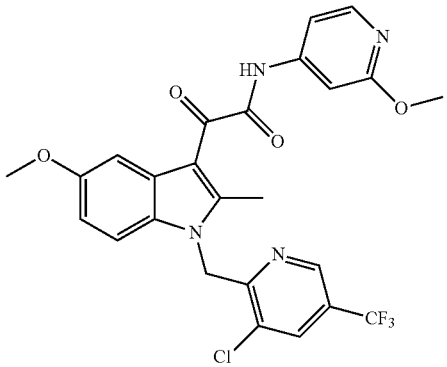

To a suspension of 5-methoxy-2-methyl-1H-indole (0.280 g, 1.74 mmol) in acetonitrile (5 mL) was added 3-chloro-2-(chloromethyl)-5-(trifluoromethyl)pyridine (0.400 g, 1.74 mmol) and potassium carbonate (0.481 g, 0.348 mmol) was heated to 70° C. for 18 hrs after which the reaction mixture was cooled to room temperature, diluted in water (30 mL), extracted with dichloromethane (3×20 mL), washed with saturated sodium chloride solution (1×50 mL), dried (sodium sulfate), filtered and concentrated to a residue. Purification was achieved by silica gel chromatography using 0 to 40% ethyl acetate in hexanes to afford 1-((3-chloro-5-(trifluoromethyl)pyridin-2-yl)methyl)-5-methoxy-2-methyl-1H-indole (129 mg, 0.218 mmol, 13% yield) as a solid.

1-((3-chloro-5-(trifluoromethyl)pyridin-2-yl)methyl)-5-methoxy-2-methyl-1H-indole was synthesized as a solid in 18% yield starting from 1-((3-chloro-5-(trifluoromethyl)pyridin-2-yl)methyl)-5-methoxy-2-methyl-1H-indole using general procedure G. $^1$H NMR (400 MHz, CDCl$_3$) δ (ppm): 9.07 (s, 1H), 8.58 (s, 1H), 8.15 (d, 1H), 7.99 (d, 1H), 7.79 (d, 1H), 7.29 (s, 1H), 7.17 (dd, 1H), 7.06 (d, 1H), 6.84 (dd, 1H), 5.60 (s, 2H), 3.99 (s, 3H), 3.86 (s, 3H), 2.74 (s, 3H).

2-(5-methoxy-2-methyl-1-(pyridin-2-ylmethyl)-1H-indol-3-yl)-N-(2-methoxypyridin-4-yl)-2-oxoacetamide (77)

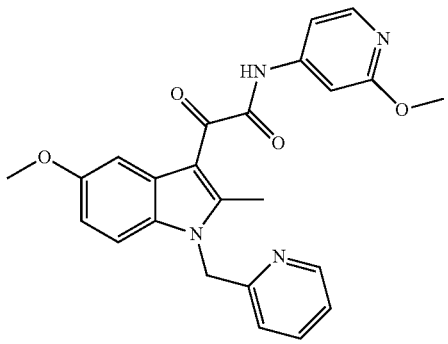

To a solution of 5-methoxy-2-methyl-1H-indole (1.00 g, 6.20 mmol) in N,N-dimethylformamide (10 mL) at 0° C. was added sodium hydride (0.372 g, 9.31 mmol). The reaction was stirred at room temperature for 20 minutes, after which 2-(bromomethyl)pyridine hydrobromide (1.88 g, 7.44 mmol) was added. The reaction mixture was stirred at 80° C. for 24 hours, after which it was diluted with water, extracted with ethyl acetate (3×50 mL), washed with water, then washed with saturated sodium bicarbonate solution, dried (magnesium sulfate), filtered and concentrated. Purification was achieved by silica gel chromatography (ISCO 80 g) using 0 to 80% ethyl acetate in hexanes to afford 5-methoxy-2-methyl-1-(pyridin-2-ylmethyl)-1H-indole as a yellow-brown solid in 36% yield.

2-(5-methoxy-2-methyl-1-(pyridin-2-ylmethyl)-1H-indol-3-yl)-N-(2-methoxypyridin-4-yl)-2-oxoacetamide was synthesized as a yellow solid in 8% yield starting from 5-methoxy-2-methyl-1-(pyridin-2-ylmethyl)-1H-indole using general procedure G. $^1$H NMR (400 MHz, CDCl$_3$) G (ppm): 9.33 (s, 1H), 8.58 (d, 1H), 8.12 (s, 1H), 7.70 (s, 1H), 7.57 (m, 1H), 7.31 (s, 1H), 7.19 (m, 2H), 7.14 (s, 1H), 6.86 (d, 1H), 6.71 (d, 1H), 5.41 (s, 2H), 3.96 (s, 3H), 3.81 (s, 3H), 2.65 (s, 3H).

2-(5-methoxy-2-methyl-1-(pyridin-3-ylmethyl)-1H-indol-3-yl)-N-(2-methoxypyridin-4-yl)-2-oxoacetamide (78)

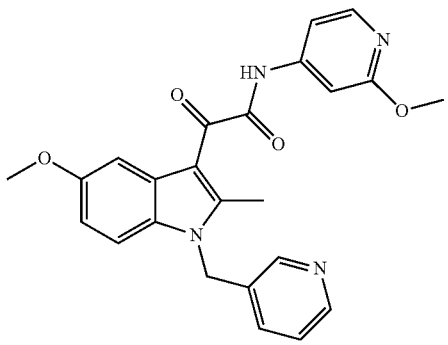

To a solution of 5-methoxy-2-methyl-1H-indole (1.70 g, 10.6 mmol) in N,N-dimethylformamide (10 mL) at 0° C. was added sodium hydride (0.633 g, 15.8 mmol). The reaction was stirred at room temperature for 20 minutes, after which 3-(bromomethyl)pyridine hydrobromide (2.67 g, 10.6 mmol) was added. The reaction mixture was stirred at 80° C. for 24 hours, after which it was diluted with water, extracted with ethyl acetate (3×100 mL), washed with water, then washed with saturated sodium bicarbonate solution, dried (magnesium sulfate), filtered and concentrated. Purification was achieved by silica gel chromatography (ISCO 80 g) using 0 to 80% ethyl acetate in hexanes to afford 5-methoxy-2-methyl-1-(pyridin-2-ylmethyl)-1H-indole as a yellow-brown solid in 34% yield.

2-(5-methoxy-2-methyl-1-(pyridin-3-ylmethyl)-1H-indol-3-yl)-N-(2-methoxypyridin-4-yl)-2-oxoacetamide was synthesized as a yellow solid in 2% yield starting from 5-methoxy-2-methyl-1-(pyridin-3-ylmethyl)-1H-indole using general procedure G as a yellow solid in 2.21% yield. $^1$H NMR (400 MHz, CDCl$_3$) δ (ppm): 9.17 (s, 1H), 8.55 (d, 1H), 8.48 (s, 1H), 8.13 (d, 1H), 7.75 (s, 1H), 7.26 (m, 1H, isochronous with CDCl$_3$), 7.21 (m, 2H), 7.14 (s, 1H), 7.12 (d, 1H), 6.88 (d, 1H), 5.34 (s, 2H), 3.95 (s, 3H), 3.85 (s, 3H), 2.66 (s, 3H).

2-(1-((5-chloropyridin-2-yl)methyl)-5-methoxy-2-methyl-1H-indol-3-yl)-N-(2-methoxypyridin-4-yl)-2-oxoacetamide (79)

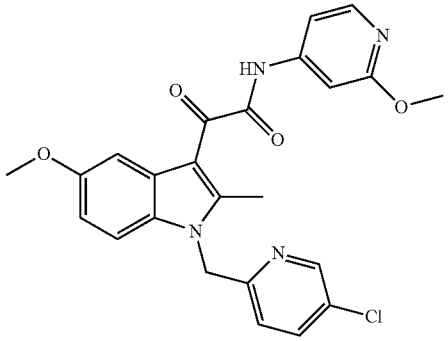

This compound was synthesized as a yellow solid in starting from 5-chloro-2-(chloromethyl)pyridine using general route 3. $^1$H NMR (400 MHz, CDCl$_3$) δ (ppm): 9.15 (s, 1H), 8.54 (s, 1H), 8.12 (d, 1H), 7.73 (s, 1H), 7.54 (d, 1H), 7.25 (s, 1H, isochronous with CDCl$_3$), 7.17 (d, 1H), 7.11 (d, 1H), 6.87 (d, 1H), 6.67 (d, 1H), 5.37 (s, 2H), 3.95 (s, 3H), 3.83 (s, 3H), 2.66 (s, 3H).

2-(1-((3,5-difluoropyridin-2-yl)methyl)-5-methoxy-2-methyl-1H-indol-3-yl)-N-(2-methoxypyridin-4-yl)-2-oxoacetamide (81)

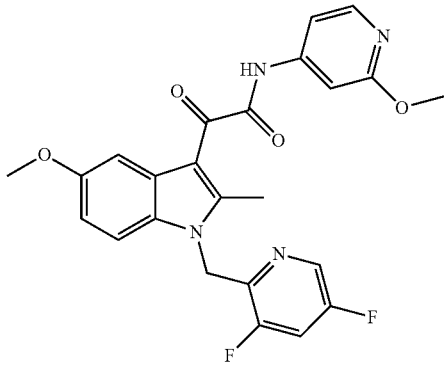

2-(1-((3,5-difluoropyridin-2-yl)methyl)-5-methoxy-2-methyl-1H-indol-3-yl)-N-(2-methoxypyridin-4-yl)-2-oxoacetamide was synthesized as a yellow solid starting from 3,5-Difluoro-2-(chloromethyl)pyridine using general route 3. $^1$H NMR (400 MHz, CDCl$_3$) δ (ppm): 8.99 (s, 1H), 8.25 (s, 1H), 8.14 (d, 1H), 7.72 (s, 1H), 7.30 (d, 1H), 7.24 (m, 2H), 7.14 (d, 1H), 6.87 (d, 1H), 5.46 (s, 2H), 3.96 (s, 3H), 3.85 (s, 3H), 2.84 (s, 3H).

2-(1-((3,5-dichloropyridin-2-yl)methyl)-5-methoxy-2-methyl-1H-indol-3-yl)-N-(2-methoxypyridin-4-yl)-2-oxoacetamide (82)

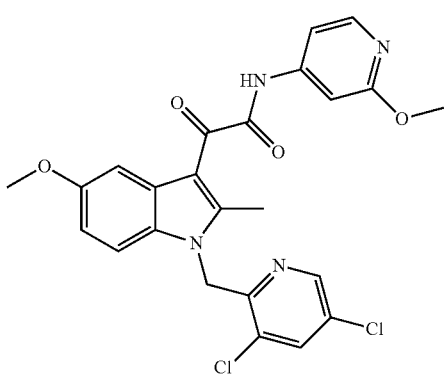

2-(1-((3,5-dichloropyridin-2-yl)methyl)-5-methoxy-2-methyl-1H-indol-3-yl)-N-(2-methoxypyridin-4-yl)-2-oxoacetamide was synthesized as a yellow solid starting from 3,5-dichloro-2-(chloromethyl)pyridine using general route 3. $^1$H NMR (400 MHz, CDCl$_3$) δ (ppm): 9.02 (s, 1H), 8.25 (s, 1H), 8.14 (d, 1H), 7.70 (s, 1H), 7.16-7.26 (m, 3H), 7.15 (d, 1H), 6.87 (d, 1H), 5.40 (s, 2H), 3.96 (s, 3H), 3.84 (s, 3H), 2.83 (s, 3H).

2-(5-methoxy-2-methyl-1-(pyrimidin-2-ylmethyl)-1H-indol-3-yl)-N-(2-methoxypyridin-4-yl)-2-oxoacetamide (83)

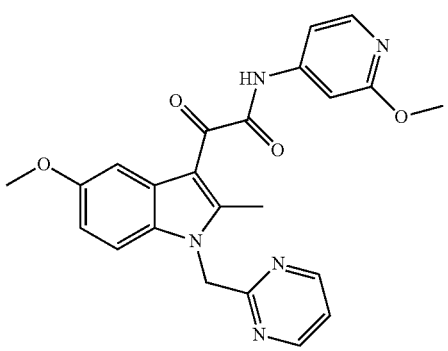

2-(5-methoxy-2-methyl-1-(pyrimidin-2-ylmethyl)-1H-indol-3-yl)-N-(2-methoxypyridin-4-yl)-2-oxoacetamide was synthesized as a yellow solid using general route 3. $^1$H NMR (400 MHz, CDCl$_3$) δ (ppm): 9.08 (s, 1H), 8.67 (d, 2H), 8.13 (d, 1H), 7.73 (s, 1H), 7.15-7.27 (m, 4H), 6.86 (d, 1H), 5.48 (s, 2H), 3.95 (s, 3H), 3.83 (s, 3H), 2.78 (s, 3H).

2-(5-methoxy-2-methyl-1-((5-methylpyridin-2-yl)methyl)-1H-indol-3-yl)-N-(2-methoxypyridin-4-yl)-2-oxoacetamide (84)

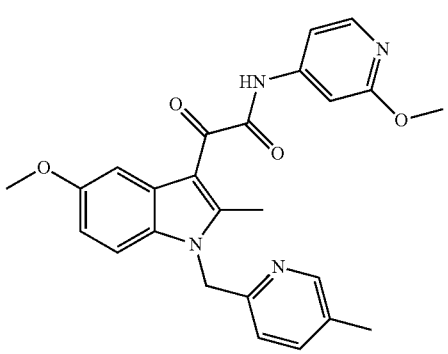

2-(5-methoxy-2-methyl-1-((5-methylpyridin-2-yl)methyl)-1H-indol-3-yl)-N-(2-methoxypyridin-4-yl)-2-oxoacetamide was synthesized as a yellow solid using general route 3. $^1$H NMR (400 MHz, CDCl$_3$) δ (ppm): 9.36 (s, 1H), 8.37 (s, 1H), 8.10 (d, 1H), 7.67 (s, 1H), 7.32-7.26 (m, 2H), 7.17 (d, 1H), 7.09 (d, 1H), 6.83 (d, 1H), 6.55 (d, 1H), 5.28 (s, 2H), 3.93 (s, 3H), 3.77 (s, 3H), 2.58 (s, 3H), 2.26 (s, 3H).

2-(1-((5-fluoropyridin-2-yl)methyl)-2,5-dimethyl-1H-indol-3-yl)-N-(2-methoxypyridin-4-yl)-2-oxoacetamide (85)

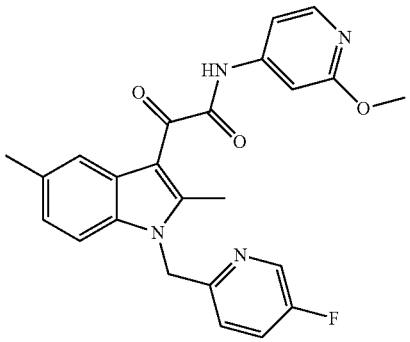

2-(1-((5-fluoropyridin-2-yl)methyl)-2,5-dimethyl-1H-indol-3-yl)-N-(2-methoxypyridin-4-yl)-2-oxoacetamide was synthesized as a yellow solid using general route 3. $^1$H NMR (400 MHz, CDCl$_3$) δ (ppm): 9.18 (s, 1H), 8.43 (s, 1H), 8.12 (d, 1H), 7.94 (s, 1H), 7.23-7.28 (m, 2H), 7.18 (d, 1H), 7.16 (d, 1H), 7.06 (d, 1H), 6.73 (m, 1H), 5.36 (s, 2H), 3.95 (s, 3H), 2.65 (s, 3H), 2.42 (s, 3H).

2-(1-(4-chlorobenzyl)-5,6-dimethoxy-2-methyl-1H-indol-3-yl)-N-(2-methoxypyridin-4-yl)-2-oxoacetamide (44)

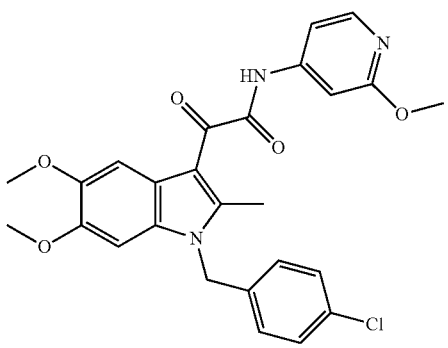

To a 0° C. solution of 5,6-dimethoxy-1H-indole-2-carboxylic acid (2.22 g, 10.0 mmol) in 1,4-dioxane (20 mL) was added, dropwise, a 2M in tetrahydrofuran solution of lithium aluminum hydride (25.1 mL, 50.2 mmol). The reaction mixture was warmed to room temperature for an hour then heated to reflux for 30 hours. The reaction was then cooled to 0° C., after which ice water (5 mL) was cautiously added, followed by an additional 20 mL of water. The reaction mixture was extracted with ethyl acetate (3×20 mL), washed with saturated sodium chloride solution (3×20 mL), dried (sodium sulfate), filtered and concentrated to a solid. Purification was achieved by column chromatography (Biotage, 50 g), using 20 to 100% ethyl acetate in hexanes to afford 5,6-dimethoxy-2-methyl-1H-indole (400 mg, 2.09 mmol, 21% yield) as a solid.

2-(1-(4-chlorobenzyl)-5,6-dimethoxy-2-methyl-1H-indol-3-yl)-N-(2-methoxypyridin-4-yl)-2-oxoacetamide was synthesized as a solid in 32% yield starting from a 1:1 mixture of 1-(4-chlorobenzyl)-5,6-dimethoxy-2-methyl-1H-indole and 1,3-bis(4-chlorobenzyl)-5,6-dimethoxy-2-methyl-1H-indole using general procedure G. (1,3-bis(4-chlorobenzyl)-5,6-dimethoxy-2-methyl-1H-indole does not react in this step and is easily separated from the reaction mixture). $^1$H NMR (400 MHz, CDCl$_3$) δ (ppm): 9.06 (br. s, 1H), 8.14 (d, 1H), 7.80 (s, 1H), 7.24-7.30 (m, 3H), 7.15 (d, 1H), 6.94 (d, 2H), 6.66 (s, 1H), 5.31 (s, 2H), 3.96 (s, 3H), 3.88 (s, 3H), 2.65 (s, 3H). LCMS 1.78 min, [ES]$^+$ found 493.94

2-(1-(4-chlorobenzyl)-4-methoxy-2-methyl-1H-indol-3-yl)-N-(2-methoxypyridin-4-yl)-2-oxoacetamide (45)

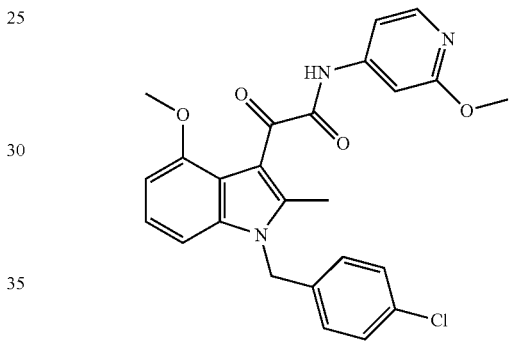

To a 0° C. solution of methyl 4-methoxy-1H-indole-2-carboxylate (1.00 g, 4.87 mmol) in 1,4-dioxane (20 mL) was added, dropwise, a 2M in tetrahydrofuran solution of lithium aluminum hydride (12.2 mL, 24.4 mmol). The reaction mixture was warmed to room temperature for an hour then heated to reflux for 15 hours after which the reaction was complete. The reaction mixture was then cooled to 0° C., after which ice water (5 mL) was cautiously added, followed by an additional 20 mL of water. The reaction mixture was extracted with ethyl acetate (3×20 mL), washed by saturated sodium chloride solution (3×20 mL), dried (sodium sulfate), filtered and concentrated to afford 4-methoxy-2-methyl-1H-indole (0.780 g, 4.84 mmol, 99% yield) as a solid.

2-(1-(4-chlorobenzyl)-4-methoxy-2-methyl-1H-indol-3-yl)-N-(2-methoxypyridin-4-yl)-2-oxoacetamide was synthesized as a yellow solid starting from 4-methoxy-2-methyl-1H-indole using general procedure G. $^1$H NMR (400 MHz, CDCl$_3$) δ (ppm): 8.45 (br. s, 1H), 8.13 (d, 1H), 7.28 (d, 2H), 7.10-7.21 (m, 3H), 6.97 (d, 2H), 6.85 (d, 1H), 6.62 (d, 1H), 5.35 (s, 2H), 3.95 (s, 3H), 3.71 (s, 3H), 2.56 (s, 3H).

123

2-(1-(4-chlorobenzyl)-5-methoxy-2-methyl-1H-indol-3-yl)-N-(2-methoxypyrimidin-4-yl)-2-oxoacetamide (46)

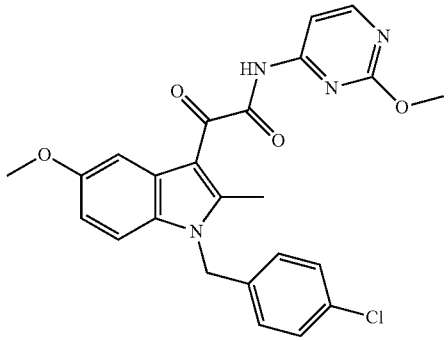

2-(1-(4-chlorobenzyl)-5-methoxy-2-methyl-1H-indol-3-yl)-N-(2-methoxypyrimidin-4-yl)-2-oxoacetamide was synthesized as a yellow solid in 29% yield using a mixture of 1-(4-chlorobenzyl)-5-methoxy-2-methyl-1H-indole and 1,3-bis(4-chlorobenzyl)-5-methoxy-2-methyl-1H-indole using general procedure G (1,3-bis(4-chlorobenzyl)-5-methoxy-2-methyl-1H-indole does not react in this step and is easily separated from the reaction mixture). $^1$H NMR (400 MHz, CDCl$_3$) δ (ppm): 9.42 (br. s, 1H), 8.52 (d, 1H), 7.95 (d, 1H), 7.74 (d, 1H), 7.29 (d, 2H), 7.13 (d, 1H), 6.96 (d, 2H), 6.88 (d, 1H), 5.34 (s, 2H), 4.00 (s, 3H), 3.87 (s, 3H), 2.67 (s, 3H).

N-(2-chloro-6-methoxypyridin-4-yl)-2-(1-(4-chlorobenzyl)-5-methoxy-2-methyl-1H-indol-3-yl)-2-oxoacetamide (47)

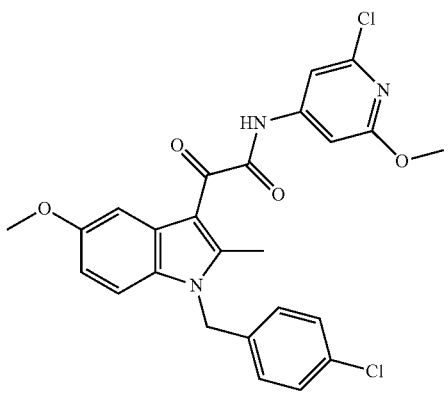

N-(2-chloro-6-methoxypyridin-4-yl)-2-(1-(4-chlorobenzyl)-5-methoxy-2-methyl-1H-indol-3-yl)-2-oxoacetamide was synthesized as a yellow solid in 70% yield using a mixture of 1-(4-chlorobenzyl)-5-methoxy-2-methyl-1H-indole and 1,3-bis(4-chlorobenzyl)-5-methoxy-2-methyl-1H-indole using general procedure G (1,3-bis(4-chlorobenzyl)-5-methoxy-2-methyl-1H-indole does not react in this step and is easily separated from the reaction mixture). $^1$H NMR (400 MHz, CDCl$_3$) δ (ppm): 9.20 (br. s, 1H), 7.74 (d, 1H), 7.30 (d, 1H), 7.27 (s, 1H), 7.25 (d, 1H), 7.09 (d, 1H), 7.08 (s, 1H), 6.93 (d, 2H), 6.85 (d, 1H), 5.27 (s, 2H), 3.94 (s, 3H), 3.85 (s, 3H), 2.63 (s, 3H). LCMS: 1.77 min, [ES]$^+$ found 498.36.

124

2-(1-(4-chlorobenzyl)-6-methoxy-2-methyl-1H-indol-3-yl)-N-(2-methoxypyridin-4-yl)-2-oxoacetamide (49)

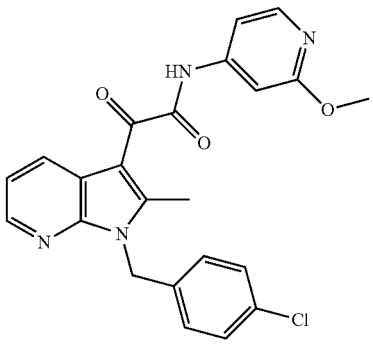 [SMILES: COc1cc(NC(=O)C(=O)c2c(C)n(Cc3ccc(Cl)cc3)c3ncccc23)ccn1]

2-(1-(4-chlorobenzyl)-6-methoxy-2-methyl-1H-indol-3-yl)-N-(2-methoxypyridin-4-yl)-2-oxoacetamide was synthesized as a yellow solid using general route 3. $^1$H NMR (400 MHz, CDCl$_3$) δ (ppm): 9.20 (br. s, 1H), 8.60 (d, 1H), 8.40 (d, 1H), 8.10 (d, 1H), 7.22-7.30 (m, 4H), 7.20 (d, 1H), 7.10 (d, 2H), 5.60 (d, 2H), 4.00 (s, 3H), 2.90 (s, 3H).

2-(1-(4-chlorobenzyl)-5-methoxy-2-methyl-1H-indol-3-yl)-N-(2-hydroxypyridin-4-yl)-2-oxoacetamide (50)

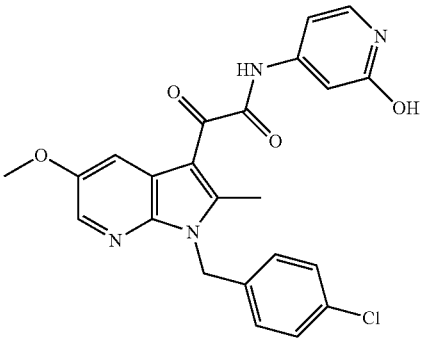 [SMILES: COc1cnc2c(c1)c(C(=O)C(=O)Nc1ccnc(O)c1)c(C)n2Cc1ccc(Cl)cc1]

2-(1-(4-chlorobenzyl)-5-methoxy-2-methyl-1H-indol-3-yl)-N-(2-hydroxypyridin-4-yl)-2-oxoacetamide was synthesized as a yellow solid in a 10% yield starting from a mixture of 1-(4-chlorobenzyl)-5-methoxy-2-methyl-1H-indole and 1,3-bis(4-chlorobenzyl)-5-methoxy-2-methyl-1H-indole using general procedure G (1,3-bis(4-chlorobenzyl)-5-methoxy-2-methyl-1H-indole does not react in this step and is easily separated from the reaction mixture). $^1$H NMR (400 MHz, CDCl$_3$) δ (ppm): 8.10 (d, 1H), 7.78 (d, 1H), 7.28 (d, 2H), 7.11 (d, 1H), 6.92 (d, 2H), 6.85 (d, 1H), 6.50 (d, 1H), 6.45 (d, 1H), 5.33 (s, 2H), 4.28 (br. s, 1H), 3.86 (s, 3H), 2.78 (s, 3H).

2-(1-(4-chlorobenzyl)-7-methoxy-2-methyl-1H-indol-3-yl)-N-(2-methoxypyridin-4-yl)-2-oxoacetamide (51)

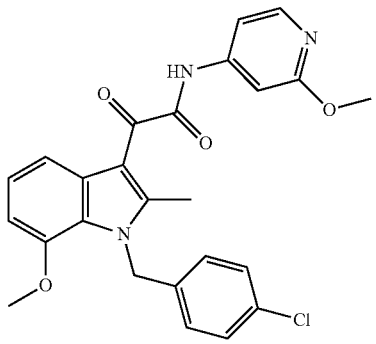 [SMILES: COc1cc(NC(=O)C(=O)c2c(C)n(Cc3ccc(Cl)cc3)c3c(OC)cccc23)ccn1]

To a 0° C. solution of 7-methoxy-1H-indole-2-carboxylic acid (1.91 g, 9.99 mmol) in 1,4-1,4-dioxane (20 mL) was added, dropwise, a 2M in tetrahydrofuran solution of lithium aluminum hydride (12.2 mL, 24.4 mmol). The reaction mixture was warmed to room temperature for an hour then heated to reflux for 20 hours after which the reaction was cooled to 0° C., carefully quenched by the addition of ice water (5 mL), diluted with water (20 mL), extracted with ethyl acetate (3×20 mL), washed by saturated sodium chloride solution (3×20 mL), dried (sodium sulfate), filtered and concentrated to afford a solid. Purification was achieved by silica gel chromatography (Biotage 25 g) using 10 to 100% ethyl acetate in hexanes to afford 4-methoxy-2-methyl-1H-indole (0.900 g, 5.59 mmol, 56% yield) as a solid.

2-(1-(4-chlorobenzyl)-7-methoxy-2-methyl-1H-indol-3-yl)-N-(2-methoxypyridin-4-yl)-2-oxoacetamide was synthesized as a yellow solid starting from 4-methoxy-2-methyl-1H-indole using general route 3. 1H NMR (400 MHz, CDCl$_3$) δ (ppm): 9.02 (br. s, 1H), 8.12 (d, 1H), 7.74 (d, 1H), 7.24-7.26 (m, 3H), 7.19 (d, 1H), 7.16 (d, 1H), 6.93 (d, 2H), 6.72 (d, 1H), 5.67 (s, 2H), 3.95 (s, 3H), 3.78 (s, 3H), 2.57 (s, 3H). LCMS: 2.01 min, [ES]$^+$ found 463.91.

N-(3-chloro-2-methoxypyridin-4-yl)-2-(1-(4-chlorobenzyl)-5-methoxy-2-methyl-1H-indol-3-yl)-2-oxoacetamide (52)

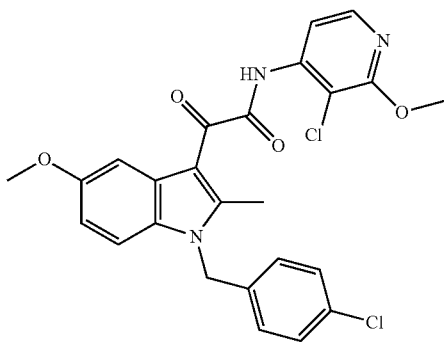

N-(3-chloro-2-methoxypyridin-4-yl)-2-(1-(4-chlorobenzyl)-5-methoxy-2-methyl-1H-indol-3-yl)-2-oxoacetamide was synthesized as a yellow solid in 11% yield starting from a mixture of 1-(4-chlorobenzyl)-5-methoxy-2-methyl-1H-indole and 1,3-bis(4-chlorobenzyl)-5-methoxy-2-methyl-1H-indole using general procedure G (1,3-bis(4-chlorobenzyl)-5-methoxy-2-methyl-1H-indole does not react in this step and is easily separated from the reaction mixture). $^1$H NMR (400 MHz, CDCl$_3$) δ (ppm): 8.16 (br. s, 1H), 7.48 (s, 1H), 7.25-7.27 (m, 3H), 7.06 (d, 1H), 7.03 (d, 1H), 6.92 (d, 2H), 6.82 (d, 1H), 5.25 (s, 2H), 4.05 (s, 3H), 3.77 (s, 3H), 2.58 (s, 3H). LCMS, 2.62 min, [ES]$^+$ found 498.36.

2-(1-(4-chlorobenzyl)-5-methoxy-2-methyl-1H-indol-3-yl)-N-(3-fluoro-2-methoxypyridin-4-yl)-2-oxoacetamide (53)

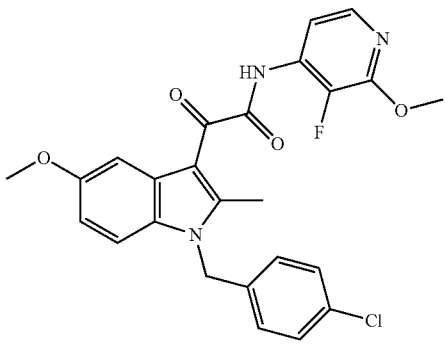

To a room temperature solution of 2-methoxypyridin-4-amine (620 mg, 5.00 mmol) in acetonitrile (5 mL) was added Selectfluor (1.77 g, 5.00 mmol). The reaction was stirred at room temperature for 18 hours, after which water (10 mL) was added to reaction mixture, and the resulting mixture was extracted with ethyl acetate (3×10 mL), washed with saturated sodium chloride solution (3×10 mL), dried (sodium sulfate) and concentrated to a solid. Purification was achieved by silica gel chromatography (Biotage 25 g) using 10 to 100% ethyl acetate in hexanes to afford 3-fluoro-2-methoxypyridin-4-amine (0.100 g, 0.700 mmol, 14% yield) as a solid.

2-(1-(4-chlorobenzyl)-5-methoxy-2-methyl-1H-indol-3-yl)-N-(3-fluoro-2-methoxypyridin-4-yl)-2-oxoacetamide was synthesized as a yellow solid in 18% yield starting from a mixture of 1-(4-chlorobenzyl)-5-methoxy-2-methyl-1H-indole and 1,3-bis(4-chlorobenzyl)-5-methoxy-2-methyl-1H-indole using general procedure G (1,3-bis(4-chlorobenzyl)-5-methoxy-2-methyl-1H-indole does not react in this step and is easily separated from the reaction mixture). $^1$H NMR (400 MHz, CDCl$_3$) δ (ppm): 8.01 (br. s, 1H), 7.50 (s, 1H), 7.25-7.28 (m, 3H), 7.15 (d, 1H), 6.89-6.93 (m, 3H), 6.83 (d, 1H), 5.25 (s, 2H), 4.01 (s, 3H), 3.80 (s, 3H), 2.60 (s, 3H).

2-(1-(4-chlorobenzyl)-5-methoxy-2-methyl-1H-indol-3-yl)-N-(5-fluoro-2-methoxypyridin-4-yl)-2-oxoacetamide (54)

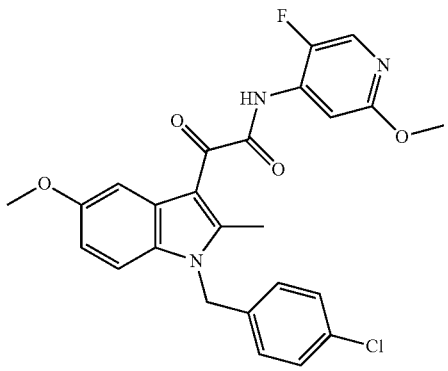

2-(1-(4-chlorobenzyl)-5-methoxy-2-methyl-1H-indol-3-yl)-N-(5-fluoro-2-methoxypyridin-4-yl)-2-oxoacetamide was synthesized as a yellow solid in 12% yield starting from a mixture of 1-(4-chlorobenzyl)-5-methoxy-2-methyl-1H-indole and 1,3-bis(4-chlorobenzyl)-5-methoxy-2-methyl-1H-indole using general procedure G (1,3-bis(4-chlorobenzyl)-5-methoxy-2-methyl-1H-indole does not react in this step and is easily separated from the reaction mixture). $^1$H NMR (400 MHz, CDCl$_3$) δ (ppm): 9.35 (br. s, 1H), 8.03 (d, 1H), 7.96 (d, 1H), 7.79 (d, 1H), 7.29 (d, 2H), 7.13 (d, 1H), 6.96 (d, 2H), 6.88 (d, 1H), 5.34 (s, 2H), 3.93 (s, 3H), 3.88 (s, 3H), 2.68 (s, 3H). LCMS, 2.09 min, [ES]$^+$ found 481.90.

2-(1-(4-chlorobenzyl)-5,6-dimethoxy-2-methyl-1H-indol-3-yl)-N-(2-methoxypyridin-4-yl)-2-oxoacetamide (57)

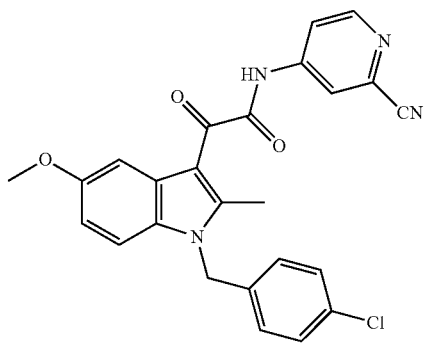 [SMILES: COc1ccc2c(c1)c(C(=O)C(=O)Nc1ccnc(C#N)c1)c(C)n2Cc1ccc(Cl)cc1]

2-(1-(4-chlorobenzyl)-5,6-dimethoxy-2-methyl-1H-indol-3-yl)-N-(2-methoxypyridin-4-yl)-2-oxoacetamide was synthesized as a yellow solid in 41% yield starting from a mixture of 1-(4-chlorobenzyl)-5-methoxy-2-methyl-1H-indole and 1,3-bis(4-chlorobenzyl)-5-methoxy-2-methyl-1H-indole using general procedure G (1,3-bis(4-chlorobenzyl)-5-methoxy-2-methyl-1H-indole does not react in this step and is easily separated from the reaction mixture). $^1$H NMR (400 MHz, CDCl$_3$) δ (ppm): 9.41 (br. s, 1H), 8.66 (d, 1H), 8.25 (d, 1H), 7.79 (d, 1H), 7.76 (d, 1H), 7.29 (d, 2H), 7.15 (d, 1H), 6.93 (d, 2H), 6.89 (d, 1H), 5.35 (s, 2H), 3.89 (s, 3H), 2.69 (s, 3H). LCMS: 1.86 min, [ES]$^+$ found 458.90.

2-(6-chloro-1-(4-chlorobenzyl)-5-methoxy-2-methyl-1H-indol-3-yl)-N-(2-methoxypyridin-4-yl)-2-oxoacetamide (55)

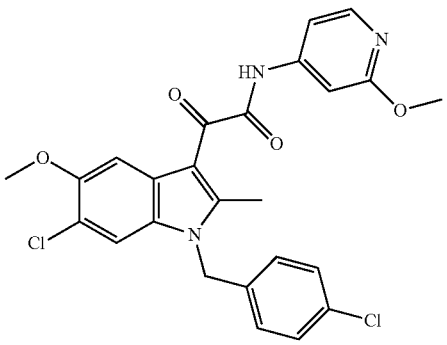

2-(6-chloro-1-(4-chlorobenzyl)-5-methoxy-2-methyl-1H-indol-3-yl)-N-(2-methoxypyridin-4-yl)-2-oxoacetamide was synthesized as a yellow solid starting from 6-chloro-1-(4-chlorobenzyl)-5-methoxy-2-methyl-1H-indole using general route 3. $^1$H NMR (400 MHz, CDCl$_3$) δ (ppm): 9.12 (br. s, 1H), 8.14 (d, 1H), 7.84 (s, 1H), 7.29 (d, 2H), 7.24 (d, 1H), 7.21 (s, 1H), 7.15 (d, 1H), 6.92 (d, 2H), 5.25 (s, 2H), 3.95 (s, 3H), 3.94 (s, 3H), 2.64 (s, 3H). LCMS, 2.03 min, [ES]$^+$ found 498.34.

2-(1-(4-chlorobenzyl)-4,5-dimethoxy-2-methyl-1H-indol-3-yl)-N-(2-methoxypyridin-4-yl)-2-oxoacetamide (56)

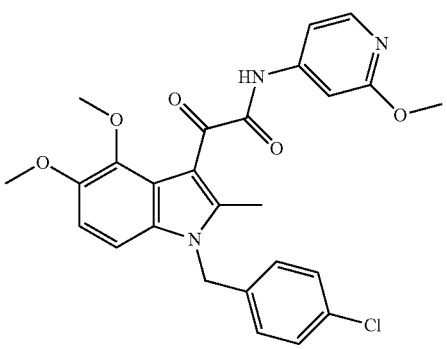

2-(1-(4-chlorobenzyl)-4,5-dimethoxy-2-methyl-1H-indol-3-yl)-N-(2-methoxypyridin-4-yl)-2-oxoacetamide was synthesized as a yellow solid starting from 4,5-dimethoxy-2-methyl-1H-indole using general route 3. $^1$H NMR (400 MHz, CDCl$_3$) δ (ppm): 8.48 (br. s, 1H), 8.13 (d, 1H), 7.30 (d, 1H), 7.27 (d, 1H), 7.22 (d, 1H), 7.19 (d, 1H), 6.98 (d, 2H), 6.90 (d, 2H), 5.27 (s, 2H), 3.95 (s, 3H), 3.84 (s, 3H), 3.81 (s, 3H), 2.54 (s, 3H).

2-(1-(4-chlorobenzyl)-4-fluoro-5-methoxy-2-methyl-1H-indol-3-yl)-N-(2-methoxypyridin-4-yl)-2-oxoacetamide (59)

2-(1-((5-chloropyridin-2-yl)methyl)-2,5-dimethyl-1H-indol-3-yl)-N-(2-methoxypyridin-4-yl)-2-oxoacetamide (61)

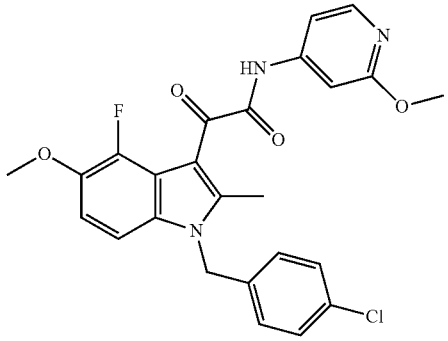

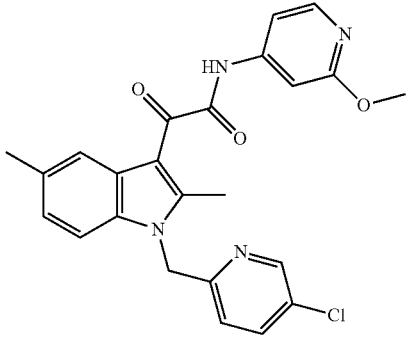

2-(1-(4-chlorobenzyl)-4-fluoro-5-methoxy-2-methyl-1H-indol-3-yl)-N-(2-methoxypyridin-4-yl)-2-oxoacetamide was synthesized as a yellow solid using general route 3. $^1$H NMR (400 MHz, CDCl$_3$) δ (ppm): 9.76 (br. s, 1H), 8.11 (d, 1H), 7.29 (d, 2H), 7.21 (d, 1H), 7.18 (d, 1H), 6.96 (d, 2H), 6.90 (d, 1H), 6.88 (d, 1H), 5.26 (s, 2H), 3.94 (s, 3H), 3.87 (s, 3H), 2.57 (s, 3H). LCMS, 1.80 min, [ES]$^+$ found 481.90.

2-(1-((5-chloropyridin-2-yl)methyl)-2,5-dimethyl-1H-indol-3-yl)-N-(2-methoxypyridin-4-yl)-2-oxoacetamide was synthesized as a yellow solid using general route 3. $^1$H NMR (400 MHz, CDCl$_3$) δ (ppm): 9.01 (br. s, 1H), 8.56 (d, 1H), 8.15 (d, 1H), 7.98 (s, 1H), 7.55 (d, 1H), 7.26 (d, 1H), 7.18 (d, 1H), 7.12 (d, 1H), 7.08 (d, 1H), 6.68 (d, 1H), 5.43 (s, 2H), 3.96 (s, 3H), 2.70 (s, 3H), 2.46 (s, 3H). LCMS: 1.75 min, [ES]$^+$ found 448.90.

2-(6-chloro-1-((5-chloropyridin-2-yl)methyl)-5-methoxy-2-methyl-1H-indol-3-yl)-N-(2-methoxypyridin-4-yl)-2-oxoacetamide (60)

2-(1-((5-chloropyridin-2-yl)methyl)-2-methyl-5-nitro-1H-indol-3-yl)-N-(2-methoxypyridin-4-yl)-2-oxoacetamide (62)

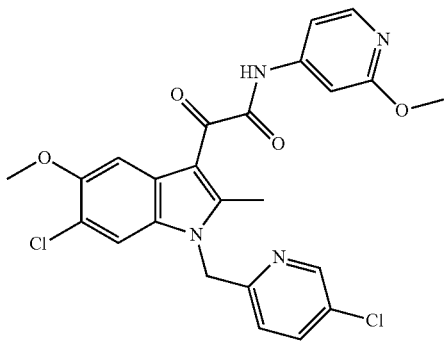

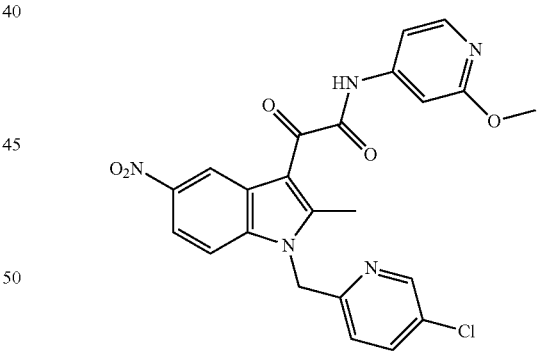

2-(6-chloro-1-((5-chloropyridin-2-yl)methyl)-5-methoxy-2-methyl-1H-indol-3-yl)-N-(2-methoxypyridin-4-yl)-2-oxoacetamide was synthesized as a yellow using general route 3. $^1$H NMR (400 MHz, CDCl$_3$) δ (ppm): 9.17 (br. s, 1H), 8.58 (d, 1H), 8.17 (d, 1H), 7.81 (s, 1H), 7.58 (d, 1H), 7.26 (d, 2H), 7.18 (d, 1H), 6.76 (d, 1H), 5.38 (s, 2H), 3.96 (s, 3H), 3.94 (s, 3H), 2.69 (s, 3H). LCMS: 1.80 min, [ES]$^+$ found 499.35.

2-(1-((5-chloropyridin-2-yl)methyl)-2-methyl-5-nitro-1H-indol-3-yl)-N-(2-methoxypyridin-4-yl)-2-oxoacetamide was synthesized as a yellow solid using general route 3. $^1$H NMR (400 MHz, DMSO-d$_6$) δ (ppm): 11.37 (s, 1H), 8.86 (d, 1H), 8.50 (d, 1H), 8.16 (d, 1H), 8.14 (d, 1H), 8.00 (d, 1H), 7.86 (d, 1H), 7.52 (d, 1H), 7.28 (d, 1H), 7.26 (d, 1H), 5.81 (s, 2H), 3.86 (s, 3H), 2.68 (s, 3H). LCMS: 1.69 min, [ES]$^+$ found 479.87.

131

2-(5-chloro-1-((5-chloropyridin-2-yl)methyl)-2-methyl-1H-indol-3-yl)-N-(2-methoxypyridin-4-yl)-2-oxoacetamide (63)

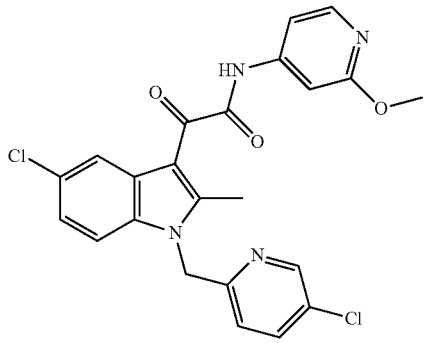 [SMILES: COc1cc(NC(=O)C(=O)c2c(C)n(Cc3ccc(Cl)cn3)c3ccc(Cl)cc23)ccn1]

2-(5-chloro-1-((5-chloropyridin-2-yl)methyl)-2-methyl-1H-indol-3-yl)-N-(2-methoxypyridin-4-yl)-2-oxoacetamide was synthesized as a yellow solid using general route 3. $^1$H NMR (400 MHz, CDCl$_3$) δ (ppm): 8.98 (br. s, 1H), 8.49 (d, 1H), 8.15 (d, 1H), 8.09 (d, 1H), 7.52 (d, 1H), 7.13 (d, 2H), 7.10 (d, 2H), 6.66 (d, 1H), 5.38 (s, 2H), 3.90 (s, 3H), 2.67 (s, 3H). LCMS: 1.85 min, [ES]$^+$ found 469.32.

2-(1-((5-chloropyridin-2-yl)methyl)-6-fluoro-5-methoxy-2-methyl-1H-indol-3-yl)-N-(2-methoxypyridin-4-yl)-2-oxoacetamide (64)

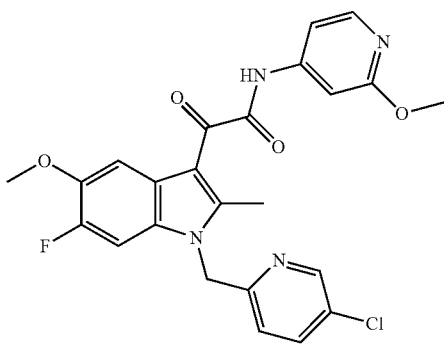

2-(1-((5-chloropyridin-2-yl)methyl)-6-fluoro-5-methoxy-2-methyl-1H-indol-3-yl)-N-(2-methoxypyridin-4-yl)-2-oxoacetamide was synthesized as a yellow solid using general route 3. $^1$H NMR (400 MHz, CDCl$_3$) δ (ppm): 9.05 (br. s, 1H), 8.55 (d, 1H), 8.15 (d, 1H), 7.89 (s, 1H), 7.59 (d, 1H), 7.24 (d, 1H), 7.15 (d, 1H), 7.01 (d, 1H), 6.73 (d, 1H), 5.38 (s, 2H), 3.96 (s, 3H), 3.95 (s, 3H), 2.72 (s, 3H). LCMS: 1.66 min, [ES]$^+$ found 482.89.

132

2-(5-chloro-1-((5-chloropyridin-2-yl)methyl)-6-methoxy-2-methyl-1H-indol-3-yl)-N-(2-methoxypyridin-4-yl)-2-oxoacetamide (67)

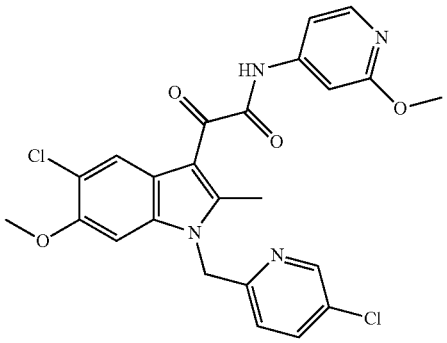

2-(5-chloro-1-((5-chloropyridin-2-yl)methyl)-6-methoxy-2-methyl-1H-indol-3-yl)-N-(2-methoxypyridin-4-yl)-2-oxoacetamide was synthesized as a yellow solid using general route 3. $^1$H NMR (400 MHz, CDCl$_3$) δ (ppm): 9.07 (br. s, 1H), 8.57 (d, 1H), 8.23 (s, 1H), 8.15 (d, 1H), 7.59 (d, 1H), 7.24 (d, 1H), 7.17 (d, 1H), 6.72 (d, 1H), 6.70 (d, 1H), 5.42 (s, 2H), 3.96 (s, 3H), 3.86 (s, 3H), 2.71 (s, 3H). LCMS: 1.75 min, [ES]$^+$ found 499.35.

2-(1-((5-chloropyridin-2-yl)methyl)-2-methyl-1H-indol-3-yl)-N-(2-methoxypyridin-4-yl)-2-oxoacetamide (68)

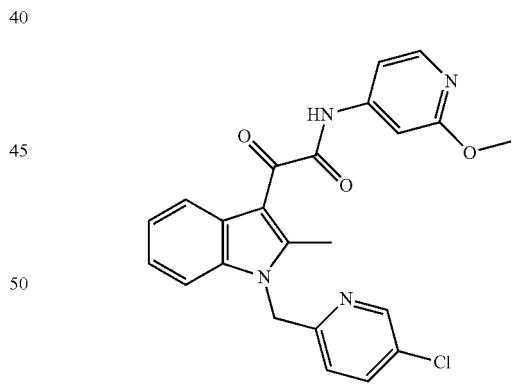

2-(1-((5-chloropyridin-2-yl)methyl)-2-methyl-1H-indol-3-yl)-N-(2-methoxypyridin-4-yl)-2-oxoacetamide was synthesized as a yellow solid in using general route 3. $^1$H NMR (400 MHz, CDCl$_3$) δ (ppm): 9.06 (br. s, 1H), 8.55 (d, 1H), 8.17 (d, 1H), 8.14 (d, 1H), 7.55 (d, 1H), 7.24-7.31 (m, 4H), 7.17 (d, 1H), 6.70 (d, 1H), 5.45 (s, 2H), 3.96 (s, 3H), 2.72 (s, 3H). LCMS: 1.63 min, [ES]$^+$ found 434.86.

2-(1-((5-methoxypyridin-2-yl)methyl)-2,5-dimethyl-1H-indol-3-yl)-N-(2-methoxypyridin-4-yl)-2-oxoacetamide (69)

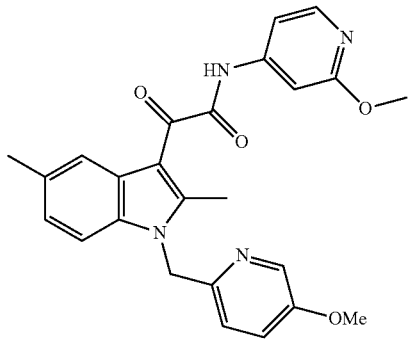

2-(1-((5-methoxypyridin-2-yl)methyl)-2,5-dimethyl-1H-indol-3-yl)-N-(2-methoxypyridin-4-yl)-2-oxoacetamide was synthesized as a yellow solid using general route 3. $^1$H NMR (400 MHz, CDCl$_3$) δ (ppm): 9.05 (br. s, 1H), 8.27 (d, 1H), 8.14 (s, 1H), 7.97 (s, 1H), 7.27 (s, 1H), 7.26 (d, 1H), 7.17 (d, 1H), 7.16 (d, 1H), 7.04 (d, 1H), 6.67 (d, 1H), 5.39 (s, 2H), 4.96 (s, 3H), 3.81 (s, 3H), 2.70 (s, 3H), 2.45 (s, 3H). LCMS, 1.55 min, [ES]$^+$ found 444.48.

2-(6-chloro-1-((3,5-dichloropyridin-2-yl)methyl)-5-methoxy-2-methyl-1H-indol-3-yl)-N-(2-methoxypyridin-4-yl)-2-oxoacetamide (70)

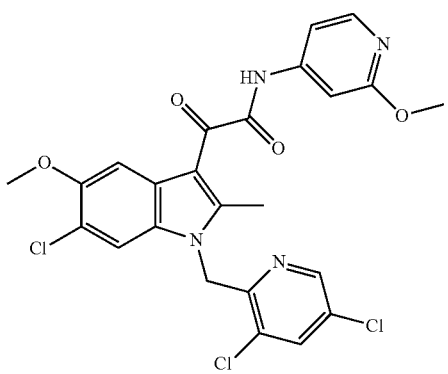

2-(6-chloro-1-((3,5-dichloropyridin-2-yl)methyl)-5-methoxy-2-methyl-1H-indol-3-yl)-N-(2-methoxypyridin-4-yl)-2-oxoacetamide was synthesized as a yellow solid in 33% yield starting from 1-((5-methoxypyridin-2-yl)methyl)-2,5-dimethyl-1H-indole using general procedure G. $^1$H NMR (400 MHz, CDCl$_3$) δ (ppm): 9.08 (br. s, 1H), 8.27 (d, 1H), 8.14 (d, 1H), 7.85 (s, 1H), 7.78 (d, 1H), 7.25 (s, 1H), 7.19 (s, 1H), 7.15 (d, 1H), 5.43 (s, 2H), 3.96 (s, 3H), 3.94 (s, 3H), 2.69 (s, 3H). LCMS: 1.96 min, [ES]$^+$ found 533.79.

2-(1-((5-chloro-3-fluoropyridin-2-yl)methyl)-6-fluoro-5-methoxy-2-methyl-1H-indol-3-yl)-N-(2-methoxypyridin-4-yl)-2-oxoacetamide (99)

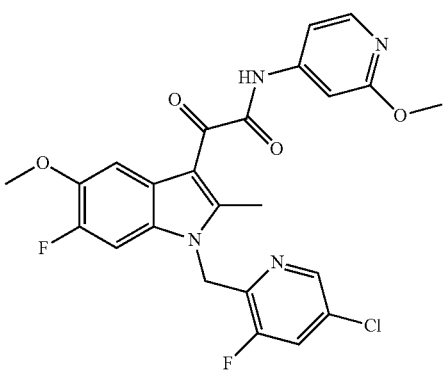

2-(1-((5-chloro-3-fluoropyridin-2-yl)methyl)-6-fluoro-5-methoxy-2-methyl-1H-indol-3-yl)-N-(2-methoxypyridin-4-yl)-2-oxoacetamide was synthesized as a light yellow solid using general route 3. Purification was achieved by silica gel chromatography using 0 to 50% ethyl acetate in hexanes over 30 minutes. $^1$H NMR (400 MHz, CDCl$_3$) δ (ppm): 9.00 (s, 1H), 8.32 (m, 1H), 8.14 (d, 1H), 7.84 (d, 1H), 7.51 (dd, 1H), 7.24-7.25 (m, 1H), 7.13-7.17 (m, 2H), 5.42 (d, 2H), 3.95 (d, 6H), 2.84 (s, 3H).

2-(1-((3,5-difluoropyridin-2-yl)methyl)-6-fluoro-5-methoxy-2-methyl-1H-indol-3-yl)-N-(2-methoxypyridin-4-yl)-2-oxoacetamide (101)

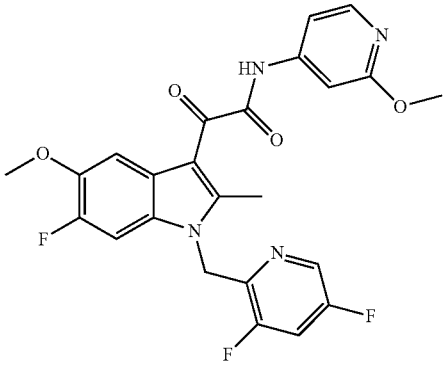

2-(1-((3,5-difluoropyridin-2-yl)methyl)-6-fluoro-5-methoxy-2-methyl-1H-indol-3-yl)-N-(2-methoxypyridin-4-yl)-2-oxoacetamide was synthesized as a white solid using general route 3. Purification was achieved by silica gel chromatography (Luknova 80 g, 20 mL/min) using 5 to 40% ethyl acetate in hexanes over 60 minutes. $^1$H NMR (400 MHz, CDCl$_3$) δ (ppm): 9.02 (br. s, 1H), 8.25 (d, 1H), 8.12 (d, 1H), 7.80 (d, 1H), 7.21-7.26 (m, 2H), 7.11-7.17 (m, 2H), 5.39 (s, 2H), 3.94 (s, 3H), 3.91 (s, 3H), 2.81 (s, 3H). LCMS: [ES]$^-$. found 483.04.

The Following Compounds were Prepared According to General Route 4

2-(1-(4-chlorobenzyl)-5-methoxy-2-methyl-1H-pyrrolo[3,2-b]pyridin-3-yl)-N-(2-methoxypyridin-4-yl)-2-oxoacetamide (36)

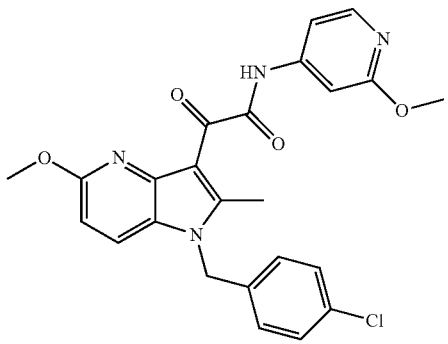

2-(1-(4-chlorobenzyl)-5-methoxy-2-methyl-1H-pyrrolo[3,2-b]pyridin-3-yl)-N-(2-methoxypyridin-4-yl)-2-oxoacetamide was synthesized according to general route 4 and general route 2.

5-methoxy-2-methyl-1H-pyrrolo[3,2-b]pyridine was synthesized as a solid starting from 6-methoxypyridin-3-amine using general route 4. LCMS: [ES]$^+$ found 163.05.

2-(1-(4-chlorobenzyl)-5-methoxy-2-methyl-1H-pyrrolo[3,2-b]pyridin-3-yl)-N-(2-methoxypyridin-4-yl)-2-oxoacetamide was synthesized as a solid starting from 5-methoxy-2-methyl-1H-pyrrolo[3,2-b]pyridine using general route 2. $^1$H NMR (400 MHz, CD$_3$OD) δ (ppm): 8.02 (d, 1H), 7.69 (d, 1H), 7.33 (m, 3H), 7.21-7.23 (m, 1H), 7.06 (d, 2H), 6.56 (d, 1H), 5.51 (s, 2H), 3.90 (s, 3H), 3.52 (s, 3H), 2.81 (s, 3H).

2-(1-(4-chlorobenzyl)-2-methyl-5-(trifluoromethyl)-1H-indol-3-yl)-N-(2-methoxypyridin-4-yl)-2-oxoacetamide (21)

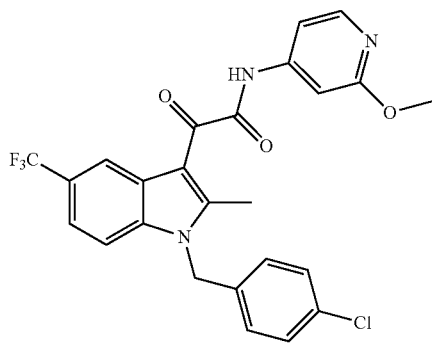 [SMILES: COc1cc(NC(=O)C(=O)c2c(C)n(Cc3ccc(Cl)cc3)c3ccc(C(F)(F)F)cc23)ccn1]

2-methyl-3-(phenylthio)-5-(trifluoromethyl)-1H-indole was synthesized as an oil in 100% yield starting with (4-(trifluoromethyl)phenyl)hydrazine hydrochloride and t-BuOH as solvent.

1-(4-chlorobenzyl)-2-methyl-3-(phenylthio)-5-(trifluoromethyl)-1H-indole was synthesized as a solid in a 22% yield starting with 2-methyl-3-(phenylthio)-5-(trifluoromethyl)-1H-indole and 1-chloro-4-(chloromethyl)benzene using general procedure B, excluding the use of potassium iodide.

1-(4-chlorobenzyl)-2-methyl-5-(trifluoromethyl)-1H-indole was synthesized as an oil in a 78% yield starting with 1-(4-chlorobenzyl)-2-methyl-3-(phenylthio)-5-(trifluoromethyl)-1H-indole following general procedure J.

2-(1-(4-chlorobenzyl)-2-methyl-5-(trifluoromethyl)-1H-indol-3-yl)-N-(2-methoxypyridin-4-yl)-2-oxoacetamide was synthesized as a solid in 35% yield starting with 1-(4-chlorobenzyl)-2-methyl-5-(trifluoromethyl)-1H-indole following general procedure G. $^1$H NMR (400 MHz, CDCl$_3$) ä (ppm): 9.08 (s, 1H), 8.55 (s, 1H), 8.16 (s, 1H), 7.49 (d, 2H), 7.18-7.31 (m, 3H), 7.16-7.17 (m, 1H), 6.94 (d, 2H), 5.41 (s, 2H), 3.97 (s, 3H), 2.73 (s, 3H).

2-(1-(4-chlorobenzyl)-2-methyl-5-(trifluoromethoxy)-1H-indol-3-yl)-N-(2-methoxypyridin-4-yl)-2-oxoacetamide (23)

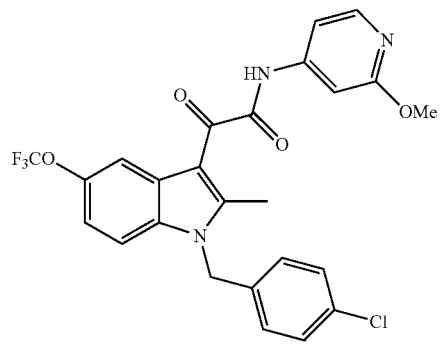 [SMILES: COc1cc(NC(=O)C(=O)c2c(C)n(Cc3ccc(Cl)cc3)c3ccc(OC(F)(F)F)cc23)ccn1]

2-(1-(4-chlorobenzyl)-2-methyl-5-(trifluoromethoxy)-1H-indol-3-yl)-N-(2-methoxypyridin-4-yl)-2-oxoacetamide was synthesized according to route 4 and route 3.

2-methyl-3-(phenylthio)-5-(trifluoromethoxy)-1H-indole was synthesized as a solid in 98% yield starting from (4-(trifluoromethoxy)phenyl)hydrazine hydrochloride and t-BuOH as solvent using procedure M.

1-(4-chlorobenzyl)-2-methyl-3-(phenylthio)-5-(trifluoromethoxy)-1H-indole was synthesized as a solid in 11% yield starting from 2-methyl-3-(phenylthio)-5-(trifluoromethoxy)-1H-indole, 1-chloro-4-(chloromethyl)benzene, acetonitrile as solvent, and excluding the use of potassium iodide using general procedure B.

1-(4-chlorobenzyl)-2-methyl-5-(trifluoromethoxy)-1H-indole was synthesized as a solid in 55% yield starting from 1-(4-chlorobenzyl)-2-methyl-3-(phenylthio)-5-(trifluoromethoxy)-1H-indole using general procedure J.

2-(1-(4-chlorobenzyl)-2-methyl-5-(trifluoromethoxy)-1H-indol-3-yl)-N-(2-methoxypyridin-4-yl)-2-oxoacetamide was synthesized as a solid in 50% yield starting from 1-(4-chlorobenzyl)-2-methyl-5-(trifluoromethoxy)-1H-indole using general procedure G. $^1$H NMR (400 MHz, CDCl$_3$) ä (ppm): 9.06 (s, 1H), 8.16 (d, 2H), 7.14-7.31 (m, 6H), 6.95 (d, 2H), 5.38 (s, 2H), 3.97 (s, 3H), 2.72 (s, 3H).

2-(5-chloro-1-(4-chlorobenzyl)-6-methoxy-2-methyl-1H-indol-3-yl)-N-(2-methoxypyridin-4-yl)-2-oxoacetamide (80)

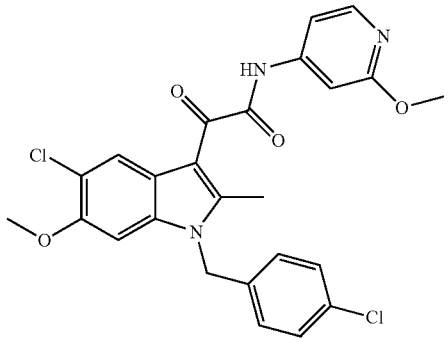

2-(5-chloro-1-(4-chlorobenzyl)-6-methoxy-2-methyl-1H-indol-3-yl)-N-(2-methoxypyridin-4-yl)-2-oxoacetamide was synthesized using route 4 and route 3.

5-chloro-6-methoxy-2-methyl-1H-indole was synthesized as an orange oil using general route 4.

2-(5-chloro-1-(4-chlorobenzyl)-6-methoxy-2-methyl-1H-indol-3-yl)-N-(2-methoxypyridin-4-yl)-2-oxoacetamide was synthesized as a yellow solid starting from 5-chloro-6-methoxy-2-methyl-1H-indole using general route 3. $^1$H NMR (400 MHz, CDCl$_3$) ä (ppm): 9.07 (s, 1H), 8.25 (s, 1H), 8.15 (d, 1H), 7.31 (d, 2H), 7.24 (d, 1H), 7.17 (d, 1H), 6.95 (d, 2H), 6.67 (s, 1H), 5.31 (s, 2H), 3.96 (s, 3H), 3.85 (s, 3H), 2.66 (s, 3H).

2-(4-chloro-1-(4-chlorobenzyl)-5-methoxy-2-methyl-1H-indol-3-yl)-N-(2-methoxypyridin-4-yl)-2-oxoacetamide (58)

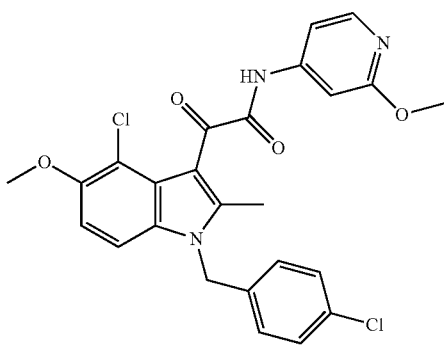

2-(4-chloro-1-(4-chlorobenzyl)-5-methoxy-2-methyl-1H-indol-3-yl)-N-(2-methoxypyridin-4-yl)-2-oxoacetamide was synthesized using route 4 and route 3.

4-chloro-5-methoxy-2-methyl-1H-indole was synthesized using route 4.

2-(4-chloro-1-(4-chlorobenzyl)-5-methoxy-2-methyl-1H-indol-3-yl)-N-(2-methoxypyridin-4-yl)-2-oxoacetamide was synthesized as a yellow solid starting from 4-chloro-5-methoxy-2-methyl-1H-indole using general route 3. $^1$H NMR (400 MHz, CDCl$_3$) δ (ppm): 8.84 (br. s, 1H), 8.12 (d, 1H), 7.30 (d, 2H), 7.19 (d, 2H), 7.10 (d, 1H), 6.96 (d, 1H), 6.92 (d, 2H), 5.30 (s, 2H), 3.94 (s, 3H), 3.90 (s, 3H), 2.50 (s, 3H). LCMS: 1.90 min, [ES]$^+$ found 498.36.

2-(1-(4-chlorobenzyl)-6-fluoro-5-methoxy-2-methyl-1H-indol-3-yl)-N-(2-methoxypyridin-4-yl)-2-oxoacetamide (72)

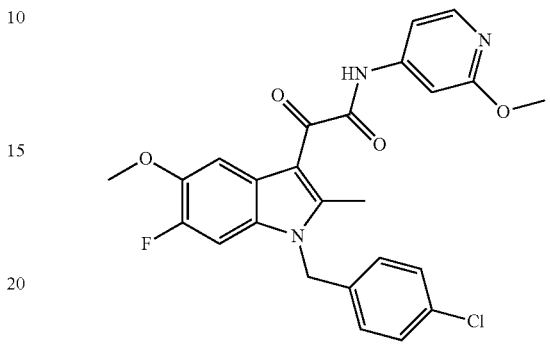

2-(1-(4-chlorobenzyl)-6-fluoro-5-methoxy-2-methyl-1H-indol-3-yl)-N-(2-methoxypyridin-4-yl)-2-oxoacetamide was synthesized using route 4 and route 3.

6-fluoro-5-methoxy-2-methyl-1H-indole was synthesized using route 4.

2-(1-(4-chlorobenzyl)-6-fluoro-5-methoxy-2-methyl-1H-indol-3-yl)-N-(2-methoxypyridin-4-yl)-2-oxoacetamide was synthesized as a yellow starting from 6-fluoro-5-methoxy-2-methyl-1H-indole using general procedure 3. $^1$H NMR (400 MHz, CDCl$_3$) δ (ppm): 9.04 (br. s, 1H), 8.14 (d, 1H), 7.90 (d, 1H), 7.29 (d, 2H), 7.25 (d, 1H), 7.14 (dd, 1H), 6.95 (d, 1H), 6.93 (d, 2H), 5.28 (s, 2H), 3.96 (s, 6H), 2.68 (s, 3H). LCMS: [ES]$^+$ found 482.0.

2-(1-(4-chlorobenzyl)-5-methoxy-2,6-dimethyl-1H-indol-3-yl)-N-(2-methoxypyridin-4-yl)-2-oxoacetamide (74)

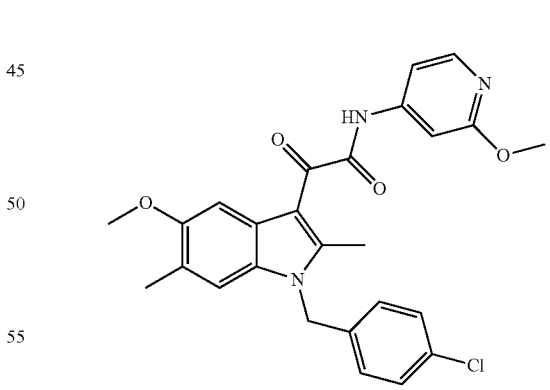

2-(1-(4-chlorobenzyl)-5-methoxy-2,6-dimethyl-1H-indol-3-yl)-N-(2-methoxypyridin-4-yl)-2-oxoacetamide was synthesized using general route 4 and general route 3.

5-methoxy-2,6-dimethyl-1H-indole was synthesized as a solid using general route 4. LCMS: [ES]$^+$ found 176.0.

2-(1-(4-chlorobenzyl)-5-methoxy-2,6-dimethyl-1H-indol-3-yl)-N-(2-methoxypyridin-4-yl)-2-oxoacetamide was synthesized as a yellow solid starting from 15-methoxy-2,6-dimethyl-1H-indole using general route 3. $^1$H NMR (400

MHz, CDCl₃) ä (ppm): 9.05 (br. s, 1H), 8.13 (d, 1H), 7.72 (s, 1H), 7.27 (d, 2H), 7.25 (d, 1H), 7.14 (dd, 1H), 6.96 (s, 1H), 6.93 (d, 2H), 5.30 (s, 2H), 3.96 (s, 3H), 3.90 (s, 3H), 2.65 (s, 3H), 2.28 (s, 3H). LCMS: [ES]⁺ found 478.0.

The following compounds or precursors of compounds were not prepared according to any of the general routes:

2-methyl-1H-pyrrolo[3,2-b]pyridine

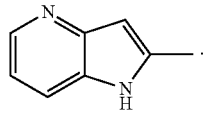

To a 10° C. solution of 2-chloropyridin-3-amine (2.00 g, 15.6 mmol) in 1,4-dioxane (20 mL) was added an aqueous solution of 1M sodium hydroxide (31.2 mL, 31.2 mmol). To this reaction mixture was added ethyl chloroformate (1.80 mL, 18.7 mmol), and the reaction was warmed to room temperature. After 2 hours, an additional ethyl chloroformate (0.8 mL) was added, and the reaction was stirred at room temperature for 12 hours, after which it was complete by LCMS analysis. The reaction mixture was diluted in water (50 mL), extracted with ethyl acetate (3×50 mL), washed with saturated sodium chloride solution (1×50 mL), dried (sodium sulfate), filtered and concentrated to afford a yellow oil which was purified on silica gel (ISCO 80 g, 20 mL/min) using 15% ethyl acetate in hexanes over 60 minutes. Ethyl 2-chloropyridin-3-ylcarbamate (2.21 g, 11.0 mmol, 71% yield) was isolated as a white solid. ¹H NMR (400 MHz, CDCl₃) δ (ppm): 8.51 (d, 1H), 8.07 (dd, 1H), 7.23-7.27 (m, 1H), 7.13 (br. s, 1H), 4.28 (q, 2H), 1.34 (t, 3H).

To a suspension of lithium chloride (341 mg, 8.05 mmol) in 1,4-dioxane (16.4 mL) was added ethyl 2-chloropyridin-3-ylcarbamate (660 mg, 3.29 mmol), tributyl(prop-1-ynyl)stannane (1.00 mL, 3.29 mmol) and Pd(Ph₃P)₄ (76.0 mg, 0.0660 mmol). The mixture was refluxed for 1.5 hours, after which the reaction showed >75% product with some starting material remaining. The reaction was continued heating for 12 hours (overnight), after which it was cooled, diluted with water, extracted with ethyl acetate (3×50 mL), washed with saturated aqueous sodium hydrogen carbonate solution (3×50 mL), followed by brine (3×50 mL), dried (sodium sulfate), filtered and concentrated to a residue. Purification was achieved by silica gel chromatography (Luknova 120 g, 20 mL/min) using 10 to 60% ethyl acetate in hexanes over 60 minutes affording ethyl 2-(prop-1-ynyl)pyridin-3-ylcarbamate (420 mg, 2.06 mmol, 63% yield) as a gold oil. ¹H NMR (400 MHz, CDCl₃) ä (ppm): 8.45 (d, 1H), 8.21 (dd, 1H), 7.34 (br. s, 1H), 7.21 (dd, 1H), 4.27 (q, 2H), 2.19 (s, 3H), 1.34 (t, 3H).

To a solution of ethyl 2-(prop-1-ynyl)pyridin-3-ylcarbamate (400 mg, 1.96 mmol) in absolute ethanol (653 µL) was added solid sodium hydroxide (400 mg, 5.88 mmol). The reaction was heated to 80° C. for 1.5 hours, after which the reaction mixture was cooled, diluted in water, extracted with dichloromethane (3×50 mL), dried (sodium sulfate), filtered and concentrated to a pink solid. This solid was isolated ~90% pure as 2-methyl-1H-pyrrolo[3,2-b]pyridine (250 mg, 1.70 mmol, 87% yield), and used without further purification in the next step. ¹H NMR (400 MHz, CDCl₃) ä (ppm): 8.39 (dd, 1H), 8.22 (br. s, 1H), 7.55 (d, 1H), 7.02 (dd, 1H), 6.44 (s, 1H), 2.51 (s, 3H).

2-methyl-1H-indole-5-carbonitrile

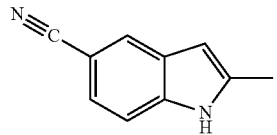

A suspension of 5-bromo-2-methyl-1H-indole (5.07 g, 24.1 mmol) and copper(I) cyanide (10.8 g, 121 mmol) was heated in N-methyl pyrrolidinone (34.5 mL) at 150° C. After 3 hours, the reaction was quenched by the addition of water (100 mL), and diluted in ethyl acetate (100 mL). Ethylenediamine (30 mL) was added and the biphasic mixture was stirred for 15 minutes. The organic layer was extracted with ethyl acetate (4×250 mL), washed with brine (3×200 mL), dried (sodium sulfate), filtered, and concentrated to a brown residue. Purification was achieved by column chromatography on silica gel (Luknova 40 g, 20 mL/min) using 25-60% ethyl acetate in hexanes over 60 minutes to afford 2-methyl-1H-indole-5-carbonitrile (1.85 g, 11.9 mmol, 49% yield) as a white solid. ¹H NMR (400 MHz, CDCl₃) δ (ppm): 8.15 (br. s, 1H), 7.86 (d, 1H), 7.31-7.55 (m, 2H), 6.30 (s, 1H), 2.48 (s, 3H).

(5-chloropyrazin-2-yl)methyl methanesulfonate

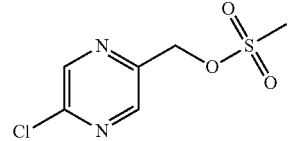

To a solution of 5-chloropyrazine-2-carboxylic acid (3.21 g, 20.3 mmol) in diethyl ether (20 mL) and methanol (20.0 mL) was added a 2M solution in diethyl ether of trimethylsilyldiazomethane (20.3 mL, 40.5 mmol). A vigorous bubbling was observed initially, and LCMS after 30 minutes indicated that the reaction was complete. Concentration of the reaction mixture afforded methyl 5-chloropyrazine-2-carboxylate (3.53 g, 20.5 mmol, 101% yield) as a tan solid. This material was shown to be >95% pure by ¹H NMR analysis and was used in the subsequent step without any purification. ¹H NMR (400 MHz, CDCl₃) δ (ppm): 9.09 (s, 1H), 8.70 (s, 1H), 4.04 (s, 3H).

To a 0° C. solution of methyl 5-chloropyrazine-2-carboxylate (3.50 g, 20.3 mmol) in tetrahydrofuran (101 mL) was added a 1M solution in tetrahydrofuran of diisobutylaluminum hydride (42.6 mL, 42.6 mmol). The reaction was stirred at 0° C. for 2 hours, after which it was quenched by the addition of methanol (2 mL). To this mixture was added saturated sodium-potassium tartrate solution, and the resulting reaction mixture was extracted with ethyl acetate (3×100 mL), dried (sodium sulfate), filtered and concentrated to brown residue. Purification was achieved by column chromatography on silica gel (Luknova 120 g, 20 mL/min) using 30 to 100% ethyl acetate in hexanes over 60 minutes to afford (5-chloropyrazin-2-yl)methanol (1.45 g, 10.0 mmol, 50% yield) as a tan solid. ¹H NMR (400 MHz, CDCl₃) ä (ppm): 8.56 (s, 1H), 8.45 (s, 1H), 4.84 (s, 3H), 2.79 (br. s, 1H).

To a 0° C. solution of (5-chloropyrazin-2-yl)methanol (648 mg, 4.48 mmol) in dichloromethane (12 mL) was added triethylamine (1.87 mL, 13.5 mmol) followed by dropwise addition of methanesulfonyl chloride (0.699 mL, 8.97 mmol). After 20 minutes, analysis by LCMS indicated the complete conversion to the mesylate product. The reaction mixture was concentrated to afford (5-chloropyrazin-2-yl)methyl methanesulfonate (787 mg, 3.53 mmol, 79% yield) as an oil. The material was used crude in the next step without further purification.

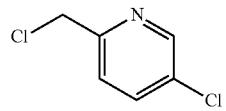

5-chloro-2(chloromethyl)pyridine

To a 0° C. solution of 5-chloropicolinic acid (3.00 g, 19.0 mmol) in dichloromethane (20 mL) was added sulfurous dichloride (2.78 mL, 38.1 mmol), after which the reaction was warmed to room temperature and stirred at that temperature for 4 hours. The reaction was then concentrated to dryness, then reconstituted in dichloromethane (5 mL). Methanol (10 mL) was added to the reaction mixture, and the reaction was allowed to stir at room temperature for 12 hours, after which it was then diluted with water, extracted with ethyl acetate (3×50 mL), washed with water, then washed with saturated sodium bicarbonate solution, dried (magnesium sulfate), filtered and concentrated. Purification was achieved by silica gel chromatography (ISCO 80 g) using 0 to 80% ethyl acetate in hexanes to afford methyl 5-chloropicolinate was as an off-white solid (2.75 g, 15.2 mmol, 80% yield).

To a 0° C. solution of methyl 5-chloropicolinate (2.70 g, 15.7 mmol) in methanol (50 mL) was added sodium borohydride (1.79 g, 47.2 mmol), after which the reaction was warmed to room temperature and stirred at that temperature for 4 hours. The reaction mixture was then concentrated to a residue which was treated with 1M hydrochloric acid solution (15 mL), extracted with ethyl acetate (3×100 mL), washed with water, then washed with saturated sodium bicarbonate solution, dried (magnesium sulfate), filtered and concentrated. Purification was achieved by silica gel chromatography (ISCO 80 g) using 0 to 60% ethyl acetate in hexanes to afford (5-chloropyridin-2-yl)methanol was as an off-white solid (2.15 g, 14.9 mmol, 95% yield).

To a 0° C. solution of (5-chloropyridin-2-yl)methanol (2.10 g, 14.6 mmol) in dichloromethane (10 mL) was added sulfurous dichloride (1.60 mL, 21.9 mmol) followed by N,N-dimethylformamide (50 µL), after which the reaction was warmed to room temperature and stirred at that temperature for 4 hours. The reaction mixture was then concentrated to a residue which was reconstituted in water (15 mL), ethyl acetate (15 mL), and saturated sodium bicarbonate solution (15 mL). The organic layers were separated and washed with saturated sodium chloride solution, dried (magnesium sulfate), filtered and concentrated. Purification was achieved by silica gel chromatography (ISCO 40 g) using 0 to 50% ethyl acetate in hexanes to afford 5-chloro-2(chloromethyl)pyridine as an light brown oil (2.11 g, 13.0 mmol, 89% yield).

3,5-Difluoro-2-(chloromethyl)pyridine

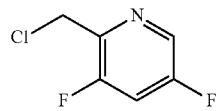

3,5-Difluoro-2-(chloromethyl)pyridine was prepared by using the procedure for the preparation of 3,5-dichloro-2-(chloromethyl)pyridine. $^1$H NMR (300 MHz, CDCl$_3$) δ (ppm): 8.31 (s, 1H), 7.22-7.26 (m, 1H), 4.69 (s, 2H).

3,5-dichloro-2-(chloromethyl)pyridine

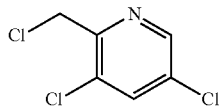

To a 0° C. solution of 5-chloropicolinic acid (5.00 g, 26.0 mmol) and N,N-dimethylformamide (1 drop) in dichloromethane (20 mL) was added oxalyl chloride (3.28 g, 26.0 mmol) dropwise, after which the reaction mixture was allowed to warm up to room temperature and stirred at that temperature for two hours. The reaction was then cooled again to 0° C., after which methanol (10 mL) was added dropwise to the reaction mixture, and the reaction was allowed to stir at room temperature for one hour where it was shown as complete by LCMS analysis. The reaction mixture was washed with saturated sodium bicarbonate solution, dried (magnesium sulfate), filtered and concentrated to afford methyl 3,5-dichloropyridine-2-carboxylate (5.36 g, 26.0 mmol, 100% yield) as a white solid.

To a 0° C. solution of methyl 3,5-dichloropyridine-2-carboxylate (5.00 g, 24.3 mmol) in methanol (40 mL) was added sodium borohydride (1.80 g, 48.5 mmol), after which the reaction was warmed to room temperature and stirred at that temperature for two hours. The reaction mixture was then quenched by the addition of water (5 mL), concentrated to a residue, reconstituted in water (60 mL), extracted with ethyl acetate (2×60 mL), dried (magnesium sulfate), filtered and concentrated to afford (3,5-dichloropyridin-2-yl)methanol (2.90 g, 16.3 mmol, 67% yield) as a viscous oil. This material was used in the subsequent step without any purification.

To a 0° C. solution of (3,5-dichloropyridin-2-yl)methanol (2.90 g, 16.3 mmol) in dichloromethane (50 mL) was added thionyl chloride (2.31 g, 19.6 mmol) dropwise, after which the reaction mixture was allowed to warm up to room temperature and stirred at that temperature for two hours. The reaction mixture was washed by the addition of saturated sodium bicarbonate solution (1×40 mL) and the organic layer was separated, dried (sodium sulfate), filtered and concentrated to a residue. Purification was achieved by silica gel chromatography using 9% ethyl acetate in hexanes to afford 3,5-dichloro-2-(chloromethyl)pyridine (2.40 g, 12.2 mmol, 75% yield) as an off-white solid. $^1$H NMR (300 MHz, CDCl$_3$) δ (ppm): 8.36 (s, 1H), 7.56 (s, 1H), 4.66 (s, 2H).

5-chloro-2-chloromethyl-3-fluoro-pyridine hydrochloride

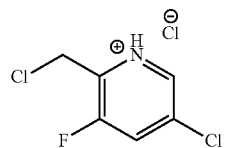

To a −15° C. solution of 5-chloro-3-fluoropyridine-2-carboxylic acid (4.80 g, 27.3 mmol) in tetrahydrofuran (96 mL) was added isobutyl chloroformate (3.73 g, 27.34 mmol), dropwise, followed by triethylamine (3.80 mL, 27.3 mmol), resulting in a tan suspension. This reaction mixture was stirred at −25° C. for 20 minutes, after which the solids were removed by filtration. The remaining filtrate was cooled 0° C., after which a solution of sodium borohydride (1.55 g, 40.1 mmol) in water (15 mL) was added, and the resulting reaction mixture was warmed to room temperature and stirred for 18 hours, then diluted with water (100 mL), adjusted to pH-7 with 2 mL of a 10% hydrochloric acid solution, extracted with ethyl acetate (2×80 mL), dried (sodium sulfate), filtered and concentrated. Purification was achieved by silica gel chromatography using 0.5% methanol in dichloromethane to afford (5-chloro-3-fluoro-pyridin-2-yl)-methanol (2.33 g, 14.4 mmol, 53.0%) as a white solid.

To a room temperature solution of (5-chloro-3-fluoro-pyridin-2-yl)-methanol (1.87 g, 11.6 mmol) in dichloromethane (19 mL) was added thionyl chloride (2.80 mL, 38.6 mmol), and the resulting suspension was refluxed for one hour. The reaction mixture was then concentrated, and the resulting residue was triturated with diethyl ether afford 5-chloro-2-chloromethyl-3-fluoro-pyridine hydrochloride as a tan solid (1.70 g, 7.85 mmol, 68% yield). $^1$H NMR (400 MHz, CDCl$_3$) δ (ppm): 8.41 (s, 1H), 7.51 (d, 1H), 4.71 (s, 2H).

4,5-dimethoxy-2-methyl-1H-indole

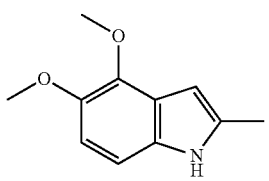

To a 0° C. solution of 4,5-dimethoxy-1H-indole-2-carboxylic acid (1.01 g, 4.97 mmol) in 1,4-dioxane (20 mL) was added, dropwise, a 2M in tetrahydrofuran solution of lithium aluminum hydride (12.43 mL, 50.2 mmol). The reaction mixture was warmed to room temperature for an hour then heated to reflux for 30 hours after which the reaction was cooled to 0° C., carefully quenched by the addition of ice water (5 mL), diluted with water (20 mL), extracted with ethyl acetate (3×20 mL), washed by saturated sodium chloride solution (3×20 mL), dried (sodium sulfate), filtered and concentrated to afford a solid. Purification was achieved by silica gel chromatography (Biotage 25 g) using 50 to 80% ethyl acetate in hexanes to afford (4,5-dimethoxy-1H-indol-2-yl)methanol (0.600 g, 2.89 mmol, 58% yield) as a solid.

To a room temperature solution of (4,5-dimethoxy-1H-indol-2-yl)methanol (100 mg, 0.483 mmol) in dichloromethane (5 mL) was added triethylsilane (0.462 mL, 2.90 mmol) followed by 2,2,2-trifluoroacetic acid (0.480 mL, 6.27 mmol). The resulting reaction mixture was stirred at room temperature for two hours (after which it was shown to be complete by LCMS analysis), quenched by the addition of saturated sodium chloride solution, extracted with dichloromethane (3×15 mL) washed with saturated sodium chloride solution (3×15 mL), dried (sodium sulfate), filtered and concentrated to a solid. Purification was achieved by column chromatography (Biotage, 10 g) using 10 to 80% ethyl acetate in hexanes to afford 4,5-dimethoxy-2-methyl-1H-indole (50.0 mg, 0.262 mmol, 54% yield) as a solid.

2-methyl-1H-pyrrolo[3,2-c]pyridine

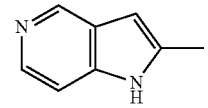

Prop-1-yne (1.06 mL, 18.7 mmol) was condensed at −78° C., after which a reddish-brown solution of tert-butyl 3-iodopyridin-4-ylcarbamate (2.00 g, 6.25 mmol, Alfa Aesar), copper (I) iodide (0.119 g, 0.625 mmol), bis(triphenylphosphine)palladium (II) chloride (0.219 g, 0.312 mmol), and triethylamine (4.79 mL, 34.4 mmol) in N,N-dimethylformamide (5.3 mL) was added. The reaction became olive green upon addition at −78° C., and was then warmed to room temperature and stirred at room temperature for one hour. The reaction was then shown to be complete by LCMS analysis, after which the reaction mixture was diluted in water, extracted with ethyl acetate (3×50 mL), dried (sodium sulfate), filtered and concentrated to a brown residue which was purified on silica gel (ISCO 80 g, 20 mL/min) using 10 to 50% ethyl acetate in hexanes over 60 minutes. The product, tert-butyl 3-(prop-1-ynyl)pyridin-4-ylcarbamate (1.54 g, 6.63 mmol, 106% yield) was isolated as a gold oil (trapped with ~6% ethyl acetate by $^1$H NMR). $^1$H NMR (400 MHz, CDCl$_3$) δ (ppm): 8.47 (s, 1H), 8.35 (d, 1H), 8.05 (d, 1H), 7.31 (br. s, 1H), 2.18 (s, 3H), 1.55 (s, 9H).

To a solution of tert-butyl 3-(prop-1-ynyl)pyridin-4-ylcarbamate (1.54 g, 6.63 mmol, with 6% residual ethyl acetate) in MeOH (14.7 mL) was added 1,8-diazabicyclo[5.4.0]undec-7-ene (3.00 mL, 19.9 mmol). The reaction was then stirred at 70° C. for 60 hours, after which it was complete by LCMS analysis after which it was concentrated and purified directly on silica gel (Luknova 80 g, 20 mL/min) using 3 to 10% methanol in dichloromethane over 45 minutes. The product, 2-methyl-1H-pyrrolo[3,2-c]pyridine (729 mg, 5.52 mmol, 83% yield) was isolated as a tan solid. $^1$H NMR (400 MHz, CD$_3$OD) δ (ppm): 8.60 (d, 1H), 8.03 (d, 1H), 7.29 (m, 1H), 6.30 (s, 1H), 2.45 (s, 3H).

2-(3-fluoro-4-methoxyphenyl)hydrazine hydrochloride

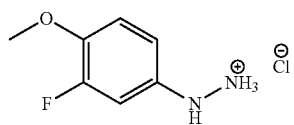

This compound was synthesized as a white solid in 54% yield staring from 3-fluoro-4-methoxyaniline using general procedure H. As part of the purification/isolation process, the hydrazine hydrochloride salt that is generated using general procedure H was reconstituted in water (100 mL) and a 3M aqueous sodium hydroxide solution (200 mL), extracted with diethyl ether (2×200 mL), washed with saturated sodium bicarbonate solution (2×100 mL), washed successively with water (2×20 mL) and saturated sodium chloride solution (2×20 mL), dried (sodium sulfate), filtered and concentrated to afford 2-(3-fluoro-4-methoxyphenyl)hydrazine as a light yellow solid (15.0 g, 96.1 mmol, 54% yield). A portion of 2-(3-fluoro-4-methoxyphenyl)hydrazine (5.00 g, 32.0 mmol) was dissolved in absolute ethanol (50 mL), to which a solution hydrogen chloride (15 mL, 2.5M in ethanol) was added. The resulting precipitate was filtered, washed with ethyl acetate (2×40 mL), and dried to afford 2-(3-fluoro-4-methoxyphenyl)hydrazine hydrochloride as an off-white solid (4.7 g).

1-(4-chlorobenzyl)-3-(2-(2-methoxypyridin-4-ylamino)-2-oxoacetyl)-2-methyl-1H-indole-5-carboxylic acid (4)

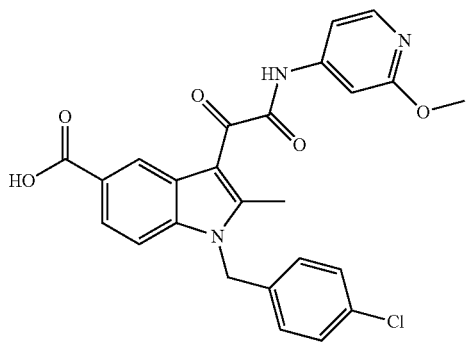 [SMILES: COc1cc(NC(=O)C(=O)c2c(C)n(Cc3ccc(Cl)cc3)c3ccc(C(=O)O)cc23)ccn1]

To a slurry of 1-(4-chlorobenzyl)-2-methyl-1H-indole-5-carboxylic acid (350 mg, 1.17 mmol) in diethyl ether (50 mL) and methanol (50.0 mL) was added a 2M solution in diethyl ether of trimethylsilyldiazomethane (2.92 mL, 5.84 mmol). The reaction was stirred at room temperature for 30 minutes, after which the slurry became homogeneous and gold in color. The reaction mixture was concentrated to afford the product, methyl 1-(4-chlorobenzyl)-2-methyl-1H-indole-5-carboxylate (350 mg, 1.12 mmol, 96% yield) as a tan solid, which was used in the subsequent step without any purification. $^1$H NMR (400 MHz, CDCl$_3$) δ (ppm): 8.16 (d, 1H), 7.66 (dd, 1H), 7.07-7.10 (m, 2H), 7.01 (d, 1H), 6.71 (d, 2H), 6.27 (s, 1H), 5.12 (s, 2H), 3.76 (s, 3H), 2.20 (s, 3H).

Methyl 1-(4-chlorobenzyl)-3-(2-(2-methoxypyridin-4-ylamino)-2-oxoacetyl)-2-methyl-1H-indole-5-carboxylate was synthesized as a white solid in 56% yield starting from methyl 1-(4-chlorobenzyl)-2-methyl-1H-indole-5-carboxylate using general procedure G. $^1$H NMR (400 MHz, CDCl$_3$) δ (ppm): 9.06 (s, 1H), 8.90 (s, 1H), 8.16 (d, 1H), 7.97 (dd, 1H), 7.24-7.30 (m, 4H), 7.19 (dd, 1H), 6.95 (d, 2H), 5.40 (s, 2H), 3.97 (s, 3H), 3.94 (s, 3H), 2.71 (s, 3H).

To a solution of methyl 1-(4-chlorobenzyl)-3-(2-(2-methoxypyridin-4-ylamino)-2-oxoacetyl)-2-methyl-1H-indole-5-carboxylate (46.8 mg, 0.0950 mmol) in tetrahydrofuran (3 mL) and water (3 mL) was added a 1M solution of aqueous sodium hydroxide (0.285 mL, 0.285 mmol). The reaction mixture was stirred at room temperature for 30 minutes, after which additional 1M solution of aqueous sodium hydroxide (0.285 mL, 0.285 mmol) was added. After stirring at room temperature for 30 minutes, the reaction mixture was heated to 60° C. for 20 minutes, then dropped to 40° C. and stirred at this temperature overnight (14 hours). After cooling to room temperature, the tetrahydrofuran was removed, and the resulting residue was diluted in water, neutralized by the addition of aqueous 6M hydrochloric acid solution (95 μL), extracted with ethyl acetate (3×30 mL), dried (sodium sulfate), filtered and concentrated to afford a residue which was purified on silica gel (Luknova 12 g, 10 mL/min) using 3 to 9% MeOH in dichloromethane over 60 minutes affording 1-(4-chlorobenzyl)-3-(2-(2-methoxypyridin-4-ylamino)-2-oxoacetyl)-2-methyl-1H-indole-5-carboxylic acid (19.7 mg, 0.0410 mmol, 43% yield) as a gold solid. $^1$H NMR (400 MHz, CD$_3$OD) δ (ppm): 8.79 (s, 1H), 8.06 (s, 1H), 7.93 (dd, 1H), 7.45 (d, 1H), 7.31-7.33 (m, 3H), 7.24 (dd, 1H), 7.05 (d, 2H), 5.56 (s, 2H), 3.91 (s, 3H), 2.67 (s, 3H).

(1-(4-chlorobenzyl)-3-(2-(2-methoxypyridin-4-ylamino)-2-oxoacetyl)-2-methyl-1H-indol-5-yl)methyl acetate (10)

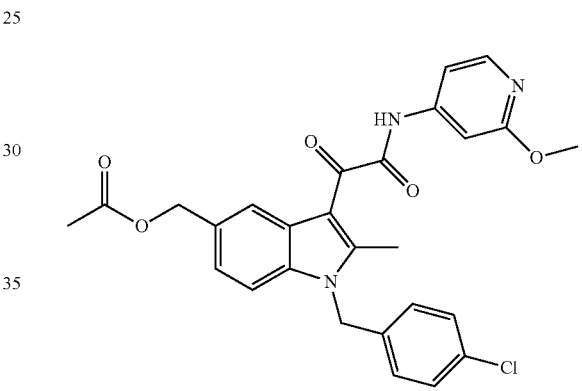

To a 0° C. solution of 1-(4-chlorobenzyl)-2-methyl-1H-indole-5-carboxylic acid (515 mg, 1.72 mmol) in tetrahydrofuran (10.7 mL) was added a 1M solution of borane-tetrahydrofuran complex (3.44 mL, 3.44 mmol) dropwise over 5 minutes. The reaction was maintained at 0° C. for 2 hours, after which additional 0.1M solution of borane-tetrahydrofuran complex (0.5 mL) solution was added. The reaction was allowed to warm up to temperature and after 30 minutes, the reaction mixture was quenched by the addition of methanol (2 mL), extracted with ethyl acetate (3×50 mL), washed with saturated sodium bicarbonate solution (3×50 mL), dried (sodium sulfate), filtered and concentrated to a clear residue which solidified to a white solid under vacuum. Purification of this material was achieved by silica gel column chromatography (Luknova 40 g, 20 mL/min) using 20 to 75% ethyl acetate over 40 minutes. Fractions 10-33 were collected and concentrated to afford (1-(4-chlorobenzyl)-2-methyl-1H-indol-5-yl)methanol (390 mg, 1.37 mmol, 79% yield) as a white solid. $^1$H NMR (400 MHz, CDCl$_3$) δ (ppm): 7.55 (s, 1H), 7.23 (d, 2H), 7.14 (m, 2H), 6.87 (d, 2H), 6.32 (s, 1H), 5.27 (s, 2H), 4.75 (d, 2H), 2.36 (s, 3H).

To a 0° C. solution of 1-(4-chlorobenzyl)-2-methyl-1H-indol-5-yl)methanol (482 mg, 1.69 mmol) in dichloromethane (15 mL) was added triethylamine (0.282 mL, 2.02 mmol), followed by acetic anhydride (0.167 mL, 1.77 mmol) and DMAP (10.3 mg, 0.0840 mmol). The reaction was stirred at 0° C. for 2 hours, the reaction was about 90% complete by LCMS analysis. The reaction was stored in the freezer for 12 hours, after which it was extracted with dichloromethane (3×50 mL), dried (sodium sulfate), filtered and concentrated to afford (1-(4-chlorobenzyl)-2-methyl-1H-indol-5-yl)methyl acetate (512 mg, 1.562 mmol, 93% yield) as a yellow oil. This material was used in the next step without further purification. $^1$H NMR (400 MHz, CDCl$_3$) δ (ppm): 7.56 (s, 1H), 7.23 (d, 2H), 7.10-7.16 (m, 2H), 6.88 (d, 2H), 6.33 (s, 1H), 5.26 (s, 2H), 5.18 (s, 2H), 2.35 (s, 3H), 2.08 (s, 3H).

(1-(4-chlorobenzyl)-3-(2-(2-methoxypyridin-4-ylamino)-2-oxoacetyl)-2-methyl-1H-indol-5-yl)methyl acetate was synthesized as a white solid in 67% yield starting from methyl 1-(4-chlorobenzyl)-2-methyl-1H-indole-5-carboxylate using general procedure G. $^1$H NMR (400 MHz, CDCl$_3$) δ (ppm): 9.02 (s, 1H), 8.22 (s, 1H), 8.15 (s, 1H), 7.21-7.29 (m, 5H), 7.16 (dd, 1H), 6.94 (d, 2H), 5.37 (s, 2H), 5.22 (s, 2H), 3.96 (s, 3H), 2.70 (s, 3H), 2.09 (s, 3H).

2-(1-(4-chlorobenzyl)-5-(hydroxymethyl)-2-methyl-1H-indol-3-yl)-N-(2-methoxypyridin-4-yl)-2-oxoacetamide (8)

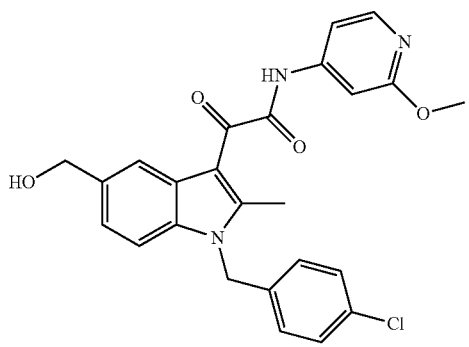 [SMILES: COc1cc(NC(=O)C(=O)c2c(C)n(Cc3ccc(Cl)cc3)c3ccc(CO)cc23)ccn1]

To a 0° C. solution of (1-(4-chlorobenzyl)-3-(2-(2-methoxypyridin-4-ylamino)-2-oxoacetyl)-2-methyl-1H-indo-5-yl)methyl acetate (173 mg, 0.342 mmol) in tetrahydrofuran (3.4 mL) and water (3.4 mL) was added an aqueous 3M solution of sodium hydroxide (342 µl, 1.03 mmol). After 2 hours, the reaction was warmed to room temperature, after which additional of 3M sodium hydroxide solution was added (114 µL, 0.343 mmol), and the reaction was stirred for 30 minutes at room temperature. The reaction mixture was then concentrated to remove the tetrahydrofuran and diluted in water, quenched by the addition of 6M hydrochloric acid solution (230 µL), extracted with ethyl acetate (3×50 mL), dried (sodium sulfate), filtered and concentrated to a solid. Purification on silica gel (Luknova 120 g, 20 mL/min) using 15 to 60% ethyl acetate in hexanes over 60 minutes afforded 2-(1-(4-chlorobenzyl)-5-(hydroxymethyl)-2-methyl-1H-indol-3-yl)-N-(2-methoxypyridin-4-yl)-2-oxoacetamide (121 mg, 0.257 mmol, 75% yield) as a pale yellow solid. $^1$H NMR (400 MHz, CD$_3$OD) δ (ppm): 8.04-8.07 (m, 2H), 7.42 (d, 1H), 7.22-7.32 (m, 5H), 7.04 (d, 2H), 5.53 (d, 2H), 4.88 (s, 2H), 3.92 (s, 3H), 2.67 (s, 3H).

2-(1-(4-chlorobenzyl)-5-((dimethylamino)methyl)-2-methyl-1H-indol-3-yl)-N-(2-methoxypyridin-4-yl)-2-oxoacetamide (26)

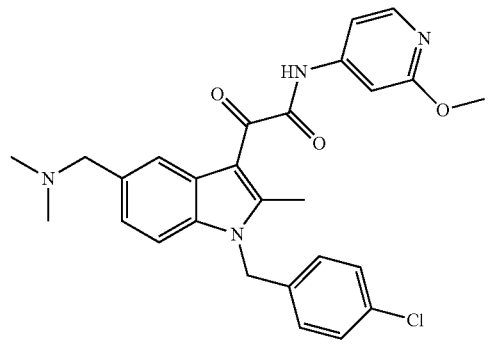

To a 0° C. solution of pyridinium chlorochromate (20.6 mg, 0.0950 mmol) adsorbed onto celite (200 mg) in dichloromethane (2 mL) was added a solution of 2-(1-(4-chlorobenzyl)-5-(hydroxymethyl)-2-methyl-1H-indol-3-yl)-N-(2-methoxypyridin-4-yl)-2-oxoacetamide (43.0 mg, 0.0930 mmol) in dichloromethane (6 mL). After 4 hours, an additional 20 mg of pyridinium chlorochromate (20 mg) adsorbed onto celite (200 mg) was added to the reaction, and the reaction mixture was stirred at room temperature overnight (15 hours), after which LCMS analysis indicated that the reaction was complete. The reaction was filtered through celite with dichloromethane as the solvent and the resulting filtrate was concentrated to afford 2-(1-(4-chlorobenzyl)-5-formyl-2-methyl-1H-indol-3-yl)-N-(2-methoxypyridin-4-yl)-2-oxoacetamide (40.5 mg, 0.0880 mmol, 95% yield) as an orange solid. This material was used in the subsequent step without any purification.

A 40% wt. solution of dimethylamine (23.0 µL, 0.181 mmol) and 2-(1-(4-chlorobenzyl)-5-formyl-2-methyl-1H-indol-3-yl)-N-(2-methoxypyridin-4-yl)-2-oxoacetamide (101 mg, 0.218 mmol) in 1,2-dichloroethane (3.6 mL) was sonicated for 5 minutes after which solid sodium triacetoxyborohydride (61.5 mg, 0.290 mmol) was added. The reaction mixture was stirred for one hour after which dimethylamine hydrochloride (22.2 mg, 0.272 mmol) was added portionwise (two additions over a one hour period). The reaction was then complete by LCMS analysis, after which it was stopped, quenched with saturated sodium bicarbonate solution (20 mL) extracted with diethyl ether (3×25 mL), and dried (sodium sulfate). Reconstitution of this crude product in dichloromethane afforded a precipitate which was filtered and further purified by silica gel chromatography using 0 to 100% ethyl acetate in hexanes to afford 2-(1-(4-chlorobenzyl)-5-((dimethylamino)methyl)-2-methyl-1H-indol-3-yl)-N-(2-methoxypyridin-4-yl)-2-oxoacetamide (3.7 mg, 7.5 mol, 4% yield) as a solid. $^1$H NMR (400 MHz, CD$_3$OD) δ (ppm): 8.07 (d, 1H), 7.98 (s, 1H), 7.44 (d, 1H), 7.31-7.33 (m, 3H), 7.22-7.26 (m, 2H), 7.05 (d, 2H), 5.54 (s, 2H), 3.92 (s, 3H), 3.63 (s, 2H), 2.68 (s, 3H), 2.27 (s, 6H).

2-(1-(4-chlorobenzyl)-2-methyl-5-((methylamino)methyl)-1H-indol-3-yl)-N-(2-methoxypyridin-4-yl)-2-oxoacetamide (25)

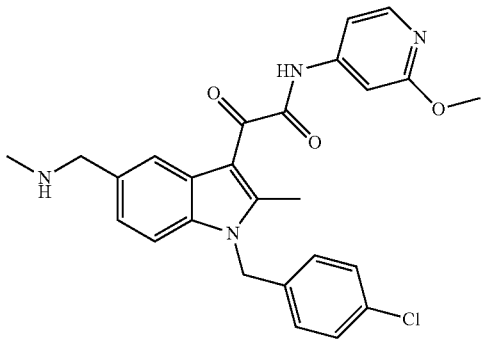

A 2M in tetrahydrofuran solution of methylamine (0.045 mL, 0.090 mmol) and 2-(1-(4-chlorobenzyl)-5-formyl-2-methyl-1H-indol-3-yl)-N-(2-methoxypyridin-4-yl)-2-oxoacetamide (0.0500 g, 0.108 mmol) in 1,2-dichloroethane (1.8 mL) was sonicated for 5 minutes after which solid sodium triacetoxyborohydride (31.0 mg, 0.144 mmol) was added. The reaction mixture was stirred for one hour after which it was complete by LCMS analysis. The reaction was quenched by the addition of saturated sodium bicarbonate solution (10 mL) extracted with diethyl ether (3×50 mL), washed with saturated sodium chloride solution, dried (sodium sulfate), filtered and concentrated to a residue. Purification was achieved by silica gel chromatography using 0 to 100% of a 1:49 triethylamine:ethyl acetate solution in hexanes to afford 2-(1-(4-chlorobenzyl)-2-methyl-5-((methylamino)methyl)-1H-indol-3-yl)-N-(2-methoxypyridin-4-yl)-2-oxoacetamide (11.6 mg, 0.024 mmol, 27% yield). $^1$H NMR (400 MHz, CD$_3$OD) δ (ppm): 8.06 (d, 1H), 8.02 (s, 1H), 7.60-7.72 (m, 1H), 7.42 (d, 1H), 7.22-7.32 (m, 4H), 7.04 (d, 2H), 5.53 (s, 2H), 3.91 (s, 3H), 3.81 (s, 2H), 3.21 (m, 1H), 2.67 (s, 3H), 2.37 (s, 3H).

2-(1-(4-chlorobenzyl)-5-(methoxymethyl)-2-methyl-1H-indol-3-yl)-N-(2-methoxypyridin-4-yl)-2-oxoacetamide (11)

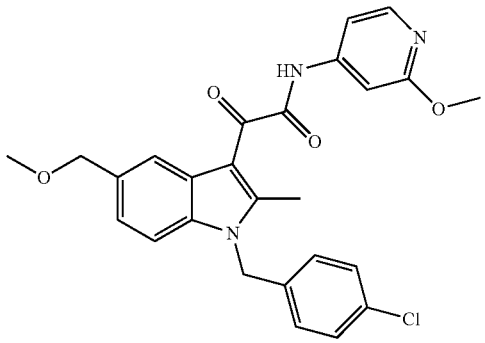

To a 0° C. solution of (1-(4-chlorobenzyl)-2-methyl-1H-indol-5-yl)methanol (126 mg, 0.440 mmol) in tetrahydrofuran (4.4 mL) was added a 60% oil dispersion of sodium hydride (21.11 mg, 0.528 mmol). After initial bubbling ceased, iodomethane (33 μL, 0.53 mmol) was added. The reaction mixture was warmed to room temperature and stirred for two hours, after which it was heated to 60° C. and stirred for 14 hours. About 15-20% of product was detected by LCMS analysis, so additional 60% sodium hydride (25 mg) was added, followed by additional iodomethane (100 μL), and the reaction mixture continued to stir at 60° C. After 24 hours from this second addition, a third addition of sodium hydride (25 mg) and iodomethane (100 μL) was added, after which the reaction was heated at 60° C. for 4 days, resulting in a ~1:1 mixture of starting material:product. The reaction was quenched by the addition of saturated ammonium chloride solution, extracted with dichloromethane (3×50 mL), dried (sodium sulfate), filtered and concentrated to a residue. Purification was achieved by silica gel chromatography (Luknova 40 g, 20 mL/min) using 15 to 50% ethyl acetate in hexanes over 40 minutes affording 1-(4-chlorobenzyl)-5-(methoxymethyl)-2-methyl-1H-indole (37.6 mg, 0.125 mmol, 29% yield) as a clear, colorless oil. The starting material, (1-(4-chlorobenzyl)-2-methyl-1H-indol-5-yl)methanol, was recovered in 33% yield. $^1$H NMR (400 MHz, CDCl$_3$) δ (ppm): 7.53 (s, 1H), 7.25 (d, 2H), 7.12-7.25 (m, 2H), 6.87 (d, 2H), 6.32 (s, 1H), 5.26 (s, 2H), 4.53 (s, 2H), 3.31 (s, 3H), 2.35 (s, 3H).

2-(1-(4-chlorobenzyl)-5-(methoxymethyl)-2-methyl-1H-indol-3-yl)-N-(2-methoxypyridin-4-yl)-2-oxoacetamide was synthesized as a yellow solid in 55% yield starting from 1-(4-chlorobenzyl)-5-(methoxymethyl)-2-methyl-1H-indole using general procedure G. $^1$H NMR (400 MHz, CDCl$_3$) δ (ppm): 8.13-8.17 (m, 2H), 7.25-7.29 (m, 3H), 7.23 (d, 2H), 7.16 (dd, 1H), 6.95 (d, 2H), 5.37 (s, 2H), 4.57 (s, 2H), 3.97 (s, 3H), 3.40 (s, 3H), 2.69 (s, 3H).

2-(1-(4-chlorobenzyl)-5-(diethylamino)-2-methyl-1H-indol-3-yl)-N-(2-methoxypyridin-4-yl)-2-oxoacetamide (24)

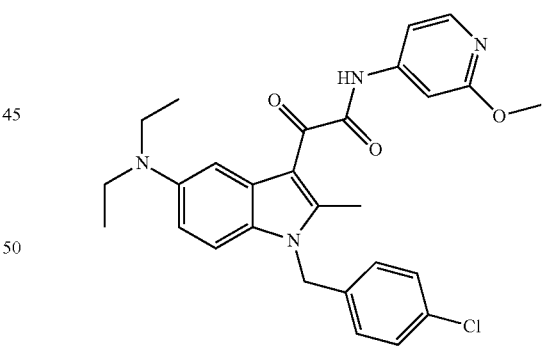

To a 0° C. solution of 1-(4-chlorobenzyl)-2-methyl-5-nitro-1H-indole (0.200 g, 0.665 mmol) in tetrahydrofuran (9.5 mL) was slowly added a 2M in tetrahydrofuran solution of lithium aluminum hydride (0.831 mL, 1.66 mmol). The reaction was allowed to come up to room temperature over one hour, after which it was shown as complete by LCMS analysis. The reaction mixture was carefully quenched by the careful addition of saturated ammonium bicarbonate solution (20 mL), extracted with dichloromethane (3×100 mL), dried (sodium sulfate), filtered and concentrated to a residue. Purification was achieved by silica gel chromatography using 0 to 100% ethyl acetate in hexanes to afford 1-(4-chlorobenzyl)-2-methyl-1H-indol-5-amine (0.160 g, 0.591 mmol, 89% yield) as a solid.

To a solution of 1-(4-chlorobenzyl)-2-methyl-1H-indol-5-amine (0.500 g, 1.85 mmol) in 1,2-dichloroethane (9.2 mL) was added acetaldehyde (0.156 mL, 2.77 mmol) followed by sodium triacetoxyborohydride (0.704 g, 3.32 mmol). The reaction mixture was stirred at room temperature for one hour, after which it was shown as complete by LCMS analysis. The reaction mixture was quenched by the addition of 10% sodium hydroxide solution, extracted with ether (3×50 mL) dried (sodium sulfate), filtered and concentrated to a residue. Purification was achieved by silica gel chromatography using 0 to 100% ethyl acetate in hexanes to afford 1-(4-chlorobenzyl)-N,N-diethyl-2-methyl-1H-indol-5-amine (0.0630 g, 0.193 mmol, 10% yield) as a solid.

To a solution of 1-(4-chlorobenzyl)-N,N-diethyl-2-methyl-1H-indol-5-amine (0.0630 g, 0.193 mmol) in dichloromethane (1.9 mL) at −78° C. was added oxalyl chloride (0.0190 mL, 0.212 mmol) resulting in a red reaction color. The reaction mixture was slowly warmed up to room temperature over several hours, after which it was concentrated to dryness. The resulting solid was reconstituted in dichloromethane (2 mL) and cooled to −78° C. To this mixture was added 2-methoxypyridin-4-amine (0.0240 g, 0.193 mmol), followed by triethylamine (0.054 mL, 0.39 mmol). LCMS analysis indicated exclusive presence of the carboxylic acid species, upon which the solvent was removed and the resulting residue was diluted in water. This solution was washed with ethyl acetate (1×30 mL), after which the aqueous layer was acidified with 3M aqueous hydrochloric acid solution (0.097 mL), back-extracted with ethyl acetate (3×50 mL), dried (sodium sulfate), filtered and concentrated to afford 2-(1-(4-chlorobenzyl)-5-(diethylamino)-2-methyl-1H-indol-3-yl)-2-oxoacetic acid (0.077 g, 0.193 mmol, 100% yield) as a solid. This material was used in the next step without any purification.

2-(1-(4-chlorobenzyl)-5-(diethylamino)-2-methyl-1H-indol-3-yl)-N-(2-methoxypyridin-4-yl)-2-oxoacetamide was synthesized as a solid in 31% yield starting from 2-(1-(4-chlorobenzyl)-5-(diethylamino)-2-methyl-1H-indol-3-yl)-2-oxoacetic acid using general procedure D. $^1$H NMR (400 MHz, CDCl$_3$) δ (ppm): 8.94 (s, 1H), 8.13 (d, 1H), 7.58 (d, 1H), 7.23-7.29 (m, 3H), 7.15 (d 1H), 7.06 (d, 1H), 6.96-7.00 (m, 2H), 6.73 (dd, 1H), 5.29 (s, 2H), 3.96 (s, 3H), 3.38 (q, 4H), 2.66 (s, 3H), 1.17 (t, 6H).

1-(4-chlorobenzyl)-3-(2-(2-methoxypyridin-4-ylamino)-2-oxoacetyl)-2-methyl-1H-indol-5-yl acetate (1)

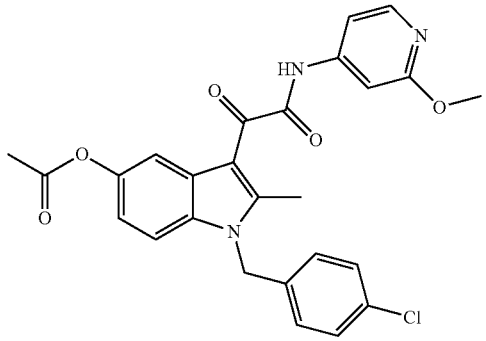 [SMILES: COc1cc(NC(=O)C(=O)c2c(C)n(Cc3ccc(Cl)cc3)c3ccc(OC(C)=O)cc23)ccn1]

1-(4-chlorobenzyl)-5-methoxy-2-methyl-1H-indole was synthesized using 2-methyl-5-(methoxy)-1H-indole (Aldrich) and 4-chlorobenzyl chloride (Aldrich) in DMSO as a 5:1 mixture of 1-(4-chlorobenzyl)-2-methyl-5-(methoxy)-1H-indole and 1,3-bis(4-chlorobenzyl)-2-methyl-5-(methoxy)-1H-indole in 69% yield using general procedure E.

To a room temperature solution of 1-(4-chlorobenzyl)-5-methoxy-2-methyl-1H-indole (174 mg, 0.609 mmol) in dichloromethane (2.1 mL) was added a 1M boron tribromide in dichloromethane solution (2.44 mL, 2.44 mmol). The reaction became brownish-red in color and was stirred at room temperature for one hour after which the reaction was complete. The reaction was then poured over ice and extracted with dichloromethane (3×40 mL), dried (sodium sulfate), filtered and concentrated to a pinkish-tan solid, 1-(4-chlorobenzyl)-2-methyl-1H-indol-5-ol (187 mg isolated, an aromatic impurity was identified in this reaction mixture which was not separated out). The mixture was carried on to the next step without further purification. $^1$H NMR (400 MHz, CDCl$_3$) δ (ppm): 7.19-7.25 (m, 3H), 6.97-7.03 (m, 2H), 6.87 (d, 2H), 6.66 (dd, 1H), 6.21 (s, 1H), 5.22 (s, 2H), 2.33 (s, 3H).

To a 0° C. solution of 1-(4-chlorobenzyl)-2-methyl-1H-indol-5-ol (185.3 mg, 0.682 mmol) in dichloromethane (10 mL) was added acetic anhydride (70.8 µl, 0.750 mmol) and triethylamine (105 µl, 0.750 mmol), followed by 4-dimethylaminopyridine (8.33 mg, 0.0680 mmol). After 30 minutes, another 0.3 equivalents of acetic anhydride and triethylamine were added. After 30 minutes, the reaction was complete, then diluted in water and extracted with dichloromethane (3×30 mL), dried (sodium sulfate), filtered and concentrated to a 5:1 mixture of afford 1-(4-chlorobenzyl)-2-methyl-1H-indol-5-yl acetate and 1,3-bis(4-chlorobenzyl)-2-methyl-1H-indol-5-yl acetate (186 mg, 0.593 mmol, 87% yield) as a waxy gum. The reaction was used in the next step without any purification. $^1$H NMR (400 MHz, CDCl$_3$) δ (ppm): 7.24-7.26 (m, 2H), 7.08-7.13 (m, 2H), 6.89 (d, 2H), 6.81 (dd, 1H), 6.21 (s, 1H), 5.25 (s, 2H), 2.34 (s, 3H), 2.31 (s, 3H).

1-(4-chlorobenzyl)-3-(2-(2-methoxypyridin-4-ylamino)-2-oxoacetyl)-2-methyl-1H-indol-5-yl acetate was synthesized using a 5:1 mixture of 1-(4-chlorobenzyl)-2-methyl-1H-indol-5-yl acetate and 1,3-bis(4-chlorobenzyl)-2-methyl-1H-indol-5-yl acetate (as described above) to afford the title product as a gold-colored solid in 50% yield using general procedure G. $^1$H NMR (400 MHz, CDCl$_3$) δ (ppm): 9.02 (br. s, 1H), 8.14 (d, 1H), 7.96 (d, 1H), 7.25-7.30 (m, 3H), 7.20 (d, 1H), 7.15 (dd, 1H), 6.95-7.00 (m, 3H), 5.31 (s, 2H), 3.96 (s, 3H), 2.67 (s, 3H), 2.33 (s, 3H).

2-(1-(4-chlorobenzyl)-5-hydroxy-2-methyl-1H-indol-3-yl)-N-(2-methoxypyridin-4-yl)-2-oxoacetamide (2)

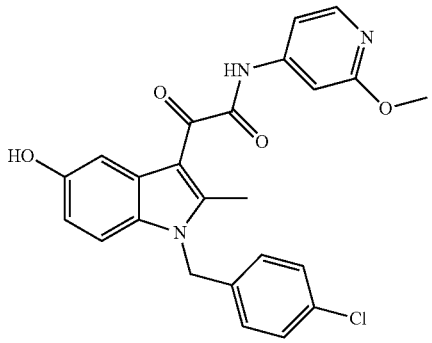 [SMILES: COc1cc(NC(=O)C(=O)c2c(C)n(Cc3ccc(Cl)cc3)c3ccc(O)cc23)ccn1]

To a solution of 1-(4-chlorobenzyl)-3-(2-(2-methoxypyridin-4-ylamino)-2-oxoacetyl)-2-methyl-1H-indol-5-yl acetate (76.0 mg, 0.154 mmol) in tetrahydrofuran (8 mL) and water (8.00 mL) was added solid lithium hydroxide hydrate (21.7 mg, 0.517 mmol). After one hour the reaction was shown as complete by LCMS analysis. The reaction was concentrated to remove tetrahydrofuran, acidified with aqueous 3N HCl solution (0.170 mL), extracted with dichloromethane (3×30 mL), dried (sodium sulfate), filtered and concentrated to 2-(1-(4-chlorobenzyl)-5-hydroxy-2-methyl-1H-indol-3-yl)-N-(2-methoxypyridin-4-yl)-2-oxoacetamide as a tan solid. A small UV-inactive impurity was detected, so the product was repurified on silica gel (Luknova 40 g, 20 mL/min) using 30 to 70% ethyl acetate in hexanes over 60 minutes to afford 2-(1-(4-chlorobenzyl)-5-hydroxy-2-methyl-1H-indol-3-yl)-N-(2-methoxypyridin-4-yl)-2-oxoacetamide (40.5 mg, 0.0900 mmol, 58% yield) as a solid. $^1$H NMR (400 MHz, CDCl$_3$) δ (ppm): 9.01 (br. s, 1H), 8.15 (d, 1H), 7.69 (d, 1H), 7.24-7.29 (m, 4H), 7.09 (d, 1H), 6.95 (d, 2H), 6.81 (dd, 1H), 5.33 (s, 2H), 3.97 (s, 3H), 2.68 (s, 3H).

1-(4-chlorobenzyl)-3-(2-(2-methoxypyridin-4-ylamino)-2-oxoacetyl)-N,N,2-trimethyl-1H-indole-5-carboxamide (6)

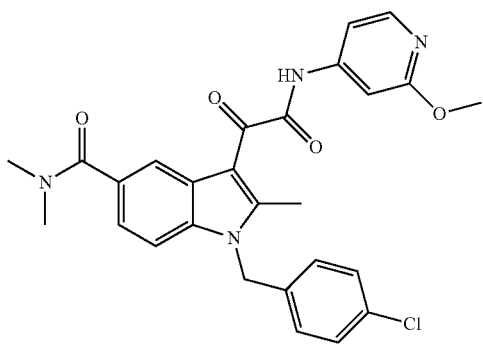

To slurry of 1-(4-chlorobenzyl)-2-methyl-1H-indole-5-carbonitrile (566 mg, 2.02 mmol) in absolute ethanol (5 mL) was added an aqueous 3M solution of sodium hydroxide (3.36 mL, 10.1 mmol). The reaction mixture was heated in the microwave at 170° C. for 15 minutes after which LCMS analysis of the reaction mixture indicated complete consumption of the starting material. The reaction mixture was diluted in water, washed with ethyl acetate (3×50 mL), and the aqueous layer was acidified with aqueous 3M hydrochloric acid solution, then back-extracted with ethyl acetate (3×50 mL), dried (sodium sulfate), filtered and concentrated to afford 1-(4-chlorobenzyl)-2-methyl-1H-indole-5-carboxylic acid (350 mg, 1.17 mmol, 58% yield) as a tan solid. The original organic washes from the pre-acidifed reaction mixture were concentrated to afford 1-(4-chlorobenzyl)-2-methyl-1H-indole-5-carboxamide (282 mg, 0.849 mmol, 42% yield) as an off-white solid. By $^1$H NMR, approximately 90% purity was detected of the amide product, and this material was not purified for the subsequent step. 1-(4-chlorobenzyl)-2-methyl-1H-indole-5-carboxylic acid: $^1$H NMR (400 MHz, CDCl$_3$) δ (ppm): 8.37 (s, 1H), 7.87 (d, 1H), 7.24 (d, 2H), 7.20 (d, 1H), 6.88 (d, 2H), 6.45 (s, 1H), 5.31 (s, 2H), 2.37 (s, 3H). [Carboxylic acid proton not observed]1-(4-chlorobenzyl)-2-methyl-1H-indole-5-carboxamide: $^1$H NMR (400 MHz, CDCl$_3$) δ (ppm): 8.07 (d, 1H), 7.60 (dd, 1H), 7.24 (d, 2H), 7.19 (d, 1H), 6.87 (d, 2H), 6.42 (s, 1H), 5.40-6.20 (v. br. s, 2H), 5.30 (s, 2H), 2.37 (s, 3H).

To a solution of potassium hydroxide (160 mg, 2.86 mmol) in DMSO (5 mL) was added 1-(4-chlorobenzyl)-2-methyl-1H-indole-5-carboxamide (219 mg, 0.733 mmol) followed by iodomethane (0.0940 mL, 1.50 mmol). The reaction was stirred at room temperature overnight (14 hours), after which the reaction mixture was quenched by the addition of ice, followed by saturated sodium chloride solution. The reaction mixture was extracted with dichloromethane (3×50 mL), dried (sodium sulfate), filtered and concentrated to afford a brown residue. Purification was achieved by silica gel chromatography (Luknova 40 g, 20 mL/min) using 10 to 60% ethyl acetate in hexanes over 60 minutes to afford 1-(4-chlorobenzyl)-N,N,2-trimethyl-1H-indole-5-carboxamide (139 mg, 0.425 mmol, 58% yield) as a white residue (which solidified on vacuum). 1H NMR (400 MHz, CDCl$_3$) δ (ppm): 7.64 (s, 1H), 7.13-7.22 (m, 4H), 6.85 (d, 2H), 6.35 (s, 1H), 3.00-3.19 (v. br. s, 6H), 5.26 (s, 2H), 2.34 (s, 3H).

Ethyl 2-(1-(4-chlorobenzyl)-5-(dimethylcarbamoyl)-2-methyl-1H-indol-3-yl)-2-oxoacetate was synthesized as a white solid in 47% yield starting from 1-(4-chlorobenzyl)-N,N,2-trimethyl-1H-indole-5-carboxamide and ethyl oxalyl chloride using general procedure F.

To a solution of 2-methoxypyridin-4-amine (39.5 mg, 0.319 mmol) in tetrahydrofuran (3 mL) at −30° C. was added a 1M in tetrahydrofuran solution of lithium bis(trimethylsilyl)amide (0.299 mL, 0.299 mmol). The reaction was stirred for 5 minutes, after which this cold anion solution was transferred to a solution of ethyl 2-(1-(4-chlorobenzyl)-5-(dimethylcarbamoyl)-2-methyl-1H-indol-3-yl)-2-oxoacetate (85.0 mg, 0.199 mmol) in tetrahydrofuran (5 mL) at −30° C. The reaction mixture was stirred for 1 hour, after which an additional solution of lithium 2-methoxypyridin-4-amide (3.0 equiv, generated by the addition of 700 μL of 1M lithium bis(trimethylsilyl)amide solution in tetrahydrofuran to 79.0 mg of 2-methoxypyridin-4-amine in 3 mL of tetrahydrofuran) was added. The reaction mixture was stirred at −30° C. for 1 hour, then warmed to room temperature. Upon achieving room temperature, T3P (50% solution in ethyl acetate, 1.5 mL) was added, and the reaction mixture was allowed to stir overnight (14 h), then quenched by the addition of saturated ammonium chloride solution, extracted with dichloromethane (3×50 mL), dried (sodium sulfate), filtered and concentrated to a residue. Purification using silica gel chromatography (Luknova 25 g, 20 mL/min) using 15 to 90% ethyl acetate in hexanes afforded 1-(4-chlorobenzyl)-3-(2-(2-methoxypyridin-4-ylamino)-2-oxoacetyl)-N,N,2-trimethyl-1H-indole-5-carboxamide (5.7 mg, 11 µmol, 5% yield) as a yellow solid. ¹H NMR (400 MHz, CDCl₃) δ (ppm): 9.00 (s, 1H), 8.20 (s, 1H), 8.08 (d, 1H), 7.19-7.31 (m, 5H), 7.09 (dd, 1H), 6.88 (d, 2H), 5.31 (s, 2H), 3.90 (s, 3H), 3.08 (s, 3H), 3.03 (s, 3H), 2.63 (s, 3H).

2-(5-acetyl-1-(4-chlorobenzyl)-2-methyl-1H-indol-3-yl)-N-(2-methoxypyridin-4-yl)-2-oxoacetamide (5)

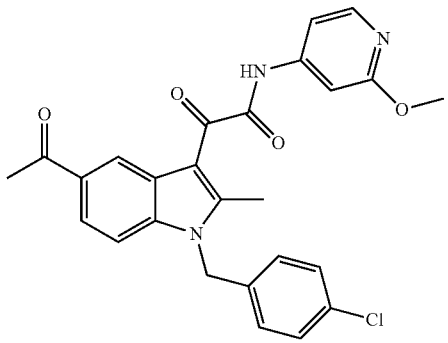 [SMILES: COc1cc(NC(=O)C(=O)c2c(C)n(Cc3ccc(Cl)cc3)c3ccc(C(C)=O)cc23)ccn1]

Methyl 2-(2-methyl-1H-indol-3-yl)-2-oxoacetate was synthesized as a pink solid in 93% yield starting from 2-methylindole using general procedure A.

To a solution of methyl 2-(2-methyl-1H-indol-3-yl)-2-oxoacetate (722 mg, 3.32 mmol) in dichloromethane (16.6 mL) was added acetyl chloride (1.65 mL, 23.4 mmol) followed by aluminum trichloride (1.33 g, 9.97 mmol). After 3 hours, about 40% conversion was observed to an acetylated product (LCMS), after which the reaction was allowed to stir at room temperature for 16 hours. The reaction mixture was then poured over ice, diluted in dichloromethane, then filtered. The layers were separated and the organic layer was extracted with dichloromethane (3×50 mL), dried (sodium sulfate), filtered and concentrated to a purple solid. First-pass purification was achieved using silica gel chromatography (Luknova 120 g, 20 mL/min) using 10 to 90% ethyl acetate in hexanes over 60 minutes to afford a 2.4/1 mixture of methyl 2-(5-acetyl-2-methyl-1H-indol-3-yl)-2-oxoacetate (mass of mixture: 370 mg). Recrystallization from 100% ethyl acetate afforded pure methyl 2-(5-acetyl-2-methyl-1H-indol-3-yl)-2-oxoacetate (233 mg, 0.638 mmol, 19% yield) as a yellow solid. The remaining mother liquor was concentrated and was shown to be roughly a 1:2 mixture of 5-acetyl:6-acetyl products, and was not pursued further. ¹H NMR (400 MHz, CDCl₃) δ (ppm): 8.94 (br. s, 1H), 8.70 (s, 1H), 7.94 (d, 1H), 7.38 (d, 1H), 4.02 (s, 3H), 2.70 (s, 3H), 2.69 (s, 3H).

Methyl 2-(5-acetyl-1-(4-chlorobenzyl)-2-methyl-1H-indol-3-yl)-2-oxoacetate was synthesized as a white solid in 93% yield starting from methyl 2-(5-acetyl-2-methyl-1H-indol-3-yl)-2-oxoacetate, 4-chlorobenzyl chloride, and acetonitrile as solvent using general procedure B. ¹H NMR (400 MHz, CDCl₃) δ (ppm): 8.66 (d, 1H), 7.93 (dd, 1H), 7.28-7.31 (m, 3H), 6.92 (d, 2H), 5.38 (s, 2H), 4.03 (s, 3H), 2.68 (s, 3H), 2.64 (s, 3H).

To a slurry of methyl 2-(5-acetyl-1-(4-chlorobenzyl)-2-methyl-1H-indol-3-yl)-2-oxoacetate (32.5 mg, 0.0850 mmol) in methyl tert-butyl ether (1.5 mL) and tetrahydrofuran (1.5 mL) was added an aqueous 1M solution of sodium hydroxide (0.085 mL, 0.085 mmol). After 2 hours, the solvents were removed and the solid sodium salt of the ketoacid was filtered, affording 27.8 mg of this intermediate. The sodium salt (27.8 mg) was diluted in acetonitrile (5 mL). Triethylamine (0.0590 mL, 0.423 mmol), 2-methoxypyridin-4-amine (11.2 mg, 0.0900 mmol), then a 50% ethyl acetate solution of T3P (0.202 mL, 0.317 mmol) were added. After 2 hours of stirring, additional triethylamine (59 µL) and T3P solution (202 µL) were added and the reaction was stirred at 65° C. for 12 hours. The reaction mixture was then cooled to room temperature, extracted with dichloromethane (3×30 mL), dried (sodium sulfate), filtered and concentrated to a yellow/brown residue. Purification on silica gel (Luknova 25 g, 20 mL/min) using 20 to 80% ethyl acetate in hexanes over 45 minutes afforded 2-(5-acetyl-1-(4-chlorobenzyl)-2-methyl-1H-indol-3-yl)-N-(2-methoxypyridin-4-yl)-2-oxoacetamide (25.8 mg, 0.0540 mmol, 64% yield) as a yellow solid. ¹H NMR (400 MHz, CDCl₃) δ (ppm): 9.38 (s, 1H), 8.85 (d, 1H), 8.23 (d, 1H), 7.92 (dd, 1H), 7.41 (s, 1H), 7.23-7.30 (m, 4H), 6.94 (d, 1H), 5.40 (s, 2H), 4.00 (s, 3H), 2.71 (s, 3H), 2.68 (s, 3H).

Tert-butyl(1-(4-chlorobenzyl)-3-(2-((2-methoxypyridin-4-yl)amino)-2-oxoacetyl)-2-methyl-1H-indol-5-yl)(methyl)carbamate (7)

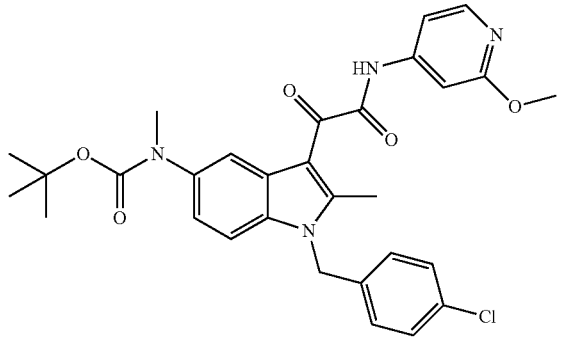 [SMILES: COc1cc(NC(=O)C(=O)c2c(C)n(Cc3ccc(Cl)cc3)c3ccc(N(C)C(=O)OC(C)(C)C)cc23)ccn1]

A solution of 1-(4-chlorobenzyl)-2-methyl-1H-indole-5-carboxylic acid (388 mg, 1.29 mmol), diphenyl phosphorazidate (0.335 mL, 1.55 mmol), and triethylamine (0.397 mL, 2.85 mmol) in t-Butanol (5.6 mL) was heated to reflux for 3 hours, after which it was cooled to room temperature, diluted in ethyl acetate and filtered through celite. The filtrate was concentrated and then purified on silica gel (Luknova 40 g, 20 mL/min) using 5 to 40% ethyl acetate over 60 minutes. The product, tert-butyl 1-(4-chlorobenzyl)-2-methyl-1H-indol-5-ylcarbamate (88.4 mg, 0.238 mmol, 18% yield) was isolated as an off-white solid. ¹H NMR (400 MHz, CDCl₃) δ (ppm): 7.61 (br. s, 1H), 7.22 (d, 2H), 6.98-7.06 (m, 2H), 6.85 (d, 2H), 6.41 (br. s, 1H), 6.26 (s, 1H), 5.23 (s, 2H), 2.32 (s, 3H), 1.52 (s, 9H).

To a 0° C. solution of tert-butyl 1-(4-chlorobenzyl)-2-methyl-1H-indol-5-ylcarbamate (88.4 mg, 0.238 mmol) in N,N-dimethylformamide (1.5 mL) was added iodomethane (0.0190 mL, 0.310 mmol), followed by a 60% dispersion of sodium hydride (10.5 mg, 0.262 mmol). The reaction mixture was warmed to room temperature and allowed to stir overnight, after which it was diluted in water, extracted with dichloromethane (3×50 mL), then ethyl acetate (1×50), washed with water (4×100 mL), dried (sodium sulfate), filtered and concentrated to a white foam. The product, tert-butyl 1-(4-chlorobenzyl)-2-methyl-1H-indol-5-yl (methyl)carbamate (78.5 mg, 0.204 mmol, 86% yield) was used in the subsequent step without any purification. $^1$H NMR (400 MHz, CDCl$_3$) δ (ppm): 7.36 (br. s, 1H), 7.23 (d, 2H), 7.08 (d, 2H), 6.89 (d, 2H), 6.29 (s, 1H), 5.24 (s, 2H), 3.28 (s, 3H), 2.34 (s, 3H), 1.43 (s, 9H).

Tert-butyl 1-(4-chlorobenzyl)-3-(2-(2-methoxypyridin-4-ylamino)-2-oxoacetyl)-2-methyl-1H-indol-5-yl(methyl)carbamate was synthesized as a pale yellow solid in 51% yield starting from tert-butyl 1-(4-chlorobenzyl)-2-methyl-1H-indol-5-yl(methyl)carbamate using general procedure G. $^1$H NMR (400 MHz, CDCl$_3$) δ (ppm): 9.01 (s, 1H), 8.14 (d, 1H), 8.06 (s, 1H), 7.24-7.30 (m, 3H), 7.14-7.16 (m, 3H), 6.96 (d, 2H), 5.32 (s, 2H), 3.96 (s, 3H), 3.32 (s, 3H), 2.69 (s, 3H), 1.44 (s, 9H).

2-(1-(4-chlorobenzyl)-2-methyl-5-(methylamino)-1H-indol-3-yl)-N-(2-methoxypyridin-4-yl)-2-oxoacetamide (9)

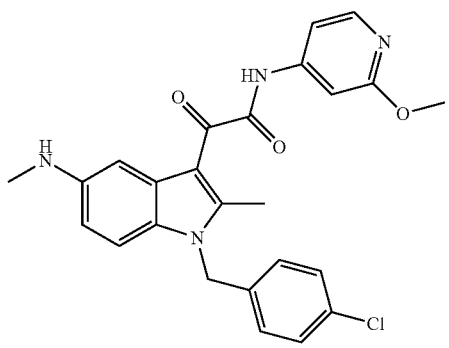

A solution of tert-butyl 1-(4-chlorobenzyl)-3-(2-(2-methoxypyridin-4-ylamino)-2-oxoacetyl)-2-methyl-1H-indol-5-yl(methyl)carbamate (58.0 mg, 0.103 mmol) and trifluoroacetic acid (0.159 mL, 2.06 mmol) in dichloromethane (5 mL) was heated to 80° C. for 20 minutes, after which LCMS analysis indicated that the deprotection was complete. The reaction mixture was poured over ice and neutralized by the addition of saturated aqueous sodium bicarbonate solution, extracted with dichloromethane (3×50 mL), dried (sodium sulfate), filtered and concentrated to afford 2-(1-(4-chlorobenzyl)-2-methyl-5-(methylamino)-1H-indol-3-yl)-N-(2-methoxypyridin-4-yl)-2-oxoacetamide (32.0 mg, 0.0691 mmol, 67%) an orange solid. The material was not purified, as it was shown to be >95% pure by 1H NMR analysis. 1H NMR (400 MHz, CDCl$_3$) δ (ppm): 8.99 (br. s, 1H), 8.13 (d, 1H), 7.48 (d, 1H), 7.24-7.28 (m, 3H), 7.15 (dd, 1H), 7.03 (d, 2H), 6.95 (d, 1H), 6.60 (dd, 1H), 5.29 (s, 2H), 3.96 (s, 3H), 3.74 (br. s, 1H), 2.89 (s, 3H), 2.65 (s, 3H).

2-(1-((6-chloropyridazin-3-yl)methyl)-5-methoxy-2-methyl-1H-indol-3-yl)-N-(2-methoxypyridin-4-yl)-2-oxoacetamide (86)

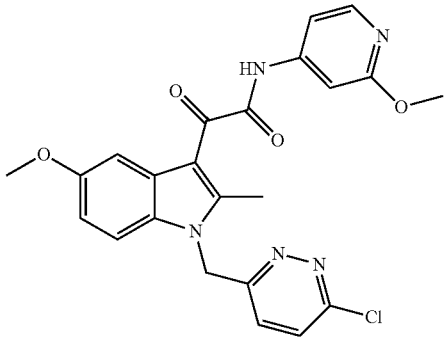

3-chloro-6-(chloromethyl)pyridazine was synthesized in 49% according to J. Med. Chem. 2005, 48, 1367-1383.

1-((6-chloropyridazin-3-yl)methyl)-5-methoxy-2-methyl-1H-indole was synthesized as a solid in 50% yield starting from 5-methoxy-2-methyl-1H-indole, 3-chloro-6-(chloromethyl)pyridazine, and DMSO as the solvent using general procedure E.

To a −78° C. solution of 1-((6-chloropyridazin-3-yl)methyl)-5-methoxy-2-methyl-1H-indole (300 mg, 1.04 mmol) in dichloromethane (10 mL) was added oxalyl dichloride (0.136 mL, 1.56 mmol), after which the resulting reaction mixture was maintained at −78° C. for one hour then warmed to room temperature. The reaction was concentrated to dryness, after which it was reconstituted in dichloromethane (10 mL) and cooled to −78° C. To this solution was added 2-methoxypyridin-4-amine (131 mg, 1.05 mmol) and triethylamine (0.220 mL, 1.56 mmol), after which the reaction mixture was stirred at −78° C. for 30 minutes, then warmed to room temperature and stirred at that temperature for 24 hours. LCMS analysis of the reaction mixture indicated a low conversion to the desired ketoamide, but indicated a sizeable amount of 2-(1-((6-chloropyridazin-3-yl)methyl)-5-methoxy-2-methyl-1H-indol-3-yl)-2-oxoacetic acid in the reaction mixture. As a result, N,N-dimethylformamide (5 mL), triethylamine (0.730 mL, 5.21 mmol), 2-methoxypyridin-4-amine (0.0660 mg, 0.527 mmol) and 2,4,6-tripropyl-1,3,5,2,4,6-trioxatriphosphinane 2,4,6-trioxide (995 mg, 3.13 mmol) were added to increase the conversion to the desired ketoamide. The mixture was stirred at room temperature for two hours, after which it was diluted in water, extracted with ethyl acetate (3×50 mL), washed with water (1×50 mL), washed with saturated sodium chloride solution (1×50 mL), dried (sodium sulfate), filtered and concentrated to a residue. Purification was achieved by silica gel chromatography (ISCO 40 g) using 5 to 80% ethyl acetate in hexanes to give 2-(1-((6-chloropyridazin-3-yl)methyl)-5-methoxy-2-methyl-1H-indol-3-yl)-N-(2-methoxypyridin-4-yl)-2-oxoacetamide (98.0 mg, 0.210 mmol, 20% yield) as a yellow solid. $^1$H NMR (400 MHz, CDCl$_3$) δ (ppm): 9.08 (s, 1H), 8.18 (s, 1H), 7.78 (s, 1H), 7.45 (s, 1H), 7.26 (s, 1H, isochronous with CDCl$_3$), 7.19 (d, 2H), 6.84 (m, 2H), 5.89 (s, 2H), 4.00 (s, 3H), 3.90 (s, 3H), 2.70 (s, 3H).

2-(1-(4-chlorobenzyl)-6-methoxy-2-methyl-1H-indol-3-yl)-N-(2-methoxypyridin-4-yl)-2-oxoacetamide (48)

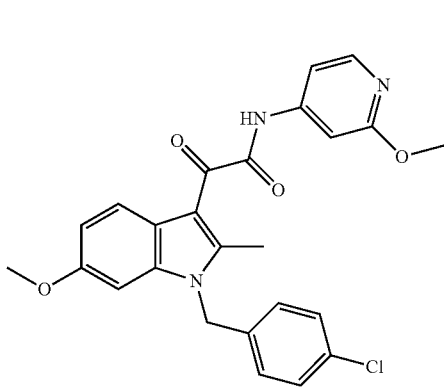

To a 0° C. solution of methyl 2-(1-(4-chlorobenzyl)-6-methoxy-2-methyl-1H-indol-3-yl)-2-oxoacetate (670 mg, 1.80 mmol) in acetonitrile (10 mL) was added a solution of sodium hydroxide (72.1 mg, 1.80 mmol) in water (4 mL). The reaction was stirred at 0° C. for one hour, after which it was complete by LCMS analysis. The reaction mixture was neutralized by the addition of 0.5M hydrochloric acid solution until a pH of 3 was achieved, diluted in water, extracted with ethyl acetate (3×10 mL), washed with saturated sodium chloride solution (3×10 mL), dried (sodium sulfate), filtered and concentrated to afford 2-(1-(4-chlorobenzyl)-6-methoxy-2-methyl-1H-indol-3-yl)-2-oxoacetic acid (610 mg, 1.70 mmol, 95% yield) as a solid. This material was used in the subsequent step without any purification.

To a −30° C., nitrogen-purged solution of 2-(1-(4-chlorobenzyl)-6-methoxy-2-methyl-1H-indol-3-yl)-2-oxoacetic acid (600 mg, 1.68 mmol) in dichloromethane (5 mL) was added oxalyl chloride (234 mg, 1.85 mmol). The reaction was stirred at −30° C. for 30 minutes, then allowed to warm to room temperature, after which it was allowed to stir for 12 hours. The reaction mixture was concentrated to dryness, reconstituted in dichloromethane (5 mL) and cooled to −30° C. To this solution was triethylamine (0.326 mL, 2.35 mmol) followed by 2-methoxypyridin-4-amine (312 mg, 2.52 mmol), after which the reaction mixture was stirred at −30° C. for 30 minutes, then allowed to warm to room temperature, after which it was allowed to stir for 12 hours. The reaction was then diluted in water (20 mL), extracted with ethyl acetate (3×20 mL), washed with saturated sodium chloride solution (3×10 mL), then dried (sodium sulfate), filtered and concentrated to afford a solid. Purification was achieved by silica gel chromatography (Biotage 25 g) using 20 to 80% ethyl acetate in hexanes to afford 2-(1-(4-chlorobenzyl)-6-methoxy-2-methyl-1H-indol-3-yl)-N-(2-methoxypyridin-4-yl)-2-oxoacetamide (78.0 mg, 0.168 mmol, 10% yield) as a brown solid. $^1$H NMR (400 MHz, CDCl$_3$) δ (ppm): 9.01 (br. s, 1H), 8.14 (d, 1H), 8.11 (d, 1H), 7.29 (d, 2H), 7.24 (s, 1H), 7.14 (d, 1H), 6.97 (d, 2H), 6.92 (d, 1H), 6.69 (d, 1H), 5.31 (s, 2H), 3.96 (s, 3H), 3.81 (s, 3H), 2.67 (s, 3H).

2-(1-(4-chlorobenzyl)-5-hydroxy-2-methyl-1H-indol-3-yl)-N-(3-chlorophenyl)-2-oxoacetamide (71)

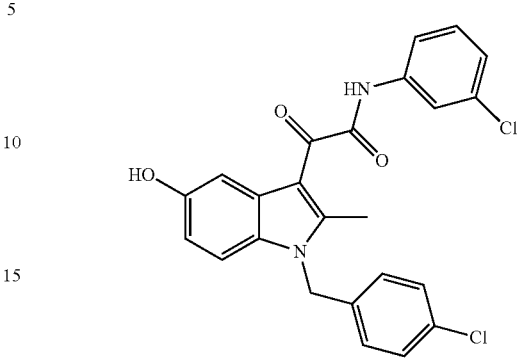

To a −78° C. solution of 2-(1-(4-chlorobenzyl)-5-methoxy-2-methyl-1H-indol-3-yl)-N-(3-chlorophenyl)-2-oxoacetamide (0.500 g, 1.07 mmol) in dichloromethane (20 mL) was added neat boron tribromide (1.00 mL, 10.6 mmol), after which the reaction mixture was allowed to warm to room temperature and stirred at that temperature for one hour. The reaction mixture was then cooled to 0° C., quenched by the addition of water (2 mL), and stirred at 0° C. for 15 minutes. The reaction mixture was diluted with water (100 mL), extracted with dichloromethane (1×100 mL) and concentrated. Purification was achieved by silica gel chromatography using 15 to 50% ethyl acetate in hexanes to afford 2-(1-(4-chlorobenzyl)-5-hydroxy-2-methyl-1H-indol-3-yl)-N-(3-chlorophenyl)-2-oxoacetamide (0.131 g, 0.268 mmol, 25% yield) as a grey solid. $^1$H NMR (400 MHz, CD$_3$OD) δ (ppm): 7.91 (m, 1H), 7.58 (br. d, 1H), 7.49 (d, 1H), 7.36 (t, 1H), 7.31 (d, 2H), 7.23 (d, 1H), 7.18 (br. d, 1H), 7.04 (d, 2H), 6.75 (dd, 1H), 5.46 (s, 2H), 2.64 (s, 3H). LCMS: [M−H]$^-$ found 452.0.

2-(5-amino-4-chloro-1-(4-chlorobenzyl)-2-methyl-1H-indol-3-yl)-N-(2-methoxypyridin-4-yl)-2-oxoacetamide (73)

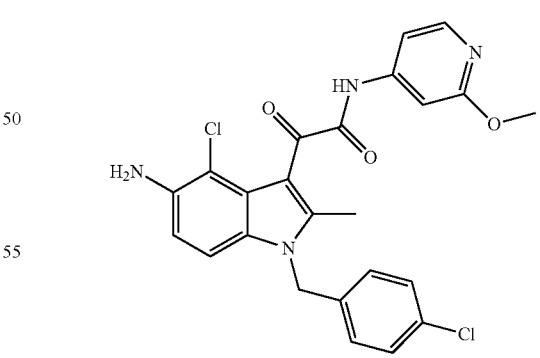

To a room temperature solution of 2-(5-amino-1-(4-chlorobenzyl)-2-methyl-1H-indol-3-yl)-N-(2-methoxypyridin-4-yl)-2-oxoacetamide (29 mg, 0.065 mmol) in N,N-dimethylformamide (3 mL) was added N-chlorosuccinimide (20 mg, 0.15 mmol) portionwise (one addition per hour, over 7 hours). The reaction mixture was diluted with ethyl acetate, washed successively with water (3×5 mL), then saturated sodium chloride solution (3×5 mL), dried (sodium sulfate), filtered and concentrated to a residue. Purification was achieved by silica gel chromatography using 20 to 80% ethyl acetate in hexanes over 20 minutes to afford 2-(5-amino-4-chloro-1-(4-chlorobenzyl)-2-methyl-1H-indol-3-yl)-N-(2-methoxypyridin-4-yl)-2-oxoacetamide (17.9 mg, 0.0370 mmol, 54% yield) as a yellow solid. $^1$H NMR (400 MHz, CDCl$_3$) δ (ppm): 8.96 (br. s, 1H), 8.12 (d, 1H), 7.27 (d, 2H), 7.22 (d, 1H), 7.17 (dd, 1H), 6.95 (d, 1H), 6.93 (d, 2H), 6.70 (d, 1H), 5.24 (s, 2H), 3.96 (br. s, 2H), 3.94 (s, 3H), 2.76 (s, 3H). LCMS: [ES]$^+$ found 484.0.

2-(1-(4-chlorobenzyl)-5-methoxy-2-methyl-1H-pyrrolo[2,3-b]pyridin-3-yl)-N-(2-methoxypyridin-4-yl)-2-oxoacetamide (38)

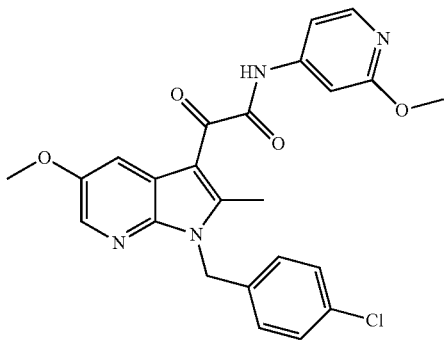

To a solution of 5-bromo-1H-pyrrolo[2,3-b]pyridine (2.00 g, 10.2 mmol) in N,N-dimethylformamide (30 mL) was added a 25% weight solution in methanol of sodium methoxide (46.4 mL, 203 mmol) followed by copper(I) bromide (2.91 g, 20.3 mmol). The reaction mixture was heated at 140° C. for 2.5 hours, after it was cooled to room temperature and concentrated to remove most of the N,N-dimethylformamide. Water (100 mL) was added followed by saturated aqueous sodium bicarbonate solution (20 mL). The mixture was extracted with EtOAc (3×50 mL), dried (magnesium sulfate), filtered and concentrated to a residue. Purification was achieved by silica gel chromatography (Biotage) using 0 to 50% ethyl acetate in hexanes over 60 minutes to afford 5-methoxy-1H-pyrrolo[2,3-b]pyridine (0.680 g, 4.59 mmol, 45% yield) as a green solid. $^1$H NMR (400 MHz, CDCl$_3$) δ (ppm): 9.90 (br. s, 1H), 8.10 (m, 1H), 7.46 (m, 1H), 7.33 (m, 1H), 6.44 (m, 1H), 3.89 (s, 3H).

To a mixture of 5-methoxy-1H-pyrrolo[2,3-b]pyridine (670 mg, 4.52 mmol), and benzyltributylammonium bromide (70.5 mg, 0.226 mmol) in dichloromethane (20 mL) was added powdered sodium hydroxide (561 mg, 14.0 mmol). The reaction mixture was cooled to 0° C., after which 4-methylbenzene-1-sulfonyl chloride (991 mg, 5.20 mmol) was added portionwise. The mixture was stirred at 0° C. for 15 min then warmed to room temperature where it was stirred for two hours, extracted with toluene (2×50 mL), dried (sodium sulfate), filtered and concentrated. The crude product was triturated in ether and filtrated to afford the compound 5-methoxy-1-tosyl-1H-pyrrolo[2,3-b]pyridine (1.21 g, 4.01 mmol, 89% yield) as a solid. $^1$H NMR (400 MHz, CDCl$_3$) δ (ppm): 8.15 (s, 1H), 8.05 (m, 2H), 7.66 (m, 1H), 7.25-7.30 (m, 3H), 6.51 (m, 1H), 3.83 (s, 3H), 2.35 (s, 3H).

To a −60° C. solution of 5-methoxy-1-tosyl-1H-pyrrolo[2,3-b]pyridine (1.20 g, 3.97 mmol) in tetrahydrofuran (25 mL) was added 2M in tetrahydrofuran/ethylbenzene/toluene solution of lithium diisopropyl amide (3.97 mL, 7.94 mmol). The reaction mixture was stirred at −60° C. for 30 minutes, after which iodomethane (0.298 mL, 4.76 mmol) was added, after which the reaction mixture was room temperature. Upon warming, the reaction was poured into ice water, extracted with ethyl acetate (3×50 mL), washed with water (3×50 mL), saturated sodium chloride solution (3×50 mL), dried (magnesium sulfate), filtered and concentrated. Purification was achieved by silica gel chromatography (Biotage) using 0 to 50% ethyl acetate in hexanes to afford 5-methoxy-2-methyl-1-tosyl-1H-pyrrolo[2,3-b]pyridine (0.550 g, 1.74 mmol, 44% yield). $^1$H NMR (400 MHz, CDCl$_3$) δ (ppm): 8.08 (s, 1H), 7.96 (d, 2H), 7.26 (m, 2H), 7.16 (m, 1H), 6.20 (s, 1H), 3.83 (s, 3H), 2.69 (s, 3H), 2.35 (s, 3H).

A solution of 5-methoxy-2-methyl-1-tosyl-1H-pyrrolo[2,3-b]pyridine (1.14 g, 3.60 mmol) and sodium hydroxide (14.4 g, 360 mmol) in methanol (70 mL) and water (70 mL) was heated at 80° C. for 30 minutes, after which it was cooled to room temperature, poured into to ice water, extracted with ethyl acetate (3×50 mL), washed with saturated sodium chloride solution (3×50 mL), dried (magnesium sulfate), filtered and concentrated to afford 5-methoxy-2-methyl-1H-pyrrolo[2,3-b]pyridine (0.550 g, 3.39 mmol, 94% yield) as a solid. $^1$H NMR (400 MHz, CDCl$_3$) δ (ppm): 9.48 (b, 1H), 7.97 (m, 1H), 7.33 (m, 1H), 6.10 (m, 1H), 3.89 (s, 3H) 2.49 (s, 3H). This material was used in the subsequent step without any purification.

2-(1-(4-chlorobenzyl)-5-methoxy-2-methyl-1H-pyrrolo[2,3-b]pyridin-3-yl)-N-(2-methoxypyridin-4-yl)-2-oxoacetamide was synthesized as a yellow solid in 55% yield starting from 1-(4-chlorobenzyl)-5-methoxy-2-methyl-1H-pyrrolo[2,3-b]pyridin using general procedure D. $^1$H NMR (400 MHz, CDCl$_3$) δ (ppm): 9.13 (br. s, 1H), 8.10-8.17 (m, 3H), 7.25-7.27 (m, 3H), 7.14 (d, 1H), 7.06 (m, 2H), 5.55 (s, 2H), 3.96 (s, 3H), 3.93 (s, 3H), 2.70 (s, 3H).

2-(1-(4-chlorobenzyl)-5-methoxy-2-methyl-11H-pyrrolo[3,2-b]pyridin-3-yl)-N-(2-methoxypyridin-4-yl)-2-oxoacetamide was synthesized as a solid starting from methoxy-2-methyl-1H-pyrrolo[3,2-b]pyridine using general route 2. $^1$H NMR (400 MHz, CD$_3$OD) δ (ppm): 8.02 (d, 1H), 7.69 (d, 1H), 7.33 (m, 3H), 7.21-7.23 (m, 1H), 7.06 (d, 2H), 6.56 (d, 1H), 5.51 (s, 2H), 3.90 (s, 3H), 3.52 (s, 3H), 2.81 (s, 3H).

2-(5-methoxy-2-methyl-1-(4-(methylsulfonyl)benzyl)-1H-indol-3-yl)-N-(2-methoxypyridin-4-yl)-2-oxoacetamide (39)

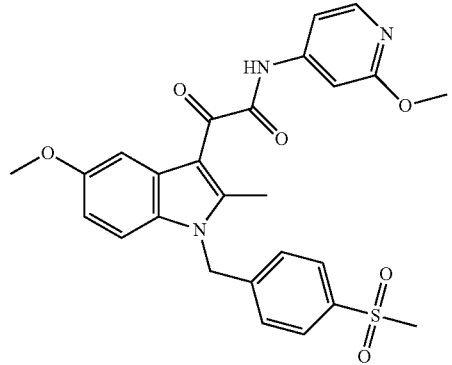

2-(5-methoxy-2-methyl-1-(4-(methylsulfonyl)benzyl)-1H-indol-3-yl)-N-(2-methoxypyridin-4-yl)-2-oxoacetamide was synthesized according to general route 2. Except one of the intermediates was obtained according to general procedure G.

5-methoxy-2-methyl-1-(4-(methylsulfonyl)benzyl)-1H-indole was synthesized as a solid in 43% yield starting from 5-methoxy-2-methyl-1H-indole, 1-(chloromethyl)-4-(methylsulfonyl)benzene and DMSO as solvent using general procedure E. LCMS: [ES]+ found 330.19.

2-(5-methoxy-2-methyl-1-(4-(methylsulfonyl)benzyl)-1H-indol-3-yl)-2-oxoacetic acid was synthesized as a solid in 82% yield starting from 5-methoxy-2-methyl-1-(4-(methylsulfonyl)benzyl)-1H-indole using general procedure G. (General procedure G applied to this intermediate afforded the carboxylic acid as the product. The ketoamide product that was expected from this general procedure was observed in trace amounts and was not isolated). LCMS [ES]+ found 402.16.

2-(5-amino-1-(4-chlorobenzyl)-2-methyl-1H-indol-3-yl)-N-(2-methoxypyridin-4-yl)-2-oxoacetamide (20)

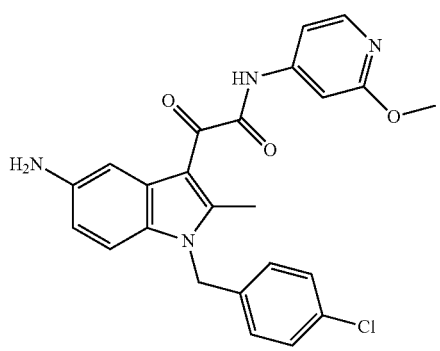

To a solution of 2-(1-(4-chlorobenzyl)-2-methyl-5-nitro-1H-indol-3-yl)-N-(2-methoxypyridin-4-yl)-2-oxoacetamide (0.182 g, 0.380 mmol) in tetrahydrofuran (1.9 mL) absolute ethanol (3.8 mL) and saturated ammonium chloride solution (1.9 mL) was added iron powder (0.127 g, 2.28 mmol). The reaction mixture was heated to 70° C. for 2 hours, after which it was cooled to room temperature and filtered through a pad of celite using ethyl acetate as the solvent (150 mL). The filtrate was dried (sodium sulfate), and concentrated to afford a residue. Purification was achieved by silica gel chromatography using 0 to 80% ethyl acetate in hexanes to afford 2-(5-amino-1-(4-chlorobenzyl)-2-methyl-1H-indol-3-yl)-N-(2-methoxypyridin-4-yl)-2-oxoacetamide as a yellow solid in 49% yield. $^1$H NMR (400 MHz, CD$_3$OD) δ (ppm): 8.04 (d, 1H), 7.44 (d, 1H), 7.27-7.30 (m, 3H), 7.20-7.22 (m, 1H), 7.14 (d, 1H), 7.00 (d, 2H), 6.70-6.73 (m, 1H), 5.38 (s, 2H), 3.90 (s, 3H), 2.57 (s, 3H).

2-(1-(4-chlorobenzyl)-5-(dimethylamino)-2-methyl-1H-indol-3-yl)-N-(2-methoxypyridin-4-yl)-2-oxoacetamide (17)

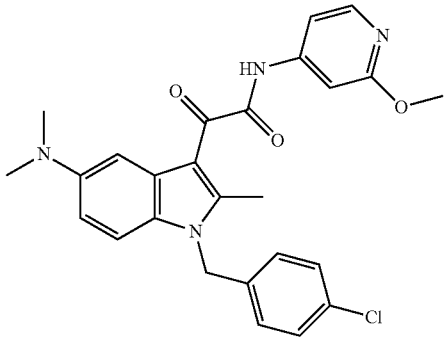

To a solution of 2-(5-amino-1-(4-chlorobenzyl)-2-methyl-1H-indol-3-yl)-N-(2-methoxypyridin-4-yl)-2-oxoacetamide (0.225 g, 0.501 mmol) in dichloromethane (3 mL) was added a 37% aqueous solution of formaldehyde (0.056 mL, 0.75 mmol) followed by sodium triacetoxyborohydride (0.191 g, 0.902 mmol). The reaction mixture was stirred at room temperature for one hour after which additional sodium triacetoxyborohydride (0.106 g) was added. After 20 minutes of stirring at room temperature, the reaction was complete by LCMS analysis, and subsequently quenched by the addition of saturated sodium bicarbonate solution (10 mL), extracted with ethyl acetate (3×20 mL), washed with saturated sodium chloride solution (1×50 mL), dried (sodium sulfate), filtered, and concentrated. Purification was achieved by silica gel chromatography using 0 to 7% of a 7:1 acetonitrile:methanol solution in dichloromethane over 60 minutes to afford 2-(1-(4-chlorobenzyl)-5-(dimethylamino)-2-methyl-1H-indol-3-yl)-N-(2-methoxypyridin-4-yl)-2-oxoacetamide (62.8 mg, 0.132 mmol, 26% yield) as a light yellow solid. $^1$H NMR (400 MHz, CDCl$_3$) δ (ppm): 9.00 (s, 1H), 8.13 (d, 1H), 7.65 (s, 1H), 7.24-7.28 (m, 3H), 7.14 (dd, 1H), 7.10 (d, 1H), 6.95 (d, 2H), 6.81 (s, 1H), 5.31 (s, 2H), 3.96 (s, 3H), 2.98 (s, 6H), 2.67 (s, 3H).

2-(5-acetamido-1-(4-chlorobenzyl)-2-methyl-1H-indol-3-yl)-N-(2-methoxypyridin-4-yl)-2-oxoacetamide (22)

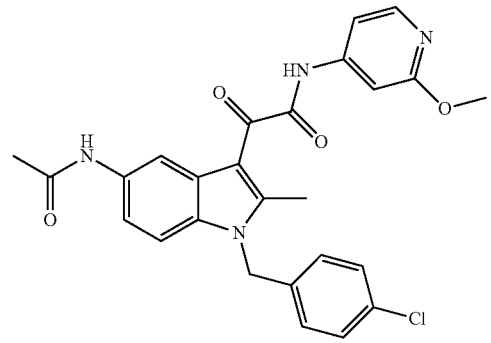 [SMILES: COc1cc(NC(=O)C(=O)c2c(C)n(Cc3ccc(Cl)cc3)c3ccc(NC(C)=O)cc23)ccn1]

To a room temperature solution of 2-(5-amino-1-(4-chlorobenzyl)-2-methyl-1H-indol-3-yl)-N-(2-methoxypyridin- 4-yl)-2-oxoacetamide (0.170 g, 0.379 mmol) in dichloromethane (1.9 mL) was added acetyl chloride (0.0270 mL, 0.379 mmol) followed by pyridine (0.0610 mL, 0.757 mmol). After five minutes, the reaction was complete by LCMS analysis. The reaction mixture was then concentrated, reconstituted in dichloromethane (5 mL) and purified using silica gel chromatography using 0 to 100% of a 1:24 triethylamine:ethyl acetate mixture in hexanes. The product, 2-(5-acetamido-1-(4-chlorobenzyl)-2-methyl-1H-indol-3-yl)-N-(2-methoxypyridin-4-yl)-2-oxoacetamide (115 mg, 0.235 mmol, 62% yield) was isolated as a solid. $^1$H NMR (400 MHz, DMSO-$d_6$) δ (ppm): 11.18 (s, 1H), 9.94 (s, 1H), 8.25 (d, 1H), 8.08 (d, 1H), 7.48-7.52 (m, 2H), 7.37-7.40 (m, 2H), 7.21-7.22 (m, 2H), 7.06 (d, 2H), 5.54 (s, 2H), 3.83 (s, 3H), 3.31 (s, 3H), 2.53 (s, 3H).

2-(1-(4-chlorobenzyl)-2-methyl-5-vinyl-1H-indol-3-yl)-N-(2-methoxypyridin-4-yl)-2-oxoacetamide (27)

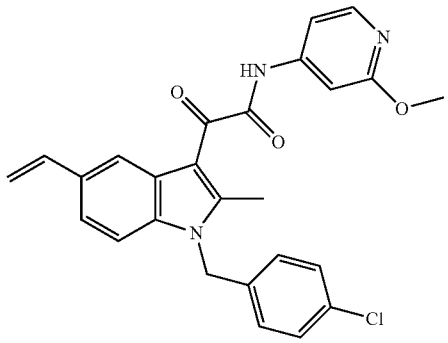 [SMILES: C=Cc1ccc2c(c1)c(C(=O)C(=O)Nc1ccnc(OC)c1)c(C)n2Cc1ccc(Cl)cc1]

To a solution of 2-(5-bromo-1-(4-chlorobenzyl)-2-methyl-1H-indol-3-yl)-N-(2-methoxypyridin-4-yl)-2-oxoacetamide (0.141 g, 0.275 mmol) in tetrahydrofuran (0.99 mL) and water (0.11 mL) was added cesium carbonate (0.269 g, 0.825 mmol), palladium(II) chloride (0.975 mg, 5.50 mol), potassium trifluoro(vinyl)borate (0.037 g, 0.28 mmol), and triphenylphosphine (4.3 mg, 0.016 mmol). The reaction mixture was purged with nitrogen and heated to 85° C. for 1 hour, after which it was cooled to room temperature and filtered through celite using dichloromethane as the solvent (75 mL). The filtrate was dried (sodium sulfate) and concentrated to a residue. Purification was achieved by silica gel chromatography using 0 to 20% methanol in dichloromethane to afford 2-(1-(4-chlorobenzyl)-2-methyl-5-vinyl-1H-indol-3-yl)-N-(2-methoxypyridin-4-yl)-2-oxoacetamide (0.0700 g, 0.152 mmol, 55% yield) as a tan solid. $^1$H NMR (400 MHz, CDCl$_3$) δ (ppm): 9.03 (s, 1H), 8.22 (s, 1H), 8.15 (d, 1H), 7.37 (dd, 1H), 7.24-7.29 (m, 3H), 7.15-7.19 (m, 2H), 6.95 (d, 2H), 6.85 (m, 1H), 5.75 (d, 1H), 5.36 (s, 2H), 5.22 (s, 1H), 3.96 (s, 3H), 2.69 (s, 3H).

2-(5-amino-1-((5-chloropyridin-2-yl)methyl)-2-methyl-1H-indol-3-yl)-N-(2-methoxypyridin-4-yl)-2-oxoacetamide (65)

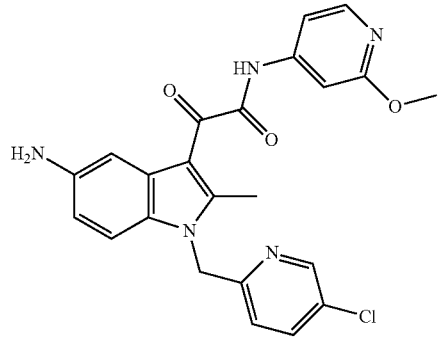

To a solution of 2-(1-((5-chloropyridin-2-yl)methyl)-2-methyl-5-nitro-1H-indol-3-yl)-N-(2-methoxypyridin-4-yl)-2-oxoacetamide (30.0 mg, 0.0630 mmol) in tetrahydrofuran (1.0 mL) absolute ethanol (2.0 mL) and saturated ammonium chloride solution (1.0 mL) was added iron powder (41.9 mg, 0.750 mmol). The reaction mixture was heated to 70° C. for one hour, after which it was cooled to room temperature, diluted in ethyl acetate (10 mL), washed with saturated sodium chloride solution, dried (sodium sulfate), and concentrated to afford 2-(5-amino-1-((5-chloropyridin-2-yl)methyl)-2-methyl-1H-indol-3-yl)-N-(2-methoxypyridin-4-yl)-2-oxoacetamide (25.0 mg, 0.0561 mmol, 89% yield) as a solid. $^1$H NMR (400 MHz, CDCl$_3$) δ (ppm): 8.91 (br. s, 1H), 8.49 (d, 1H), 8.08 (d, 1H), 7.48 (d, 1H), 7.45 (d, 1H), 7.20 (d, 1H), 7.07 (d, 1H), 6.97 (d, 1H), 6.61 (d, 1H), 6.56 (d, 1H), 5.33 (s, 2H), 3.89 (s, 3H), 2.62 (s, 3H).

2-(1-((5-chloropyridin-2-yl)methyl)-5-(dimethylamino)-2-methyl-1H-indol-3-yl)-N-(2-methoxypyridin-4-yl)-2-oxoacetamide (66)

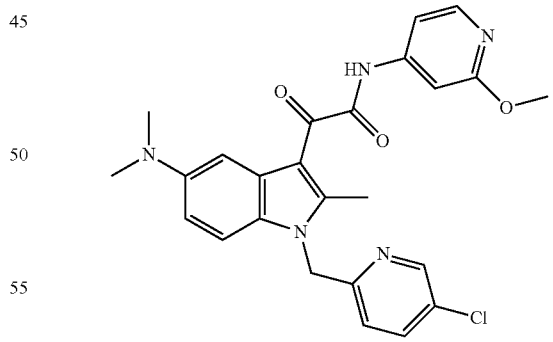

To a solution of 2-(5-amino-1-((5-chloropyridin-2-yl)methyl)-2-methyl-1H-indol-3-yl)-N-(2-methoxypyridin-4-yl)-2-oxoacetamide (25 mg, 0.056 mmol) in 1,2-dichloroethane (3 mL) was added a 37% aqueous solution of formaldehyde (6.3 µL, 0.083 mmol) followed by sodium triacetoxyborohydride (21.2 mg, 0.100 mmol). The reaction mixture was stirred at room temperature for two hours after which additional sodium triacetoxyborohydride (12 mg) was added. After 20 minutes of stirring at room temperature, the reaction was shown as complete by LCMS analysis, and subsequently quenched by the addition of saturated sodium bicarbonate solution (10 mL), diluted in ethyl acetate (10 mL), washed with saturated sodium chloride solution (3×10 mL), dried (sodium sulfate), filtered, and concentrated. Purification was achieved by silica gel chromatography (Biotage, 4 g) using 50 to 100% ethyl acetate in hexanes to afford 2-(1-(4-chlorobenzyl)-5-(dimethylamino)-2-methyl-1H-indol-3-yl)-N-(2-methoxypyridin-4-yl)-2-oxoacetamide (20.0 mg, 0.0420 mmol, 75% yield) as a yellow solid. $^1$H NMR (400 MHz, CDCl$_3$) δ (ppm): 9.05 (br. s, 1H), 8.55 (d, 1H), 8.13 (d, 1H), 7.63 (d, 1H), 7.54 (d, 1H), 7.24 (d, 1H), 7.16 (d, 1H), 7.10 (d, 1H), 6.81 (d, 1H), 6.66 (d, 1H), 5.39 (s, 2H), 3.96 (s, 3H), 2.96 (s, 6H), 2.67 (s, 3H). LCMS: 1.10 min, [ES]$^+$ found 477.94.

Biological Assays

Example 5

FAAH Inhibition Using Rat and Human Brain Homogenate Assays

The ability of compounds to inhibit FAAH was measured in human whole cell and human and rodent brain homogenates as described herein.

A. FAAH Rat Brain Membrane (RBM) Homogenate Preparation

Adult rats (Charles River CD strain, female, 200 g) were anaesthetized with isofluorane and rapidly decapitated. Each brain was quickly removed and chilled in tubes (3 brains per tube) on ice. About 25 mL of "homogenization buffer" (20 mM HEPES buffer, pH 7.0, with 1 mM MgCl$_2$) was added to 15 to 20 g of brain. The brains were homogenized on ice for 1 minute using an Omni GLH homogenizer (Omni International, Marietta, Ga.). The homogenates were then transferred to three centrifuge tubes and centrifuged at 36,500 g for 20 minutes at 4° C. The supernatant was discarded and each pellet was re-suspended in 25 mL homogenization buffer. The re-suspended material was again centrifuged (36,500 g, 20 minutes at 4° C.). Pellets were combined by re-suspension in 10 mL of homogenization buffer and incubated in a 37° C. water bath for 15 minutes. The tubes were then placed on ice for 5 minutes followed by centrifugation at 36,500 g for 20 minutes at 4° C. The supernatant was discarded and the membrane pellets were then re-suspended in 40 mL of "re-suspension buffer" (50 mM Tris-HCl buffer, pH 7.4, containing 1 mM EDTA and 3 mM MgCl$_2$). A Bradford Protein assay was performed to determine protein concentration. The protein was aliquotted into screw cap Cryo tubes each containing ~400 μL, flash-frozen in liquid nitrogen and stored at −80° C. until used for the assay. A similar protocol was used to obtain brain membrane homogenates from mice B. FAAH Human Brain Membrane (HBM) Homogenate Preparation.

Brain cerebral cortex tissue (ABS, Inc.) from 3 human donors (2 females, 1 male; 63-85 years old) was collected previously and flash-frozen in liquid nitrogen within 4 hours post-mortem interval. Tissue was stored at −80° C. Serology was negative for a defined list of infectious agents. Brain cortex samples (equal amounts from 3 donors pooled as 10 g total) were homogenized as described below.

All tissue samples were handled following Centers for Disease Control Biosafety Level 2 (BL-2) procedures for working with bio-hazardous materials by trained personnel in BL-2 certified laboratories. Brain tissue was thawed in ice-cold homogenization buffer 20 mM HEPES (pH 7.0), 1 mM MgCl$_2$. Approximately 4 mL of buffer was used per gram of tissue. Human brain tissue was homogenized in buffer in an ice-cold mortar with a pestle. Homogenates were centrifuged at 36,500×g for 20 minutes at 4° C. Supernatants were discarded. Pellets were re-suspended and homogenized in ice-cold homogenization buffer as before. The tubes were capped and incubated upright in a 37° C. water bath for 15 minutes followed by incubation on ice for 5 min. The tubes were centrifuged as before. The brain membrane microsome pellets were re-suspended using ice-cold re-suspension buffer (50 mM Tris-HCl buffer, pH 7.4, containing 1 mM EDTA and 3 mM MgCl$_2$). Protein concentrations of the brain microsome suspensions were determined using BioRad protein assay kit (BioRad). The protein was aliquotted and flash frozen as 0.2 mL aliquots in liquid nitrogen and stored at −80° C. until use.

C. Determination of FAAH Activity

FAAH activity was assayed in the respective homogenates described herein (Rat brain, Mouse brain or Human brain) with certain of the exemplary compounds described above using a modification of the method of Omeir et al. (1995 Life Sci. 56:1999) and Fowler et al. (1997 J. Pharmacol. Exp. Ther. 283:729). For the assay of FAAH activity in rat brain membrane (RBM) homogenates, RBM homogenates (7 μg protein in 20 μL final volume of 10 mM Tris pH 6.5) were mixed with 180 μL of a mixture of the following: 2.0 M unlabelled anandamide (AEA), 0.03 Ci radio labeled anandamide [ethanolamine 1-$^3$H](40-60 Ci/mmol; product number ART-626, American Radiolabelled Chemicals, St. Louis, Mo.), 1 mg/mL Bovine Serum Albumin (fatty acid-free BSA, electrophoresis grade, Sigma, St. Louis, Mo.), 10 mM Tris-HCl (pH 6.5), and 1 mM EDTA in the presence and absence of test compounds (vehicle was DMSO at a final concentration of 1%) and incubated for 10 minutes at 37° C. Samples were placed on ice to terminate the reactions.

The $^3$H-ethanolamine product and un-reacted $^3$H-anandamide substrate were then separated by either: (1) using chloroform/methanol extraction or (2) passing the reaction mixture through a glass fiber filter containing activated charcoal. Samples were extracted with chloroform/methanol by adding 0.4 mL of chloroform/methanol (1:1 v/v), vigorously mixing the samples, and separating the aqueous and organic phases by centrifugation. Radioactivity (corresponding to FAAH-catalyzed breakdown of $^3$H-anandamide) found in aliquots (0.2 mL) of the aqueous phase was determined by liquid scintillation counting with quench correction. IC$_{50}$ values were determined as described by Jonsson et al. (2001 Br. J Pharmacol. 133:1263). Alternatively, reactions were purified using a modification of the solid-phase extraction method described by Wilson et al (2003 Anal. Biochem. 318: 270). This method was modified as follows: after reactions were incubated at 37° C. for 10 minutes and chilled on ice, the reaction mixtures were acidified by adding 10 μL of sodium phosphate solution [0.5M (pH 2.0)]. Next, 90 μL aliquots of the acidified reaction mixtures were applied to activated charcoal (that had been previously washed with methanol as described by Wilson et al. (supra)) containing 80 μL of water on top of a glass fiber filter, centrifuged, and the radioactivity in the eluate was counted as described previously by Wilson et al. (supra).

FAAH activity using human homogenates was assayed based on methods adapted from Omeir et al 1995 (1) with modifications by Fowler et al. 1997 (supra). Separation of $^3$H-product and [$^3$H]-ethanolamine product was based on modifications of Wilson et al. 2003 (supra). FAAH assays were conducted in 0.2 mL (volume final) of reaction buffer per well [10 mM Tris (pH 7), 1 mM EDTA, 0.1% fatty acid free BSA (Sigma catalog #A0281), 0.5 µM anandamide (Cayman catalog #90050), 70,000 dpm of anandamide-(ethanolamine-1-[$^3$H]) (60 Ci/mmol, radiochemical purity >99%, American Radiolabeled Chemicals, Inc., catalog #ART 626)] in the presence and absence of test compounds (vehicle is DMSO at a final concentration of 1%). Reactions were initiated by adding 12.5 µg of brain microsome. Reactions were conducted at 37° C. for 10 min. The reactions were terminated by chilling the plates on ice and adding 20 µL of 0.5M of potassium phosphate buffer (adjusted to pH 2.1 with phosphoric acid). [$^3$H]-ethanolamine product and un-reacted [$^3$H]-anandamide substrate were separated by passing the reaction mixture through a glass fiber filter containing activated charcoal, and the radioactivity in the eluate was counted as described previously by Wilson et al. (supra).

Table 2 provides activity data for certain compounds tested for inhibition of FAAH using the FAAH rat, mouse and human brain homogenate assays. The known FAAH inhibitors, 3'-(aminocarbonyl)biphenyl-3-yl cyclohexylcarbamate (URB597), [1-(4-chlorobenzoyl)-5-methoxy-2-methyl-1H-indol-3-yl]acetic acid (indomethacin) and 5-benzoyl-2,3-dihydro-1H-pyrrolizine-1-carboxylic acid (Ketorolac) were used as controls in these assays.

TABLE 2

FAAH Inhibition
Average activity of the compounds of this invention, expressed as IC$_{50}$ (the concentration of the agent needed to induce 50% inhibition of the enzyme) of FAAH extracted from human and rat brain homogenates. A = Less than 100 nM; B = between 100 nM and 1 µM; C = between 1 µM and 10 µM; D = greater than 10 µM. NS means "Not Significant," which means less than 30% agonist activity when compared to the positive control.
ND means "Not Determined."

| Compound Number | Human brain Extract FAAH IC$_{50}$ | Rat Brain Extract FAAH IC$_{50}$ |
|---|---|---|
| 1 | A | A |
| 2 | A | A |
| 3 | A | A |
| 4 | C | C |
| 5 | A | A |
| 6 | B | B |
| 7 | B | B |
| 8 | A | A |
| 9 | A | A |
| 10 | A | A |
| 11 | A | A |
| 12 | A | A |
| 13 | A | A |
| 14 | A | A |
| 15 | A | A |
| 16 | B | B |
| 17 | A | A |
| 18 | A | A |
| 19 | A | A |
| 20 | A | A |
| 21 | A | A |
| 22 | A | B |
| 23 | A | A |
| 24 | C | B |
| 25 | B | C |
| 26 | B | B |
| 27 | A | A |
| 28 | B | A |
| 29 | A | A |
| 30 | A | A |
| 31 | A | A |
| 32 | A | A |
| 33 | A | A |
| 34 | A | A |

TABLE 2-continued

FAAH Inhibition
Average activity of the compounds of this invention, expressed as IC$_{50}$ (the concentration of the agent needed to induce 50% inhibition of the enzyme) of FAAH extracted from human and rat brain homogenates. A = Less than 100 nM; B = between 100 nM and 1 µM; C = between 1 µM and 10 µM; D = greater than 10 µM. NS means "Not Significant," which means less than 30% agonist activity when compared to the positive control.
ND means "Not Determined."

| Compound Number | Human brain Extract FAAH IC$_{50}$ | Rat Brain Extract FAAH IC$_{50}$ |
|---|---|---|
| 35 | B | B |
| 36 | A | A |
| 37 | A | A |
| 38 | A | A |
| 39 | C | C |
| 40 | A | A |
| 41 | A | A |
| 42 | A | A |
| 43 | B | A |
| 44 | A | A |
| 45 | A | A |
| 46 | A | A |
| 47 | A | A |
| 48 | A | A |
| 49 | A | A |
| 50 | C | C |
| 51 | B | C |
| 52 | D | D |
| 53 | B | A |
| 54 | A | A |
| 55 | A | A |
| 56 | B | C |
| 57 | A | A |
| 58 | A | B |
| 59 | A | A |
| 60 | A | A |
| 61 | A | A |
| 62 | A | A |
| 63 | A | A |
| 64 | A | A |
| 65 | B | A |
| 66 | A | A |
| 67 | A | A |
| 68 | A | A |
| 69 | A | A |
| 70 | A | A |
| 71 | A | B |
| 72 | A | A |
| 73 | B | B |
| 74 | A | A |
| 75 | A | A |
| 76 | A | A |
| 77 | B | A |
| 78 | B | B |
| 79 | A | A |
| 80 | A | A |
| 81 | A | A |
| 82 | A | A |
| 83 | C | C |
| 84 | A | A |
| 85 | A | A |
| 86 | A | A |
| 87 | A | A |
| 88 | A | A |
| 89 | A | A |
| 90 | A | A |
| 91 | A | A |
| 92 | A | A |
| 93 | A | A |
| 94 | A | A |
| 95 | A | A |
| 96 | A | A |
| 97 | A | A |
| 98 | A | A |
| 99 | A | A |
| 100 | B | A |
| 101 | A | A |

Example 6

Whole Cell Anandamide Hydrolysis Assay

FAAH activity was assayed in whole cells using methods disclosed previously (Maccarone et al., 1998 J Biol. Chem. 273:32332 and Bisogno et al., 1997 J Biol. Chem. 272: 3315). In addition to the cell lines described in Maccarone et al. and Bisogno et al., MCF7 (ATCC designation HTB-22) and T84 (ATCC designation CCL-248) cell lines were also used in these assays.

A. HeLa Cell Transfection with Human FAAH-1 cDNA expression clone for human FAAH-1 (in pcDNA3 vector) (Genbank Accession U82535; obtained from Benjamin Cravatt, Scripps Research Institute, La Jolla, Calif.) was linearized by digestion with BglII (New England Biolabs) and transfected by calcium phosphate into human HeLa cells (ATCC catalog #CCL-2). The HeLa cell line was selected as a host because it does not express FAAH or exhibit FAAH activity such that all subsequent activity can be attributed to the transfected gene. Following transfection, a stable HeLa-derived clone, designated 5c5, was isolated by single colony purification and expanded and maintained in modified Eagles medium (MEM; VWR catalog #45000-300) containing 10% fetal bovine serum (FBS), 2 mM L-glutamine, and 0.5 mg/mL G-418 (Sigma catalog #G5013).

B. FAAH Whole Cell Activity Assay

Clone 5c5 (50,000 cells in 150 µL) was seeded into 96-well plates and incubated overnight (5% $CO_2$, 37° C.). Media was carefully replaced with 180 µL DMEM/F12 medium (VWR catalog #45000-350) containing 15 mM HEPES, pH 7.4 and 0.1% fatty acid free BSA (Sigma catalog #A0281). Then, 2 µL of 100× desired final concentrations of certain exemplary compounds described herein were made up in DMSO, added to wells containing cells, and plates were incubated at 37° C. for 10 min. Next, 20 µL of 5 µM anandamide (Cayman catalog #90050) spiked with 8 µCi of anandamide-(ethanolamine-1-[$^3$H]) (American Radiolabeled Chemicals, Inc., catalog #ART 626) was added to the cells and the plates were incubated for an additional 15 min at 37° C. The reactions were terminated by chilling the plates on ice and adding 20 µL of 0.5M of potassium phosphate buffer (adjusted to pH 2.1 with phosphoric acid).

The acidified reactions were transferred to 96-well filter plates (0.25 mL capacity/well, 1.2 micron glass fiber prefilter packed above 0.65 micron pore-size PVDF membrane, Millipore catalog MSFCN6B50) containing 25 µL charcoal (neutral activated carbon, Fisher Scientific catalog C170-500) per well. Prior to the assay, charcoal was measured and loaded onto the plate using an aluminum 96-well column loading device (Millipore catalog MACL09625). The filter plate was assembled over an empty 96-well plate (Costar) using a centrifuge alignment frame (Millipore catalog MACF09604) to allow for collection of the filtrate in the receiver plate. The charcoal glass-fiber filter plates were pre-washed with methanol by centrifugation 650×g for 10 min). Next, 80 µL of water was added to the wells of the pre-washed 96 well charcoal filter plate. Then, 90 µL of the acidified reaction mixture was added to the water in the wells of the charcoal plate. The samples were centrifuged as above. The substrate remained bound to the charcoal, whereas the [$^3$H]-ethanolamine product formed flowed through and was transferred to the microplates containing scintillation cocktail and quantified in a micro-plate scintillation counter (PerkinElmer Microbeta). Control reactions with either no cells or cells treated with DMSO alone were performed in triplicate and used to define background (no cells) and 100% activity (DMSO alone).

Following subtraction of background radioactivity, data were expressed as percent inhibition relative to 100% activity and fit with a nonlinear regression curve using GraphPad Prism Software (GraphPad Software Inc). $IC_{50}$ values were calculated from the resulting dose-response curves constrained at top and bottom to 100% and 0%, respectively. Data are summarized in Table 3.

TABLE 3

Whole cell activity table.
A = Less than 100 nM; B = between 100 nM and 1 µM; C = between 1 µM and 10 µM; D = greater than 10 µM. NS means "Not Significant," which means less than 30% agonist activity when compared to the positive control. ND means "Not Determined."

| Compound Number | human FAAH whole cell $IC_{50}$ |
|---|---|
| 1 | A |
| 2 | A |
| 3 | A |
| 4 | C |
| 5 | A |
| 6 | B |
| 7 | B |
| 8 | A |
| 9 | A |
| 10 | A |
| 11 | A |
| 12 | A |
| 13 | A |
| 14 | A |
| 15 | A |
| 16 | A |
| 17 | A |
| 18 | A |
| 19 | A |
| 20 | A |
| 21 | A |
| 22 | A |
| 23 | A |
| 24 | B |
| 25 | B |
| 26 | A |
| 27 | A |
| 28 | A |
| 29 | A |
| 30 | A |
| 31 | A |
| 32 | A |
| 33 | A |
| 34 | A |
| 35 | A |
| 36 | A |
| 37 | A |
| 38 | A |
| 39 | C |
| 40 | A |
| 41 | A |
| 42 | A |
| 43 | A |
| 44 | A |
| 45 | A |
| 46 | A |
| 47 | A |
| 48 | A |
| 49 | A |
| 50 | C |
| 51 | B |
| 52 | B |
| 53 | A |
| 54 | A |
| 55 | A |
| 56 | B |
| 57 | A |

TABLE 3-continued

Whole cell activity table.
A = Less than 100 nM; B = between 100 nM and 1 μM; C = between 1 μM and 10 μM; D = greater than 10 μM. NS means "Not Significant," which means less than 30% agonist activity when compared to the positive control. ND means "Not Determined."

| Compound Number | human FAAH whole cell $IC_{50}$ |
|---|---|
| 58 | A |
| 59 | A |
| 60 | A |
| 61 | A |
| 62 | A |
| 63 | A |
| 64 | A |
| 65 | A |
| 66 | A |
| 67 | A |
| 68 | A |
| 69 | A |
| 70 | A |
| 71 | A |
| 72 | A |
| 73 | A |
| 74 | A |
| 75 | A |
| 76 | A |
| 77 | A |
| 78 | A |
| 79 | A |
| 80 | A |
| 81 | A |
| 82 | A |
| 83 | B |
| 84 | A |
| 85 | A |
| 86 | A |
| 87 | A |
| 88 | A |
| 89 | A |
| 90 | A |
| 91 | A |
| 92 | A |
| 93 | A |
| 94 | A |
| 95 | A |
| 96 | A |
| 97 | A |
| 98 | A |
| 99 | A |
| 100 | A |
| 101 | A |

Example 7

Human CB1 Cannabinoid Receptor Assay

Binding assays were used to characterize potential CB1 receptor binding affinity for the disclosed compounds and compositions.

A. CB1 Clones cDNA expression clones for human CB1 (hCB 1, Genbank Accession No. AY225225) expressed in vector pcDNA3.1+ were purchased from UMR cDNA Resource Center, Rolla, Mo. (Clone ID CNR01L000 for hCB 1).

B. Stable and Transient Transfection

Stable, HEK-293-derived cell lines that recombinantly express hCB 1 were established. In brief, the clone hCB 1 (CNR1L) was transfected into human embryonic kidney cells (HEK-293) using Lipofectamine 2000 (Gibco, Cat#11668-019) according to the manufacturer's protocol. Transfected clones were isolated by single colony purification and clones were screened for receptor expression using a whole cell, $^3$H-CP 55,940 radioligand binding assay. HEK-293 stable cells were maintained in Dulbecco's modified Eagles medium (DMEM) containing 10% fetal bovine serum, 2 mM L-glutamine and 0.5 mg/mL G-418.

C. Human CB1 Cannabinoid Receptor Radioligand Binding Assay

Membranes were isolated from transfected cells as follows. Monolayers of cultured cells were washed twice with phosphate-buffered saline (PBS). Cells were scraped into 20 mM HEPES, pH 7.4, 10 mM EDTA containing complete cocktail protease inhibitors (Roche, Catalog #11 697 498 001) and were homogenized by an electric-powered mechanical probe homogenizer (Omni GLH; probe G7-195S) for 40 seconds at 7000 rpm. Homogenates were centrifuged 10 minutes at 1000×g at 4° C. The supernatant was collected and was centrifuged for 1 hour at 40,000×g. The supernatant was then decanted and the resulting pellet was resuspended in 20 mM HEPES, pH 7.4, 5 mM $MgCl_2$, 1 mM EDTA, 10% sucrose with complete cocktail protease inhibitors. Protein concentration of membrane suspensions were measured by Bradford Protein Assay using bovine serum albumin as the standard (BioRad catalog #500-0006). Protein concentrations of membrane suspensions were adjusted with the final buffer in the range of 5 to 10 mg/mL and were stored at −80° C. until further use.

D. Cannabinoid Receptor Radioligand Binding Assay

Radioligand binding assays were performed by incubating membranes (2-10 ug protein) prepared from HEK-293 cells expressing recombinant human cannabinoid receptor, CB1, at room temperature with 0.5 nM cannabinoid receptor agonist, [$^3$H]-CP 55,940 (Perkin Elmer, catalog #NET1051) in 0.2 mL of binding buffer (50 mM Tris-HCl, pH 7.5, 5 mM $MgCl_2$, 2.5 mM EDTA) and 0.1% fatty acid free bovine serum albumin (Sigma Cat. #A0821) for 90 minutes. A rapid filtration technique using Millipore FB filter plates (Catalog #MADVNOB) and filtration apparatus (Millipore system Catalog MAVM0960R) with vacuum aspiration was used to harvest and rinse labeled membranes (8 times with 0.2 mL of chilled binding buffer). The radioactivity bound to the filters was counted with 0.05 mL of liquid scintillant (Ultra-Gold MV, PerkinElmer catalog #6013159) in a scintillation counter (Perkin Elmer Microbeta instrument). Nonspecific binding was determined in the presence of unlabeled 1 uM CP 55,940 (Sigma Aldrich, catalog #C1112). Binding data were analyzed using GraphPad Prism (GraphPad Software, Inc. San Diego, Calif.). Data expressed as a percentage of positive controls is summarized in Table 4.

TABLE 4

Human CB1 Cannabinoid Receptor activity table.
A = Less than 25%; B = between 25% and 50%; C = between 50% and 75%; D = greater than 75%.

| Compound Number | CB1 binding % (at 1 μM) | CB1 binding % (at 10 μM) |
|---|---|---|
| 1 | B | C |
| 2 | A | C |
| 3 | A | A |
| 4 | A | A |
| 5 | C | D |
| 6 | A | B |
| 7 | B | C |
| 8 | B | D |
| 9 | C | D |
| 10 | C | D |
| 11 | C | D |
| 12 | A | B |
| 13 | B | C |

TABLE 4-continued

Human CB1 Cannabinoid Receptor activity table.
A = Less than 25%; B = between 25% and 50%; C = between 50% and 75%; D = greater than 75%.

| # | | |
|---|---|---|
| 14 | C | D |
| 15 | B | C |
| 16 | A | A |
| 17 | C | D |
| 18 | A | C |
| 19 | B | C |
| 20 | A | B |
| 21 | B | C |
| 22 | A | B |
| 23 | C | D |
| 24 | C | D |
| 25 | B | C |
| 26 | A | B |
| 27 | D | D |
| 28 | A | C |
| 29 | B | B |
| 30 | B | C |
| 31 | A | C |
| 32 | A | C |
| 33 | A | C |
| 34 | A | C |
| 35 | B | C |
| 36 | D | D |
| 37 | A | C |
| 38 | B | C |
| 39 | B | C |
| 40 | A | C |
| 41 | B | B |
| 42 | A | C |
| 43 | A | B |
| 44 | B | C |
| 45 | A | B |
| 46 | A | B |
| 47 | C | C |
| 48 | A | C |
| 49 | A | C |
| 50 | A | A |
| 51 | B | C |
| 52 | A | A |
| 53 | A | A |
| 54 | C | C |
| 55 | C | D |
| 56 | A | B |
| 57 | B | C |
| 58 | A | B |
| 59 | B | C |
| 60 | C | D |
| 61 | B | C |
| 62 | A | C |
| 63 | B | C |
| 64 | C | D |
| 65 | A | B |
| 66 | C | D |
| 67 | A | B |
| 68 | A | C |
| 69 | A | C |
| 70 | A | C |
| 71 | B | D |
| 72 | D | D |
| 73 | A | A |
| 74 | C | D |
| 75 | A | C |
| 76 | B | C |
| 77 | A | B |
| 78 | A | B |
| 79 | C | D |
| 80 | A | B |
| 81 | B | C |
| 82 | B | C |
| 83 | A | A |
| 84 | B | C |
| 85 | A | C |
| 86 | A | B |
| 87 | A | C |
| 88 | A | C |
| 89 | B | C |
| 90 | B | C |
| 91 | C | D |
| 92 | D | D |
| 93 | B | C |
| 94 | B | C |
| 95 | C | D |
| 96 | C | D |
| 97 | B | C |
| 98 | C | D |

| $IC_{50}$ values | Less than 100 nM = A, between 100 nM and 1 μM = B, | between 1 μM and 10 μM = C, greater than 10 μM = D |
|---|---|---|
| 99 | | C |
| 100 | | D |
| 101 | | C |

In some embodiments, compounds of the invention display a decreased affinity for binding to the CB1 receptor. In some embodiments, compounds of the invention displayed a decreased affinity for binding to the CB1 receptor when compared to other known FAAH inhibitors. In some embodiments, compounds of the invention displayed a decreased affinity for binding to the CB1 receptor when compared to other known FAAH inhibitors having similar structures.

In some embodiments, compounds of the invention show increased selectivity for binding to FAAH relative to their binding to the CB1 receptor.

Example 8

Nonclinical Safety Profile Determination

The safety profile of the compounds can be evaluated in nonclinical toxicology studies in rodents and non-rodents. Male and female animals are administered test compound in a vehicle by an appropriate route (e.g., oral, intramuscular, intravenous) once daily for, e.g., 14 or 28 consecutive days. Additional animals receive the vehicle only and serve as the vehicle control group. Clinical observations, changes in body weights and feed consumption, ophthalmic and clinical pathology (hematology, clinical chemistry, coagulation) parameters are evaluated in each animal during the in life portion of the study. In rodents, toxicokinetic evaluations for systemic exposure determinations are conducted on separate groups of animals at each dose level of the test compound. In non-rodents, toxicokinetic evaluations are conducted on the same animals used for toxicity evaluations. Additional groups of animals can be included to assess recovery from any findings. At the end of the dosing and recovery periods, necropsy examinations are performed and organ weights, macroscopic and microscopic evaluations are conducted. Results are compared to vehicle control values using statistical analyses where appropriate. Results are used to determine the no-observed-adverse-effect-level (NOAEL) and toxicity profile in the test species.

Example 9 hERG-Related Compound Toxicity

Human ether-a-gogo-related (hERG) ion channel encodes the inward rectifying voltage gated potassium channel in the heart and has a major role during the repolarization of the cardiac action potential. It is well established that blockade of this ion channel can lead to potentially lethal arrhythmias. hERG pre-clinical safety data is often used by regulatory agencies in elucidate the toxicity profile of certain compositions. The disclosed compounds of Table 1 were tested for their ability to inhibit hERG ion channels.

hERG Testing Methods a. hERG-CHO Culture Conditions

Media components include F12 Nutrient Mixture (Ham) with GlutaMAX™ (Invitrogen, Cat#31765), Fetal Bovine Serum, Certified (Invitrogen, Cat#16000-044—not heat activated), and Geneticin® Selective Antibiotic (Invitrogen, Cat#10131-027).

One vial of frozen cells, at $1.62 \times 10^6$ cells are thawed into a T150 flask (BD Falcon 355001) with 40 mL of pre-warmed complete media. Cells are cultured at 37° C., 5% $CO_2$ for four hours prior to gently changing media. 99% of cells appear attached at this time point.

The flask is media changed at 24 hours post-thaw, the cells are imaged, media changed, and returned to the incubator. At this point, the cells appear healthy and about 25% confluent in the flask. Cells are typically passed 24-48 hours after thaw according to the following intervals and densities below. Cells are incubated at 30° C. for 48 hours prior to assay.

| Incubation Interval | Cells/T150 to Passage | Total Cell Yield/T150 |
| --- | --- | --- |
| 48 hours | $1.4 \times 10^6$ | $10.6 \times 10^6$ |
| 72 hours | $0.4 \times 10^6$ | $9.7 \times 10^6$ | b. hERG Voltage Testing Conditions

Using an automated patch clamp apparatus (IonWorks$^{HT}$), a three pulse protocol was applied by stepping from a holding potential of −80 mV to +40 mM for 2 s, to activate hERG channels. The membrane voltage was then stepped back to −50 mV for 2 s to evoke a tail current prior to returning to the holding potential for 1 s. This sequence was repeated a further two times. This voltage protocol was applied prior to drug (Pre compound) and after 600 s in the presence of drug (Post compound).

The amplitude of the hERG tail current was calculated by measuring the difference between the maximum current on stepping to −50 mV of the third pulse (i.e. peak of the outward hERG tail current) and the current measured immediately prior to activation of any hERG current. This parameter was assessed before (pre tail current amplitude) and after 600 s incubation (post tail current amplitude) in drug. In order to assess the amount of block produced by test compounds, the data was first filtered using the IonWorks™ software to exclude any cells where the seal resistance was less than 50 MOhm. The remaining data was then exported to an excel compatible data file and only currents with tail currents greater than 250 pA were analyzed. The post/pre tail current amplitude ratio for the third pulse was calculated for each drug and control, and presented as percent inhibition. Data expressed as a percentage of positive controls are summarized in Table 5.

TABLE 5 hERG Channel Inhibition %
A = Less than 25%; B = between 25% and 50%; C = between 50% and 75%; D = greater than 75%; ND means "Not Determined".

| Compound Number | hERG Channel Inhibition % (at 1 µM), vehicle-subtracted values | hERG Channel Inhibition % (at 10 µM), vehicle-subtracted values |
| --- | --- | --- |
| 1 | A | A |
| 2 | A | A |
| 3 | A | B |
| 5 | A | B |
| 6 | A | A |
| 7 | A | A |
| 9 | A | A |
| 11 | A | B |
| 12 | A | A |
| 13 | A | A |
| 14 | A | A |
| 15 | A | C |
| 16 | A | A |
| 17 | A | A |
| 18 | A | A |
| 19 | A | B |
| 20 | A | A |
| 21 | A | B |
| 22 | A | A |
| 23 | A | C |
| 30 | A | C |
| 31 | A | A |
| 32 | A | A |
| 33 | A | A |
| 34 | A | A |
| 36 | A | A |
| 37 | B | C |
| 38 | A | B |
| 40 | A | A |
| 41 | A | B |
| 42 | A | C |
| 43 | A | A |
| 44 | A | A |
| 45 | A | A |
| 46 | A | A |
| 47 | A | A |
| 48 | A | A |
| 51 | A | A |
| 52 | A | A |
| 53 | A | A |
| 54 | A | A |
| 55 | A | A |
| 59 | A | B |
| 60 | A | B |
| 61 | B | C |
| 63 | A | C |
| 64 | A | B |
| 67 | A | A |
| 68 | A | A |
| 69 | A | A |
| 70 | A | A |
| 71 | A | A |
| 72 | A | B |
| 77 | A | A |
| 78 | A | B |
| 79 | A | A |
| 80 | A | A |
| 81 | A | A |
| 82 | A | A |
| 84 | A | A |
| 85 | A | B |
| 87 | A | A |
| 88 | A | A |
| 89 | A | A |
| 90 | A | A |
| 91 | ND | ND |
| 92 | A | A |
| 93 | A | A |
| 94 | A | A |
| 95 | ND | ND |
| 96 | A | A |
| 97 | A | A |

TABLE 5-continued hERG Channel Inhibition %
A = Less than 25%; B = between 25% and 50%; C = between 50% and 75%; D = greater than 75%; ND means "Not Determined".

| Compound Number | hERG Channel Inhibition % (at 1 µM), vehicle-subtracted values | hERG Channel Inhibition % (at 10 µM), vehicle-subtracted values |
| --- | --- | --- |
| 98 | A | A |
| 99 | A | A |
| 100 | A | A |
| 101 | A | A |

In some embodiments, the compounds of the invention displayed decreased inhibition of the hERG channel. In some embodiments, the compounds of the invention displayed a decreased inhibition of the hERG channel when compared to other known FAAH inhibitors. In some embodiments, the compounds of the invention displayed a decreased inhibition of the hERG channel when compared to other known FAAH inhibitors having similar structures.

Example 10

Pharmacokinetic Studies

Pharmacokinetic studies were conducted to determine absorption and distribution profiles of the disclosed compounds which were orally administered to rats.

a. Compound Administration and Blood Preparation

Compounds were formulated in a 1% DMA/99% Vitamin E TPGS vehicle. Prepared compounds were dosed via oral gavage (PO). Following the appropriate pretreatment time of 2 hours, rats were anesthetized with isoflurane gas. Blood was collected into tubes containing EDTA via retro-orbital eye bleed. Whole blood was spun in a micro-centrifuge at approximately 13,000 rpm for 5 minutes at room temperature. Separated plasma was subsequently aliquoted into eppendorf tubes. Samples were stored at −80° C. until prepped for analysis.

b. FAAH Plasma Sample Preparation (KS Method)

Plasma samples were thawed and the required amount of plasma for standards, blanks and dilutions were made. The dilutions were prepared before plating. Preparation of crash solution included cold acetonitrile+0.1% formic acid and 25 ng/mL of a FAAH inhibitor used as internal standard. solvent standards of the FAAH inhibitor being studied were preparation at 10, 30, 100, 300, 1000, 3000, 10000, 30000, 100000, and 300000 ng/mL in DMSO. Then a plasma standard curve was generated from the solvent standards (final concentrations of standards in plasma were: 0.1, 0.3, 1, 3, 10, 30, 100, 300, 1000, 3000 ng/mL). 50 µL of each plasma sample/dilution, standard, or blank was transferred into 96-well plates. To each well, 200 µL of cold crash solution was added. The plate was covered and gently vortexed. The plate was centrifuged at 3500 rpm, 4° C. for 10 min. 200 µL of each supernatant was transferred into new plates. The plates were dried under nitrogen in a TurboVap at 55° C. The sample in each well was re-suspended with 100 µL of 30% acetonitrile, covered and vortexed gently. The well solutions were analyzed by the LC/MS/MS conditions and specifications below.

c. LC/MS/MS Conditions:

HPLC column was a Clipeus C8, 2.1×30 mm, 5 µm, with Basic 8 guard column using 20 µL injections. Mobile phase used was mobile phase A: 0.1% Formic Acid in water and mobile phase B: 0.1% Formic Acid in 85:10:5 ACN:IPA: H$_2$O. The flow rate for the run was 0.5 mL/min and the gradient for the 4 minute total run time was: 0.0 minutes 35% B; 0.5 minutes 35% B; 1.5 minutes 95% B; 2.3 minutes 95% B; and 2.4 minutes 35% B.

TABLE 6

Plasma PK levels at 2 hours in Rats
A = Less than 10 nM; B = between 10 nM and 100 nM; C = between 100 nM and 1000 nM; D = greater than 1000 nM; ND = Not Determined.

| Compound Number | 2 hr plasma level- ng/mL (rat, 10 mg/kg PO, 2 hr) |
| --- | --- |
| 1 | A |
| 2 | A |
| 5 | C |
| 8 | C |
| 9 | C |
| 10 | C |
| 11 | C |
| 12 | C |
| 13 | C |
| 14 | D |
| 15 | D |
| 17 | C |
| 18 | D |
| 19 | C |
| 20 | C |
| 21 | C |
| 22 | B |
| 23 | C |
| 28 | D |
| 29 | D |
| 30 | C |
| 31 | D |
| 32 | C |
| 33 | C |
| 34 | D |
| 36 | C |
| 37 | C |
| 38 | C |
| 41 | D |
| 42 | C |
| 43 | D |
| 44 | C |
| 45 | C |
| 46 | C |
| 47 | C |
| 48 | C |
| 49 | C |
| 54 | A |
| 55 | C |
| 57 | C |
| 59 | C |
| 60 | D |
| 61 | D |
| 63 | C |
| 64 | C |
| 66 | D |
| 67 | D |
| 68 | D |
| 69 | C |
| 70 | C |
| 71 | A |
| 72 | C |
| 74 | C |
| 75 | D |
| 76 | C |
| 77 | C |
| 79 | D |
| 81 | D |
| 82 | D |
| 84 | D |
| 85 | D |
| 86 | D |
| 87 | D |
| 88 | D |
| 89 | C |
| 90 | D |
| 91 | ND |

TABLE 6-continued

Plasma PK levels at 2 hours in Rats
A = Less than 10 nM; B = between 10 nM and 100 nM; C = between
100 nM and 1000 nM; D = greater than 1000 nM; ND = Not Determined.

| Compound Number | 2 hr plasma level- ng/mL (rat, 10 mg/kg PO, 2 hr) |
|---|---|
| 92 | ND |
| 93 | C |
| 94 | D |
| 95 | ND |
| 96 | C |
| 97 | C |
| 98 | C |
| 99 | D |
| 100 | ND |
| 101 | D |

In some embodiments, the compounds of the invention displayed an increase in plasma exposure (i.e. absorption and distribution). In some embodiments, the compounds of the invention displayed an increase in plasma exposure when compared to other known FAAH inhibitors. In some embodiments, the compounds of the invention displayed an increase in plasma exposure when compared to other known FAAH inhibitors having similar structures.

Example 11

Reduction of Spasticity in a Mouse Model of Multiple Sclerosis

The anti-spastic effect of compounds can be assessed in the mouse chronic relapsing experimental autoimmune encephalomyelitis (CREAE) model of multiple sclerosis as previously described in Baker et al, 1990 J. Neuroimmunol. 28: 261; Baker et al. 2000 Nature 404: 84; and Baker et al., 2001 FASEB J. 15: 300. CREAE is induced in Biozzi ABH mice by subcutaneous injection of syngeneic spinal cord homogenate in Freund's complete adjuvant on Day 0 and Day 7. A proportion of the inoculated mice (approximately 50-60%) develop hindlimb spasticity between 60 and 80 days post-inoculation. Spasticity is assessed by measuring the force required to bend individual hind limbs to full flexion against a strain gauge. To assess the effect of a compound on spasticity, selected doses are administered to spastic CREAE mice by an appropriate route (e.g., oral, intraperitoneal, or intravenous). Spasticity is measured pre-dose and at various times after compound administration (for example 1, 2, 4 and 24 hours post-dose). The mean force of resistance to hindlimb flexion at each post-dose timepoint is compared to the mean pre-dose force using an appropriate statistical test (e.g. analysis of variance or paired t-tests). FAAH inhibitors and their elevation of endo-cannabinoids would be expected to control spasticity in this animal disease model see, for example, Baker et al. 2001 supra) and Ligresti et al. 2006 Br. J. Pharmacol. 147(1): 83).

Example 12

Neuroprotection in a Mouse Model of Multiple Sclerosis

Agents can be tested for their ability to inhibit neurodegeneration in the mouse chronic relapsing experimental autoimmune encephalomyelitis (CREAE) model of multiple sclerosis as described in Baker et al. 1990 supra; Pryce et al. 2003 Brain 126:2191; and Al-Izki et al. 2011 J. Mult. Scler. Epub. 1 April CREAE is induced in Biozzi ABH mice by subcutaneous injection of syngeneic spinal cord homogenate in Freund's complete adjuvant on Day 0 and Day 7. An additional injection of spinal cord homogenate is administered on Day 28 during the post-acute remission period to induce a paralytic relapse, which leads to the accumulation of nerve damage. Selected doses of test agent or negative control agent (e.g., a vehicle control) are administered by an appropriate route (e.g., oral, intraperitoneal, or intravenous) starting around Day 28, and continuing for a suitable period thereafter (e.g., 14 or 28 days). Clinical and neurological symptoms can be scored daily (e.g., starting at Day 11), and motor coordination can be assessed using the RotoRod test. At the end of the dose administration period, animals are killed and their spinal cords are rapidly removed. Nerve content of the spinal cords is determined, for example, using a neurofilament enzyme-linked immunosorbant assay (Pryce et al. 2003 supra). Results for animals treated with the test agent are compared to those for animals treated with the negative control agent. Based on previous investigations, FAAH inhibitors would be expected to inhibit neurodegeneration in this animal model (Pryce et al. 2003 supra).

Example 13

Reduction of Pain and Depression in an Animal Model of Fibromyalgia

Compounds can be tested for their ability to inhibit pain and depression in a putative animal model of fibromyalgia (Nagakura et al. 2009 Pain 146:26). Rats are administered a subcutaneous injection of reserpine (1 mg/kg) once daily for 3 consecutive days to deplete biogenic amines. Treated rats manifest symptoms of pain and depression. Muscle pain can be assessed by applying increasing pressure to a hindlimb muscle until a withdrawal response is elicited. Tactile allodynia can be assessed by measuring the hindlimb withdrawal threshold following application of Von Frey filaments of incrementally increasing weights to the plantar surface of the hind paw. Depression can be assessed by immobility time in the forced swim test. To assess the effect of a test compound in the model, selected doses are administered to the rats by an appropriate route (e.g., oral, intraperitoneal, or intravenous) approximately 5 days after reserpine treatment. Muscle pressure threshold, tactile response threshold, and immobility time in the forced swim test are measured at appropriate times after compound administration (for example 0.5, 1, 2, and 4 hours post-dose). Results are compared to pre-dose values using an appropriate statistical test.

Example 14

Behavioral Effect of FAAH Inhibitors Alone or in Combination with L-DOPA in MPTP-Lesioned Marmosets FAAH inhibitors can be tested for their ability to reduce hyperactivity or dyskinesia in stable L-DOPA induced MPTP-lesioned marmosets. L-DOPA (dopamine precursor 3,4-dihydroxyphenylalanine; levodopa) has been previously demonstrated to induce a stable marmoset model with dyskinesia and hyperactivity, see for example, Gomez-Ramirez et al. (2006) Mov. Disord. 21:839-846; Visanji et al. (2008) Mov. Disord. 23:1922-1925; and Visanji et al (2009) Neurobiol Dis. 35: 184-192). The effects of FAAH inhibitors on motor activity, parkinsonian disability, dyskinesia and psychosis can be assessed through the monitoring of behavioral responses in the group of MPTP-lesioned marmosets with stable L-DOPA-induced dyskinesia and hyperactivity.

Based on previous dose-finding studies in these animals, a dose of L-DOPA (20 mg/kg)/benserazide (5 mg/kg), can be used to elicit hyperactivity, dyskinesia and psychosis that was stable and reproducible on successive L-DOPA administrations. The effect of FAAH inhibitor alone and on L-DOPA response can be assessed. For behavioral observations, L-DOPA can be administered s.c. at a dose volume of 1 ml/kg, as L-DOPA methyl ester (Sigma, Canada) in combination with benserazide (Sigma, Canada). Based on its ability to maximally elevate plasma levels of AEA, PEA and OEA in MPTP-lesioned marmosets, a dose of 10 mg/kg FAAH inhibitor may be employed for all behavioral observations and administered orally at a dose volume of 5 ml/kg.
Treatments On days prior to behavioral assessment, animals are fed normally and receive a maintenance oral L-DOPA dose at 9:00 a.m. At 4:00 p.m. animals are administered either vehicle (p.o.) or FAAH inhibitor (10 mg/kg, p.o.). On days of behavioral assessment, animals are fed their normal diet between 7:00-7:30 a.m. after which time all food is removed from their cages. Water is available ad libitum. At approximately 9:00 a.m., each animal receives either vehicle (p.o.) or FAAH inhibitor (p.o.). Two hours after this, at approximately 11:00 a.m., animals receive either vehicle or L-DOPA (s.c.) treatment. Behavioral assessment, as described below commences directly following this second treatment.

To prevent any confounding effects of prior treatment with oral FAAH inhibitor on the assessment of response to vehicle treatment, the order of these treatments are randomized in each animal. A minimum of 48 h is left between behavioral observations in the same animal.
Behavioral Assessment of Marmoset Behavior After administration of final treatment (L-DOPA, s.c.), animals can be placed immediately into observation cages (0.8×0.8×0.7 m) containing food, water and a wooden perch and left undisturbed for the 6 h duration of the experiment. Behavior can be monitored via recorded DVD footage and analyzed post hoc by a movement disorder neurologist blinded to the treatment. Methods for assessment of behavior are essentially as described previously in Fox et al. 2006 Arch. Neurol. 63:134; and Gomez-Ramirez et al. 2006 Mov Disord. 21:839. L-DOPA-induced dyskinesia and psychosis can be independently assessed after 2-4 hours after injection with L-DOPA. During this period, for each 10 min epoch, dyskinesia and psychosis can be rated from 0 to 4: 0=absent; 1=mild, fleeting, rare, present less than 30% of the observation period; 2=moderate, not interfering with normal activity, present more than 30% of the observation period; 3=marked, at times interfering with normal activity, present less than 70% of the observation period; 4=severe, continuous, replacing normal activity, present more than 70% of the observation period. For dyskinesia, chorea and dystonia can be graded separately and the score given to represent the most disabling dyskinesia observed, whether chorea or dystonia, in any 10-minute period of assessment. For psychosis, hyperkinesia, response to non-apparent stimuli (hallucinatory behavior), repetitive grooming and stereotypies can be graded separately. For this measure, the score given represented the most disabling of any of the four sub-score levels observed, in any 10 min period of assessment.

In addition, a quantitative assessment of marmoset activity can be made using computer-operated passive infra-red sensors, essentially as described previously in Maccarrone et al. 2003 J. Neurochem. 85:1018; and Visanji et al. 2009 J Pharm Exp Ther 328: 276. A single sensor containing a hemispherical lens (Guardall, Mississauga, ON, Canada) is mounted 1.5 m above the top of each the observation cage. The sensor is positioned so that motion was detected throughout the entirety of the cage below. The signal is fed via an RS-232 input to a computer. Proprietary Motion Detector software (Research Electronics, Toronto Western Hospital, Toronto, ON, Canada) is utilized that displayed within Microsoft Excel (Microsoft, Redmond, Wash.). Activity counts are logged in 1-min epochs for the entire 6 h duration of the experiment and cumulated over the peak dose period of 2-4 h.

Assessment of marmoset hyperactivity is further assessed over time by quantifying the average activity of counts per minute of the same animals obtained prior to administration of MPTP (i.e., in the normal state). Activity over the same period of 2-4 h is calculated and used to identify minutes of high activity (a minute when activity was above the average per minute of the animal prior to MPTP). High activity counts (the total counts obtained in high activity minutes) are cumulated. High activity time (the number of high activity minutes) is also calculated.

Example 15

Effect of FAAH Inhibitors on Cortagine-Induced Visceral Hypersensitivity in Rats The cortagine-induced visceral hypersensitivity rodent model has been developed to investigate the effect of compounds on visceral pain. For this experiment, male Sprague Dawley (SD) rats (250-275 g, Harlan Labs, Indianapolis, Ind.) are kept under standard conditions of humidity and temperature and a 12-hour light/dark cycle (lights on 6.00 a.m.). Animals can be group housed and have access to food ad libitum. Prior to the start of studies, animals are acclimatized to handling and administration of treatments (oral syringe feeding and subcutaneous injection). At the end of the experiments, animals are sacrificed by $CO_2$ gas inhalation followed by thoracotomy or isoflurane anesthesia followed by decapitation with appropriate approved animal protocols.
A. Rodent Model On the day of the experiments, rats are injected intraperitoneally (IP) with cortagine (10 μg/kg, 0.8 ml/kg in DMSO/cremophor/isotonic saline (1:1:8 v:v:v). Cortagine, a selective corticotropin releasing factor receptor 1 ($CRF_1$) agonist, prepared as described previously (Rivier et al. 2007 J. Med. Chem. 50:1668), can be stored in a powder form at −80° C. and prepared in sterile water (12.5 μg/ml) immediately before use. This dose had previously been established to show a significant increase in defecation, induction of diarrhea and increase in colonic motility, permeability and visceral pain in rats. (Larauche et al. 2009 Am. J. Physiol. Gastrointest. Liver Physiol. 297: G215)
B. Test Compounds FAAH inhibitors can be formulated as suspensions in DMSO/cremophor/isotonic saline (1:1:8 v:v:v). The concentrations of FAAH inhibitors compound suspensions can be 6 mg/ml for 30 mg/kg dose; 2 mg/ml for the 10 mg/kg dose; or 1.5 mg/ml for the 3 mg/kg dose. Vehicle treatment can be administered to rats by per os (PO) route at dose-volume of 5 ml/kg. FAAH inhibitor treatment can be administered to rats by subcutaneous (SC) route at dose volume of 2 ml/kg. The vehicle for the PO route was DMSO/cremophor/isotonic saline (1:1:8 v:v:v). Test agents can be administered to non-fasted rats which are restrained by hand. The regimen of administration of FAAH inhibitors can involve one delivery (PO or SC) performed 120 min before IP injection of cortagine.

C. Measurement of Visceral Pain

Visceral pain is assessed using a non-invasive pressure transducer system referred to as "sensor balloon" as previously described (Larauche et al. 2009 supra; Ness et al. 1988 Brain Res. 450:153). Adult non-fasted SD rats, a 4-5 cm "sensor balloon" lubricated with surgical lubricant (Surgilube, Fougera, Melville) is inserted intra-anally under brief isoflurane anesthesia. The "sensor balloon" can be positioned such that its distal end is 1 cm proximal to the anal verge and secured in place by tapping the balloon catheter to the tail. Rats are placed individually in Boolman's cage and allowed to recover from anesthesia and habituation. The colorectal procedure can be performed using the Distender Series IIir dual barostat (G&J Electronics Inc, Toronto, Ontario). The colorectal distension ("CRD") protocol consists of 2 CRD at 60 mmHg to unfold the balloon followed by 2 sets of CRD at 10, 20, 40 and 60 mmHg, 20 s duration, 4-min inter-stimulus interval. The intra-luminal colonic pressure (ICP) can be recorded for 20 s before, during and after termination of CRD. The AUC of ICP during CRD over non-distended ICP (before CRD) can be recorded as the VRM (visceromotor response, see Larauche et al. 2009 supra. To examine the pressure-response relationship and adjust for inter-individual variation of the signal, ICP amplitudes can be normalized as percent of the VRM response to the highest (60 mmHg) in the $1^{st}$ set of CRD for each rat. VRM to the $1^{st}$ set of CRD before treatment represents baseline VRM at different pressures of distention and is averaged for each group of rats. Rats can also be visually observed for any other behavioral responses.

D. Experimental Protocol

All the experiments can be performed on conscious male non-fasted SD rats and at the same time in the morning to avoid circadian variations that may influence experimental results.

Rats are habituated to oral gavage (once/day) and to Bollman's cages (4 h/day) for 3 consecutive days preceding the treatment. They are placed in a quiet rat room 48 h before the experimental day and are not disturbed outside of the training/gavage sessions. On the day of the experiment, at 6:30 am, animals can be equipped with distension balloons and placed in Bollman's cages before being brought to the experimental room, where they are left 20 min to recover from anesthesia. At the end of the 20 min recovery period, a baseline CRD (CRD#1) of 40 min is performed at 10, 20, 40, 60 mmHg and the visceromotor response (VMR) assessed. Immediately after the end of the first CRD, rats receive an oral gavage of vehicle (DMSO/cremophor/isotonic saline (1:1:8 v:v:v), 1.5 ml), or FAAH inhibitor in vehicle. Two hours after, cortagine (10 μg/kg in vehicle, IP) can be injected. Fifteen minutes after cortagine injection, a second CRD (CRD#2) of 40 min can be performed. At the end of the distension, the balloons are removed prior to placing the rats back into their home cages (~15 min).

SD rats with cortagine injected IP would be expected to experience visceral hypersensitivity to colorectal distension and visceral pain demonstrated through higher responses over baseline. Effective FAAH inhibitors would prevent or reduce the visceral hypersensitivity induced by IP injection of cortagine.

Example 16

Reduction of Scratching in a Mouse Model of an Acute Allergenic Response

The effects of the disclosed compounds on pruritus (itch) can be assessed using a mouse model of an acute allergenic response (Sugimoto et al. 1998 Eur J Pharmacol. 351: 1-5; Schlosburg et al. 2009 J Pharmacol Exp Ther. 329:314). Groups of mice (e.g., C57Bl6/J strain weighing approximately 20-25 g) are pretreated with selected doses of test compound or a vehicle control agent administered by an appropriate route (e.g., oral, intraperitoneal, or intravenous). Each mouse is then given an injection of compound 48/80 (a mast cell degranulating compound) under the scruff at the most dorsal point of the back just beneath the head in order to elicit short-term scratching behavior in the affected area. Behavior is then recorded and analyzed. The scratching response is tracked as hind leg scratching of the injection site and surrounding areas. Inactivity can also be monitored. The total number of seconds of a specific behavior (e.g., hind leg scratching) over a total observation period is scored, and the mean and standard error of the mean for each group is calculated. Differences between means can be analyzed by an appropriate statistical test (e.g. analysis of variance or paired t-tests).

Example 17

Reduction of Anxiety-Like Behavior in the Mouse Marble Burying Assay

The mouse marble burying assay can be used to assess the effects of compounds described herein on compulsive, anxiety-like behavior, and is considered a model of obsessive compulsive disorder (Deacon 2006 Nat Protoc. 1: 122; Kinsey et al. 2011 Pharmacol Biochem Behav. 98: 21). Groups of mice (e.g., C57Bl6/J strain weighing approximately 20-25 g) are pretreated with selected doses of a test compound or a vehicle control agent administered by an appropriate route (e.g., oral, intraperitoneal, or intravenous). To assess marble burying behavior, each mouse is placed in a cage filled to a depth of about 5 cm with bedding, in which approximately 20 marbles (approximately 10 mm in diameter) are arranged in a grid-like fashion across the surface of the bedding. After an appropriate time (e.g., approximately 20 min), the mouse is carefully removed from the cage and the number of buried marbles is determined. The mean and standard error of the mean for each group of mice is calculated. Differences between means can be analyzed by an appropriate statistical test (e.g. analysis of variance or paired t-tests.)

Example 18

Reduction of Bladder Hypersensitivity in a Rat Model of Overactive Bladder

The effects of the disclosed compounds on urinary bladder overactivity can be assessed using the acetic acid-induced bladder hypersensitivity model in the rat. Groups of female rats (e.g., Sprague-Dawley rats weighing approximately 200-250 grams) are pretreated with selected doses of test compound or a vehicle control agent administered by an appropriate route (e.g., oral, intraperitoneal, or intravenous). Cystometrograms are measured under continuous anesthesia during intravesical infusion of saline or dilute acetic acid (e.g., at a flow rate of 0.1 ml/min for 60 min) to induce repetitive micturitions. Urological parameters such as micturition reflex frequency and amplitude can be determined from the cystometrograms measured at baseline and after compound treatment. The mean and standard error of the mean for each group is calculated. Differences between group means can be analyzed by an appropriate statistical test (e.g. analysis of variance or paired t-tests.)

Other Embodiments

It is to be understood that while the invention has been described in conjunction with the detailed description thereof, the foregoing description is intended to illustrate and not limit the scope of the invention, which is defined by the scope of the appended claims. Other aspects, advantages and modifications are within the scope of the following claims.

We claim:

1. A compound selected from Table 1, or a pharmaceutically acceptable salt thereof;

TABLE 1

| Structure | Compound Number |
|---|---|
| 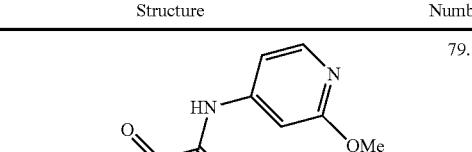 | 79. |

2. A pharmaceutical composition comprising a compound of claim 1, or a pharmaceutically acceptable salt thereof, and a pharmaceutically acceptable carrier, vehicle or adjuvant.

3. The pharmaceutical composition of claim 2, further comprising at least one additional therapeutic agent.

4. The pharmaceutical composition of claim 3, wherein the additional therapeutic agent is selected from the group consisting of painkillers, non-steroidal anti-inflammatory drugs (NSAIDs), cannabinoid receptor agonists, opiate receptor agonists, anti-infective agents, sodium channel blockers, N-type calcium channel blockers, local anesthetics, VR1 agonists and antagonists, agents used for migraines, topical agents used in the treatment of localized pruritus, anti-inflammatory and/or immunosuppressive agents, agents designed to treat tobacco abuse (e.g., nicotine receptor partial agonists and nicotine replacement therapies), ADD/ADHD agents, agents to treat alcoholism such as opioid antagonists, agents for reducing alcohol withdrawal symptoms such as benzodiazepines and beta-blockers, antihypertensive agents such as ACE inhibitors and Angiotensin II Receptor blockers, Renin inhibitors, vasodilators, agents used to treat glaucoma such as direct-acting Miotics (cholinergic agonists), indirect-acting Miotics (cholinesterase inhibitors) or Carbonic anhydrase inhibitors, selective adrenergic agonists, Osmotic diuretics, antidepressants such as SSRIs, tricyclic antidepressants, dopaminergic antidepressants, cognitive improvement agents, acetylcholinesterase inhibitors, anti-emetic agents (e.g., 5HT3 antagonists), neuroprotective agents, neuroprotective agents currently under investigation, antipsychotic medications, agents used for multiple sclerosis, disease-modifying anti-rheumatic drugs (DMARDS), biological response modifiers (BRMs), COX-2 selective inhibitors, COX-1 inhibitors, immunosuppressives, PDE4 inhibitors, corticosteroids, histamine H1 receptor antagonists, histamine H2 receptor antagonists, proton pump inhibitors, leukotriene antagonists, 5-lipoxygenase inhibitors, nicotinic acetylcholine receptor agonists, P2X3 receptor antagonists, NGF agonists and antagonists, NK1 and NK2 antagonists, NMDA antagonist, potassium channel modulators, GABA modulators, anti-cancer agents such as tyrosine kinase inhibitors, anti-hyperlipidemia drugs, appetite suppressing agents, anti-diabetic medications such as insulin, GI (gastrointestinal) agents, and serotonergic and noradrenergic modulators.

* * * * *